(12) United States Patent
Van Zyl et al.

(10) Patent No.: US 9,243,256 B2
(45) Date of Patent: Jan. 26, 2016

(54) BIOFUEL PRODUCTION

(75) Inventors: Willem Heber Van Zyl, Stellenbosch (ZA); Tania Jooste, Northcliff (ZA); Johann Ferdinand Gorgens, Stellenbosch (ZA); Maryna Saayman, Durbanville (ZA); Lorenzo Favaro, Scorze (IT); Marina Basaglia, Piove di Sacco (IT); Sergio Casella, Pisa (IT)

(73) Assignees: Stellenbosch University, Stellenbosch (ZA); Universita Degli Studi Di Padova, Padua (IT)

(*) Notice: Subject to any disclaimer, the term of this patent is extended or adjusted under 35 U.S.C. 154(b) by 491 days.

(21) Appl. No.: 13/640,902

(22) PCT Filed: Apr. 12, 2010

(86) PCT No.: PCT/IB2010/000795
§ 371 (c)(1),
(2), (4) Date: May 21, 2013

(87) PCT Pub. No.: WO2011/128712
PCT Pub. Date: Oct. 20, 2011

(65) Prior Publication Data
US 2013/0244295 A1   Sep. 19, 2013

(51) Int. Cl.
| | |
|---|---|
| C12N 1/14 | (2006.01) |
| C12N 9/30 | (2006.01) |
| C12N 9/34 | (2006.01) |
| C12N 15/00 | (2006.01) |
| C12N 1/20 | (2006.01) |
| C12P 7/00 | (2006.01) |
| C07H 21/04 | (2006.01) |
| C12N 15/81 | (2006.01) |
| C12N 9/24 | (2006.01) |
| C12P 7/06 | (2006.01) |
| C12P 19/14 | (2006.01) |

(52) U.S. Cl.
CPC .............. *C12N 15/81* (2013.01); *C12N 9/2402* (2013.01); *C12N 9/242* (2013.01); *C12N 9/2428* (2013.01); *C12P 7/06* (2013.01); *C12P 19/14* (2013.01); *Y02E 50/17* (2013.01)

(58) Field of Classification Search
CPC .............................. C12N 9/2402; C12P 7/00
See application file for complete search history.

(56) References Cited

U.S. PATENT DOCUMENTS

| 2006/0060126 A1 | 3/2006 | Dove et al. |
| 2009/0037574 A1 | 2/2009 | Machida |

FOREIGN PATENT DOCUMENTS

| ZA | 2004/06714 A | 11/2005 |

OTHER PUBLICATIONS

Eksteen et al. Starch fermentation by recombinant *Saccharomyces cerevisiae* strains expressing the alpha-amylase and glucoamylase genes from lipomyces kononenkoae and saccharomycopsis fibuligera. Biotechnol Bioeng. Dec. 20, 2003;84(6):639-46.*
Xu et al. A5HNU1—UniProtKB/TrEMBL Database. Jun. 2007.*
Knox, et al., "Starch Fermentation Characteristics of *Saccharomyces cerevisiae* Strains Transformed with Amylase Genes from Lipomyces Kononenkoae and Saccharomycopsis Fibuligera," Enzyme and Microbial Technology, 2004, vol. 34, pp. 453-460.
Thorsen et al., "Identification and Characterization of Glucoamylase from the Fungus Thermomyces Languginosus," Biochimica et Biophysica Acta, 2006, vol. 1764, pp. 671-676.
Chapter 14 of Branduardi and Porro, Yeast: Molecular and Cell Biology, 2nd ed, edited by H. Feldmann, 2012, 26 pages.

* cited by examiner

*Primary Examiner* — Yong Pak
(74) *Attorney, Agent, or Firm* — Wilmer Cutler Pickering Hale and Dorr LLP

(57) ABSTRACT

The invention relates to the combination of the TLG1 glucoamylase from *Thermomyces lanuginoses* with: (i) the SFA1 alpha-amylase from *Saccharomycopsis fibuligera*; and/or (ii) the LKA alpha-amylase. The enzyme combinations may be expressed in a host cell (e.g. in *Saccharomyces cerevisiae*) or provided as an enzyme composition. Methods for making the enzyme combinations of the invention are provided. The invention also relates to a yeast strain which exhibits amylolytic activity and promising fermentative abilities. Processes for producing a fermentation product (in particular alcohol) from starch-containing material are described.

18 Claims, 37 Drawing Sheets

Figure 4

```
1     GAATTCCAACATGGTTTCCTTCACTTCTTTGTTGGCCGGTGTCGCTGCCATTTCTGGTGT
1                 M  V  S  F  T  S  L  L  A  G  V  A  A  I  S  G  V

61    CTTGGCTGCTCCAGCTGCTGAAGTTGAACCAGTTGCCGTCGAAAAGAGAACTTTGGATTC
21     L  A  A  P  A  A  E  V  E  P  V  A  V  E  K  R  T  L  D  S

121   CTGGTTGTCTAACGAAGCCACTGTTGCTAGAACTGCTATTTTGAACAACATCGGTGCCGA
41     W  L  S  N  E  A  T  V  A  R  T  A  I  L  N  N  I  G  A  D

181   CGGTGCTTGGGTTTCCGGTGCTGACTCCGGTATTGTTGTTGCTTCCCCATCCACCGATAA
61     G  A  W  V  S  G  A  D  S  G  I  V  V  A  S  P  S  T  D  N

241   CCCAGACTACTTCTACACCTGGACTAGAGACTCCGGTTTGGTCATTAAGACTTTGGTTGA
81     P  D  Y  F  Y  T  W  T  R  D  S  G  L  V  I  K  T  L  V  D

301   CTTGTTCAGAAACGGTGATACTGACTTGTTGTCTACCATTGAACACTACATTTCTTCCCA
101    L  F  R  N  G  D  T  D  L  L  S  T  I  E  H  Y  I  S  S  Q

361   AGCTATCATCCAAGGTGTTTCCAACCCATCTGGTGACTTGTCTTCCGGTGGTTTGGGTGA
121    A  I  I  Q  G  V  S  N  P  S  G  D  L  S  S  G  G  L  G  E

421   ACCAAAGTTCAACGTCGATGAAACCGCTTACACTGGTTCTTGGGGTAGACCACAAAGAGA
141    P  K  F  N  V  D  E  T  A  Y  T  G  S  W  G  R  P  Q  R  D

481   TGGTCCAGCCTTGAGAGCTACTGCCATGATCGGTTTCGGTCAATGGTTGTTGGATAACGG
161    G  P  A  L  R  A  T  A  M  I  G  F  G  Q  W  L  L  D  N  G

541   TTACACTTCCGCTGCTACCGAAATCGTTTGGCCATTGGTTAGAAACGACTTGTCCTACGT
181    Y  T  S  A  A  T  E  I  V  W  P  L  V  R  N  D  L  S  Y  V

601   CGCTCAATACTGGAACCAAACCGGTTACGACTTGTGGGAAGAAGTTAACGGTTCTTCTTT
201    A  Q  Y  W  N  Q  T  G  Y  D  L  W  E  E  V  N  G  S  S  F

661   CTTCACCATCGCCGTCCAACACAGAGCCTTGGTTGAAGGTTCCGCTTTCGCTACCGCTGT
221    F  T  I  A  V  Q  H  R  A  L  V  E  G  S  A  F  A  T  A  V

721   CGGTTCCTCTTGTTCCTGGTGTGATTCTCAAGCTCCACAAATCTTGTGTTACTTGCAATC
241    G  S  S  C  S  W  C  D  S  Q  A  P  Q  I  L  C  Y  L  Q  S

781   TTTCTGGACCGGTTCTTACATCTTGGCTAACTTCGATTCCTCTAGATCCGGTAAGGACAC
261    F  W  T  G  S  Y  I  L  A  N  F  D  S  S  R  S  G  K  D  T

841   CAACACTTTGTTGGGTTCTATCCACACCTTCGATCCAGAAGCTGGTTGTGACGACTCTAC
281    N  T  L  L  G  S  I  H  T  F  D  P  E  A  G  C  D  D  S  T

901   TTTCCAACCATGTTCTCCAAGAGCTTTGGCTAACCACAAGGAAGTCGTTGACTCTTTCAG
301    F  Q  P  C  S  P  R  A  L  A  N  H  K  E  V  V  D  S  F  R

961   ATCCATCTACACCTTGAACGACGGTTTGTCCGATTCTGAAGCTGTTGCTGTCGGTAGATA
321    S  I  Y  T  L  N  D  G  L  S  D  S  E  A  V  A  V  G  R  Y

1021  CCCAGAAGATTCCTACTACAACGGTAACCCATGGTTCTTGTGTACTTTGGCTGCTGCTGA
341    P  E  D  S  Y  Y  N  G  N  P  W  F  L  C  T  L  A  A  A  E

1081  ACAATTGTACGACGCTTTGTACCAATGGGATAAGCAAGGTTCCTTGGAAATTACTGACGT
361    Q  L  Y  D  A  L  Y  Q  W  D  K  Q  G  S  L  E  I  T  D  V

1141  CTCCTTGGACTTCTTCAAGGCTTTGTACTCTGGTGCTGCTACTGGTACTTACTCCTCTTC
```

1201        CTCTTCTACCTACTCCTCCATTGTTTCCGCTGTTAAGACCTTCGCTGATGGTTTCGTTTC
401            S  S  T  Y  S  S  I  V  S  A  V  K  T  F  A  D  G  F  V  S

1261        TATCGTCGAAACCCACGCTGCTTCCAACGGTTCCTTGTCCGAACAATTCGACAAGTCTGA
421            I  V  E  T  H  A  A  S  N  G  S  L  S  E  Q  F  D  K  S  D

1321        CGGTGATGAATTGTCTGCTAGAGACTTGACCTGGTCTTACGCTGCTTTGTTGACCGCTAA
441            G  D  E  L  S  A  R  D  L  T  W  S  Y  A  A  L  L  T  A  N

1381        CAACAGAAGAAACTCTGTTGTTCCACCATCTTGGGGTGAAACTTCCGCTTCTTCCGTTCC
461            N  R  R  N  S  V  V  P  P  S  W  G  E  T  S  A  S  S  V  P

1441        AGGTACTTGTGCTGCCACTTCTGCTTCCGGTACTTACTCTTCCGTCACTGTTACCTCCTG
481            G  T  C  A  A  T  S  A  S  G  T  Y  S  S  V  T  V  T  S  W

1501        GCCATCCATCGTCGCTACCGGTGGTACTACCACTACTGCTACTACCACCGGTTCTGGTGG
501            P  S  I  V  A  T  G  G  T  T  T  T  A  T  T  T  G  S  G  G

1561        TGTCACCTCCACTTCCAAGACCACCACCACTGCTTCTAAGACCTCCACCACTACTTCTTC
521            V  T  S  T  S  K  T  T  T  A  S  K  T  S  T  T  T  S  S

1621        CACTTCTTGTACCACCCCAACTGCTGTTGCCGTCACTTTCGATTTGACTGCCACTACCAC
541            T  S  C  T  T  P  T  A  V  A  V  T  F  D  L  T  A  T  T  T

1681        CTACGGTGAAAACATTTACTTGGTCGGTTCCATTTCTCAATTGGGTGACTGGGAAACCTC
561            Y  G  E  N  I  Y  L  V  G  S  I  S  Q  L  G  D  W  E  T  S

1741        CGACGGTATCGCTTTGTCTGCCGACAAGTACACCTCTTCTAACCCATTGTGGTACGTTAC
581            D  G  I  A  L  S  A  D  K  Y  T  S  S  N  P  L  W  Y  V  T

1801        TGTTACTTTGCCAGCTGGTGAATCTTTCGAATACAAGTTCATCAGAGTTGAATCTGATGA
601            V  T  L  P  A  G  E  S  F  E  Y  K  F  I  R  V  E  S  D  D

1861        TTCTGTTGAATGGGAATCTGACCCAAACAGAGAATACACCGTTCCACAAGCCTGTGGTGA
621            S  V  E  W  E  S  D  P  N  R  E  Y  T  V  P  Q  A  C  G  E

1921        ATCCACCGCTACCGTTACTGACACCTGGAGATAA
641            S  T  A  T  V  T  D  T  W  R  *
```

Figure 5

```
1      AGGCCTGAATTCCAAC ATGGTTTCCTTCACCTCCTTGTTGGCCGGTGTCGCTGCTATCTC
1                       M  V  S  F  T  S  L  L  A  G  V  A  A  I  S

61     CGGTGTCTTGGCTGCTCCAGCTGCTGAAGTTGAACCAGTCGCTGTCGAAAAGAGATTGTC
21      G  V  L  A  A  P  A  A  E  V  E  P  V  A  V  E  K  R  L  S

121    TGCCGCTGAATGGAGAACTCAATCTATCTACTTCTTGTTGACCGACAGATTCGGTAGAAC
41      A  A  E  W  R  T  Q  S  I  Y  F  L  L  T  D  R  F  G  R  T

181    TGATAACTCTACCACCGCCACCTGTAACACCGGTGACCAAATCTACTGTGGTGGTTCCTG
61      D  N  S  T  T  A  T  C  N  T  G  D  Q  I  Y  C  G  G  S  W

241    GCAAGGTATCATCAACCACTTGGACTACATTCAAGGTATGGGTTTCACTGCTATCTGGAT
81      Q  G  I  I  N  H  L  D  Y  I  Q  G  M  G  F  T  A  I  W  I

301    CTCTCCAATTACTGAACAATTGCCACAAGATACCTCTGACGGTGAAGCCTACCACGGTTA
101     S  P  I  T  E  Q  L  P  Q  D  T  S  D  G  E  A  Y  H  G  Y

361    CTGGCAACAAAAGATTTACAACGTCAACTCCAACTTCGGTACTGCTGATGACTTGAAGTC
121     W  Q  Q  K  I  Y  N  V  N  S  N  F  G  T  A  D  D  L  K  S

421    TTTGTCTGACGCTTTGCACGCCAGAGGTATGTACTTGATGGTTGACGTCGTCCCAAACCA
141     L  S  D  A  L  H  A  R  G  M  Y  L  M  V  D  V  V  P  N  H

481    CATGGGTTACGCCGGTAACGGTAACGACGTTGACTACTCCGTTTTCGACCCATTCGATTC
161     M  G  Y  A  G  N  G  N  D  V  D  Y  S  V  F  D  P  F  D  S

541    TTCCTCCTACTTCCACCCATACTGTTTGATTACCGACTGGGACAACTTGACTATGGTCCA
181     S  S  Y  F  H  P  Y  C  L  I  T  D  W  D  N  L  T  M  V  Q

601    AGACTGTTGGGAAGGTGATACTATTGTCTCCTTGCCAGACTTGAACACCACTGAAACTGC
201     D  C  W  E  G  D  T  I  V  S  L  P  D  L  N  T  T  E  T  A

661    TGTCAGAACCATCTGGTACGATTGGGTCGCTGACTTGGTTTCCAACTACTCTGTTGATGG
221     V  R  T  I  W  Y  D  W  V  A  D  L  V  S  N  Y  S  V  D  G

721    TTTGAGAATTGACTCCGTCGAAGAAGTCGAACCAGATTTCTTCCCAGGTTACCAAGAAGC
241     L  R  I  D  S  V  E  E  V  E  P  D  F  F  P  G  Y  Q  E  A

781    TGCCGGTGTTTACTGTGTCGGTGAAGTTGACAACGGTAACCCAGCTTTGGATTGTCCATA
261     A  G  V  Y  C  V  G  E  V  D  N  G  N  P  A  L  D  C  P  Y

841    CCAAAAGTACTTGGACGGTGTTTTGAACTACCCAATTTACTGGCAATTGTTGTACGCTTT
281     Q  K  Y  L  D  G  V  L  N  Y  P  I  Y  W  Q  L  L  Y  A  F

901    CGAATCCTCTTCTGGTTCTATCTCCAACTTGTACAACATGATTAAGTCCGTTGCCTCCGA
301     E  S  S  S  G  S  I  S  N  L  Y  N  M  I  K  S  V  A  S  D

961    CTGTTCTGATCCAACCTTGTTGGGTAACTTCATTGAAAACCACGACAACCCAAGATTCGC
321     C  S  D  P  T  L  L  G  N  F  I  E  N  H  D  N  P  R  F  A

1021   TTCTTACACTTCCGACTACTCTCAAGCTAAGAACGTCTTGTCTTACATCTTCTTGTCTGA
341     S  Y  T  S  D  Y  S  Q  A  K  N  V  L  S  Y  I  F  L  S  D

1081   TGGTATCCCAATCGTTTACGCTGGTGAAGAACAACACTACTCTGGTGGTGACGTTCCATA
361     G  I  P  I  V  Y  A  G  E  E  Q  H  Y  S  G  G  D  V  P  Y

1141   CAACAGAGAAGCTACTTGGTTGTCCGGTTACGACACCTCCGCTGAATTGTACACTTGGAT
```

1201        CGCTACTACCAACGCCATCAGAAAGTTGGCCATCTCCGCTGATTCTGACTACATCACTTA
401            A  T  T  N  A  I  R  K  L  A  I  S  A  D  S  D  Y  I  T  Y

1261        CGCTAACGACCCAATCTACACCGATTCTAACACTATCGCCATGAGAAAGGGTACTTCCGG
421            A  N  D  P  I  Y  T  D  S  N  T  I  A  M  R  K  G  T  S  G

1321        TTCTCAAATTATCACCGTCTTGTCCAACAAGGGTTCCTCTGGTTCTTCCTACACCTTGAC
441            S  Q  I  I  T  V  L  S  N  K  G  S  S  G  S  S  Y  T  L  T

1381        TTTGTCCGGTTCTGGTTACACCTCTGGTACTAAGTTGATCGAAGCCTACACCTGTACTTC
461            L  S  G  S  G  Y  T  S  G  T  K  L  I  E  A  Y  T  C  T  S

1441        TGTTACTGTTGACTCTAACGGTGACATTCCAGTCCCAATGGCTTCTGGTTTGCCAAGAGT
481            V  T  V  D  S  N  G  D  I  P  V  P  M  A  S  G  L  P  R  V

1501        TTTGCCACCAGCTTCTGTTGTCGACTCTTCTTCTTTGTGTGGTGGTTCTGGTAACACTAC
501            L  P  P  A  S  V  V  D  S  S  S  L  C  G  G  S  G  N  T  T

1561        CACTACTACTACCGCTGCTACTTCTACTTCTAAGGCCACTACCTCTTCCTCCTCCTCTTC
521            T  T  T  T  A  A  T  S  T  S  K  A  T  T  S  S  S  S  S  S

1621        TGCTGCTGCTACCACTTCTTCCTCCTGTACTGCCACCTCTACTACCTTGCCAATTACTTT
541            A  A  A  T  T  S  S  S  C  T  A  T  S  T  T  L  P  I  T  F

1681        CGAAGAATTGGTTACCACTACTTACGGTGAAGAAGTTTACTTGTCTGGTTCCATCTCTCA
561            E  E  L  V  T  T  T  Y  G  E  E  V  Y  L  S  G  S  I  S  Q

1741        ATTGGGTGAATGGGATACCTCCGACGCTGTTAAGTTGTCTGCTGACGATTACACCTCCTC
581            L  G  E  W  D  T  S  D  A  V  K  L  S  A  D  D  Y  T  S  S

1801        TAACCCAGAATGGTCTGTCACTGTTTCTTTGCCAGTTGGTACTACCTTCGAATACAAGTT
601            N  P  E  W  S  V  T  V  S  L  P  V  G  T  T  F  E  Y  K  F

1861        CATTAAGGTTGATGAAGGTGGTTCTGTCACCTGGGAATCTGACCCAAACAGAGAATACAC
621            I  K  V  D  E  G  G  S  V  T  W  E  S  D  P  N  R  E  Y  T

1921        TGTTCCAGAATGTGGTTCCGGTTCCGGTGAAACTGTCGTCGACACTTGGAGATAA
641             V  P  E  C  G  S  G  S  G  E  T  V  V  D  T  W  R  *
```

Figure 9

```
   1    GGTACCGAATTCAGGCCTGGATCCTTAATTAAAAATGTTGTTCCAACCAACTTTGTGTGC
   1                                        M  L  F  Q  P  T  L  C  A

61    TGCTTTGGGTTTGGCTGCTTTGATTGTTCAAGGTGGTGAAGCTAGACCAGAAACTACTGT
  21     A  L  G  L  A  A  L  I  V  Q  G  G  E  A  R  P  E  T  T  V

121    TCCACATGCTACTGGTTCTTTGGATGATTTTTTGGCTGCTCAATCTCCAATTGCTTTTCA
  41     P  H  A  T  G  S  L  D  D  F  L  A  A  Q  S  P  I  A  F  Q

181    AGGTATTTTGAACAATATTGGTCCATCTGGTGCTTATTCTGAAGGTGTTAATCCAGGTGT
  61     G  I  L  N  N  I  G  P  S  G  A  Y  S  E  G  V  N  P  G  V

241    TGTTATTGCTTCTCCATCTAAACAAGATCCAGATTACTTTTACACTTGGGTTAGAGATGC
  81     V  I  A  S  P  S  K  Q  D  P  D  Y  F  Y  T  W  V  R  D  A

301    TGCTTTAACTGTTCAATACTTGGTTGAAGAATTGGTTGCTGGTAATGCTTCTTTGCAATT
 101     A  L  T  V  Q  Y  L  V  E  E  L  V  A  G  N  A  S  L  Q  F

361    CTTGATTCAAGATTACATTTCTTCACAAGCTAGATTGCAAACTGTTGAAAATCCATCTGG
 121     L  I  Q  D  Y  I  S  S  Q  A  R  L  Q  T  V  E  N  P  S  G

421    TTCTTTGTCATCTGGTGGTTTGGGTGAACCAAAATTTCATGTTGATGAAACTGCTTTTAC
 141     S  L  S  S  G  G  L  G  E  P  K  F  H  V  D  E  T  A  F  T

481    TGATTCTTGGGGAAGGCCACAAAGAGATGGTCCACCATTGAGAGCTATTGCTATGATTTC
 161     D  S  W  G  R  P  Q  R  D  G  P  P  L  R  A  I  A  M  I  S

541    TTTCGCTAACTACTTGATTGATAACGGTCATCAATCTACTGTTGAGGACATCATTTGGCC
 181     F  A  N  Y  L  I  D  N  G  H  Q  S  T  V  E  D  I  I  W  P

601    AATTGGTAGAAATGATTTGTCTTACGTTTCTCAACATTGGAATGAAACTACTTTCGATAT
 201     I  G  R  N  D  L  S  Y  V  S  Q  H  W  N  E  T  T  F  D  I

661    TTGGGAAGAAGTTCATTCTTCTTCATTTTTCACTACTGCTGTTCAATATAGAGCTTTGGT
 221     W  E  E  V  H  S  S  S  F  F  T  T  A  V  Q  Y  R  A  L  V

721    TCAAGGTTCTGCTTTGGCTTCTAAATTGGGTCATACTTGTGATAATTGTGGTTCTCAAGC
 241     Q  G  S  A  L  A  S  K  L  G  H  T  C  D  N  C  G  S  Q  A

781    TCCACAAATTTTGTGTTTCTTGCAATCTTATTGGACTGGTTCTCATATTTTGGCTAATAC
 261     P  Q  I  L  C  F  L  Q  S  Y  W  T  G  S  H  I  L  A  N  T

841    TGGTGGTGGTAGATCAGGTAAAGATGTTTCTACTATTTTGGGTGTTATTGGTTCTTTTGA
 281     G  G  G  R  S  G  K  D  V  S  T  I  L  G  V  I  G  S  F  D

901    TCCAAATGCTGATTGTGATGATGTTACTTTTCAACCATGTTCTGCTAGAGCTTTGGCTAA
 301     P  N  A  D  C  D  D  V  T  F  Q  P  C  S  A  R  A  L  A  N

961    TCATAAACAAGTTGTTGATTCTTTCAGATCAATTTACGCTATTAATGCTGGTATTCCATC
 321     H  K  Q  V  V  D  S  F  R  S  I  Y  A  I  N  A  G  I  P  S

1021    AGGTTCTGCTGTTGCTGTTGGAAGATACCCTGAAGATGTTTATCAAGGTGGTCATCCATG
 341     G  S  A  V  A  V  G  R  Y  P  E  D  V  Y  Q  G  G  H  P  W
```

Figure 9 contd.

```
1081    GTATTTGACTACTGCTGCTGCTGCAGAACAATTGTATGATGCAATTTACCAATGGAATCA
361         Y  L  T  T  A  A  A  A  E  Q  L  Y  D  A  I  Y  Q  W  N  H

1141    TGTTGGTCATATTGATATTAACGCTGTTAACTTGGATTTTTTCAAGTCAATTTATCCATC
381         V  G  H  I  D  I  N  A  V  N  L  D  F  F  K  S  I  Y  P  S

1201    TGCTGCTGAAGGTACTTATACTTCTGATTCTTCTACTTTCCAAGACATCATTTCTGCTGT
401         A  A  E  G  T  Y  T  S  D  S  S  T  F  Q  D  I  I  S  A  V

1261    TAGAACTTATGCTGATGGTTTCTTGTCTGTTATTGAAAAATACACTCCACCAGATAATTT
421         R  T  Y  A  D  G  F  L  S  V  I  E  K  Y  T  P  P  D  N  L

1321    GTTGGCTGAACAATTTCATAGAGAAACAGGTATTCCATTGTCTGCTGCTTCATTGACTTG
441         L  A  E  Q  F  H  R  E  T  G  I  P  L  S  A  A  S  L  T  W

1381    GTCTTATGCTGCTTTGAATACAGCTGCTCAAAGAAGAGCTTCTATTGTTCCATCTCCATG
461         S  Y  A  A  L  N  T  A  A  Q  R  R  A  S  I  V  P  S  P  W

1441    GAACTCTAATTCTACTGATTTGCCAGATAAATGTTCTGCTACATCTGCTACTGGTCCATA
481         N  S  N  S  T  D  L  P  D  K  C  S  A  T  S  A  T  G  P  Y

1501    TGCTACACCAACTAATACTGCTTGGCCAACTACTACTCAACCACCAGAAAGACCAGCTTG
501         A  T  P  T  N  T  A  W  P  T  T  T  Q  P  P  E  R  P  A  C

1561    TACTCCACCATCTGAAGTTACTTTGACTTTTAACGCTTTGGTTGATACTGCTTTTGGTCA
521         T  P  P  S  E  V  T  L  T  F  N  A  L  V  D  T  A  F  G  Q

1621    AAACATTTACTTGGTTGGTTCTATTCCAGAATTGGGTTCTTGGGACCCAGCTAATGCTTT
541         N  I  Y  L  V  G  S  I  P  E  L  G  S  W  D  P  A  N  A  L

1681    GTTGATGTCTGCTAAATCTTGGACTTCTGGTAATCCAGTTTGGACTTTGTCTATTTCTTT
561         L  M  S  A  K  S  W  T  S  G  N  P  V  W  T  L  S  I  S  L

1741    GCCAGCTGGTACTTCTTTTGAATACAAGTTCATTAGAAAGGATGATGGTTCTTCTGATGT
581         P  A  G  T  S  F  E  Y  K  F  I  R  K  D  D  G  S  S  D  V

1801    TGTTTGGGAATCTGATCCAAATAGATCATACAATGTTCCAAAAGATTGTGGTGCTAATAC
601         V  W  E  S  D  P  N  R  S  Y  N  V  P  K  D  C  G  A  N  T

1861    TGCTACTGTTAATTCTTGGTGGAGATAATAAGGCGCGCCAGATCTCTCGAGCTC
621         A  T  V  N  S  W  W  R  *  *
```

Figure 10

```
1     GGTACCGAATTCAGGCCTGGATCCTTAATTAAAAATGGTTTCTTTCACTTCTTTGTTGGC
1                                         M  V  S  F  T  S  L  L  A

61    TGGTGTTGCTGCTATTTCTGGTGTTTTGGCTGCTCCAGCTGCTGAAGTTGAACCAGTTGC
21     G  V  A  A  I  S  G  V  L  A  A  P  A  A  E  V  E  P  V  A

121   TGTTGAAAAAGAACTGCTGCTGAATGGAAAGAATTGTCAATTTACCAAGTTATTACTGA
41     V  E  K  R  T  A  A  E  W  K  E  L  S  I  Y  Q  V  I  T  D

181   TAGATTCGCTACTACTAATTTGACTGCTCCAGATTGTTGGATTAGAGCTTATTGTGGTGG
61     R  F  A  T  T  N  L  T  A  P  D  C  W  I  R  A  Y  C  G  G

241   TACTTGGAAAGGTTTGGAAAGAAAGTTGGATTACATTCAAAATATGGGTTTTGATGCTGT
81     T  W  K  G  L  E  R  K  L  D  Y  I  Q  N  M  G  F  D  A  V

301   TTGGATTTCTCCAGTTATTCATAACATTGAAGTTAATACTACTTGGGGTTTTGCTTTTCA
101    W  I  S  P  V  I  H  N  I  E  V  N  T  T  W  G  F  A  F  H

361   TGGTTATTGGGGTGATGATCCATATAGATTGAATGAACATTTTGGTACTGCTGCTGATTT
121    G  Y  W  G  D  D  P  Y  R  L  N  E  H  F  G  T  A  A  D  L

421   GAAATCTTTGTCTGATTCTTTGCATGCTAGAGGAATGTCTTTGATGGTTGATGTTGTTAT
141    K  S  L  S  D  S  L  H  A  R  G  M  S  L  M  V  D  V  V  I

481   TAATCATTTGGCTTCATATACTTTGCCACAAGATGTTGATTATTCTTTGTATCCAGCTCC
161    N  H  L  A  S  Y  T  L  P  Q  D  V  D  Y  S  L  Y  P  A  P

541   ATTTAATACTTCATCTGCTTTTCATCAACCATGTCCAATTGATTTTTCTAACCAATCTTC
181    F  N  T  S  S  A  F  H  Q  P  C  P  I  D  F  S  N  Q  S  S

601   TATTGAAGATTGTTGGTTGGTTACTGAACCAGCTCCAGCTTTGGTTGATTTGAAGAACGA
201    I  E  D  C  W  L  V  T  E  P  A  P  A  L  V  D  L  K  N  E

661   AGATCAAGTTATTTTGGATGCTTTGATTAACTCTGTTGTTGATTTGGTTGAAACTTACGA
221    D  Q  V  I  L  D  A  L  I  N  S  V  V  D  L  V  E  T  Y  D

721   TATTGATGGTATTAGATTGGATACTGCTAGACATGTTCCAAAACCATCTTTGGCTAAGTT
241    I  D  G  I  R  L  D  T  A  R  H  V  P  K  P  S  L  A  K  F

781   TCAAGAAAAAGTTGGTGTTTTTGTTACTGGTGAAGCATTGAATCAATCTGTTCCATACGT
261    Q  E  K  V  G  V  F  V  T  G  E  A  L  N  Q  S  V  P  Y  V

841   TGCTCAATATCAAGGTCCATTGAACTCTGCTATTAACTATCCATTGTGGTATGCTTTAGT
281    A  Q  Y  Q  G  P  L  N  S  A  I  N  Y  P  L  W  Y  A  L  V

901   TGATTCTTTTATGGGTAGAACTACTTTTGATTACTTGGAATCTGTTGTTAAATCTGAACA
301    D  S  F  M  G  R  T  T  F  D  Y  L  E  S  V  V  K  S  E  Q

961   AGCTACTTTTTCTGATGCTCATGCTTTGACTAATTTCTTGGATAATCAAGATCAACCAAG
321    A  T  F  S  D  A  H  A  L  T  N  F  L  D  N  Q  D  Q  P  R

1021  ATTTGCTTCTTATTTGGGTGATGGTAATGGTGATGATGTTTTGAGAGATGAAAATGCTGC
341    F  A  S  Y  L  G  D  G  N  G  D  D  V  L  R  D  E  N  A  A

1081  TACTTTTTTGTTTTTCGTTTCTGGTATTCCAGTTATCTACTACGGTTTCGAACAAAGATT
361    T  F  L  F  F  V  S  G  I  P  V  I  Y  Y  G  F  E  Q  R  F

1141  TGATGGTGGTTTTGATCCAGTTAATAGAGAACCAATGTGGACTTCTGGTTATAATACTTC
```

1201      TACTCCATTGTATAATTACTTGGCTAGATTGAATGCTATTAGAAAATACGCTGCTTCTAT
401         T   P   L   Y   N   Y   L   A   R   L   N   A   I   R   K   Y   A   A   S   I

1261      TACTGGTACTCAAGTTTTTTACTCTGATGATACTGTTTTTTTGGGTTCTGGTGTTTCTCA
421         T   G   T   Q   V   F   Y   S   D   D   T   V   F   L   G   S   G   V   S   H

1321      TATGGCTATGCAAAGAGGTCCATTGGTTATTGTTTTGACTAATGTTGGTCAACATATTAT
441         M   A   M   Q   R   G   P   L   V   I   V   L   T   N   V   G   Q   H   I   I

1381      TGATAACACTGGTTATACTGTTACTGGTTCTCAATTTTCTGCTGGTGATTCTTTGACTGA
461         D   N   T   G   Y   T   V   T   G   S   Q   F   S   A   G   D   S   L   T   D

1441      TTTGGTTTCTTGTACTAAGGTTAAAGTTGTTGGTGCTAATGGTACTTTTACTTCTCCATC
481         L   V   S   C   T   K   V   K   V   V   G   A   N   G   T   F   T   S   P   S

1501      TAATGGTGGTAAAGCTAGAATTTGGATTAAATCTAAGTACGCTGGTAAGTTCTGTTCTTA
501         N   G   G   K   A   R   I   W   I   K   S   K   Y   A   G   K   F   C   S   *

1561      ATAAGGCGCGCCAGATCTCTCGAGCTC
521         *
```

Figure 11

```
1     GGTACCGAATTCAGGCCTGGATCCTTAATTAAAAATGCAAATTTCTAAGGCTGCTTTGTT
1                                         M  Q  I  S  K  A  A  L  L

61    GGCTTCTTTGGCTGCTTTGGTTTATGCTCAACCAGTTACTTTGTTTAAGAGAGAAACTAA
21     A  S  L  A  A  L  V  Y  A  Q  P  V  T  L  F  K  R  E  T  N

121   CGCTGATAAGTGGAGATCACAATCAATTTACCAAATTGTTACTGATAGATTCGCTAGAAC
41     A  D  K  W  R  S  Q  S  I  Y  Q  I  V  T  D  R  F  A  R  T

181   TGATGGTGATACTTCTGCTTCTTGTAATACTGAAGATAGATTGTATTGTGGTGGTTCTTT
61     D  G  D  T  S  A  S  C  N  T  E  D  R  L  Y  C  G  G  S  F

241   TCAAGGTATTATCAAGAAGTTGGATTACATTAAGGATATGGGTTTTACTGCTATTTGGAT
81     Q  G  I  I  K  K  L  D  Y  I  K  D  M  G  F  T  A  I  W  I

301   TTCTCCAGTTGTTGAAAATATTCCAGATAATACTGCTTATGGTTATGCTTATCATGGTTA
101    S  P  V  V  E  N  I  P  D  N  T  A  Y  G  Y  A  Y  H  G  Y

361   CTGGATGAAAAACATTTACAAGATTAACGAAAATTTTGGTACTGCTGATGATTTGAAATC
121    W  M  K  N  I  Y  K  I  N  E  N  F  G  T  A  D  D  L  K  S

421   TTTGGCTCAAGAATTGCATGATAGAGACATGTTGTTGATGGTTGATATTGTTACTAATCA
141    L  A  Q  E  L  H  D  R  D  M  L  L  M  V  D  I  V  T  N  H

481   TTACGGTTCTGATGGTTCTGGTGATTCTATTGATTACTCTGAATACACTCCATTTAACGA
161    Y  G  S  D  G  S  G  D  S  I  D  Y  S  E  Y  T  P  F  N  D

541   TCAAAAGTACTTCCATAACTACTGTTTGATTTCTAACTATGATGATCAAGCTCAAGTTCA
181    Q  K  Y  F  H  N  Y  C  L  I  S  N  Y  D  D  Q  A  Q  V  Q

601   ATCTTGTTGGGAAGGTGATTCTTCTGTTGCTTTGCCAGATTTGAGAACTGAAGATTCTGA
201    S  C  W  E  G  D  S  S  V  A  L  P  D  L  R  T  E  D  S  D

661   TGTTGCTTCTGTTTTTAACTCTTGGGTTAAGGATTTTGTTGGTAACTATTCTATTGATGG
221    V  A  S  V  F  N  S  W  V  K  D  F  V  G  N  Y  S  I  D  G

721   TTTGAGAATTGATTCTGCTAAACATGTTGATCAAGGTTTTTTTCCAGATTTTGTTTCTGC
241    L  R  I  D  S  A  K  H  V  D  Q  G  F  F  P  D  F  V  S  A

781   TTCTGGTGTTTATTCTGTTGGTGAAGTTTTTCAAGGTGATCCAGCTTATACTTGTCCATA
261    S  G  V  Y  S  V  G  E  V  F  Q  G  D  P  A  Y  T  C  P  Y

841   CCAAAATTACATTCCAGGTGTTTCTAATTATCCATTGTACTACCCAACTACTAGATTTTT
281    Q  N  Y  I  P  G  V  S  N  Y  P  L  Y  Y  P  T  T  R  F  F

901   CAAGACTACTGATTCTTCTTCTTCTGAATTGACTCAAATGATTTCTTCAGTTGCTTCTTC
301    K  T  T  D  S  S  S  S  E  L  T  Q  M  I  S  S  V  A  S  S

961   TTGTTCTGATCCAACTTTGTTGACTAATTTCGTTGAAAACCATGATAATGAAAGATTTGC
321    C  S  D  P  T  L  L  T  N  F  V  E  N  H  D  N  E  R  F  A

1021  TTCTATGACTTCTGATCAATCTTTGATTTCAAACGCTATTGCTTTTGTTTTGTTGGGTGA
341    S  M  T  S  D  Q  S  L  I  S  N  A  I  A  F  V  L  L  G  D

1081  TGGTATTCCAGTTATCTACTACGGTCAAGAACAAGGTTTGTCTGGTAAATCTGATCCAAA
361    G  I  P  V  I  Y  Y  G  Q  E  Q  G  L  S  G  K  S  D  P  N

1141  CAATAGAGAAGCATTGTGGTTGTCTGGTTATAACAAAGAATCTGATTACTACAAGTTGAT
```

1201       TGCTAAAGCTAATGCTGCTAGAAATGCTGCTGTTTATCAAGATTCTTCTTACGCTACTTC
401        A  K  A  N  A  A  R  N  A  A  V  Y  Q  D  S  S  Y  A  T  S

1261       TCAATTGTCTGTTATTTTCTCTAACGATCATGTTATTGCTACTAAAAGAGGTTCTGTTGT
421        Q  L  S  V  I  F  S  N  D  H  V  I  A  T  K  R  G  S  V  V

1321       TTCTGTTTTCAACAATTTGGGTTCTTCTGGTTCTTCAGATGTTACTATTTCTAACACTGG
441        S  V  F  N  N  L  G  S  S  G  S  S  D  V  T  I  S  N  T  G

1381       TTATTCTTCAGGTGAAGATTTGGTTGAAGTTTTGACTTGTTCTACTGTTTCTGGTTCATC
461        Y  S  S  G  E  D  L  V  E  V  L  T  C  S  T  V  S  G  S  S

1441       TGATTTGCAAGTTTCTATTCAAGGTGGTCAACCACAAATTTTTGTTCCAGCTAAGTATGC
481        D  L  Q  V  S  I  Q  G  G  Q  P  Q  I  F  V  P  A  K  Y  A

1501       TTCTGATATTTGTTCTTAATAAGGCGCGCCAGATCTCTCGAGCTC
501        S  D  I  C  S  *  *
```

BIOFUEL PRODUCTION

CROSS-REFERENCE TO RELATED APPLICATIONS

This application is a National Stage Application under 35 U.S.C. §371 of and claims priority to International Patent Application No. PCT/IB2010/000795, filed Apr. 12, 2010, the contents of which are hereby incorporated by reference in their entirety.

FIELD OF THE INVENTION

The invention relates to the use of fungal enzymes and microbial systems for industrial processing, in particular for the microbial conversion of starch-containing material (e.g. raw starch) to ethanol.

All documents cited in this text ("herein cited documents") and all documents cited or referenced in herein cited documents and sequences from GenBank and other data bases referred to herein are incorporated by reference in their entirety for all purposes.

There is no admission that any of the various documents etc. cited in this text are prior art as to the present invention.

BACKGROUND

Plant biomass is a carbon-neutral renewable resource and biomass conversion, particularly cellulosic feedstock conversion, is receiving much attention as a cleaner alternative to oil and as a result of its abundance and relatively low cost. The current process of converting starch to bioethanol is well established, but the energy cost is high and, accordingly, the need to develop a more feasible process is evident.

The industrial process of converting starch to bioethanol generally involves four steps which include: (i) extraction of starch from the biomass, (ii) the conversion of the starch to yield fermentable sugars, which are then (iii) fermented to ethanol upon the addition of yeast. In the final step (iv) ethanol is refined and concentrated by distillation. Extraction of starch is accomplished via wet milling or dry milling. Starch may be converted to fermentable sugars via acid hydrolysis or enzymatic hydrolysis (enzyme hydrolysis is now generally used). Enzymatic hydrolysis is initiated when starch is pre-treated to yield a viscous slurry, which is then liquefied by heat treatment and alpha-amylase. The starch is cooked and undergoes saccharification after addition of glucoamylase. Yeast is added after cooling the mixture for fermentation of sugars to ethanol. The process includes large temperature changes (typically in the range of about 32-120° C.) using vast amounts of heating energy which significantly adds to the cost of the process. With the intention to increase net energy yield, the hydrolysis temperature required to generate glucose could be lowered to that of the fermentation step, therefore carrying out saccharification and fermentation simultaneously (SSF). Research groups currently focus on either improving the commercial hydrolysing enzymes applied in the process, or improving microbes producing the hydrolytic enzymes necessary for the process to proceed efficiently.

A raw starch hydrolyzing (RSH) enzyme cocktail, Stargen 001 (Genencor) has been developed, which converts starch into dextrins at low temperatures (<48° C.) and hydrolyses dextrins into sugars during SSF. The cocktail contains an acid-stable alpha-amylase from *Aspergillus kawachi* and glucoamylase from *Aspergillus niger*. Using the RSH enzyme saves heating energy as jet cooking is eliminated and less water and fewer chemicals are needed for the process.

To eliminate commercial enzyme purchase costs, SSF has been performed effectively with mixed cultures, where one organism is amylolytic, and the other responsible for ethanol production. The amylolytic organism acts as the saccharifying agent, therefore replacing the addition of commercial saccharifying enzymes. However, in these systems the amylolytic organism utilises most of the soluble starch for growth, which leaves little sugars for the fermentative organism to convert to ethanol.

Generating an amylolytic fermentative organism may address this shortcoming. A more cost-effective procedure where an organism produces sufficient amounts of amylolytic enzymes to sustain growth on raw unmodified starch as sole carbon source for the production of ethanol as product is depicted in FIG. 2. Applying a raw starch utilising yeast in the starch conversion process will have all the benefits from an SSF procedure, such as a lowered heating energy requirement and chemical usage. The added benefit will be elimination of the large cost associated with commercial enzyme purchase. The engineered organism producing amylolytic enzymes and ethanol would be suitable for a Consolidated Bioprocessing (CBP) process. In the long term, generation of ethanol and coproducts employing a CBP process will ensure the production of commodity chemicals and animal feeds in a sustainable manner in a biorefinery environment.

Genetic engineering is used extensively for producing hosts with desired characteristics for the starch industry. Mainly alpha-amylases and glucoamylases are expressed in heterologous hosts to ensure higher enzyme productivity compared to the native host. Expression of thermostable enzymes as well as the ability to produce more than one desirable enzyme in one host enables the generation of more competitive organisms for the industry.

Yeasts displaying glucoamylases (e.g. Kondo et al., 2002) and alpha-amylases have been previously created (Shigechi et al., 2002). However, engineering a host strain to express raw starch hydrolysing enzymes would be even more advantageous. Very few groups have reported results on yeast strains which are able to utilise raw starch as carbon source with initial approaches utilising the *Rhizopus oryzae* glucoamylase, which is secreted or displayed on the surface of the yeast (Ashikari et al., 1989; Murai et al., 1998). Several different strains have been created where the alpha-amylases from *Streptococcus bovis* has been combined with the glucoamylase in the hope to better the amylolytic activity and therefore the ethanol productivity of the generated strains (Khaw et al., 2006; Shigechi et al., 2004b). An alpha-amylase preparation from *B. licheniformis* (Murai et al., 1998) has also been used the source of alpha-amylase activity.

Kim J H et al. (2010) *Biotechnol Lett*. February 4, developed a strain of *S. cerevisiae* that produces ethanol directly from starch. Two integrative vectors were constructed to allow the simultaneous multiple integration of the *Aspergillus awamori* glucoamylase gene (GA1) and the *Debaryomyces occidentalis* alpha-amylase gene (AMY) and glucoamylase with debranching activity gene (GAM1) into the chromosomes of an industrial strain of *S. cerevisiae*. Yamakawa et al. (2010) *Appl. Microbiol. Biotechnol*. February 24. [Epub ahead of print] demonstrated batch ethanol fermentation from raw using a yeast diploid strain coexpressing the maltose transporter AGT1, alpha-amylase, and glucoamylase.

The present invention aims to provide a beneficial enzyme combination for the hydrolysis of starch for use in alcohol production processes. The invention also describes beneficial yeast strains which may find particular utility in fermentation processes and which may also be engineered to express an enzyme combination of the invention.

BRIEF DESCRIPTION OF THE INVENTION

A first aspect of the invention, provides a host cell which expresses: (i) the *Thermomyces lanuginoses* TLG1 protein and the *Saccharomycopsis fibuligera* SFA1 protein; or (ii) the *T. lanuginoses* TLG1 protein and the *L. kononenkoae* (LKA1) protein. Cells which express variants (e.g. natural biological variants, functional equivalents, active fragments and fusion proteins) of the aforementioned TLG1, SFA1 and LKA1 proteins are also included in the first aspect of the invention.

A second aspect of the invention is directed to a method for producing a composition comprising a glucoamylase and alpha-amylase combination of the invention (i.e. TLG1 in combination with one or both of SFA1 and LKA1), comprising culturing a host cell of the first aspect of the invention (and preferably a population of host cells of the first aspect of the invention) under suitable conditions for production of the glucoamylase and the alpha-amylase combination.

A third aspect of the invention provides a composition comprising a glucoamylase and alpha-amylase combination of the invention (i.e. TLG1 in combination with one or both of SFA1 and LKA1).

In a fourth aspect of the invention there is provided a strain of *S. cerevisiae* (herein designated as "s2") as deposited under the Budapest Treaty on the International Recognition of the Deposit of Microorganisms for the Purposes of Patent Procedure at DBVPG, under accession number 27P on 1 Apr. 2010, or a variant or mutant derived therefrom, and compositions or cultures comprising the same.

A fifth aspect of the invention relates to a process for producing a fermentation product, e.g. alcohol, from a starch-containing material using TLG1 in combination with one or both of SFA1 and LKA1.

A sixth aspect of the invention relates to a process for producing a fermentation product, e.g. alcohol, from a starch-containing material using s2 or a variant or mutant thereof.

A seventh aspect of the invention provides a product obtainable or obtained by the process of the second, fifth or sixth aspects of the invention.

BRIEF DESCRIPTION OF DRAWINGS

FIG. 4 Predicted protein sequence of the sGA I gene of *A. awamori* expressed in *S. cerevisiae* (Y294[ySYAG]). The XYNSEC secretion signal is italicised. The sequence identified in glucoamylases essential for raw starch hydrolysis (Goto et al., 1994) was conserved (PL(W-597)YVTVTLPA), as well as the second tryptophan (Trp) residue and is double underlined. The Gp-Iregion is indicated as italicised and single underlined text. The Cp-Iregion or SBD is indicated in italicised and double underlined text (Belshaw and Williamson, 1993; Fukuda et al., 1992). The general acid and base catalysts Glu-213 and Glu-434, as well as Tyr-85,Trp-87,Arg-89,Asp-90,Trp-154,Glu-214,Arg-339, Asp-343,Trp-351 sites which play a role in substrate transition-state stabilisation and or ground-state binding are indicated in emboldened and single underlined text. Possible N-glycosylation sites (residues NOT, NGS and NGS) are underlined by a broken line, although only the first and third sites were found to be glycosylated when expressed in yeast (Chen et al., 1994).

FIG. 5 Predicted protein sequence of the sAMYL III gene of *A. awamori* expressed in *S. cerevisiae* (Y294[ySYAA]). The XYNSEC secretion signal is indicated in italics and double underlining. Regions1-4 are emboldened and underlined and indicate conserved regions in the sequence as identified by the authors who characterised the gene for the first time (Matsubara et al., 2004b). The sequence identified for raw starch hydrolysis was also present in the AMYL III, although not perfectly conserved (PEWSVTVSLPV versus PLWYVTVTLPA), and is double underlined. The second Trp was also present. Furthermore the TSlinker characterised by O-glycosylation was also identified and is indicated as text which is single underlined and italicised (Matsubara et al., 2004). Conserved amino acids namely Arg-242, Asp-244, Glu-268, and Asp-335 (amino acid numbering of TAKA amylase sequence from *A. oryzae*), as well as Asp-244, and H-334 are indicated in as text in outline.

determined with the phenol sulphuric assay method are indicated on the y-axis. Cell DW (g l$^{-1}$) level is indicated on the secondary y-axis.

FIG. 9 DNA and Protein sequence of the synthetic (codon-optimised) glucoamylase gene from *Thermomyces lanuginoses* (TLG1). The mature protein sequence (i.e. without the secretion signal) is referred to herein as SEQ ID NO: 1. Secretionsignal(emboldenedandunderlined), putative catalytic domain (dotted underlining and putativestarchbindingdomain(doubleunderlinedand italicised) are shown as obtained by blasting protein sequence with the following engine and follow up on results: http://blast.ncbi.nlm.nih.gov/Blast.cgi "*" indicates a stop codon FIG. 10 DNA and Protein sequence of the synthetic alpha-amylase gene from *Lypomyces kononenkoae* (xsecLKA1). The mature protein sequence (i.e. without the secretion signal) is referred to herein as SEQ ID NO: 2. Secretionsignal(emboldenedandunderlined), putative catalytic domain (dotted underlining and putativestarchbindingdomain(doubleunderlinedanditalicised are shown as obtained by blasting protein sequence with the following engine and follow up on results: http://blast.ncbi.nlm.nih.gov/Blast.cgi "*" indicates a stop codon FIG. 11 DNA and Protein sequence of the synthetic alpha-amylase gene from *Saccharomycopsis fibuligera* (SFA1). The mature protein sequence (i.e. without the secretion signal) is referred to herein as SEQ ID NO: 3. Secretionsignal(emboldenedandunderlined), putative catalytic domain (dotted underlining and putativestarchbindingdomain(doubleunderlinedanditalicised are shown as obtained by blasting protein sequence with the following engine and follow up on results: http://blast.ncbi.nlm.nih.gov/Blast.cgi "*" indicates a stop codon FIG. 12 A Schematic summary of the plasmids used to generate amylase expression cassettes in this study. (a) The SFA1 gene was inserted into vector pBKD1, generating pSFA1. (b) The xsecLKA1 gene was inserted into vector pBKD1, generating pLKA1. (c) The TLG1 gene was inserted into vector pBKD2, generating pTLG1.

Figure 13:
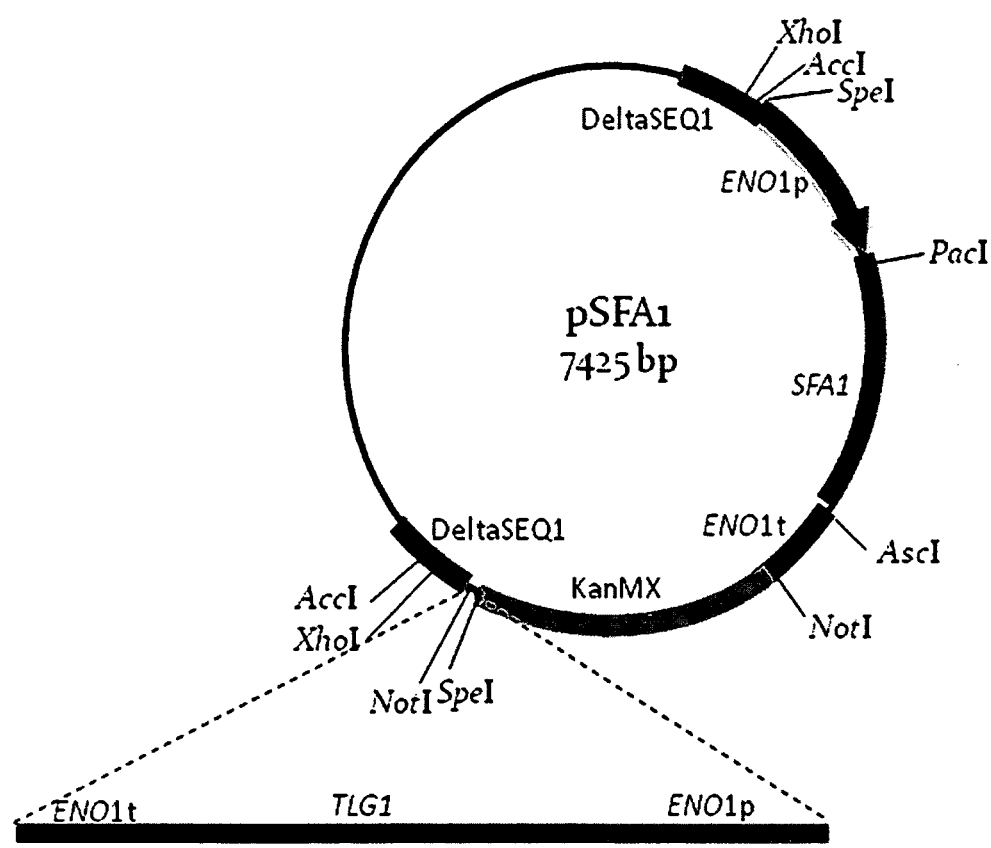

FIG. 13 A Schematic representation showing the subcloning of the ENO1P-TLG1-ENO1T cassette into pSFA1 to generate plasmid pTLGSFA. In a similar way the ENO1P-TLG1-ENO1T cassette was inserted into pLKA to yield pTLGLKA.

Figure 14:
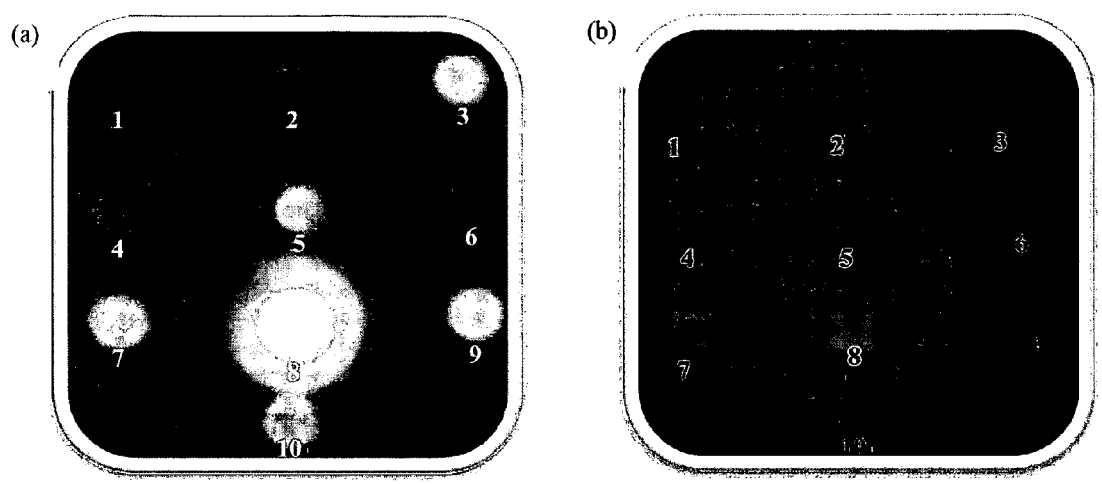

FIG. 14 Starch hydrolysis in (a) soluble starch and (b) raw starch appears as clear zones around colonies secreting functional amylases. (1) *A. awamori* synthetic glucoamylase, sGA I, (2) sGA I and *A. awamori* synthetic alpha-amylase sAMYL III, (3) sGA I and *A. awamori* wild type alpha-amylase AMYL III, (4) *Lypomyces kononenkoae* alpha-amylase LKA1, (5) *Saccharomycopsis fibuligera* alpha-amylase SFA, (6) AMYL III, (7) LKA and TLG, (8) SFA and TLG, (9) *Thermomyces lanuginoses* glucoamylase TLG1, (10) *S. cerevisiae* yMH 1000.

Figure 15:
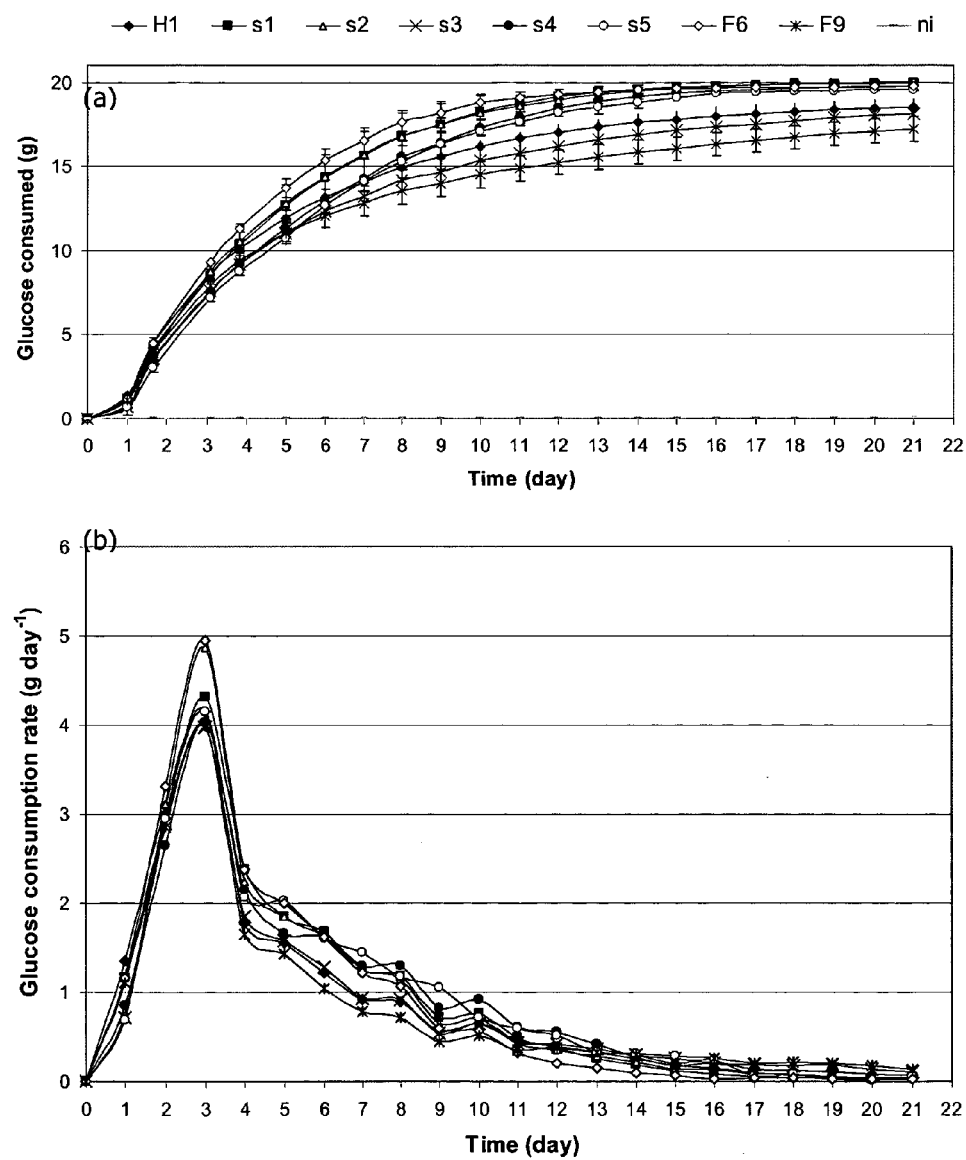

FIG. 15. Fermentative performance of *S. cerevisiae* strains in MNS medium with glucose (200 gL-1) reported as (a) cumulative sugar utilisation (grams of glucose consumed per 100 mL of MNS) and (b) daily glucose consumption rate. The experiment was conducted in triplicate (±SD).

Figure 16:
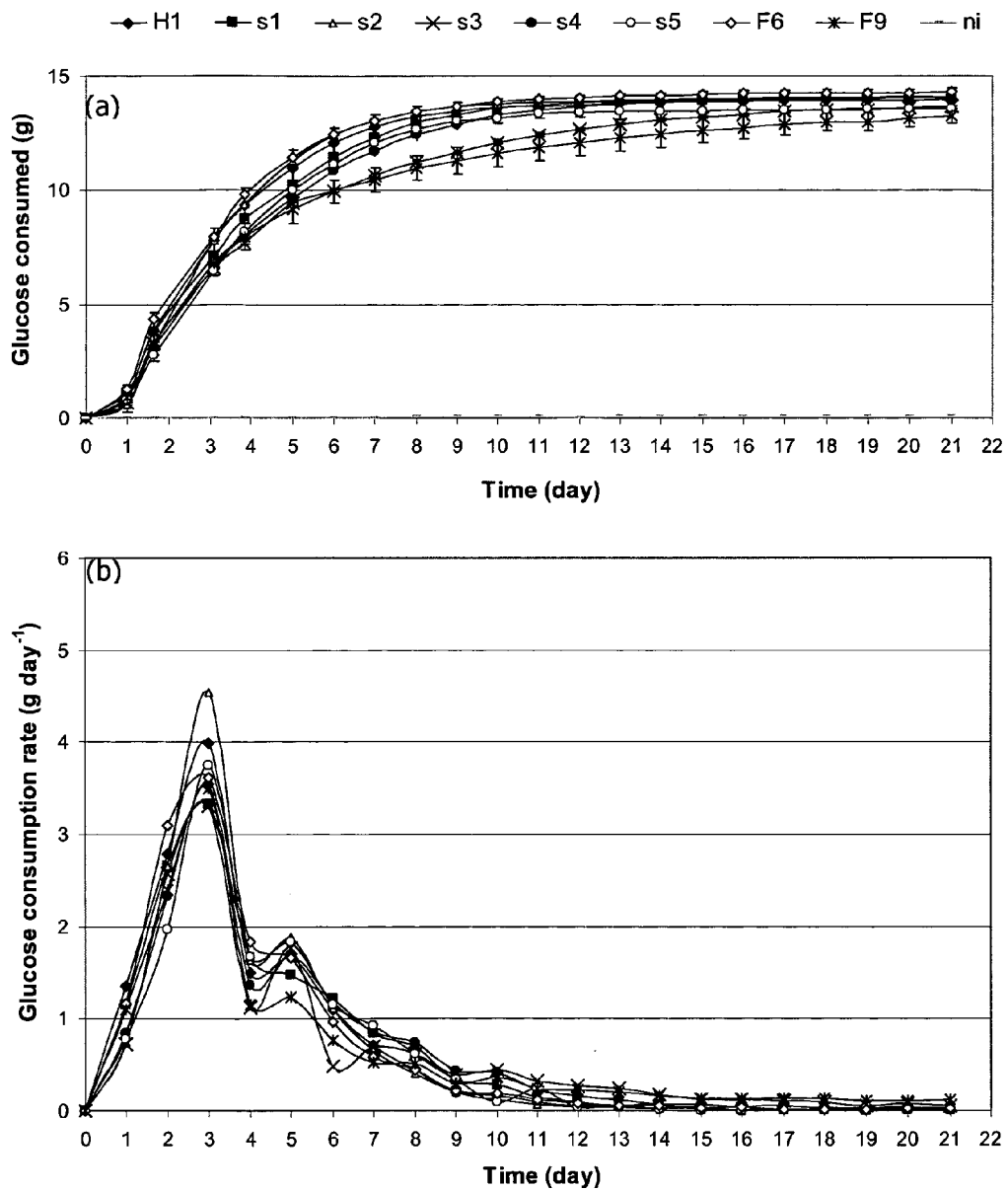

FIG. 16. Fermentative performance of *S. cerevisiae* strains in MNS medium with glucose (150 gL-1) and xylose (50 gL-1) reported as (a) cumulative sugar utilisation (grams of glucose consumed per 100 mL of MNS) and (b). daily glucose consumption rate. The experiment was conducted in triplicate (±SD).

Figure 17:
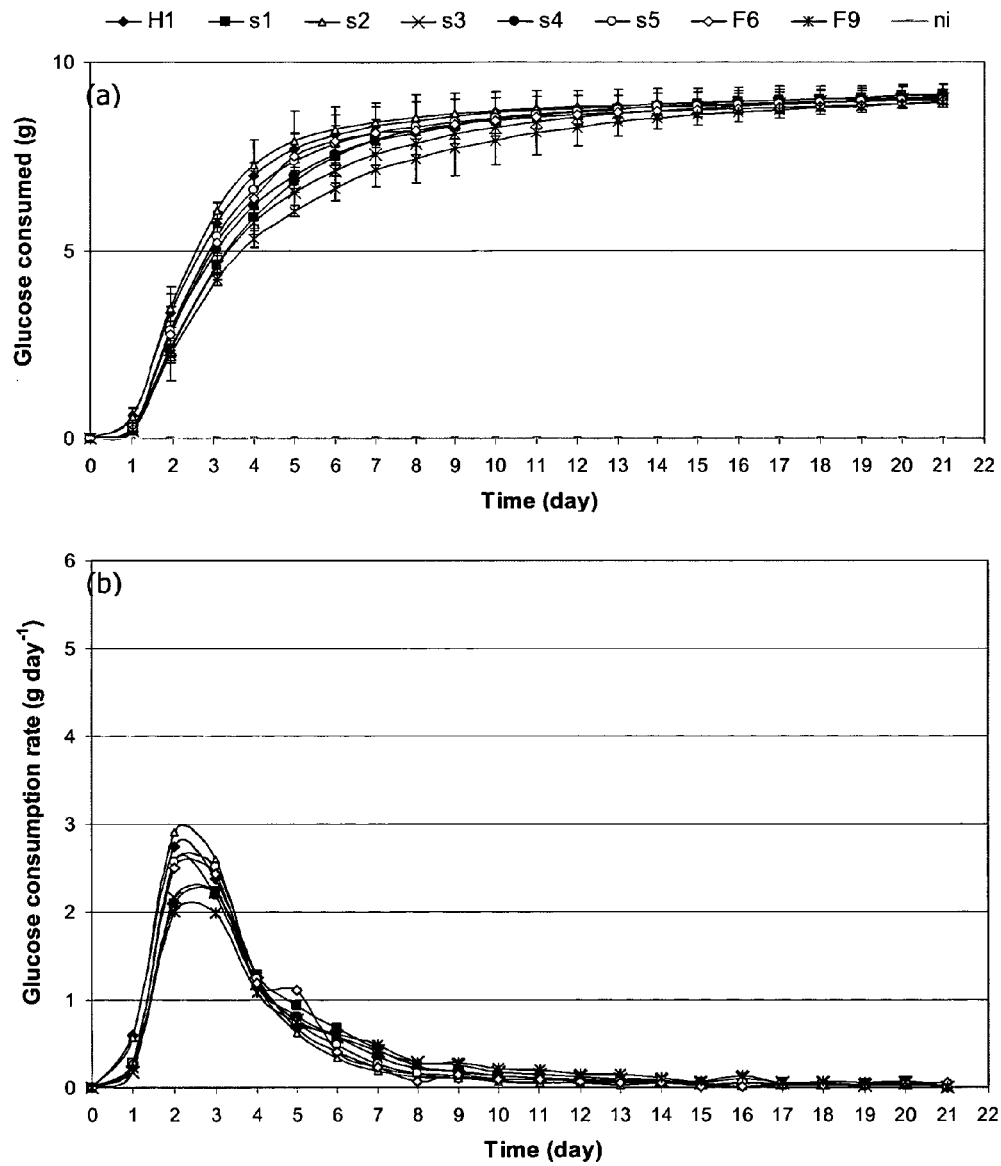

FIG. 17. Fermentative performance of *S. cerevisiae* strains in MNS medium with glucose (100 gL$^{-1}$) and xylose (100 gL$^{-1}$) reported as reported as (a) cumulative sugar utilisation (grams of glucose consumed per 100 mL of MNS) and (b). daily glucose consumption rate. The experiment was conducted in triplicate (±SD).

Figure 18:
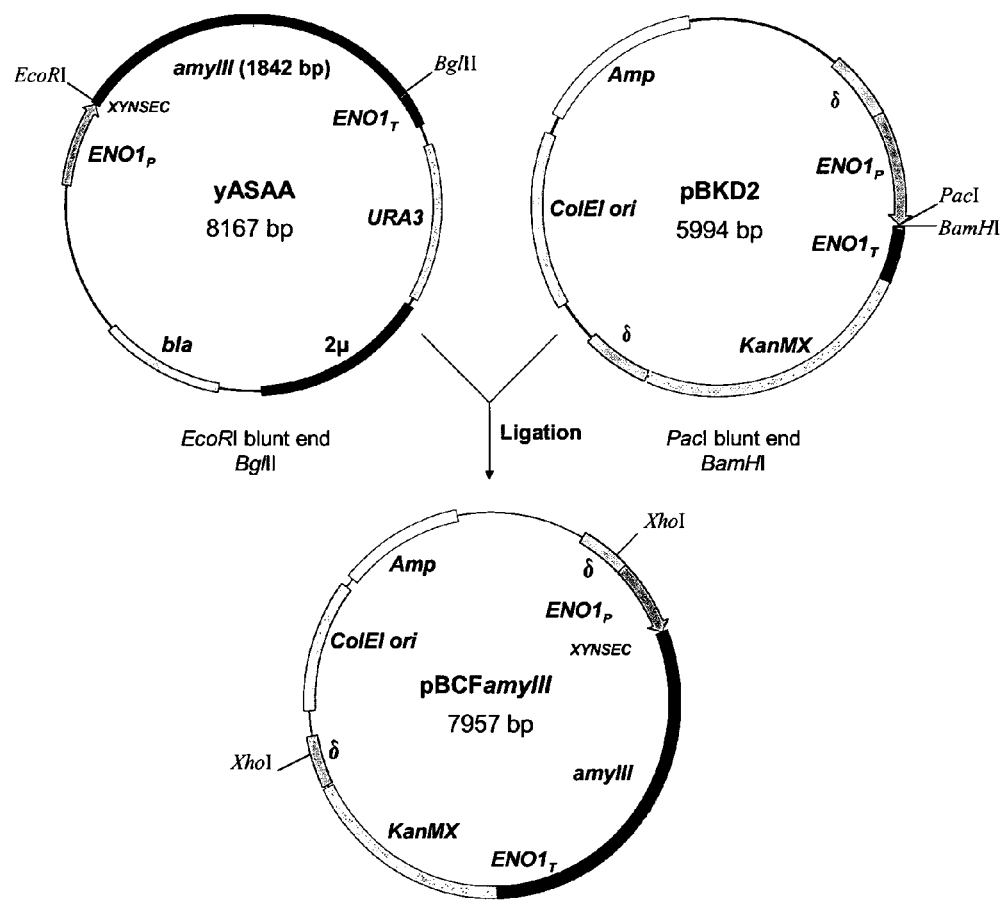

FIG. 18. Construction of the δ-integrative vector, pBC-FamyIIII, for amyIII constitutive expression in *S. cerevisiae*.

Figure 19:
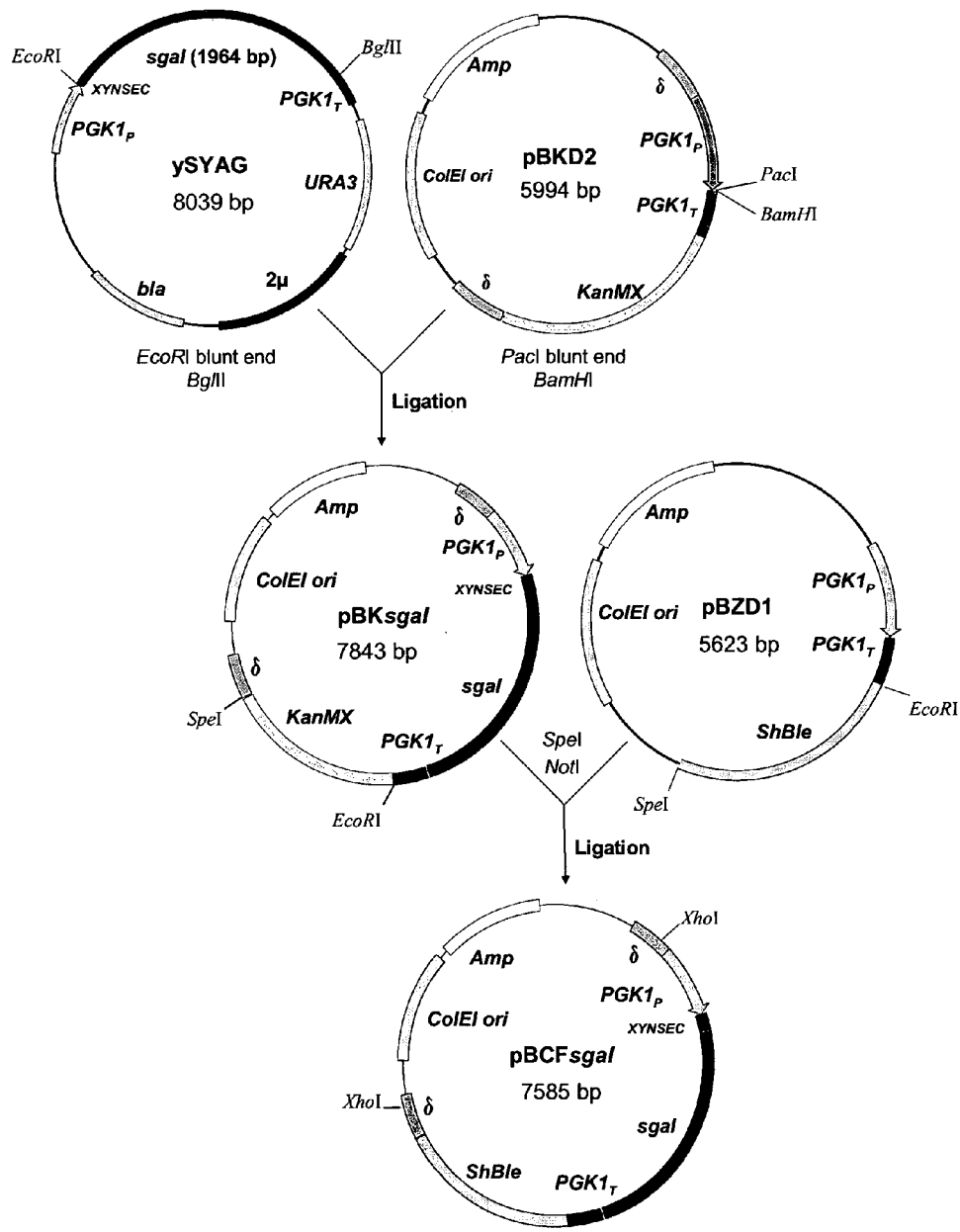

FIG. 19. Construction of the δ-integrative vector, pBCFs-gaI, for sgaI constitutive expression in *S. cerevisiae*.

Figure 20:
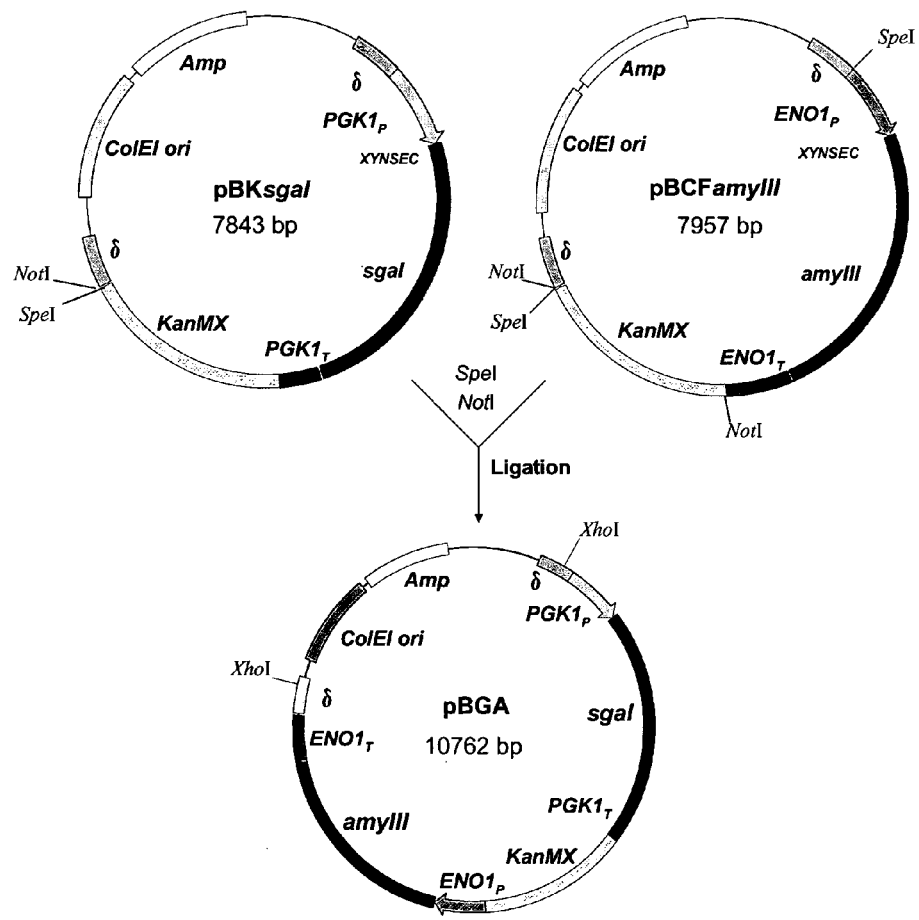

FIG. 20. Construction of the δ-integrative vector, pBGA, containing the amyIIII and sgaI cassettes for constitutive expression in *S. cerevisiae*.

Figure 21:
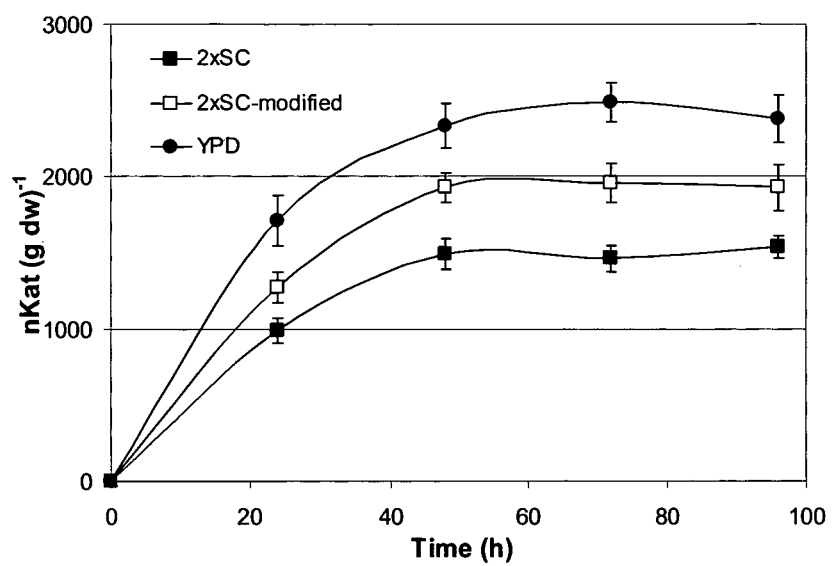

FIG. 21. Glucoamylolytic activity of *S. cerevisiae* sBCF2, recombinant of *S. cerevisiae* s2 with multiple integrations of sgaI, grown in YPD (●) 2×SC (■) and 2×SC-modified broth (□) supplemented with 0.75% yeast extract. The activity, detected at 50° C. in buffer at 4.5 pH, is expressed as nKat (g dw cells)$^{-1}$ that is the enzyme activity needed to produce 1 nmol of glucose per second per gram dry cell weight. The experiment was conducted in triplicate (±SD).

Figure 22:
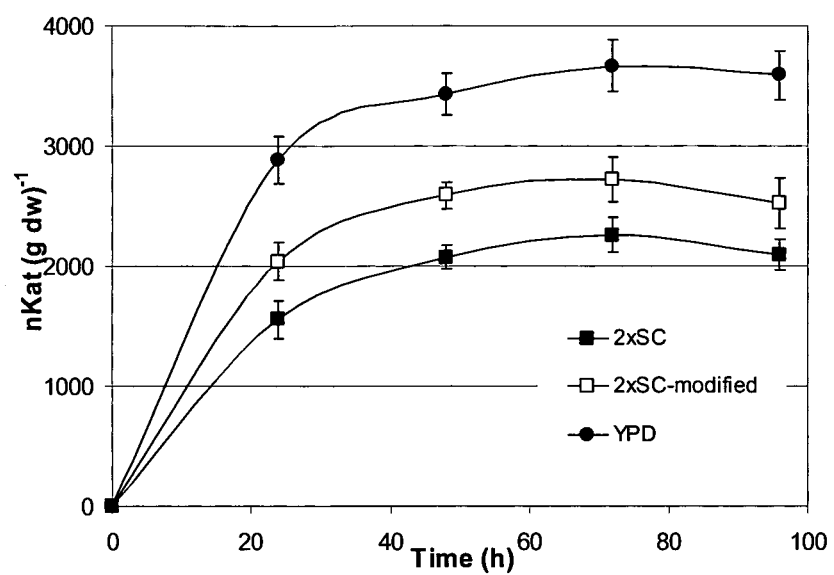

FIG. 22. Glucoamylolytic activity of *S. cerevisiae* LH4, recombinant of *S. cerevisiae* H1 with multiple integrations of sgaI, grown in YPD (●) 2×SC (■) and 2×SC-modified broth (□) supplemented with 0.75% yeast extract. The activity, detected at 50° C. in buffer at 4.5 pH, is expressed as nKat(g dw cells)$^{-1}$. The experiment was conducted in triplicate (±SD).

Figure 23:
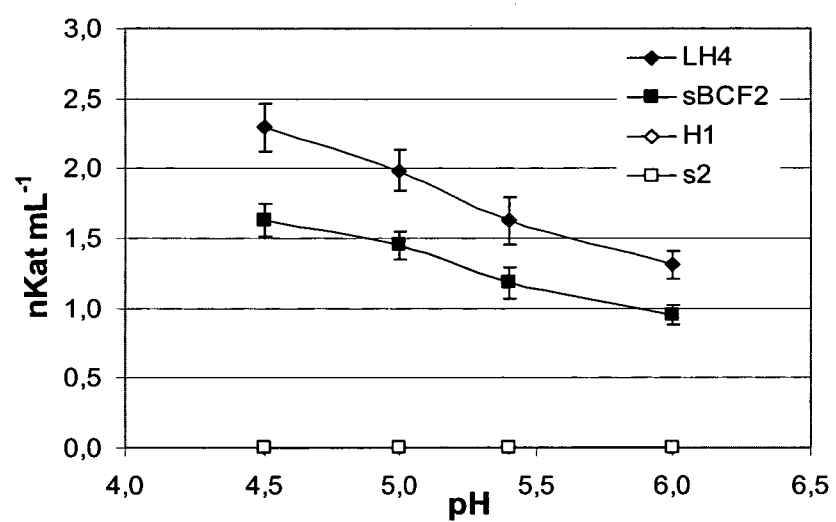

FIG. 23. Glucoamylolytic activity in cell-free culture supernatant (nKat mL$^{-1}$) of engineered strains LH4, sBCF2 and their respective wild type yeast *S. cerevisiae* H1 and s2, grown for 72 h in YPD. The assays were performed at 50° C. in citrate-phosphate buffer (0.1% soluble starch) at 4.5-5.0-5.4-6.0 pH. The experiment was conducted in triplicate (±SD).

Figure 24:
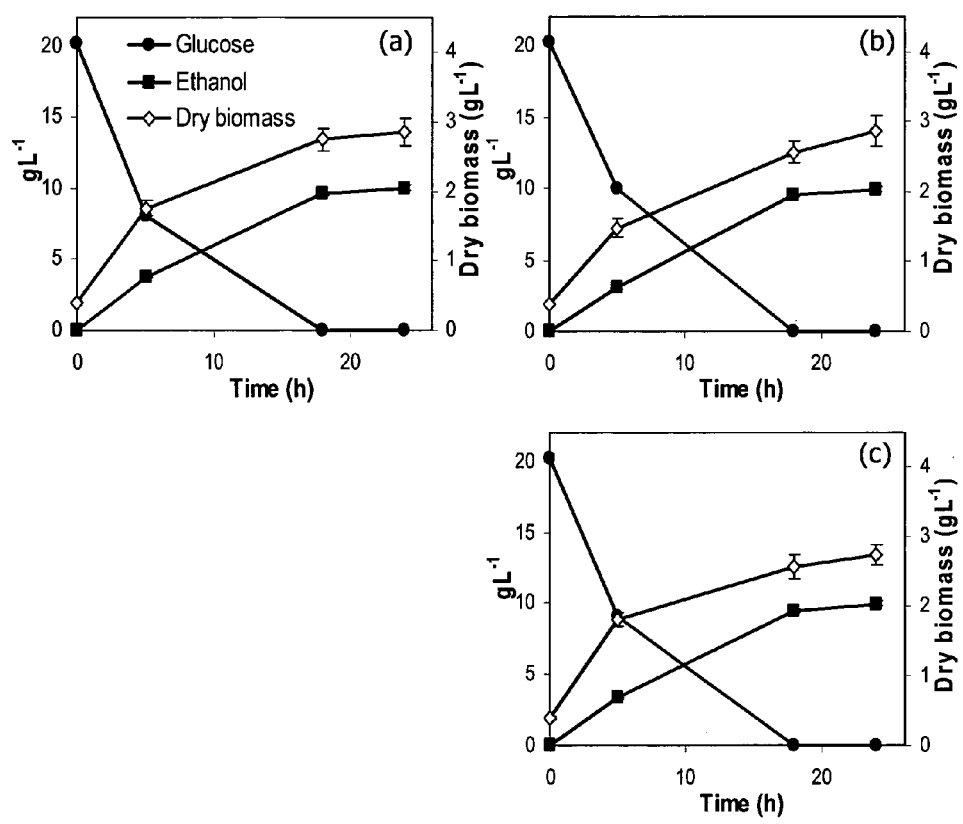

FIG. 24. Fermentation profiles of the wild-type *S. cerevisiae* s2(a) and the sBCF2(b) and sBCF6(c) engineered strains anaerobically grown in GFM medium.

Ethanol and starch concentrations (gL$^{-1}$) are indicated on the y-axis. Dry biomass (gL$^{-1}$) level is indicated on the secondary y-axis. The experiment was conducted in triplicate (±SD).

Figure 25:
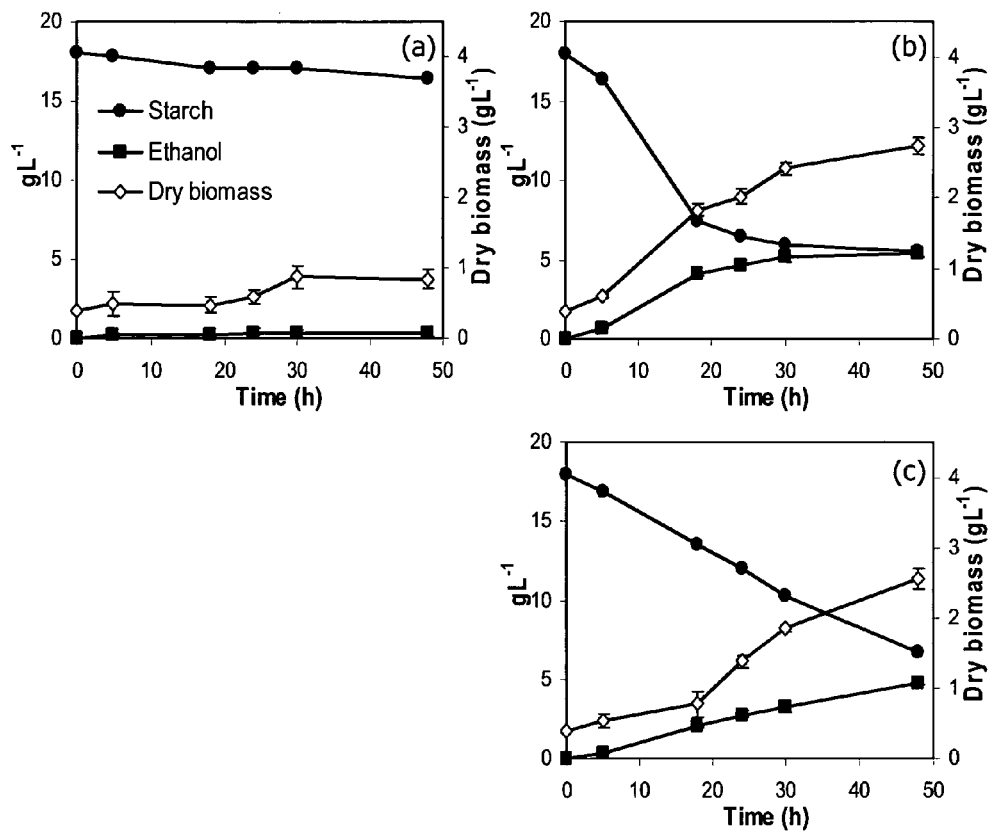

FIG. 25. Fermentation profiles of the wild-type *S. cerevisiae* s2(a) and the sBCF2(b) and sBCF6(c) engineered strains anaerobically grown in SFM medium. Ethanol and starch concentrations (gL$^{-1}$) are indicated on the y-axis. Dry biomass (gL$^{-1}$) level is indicated on the secondary y-axis. The experiment was conducted in triplicate (±SD).

Figure 26:
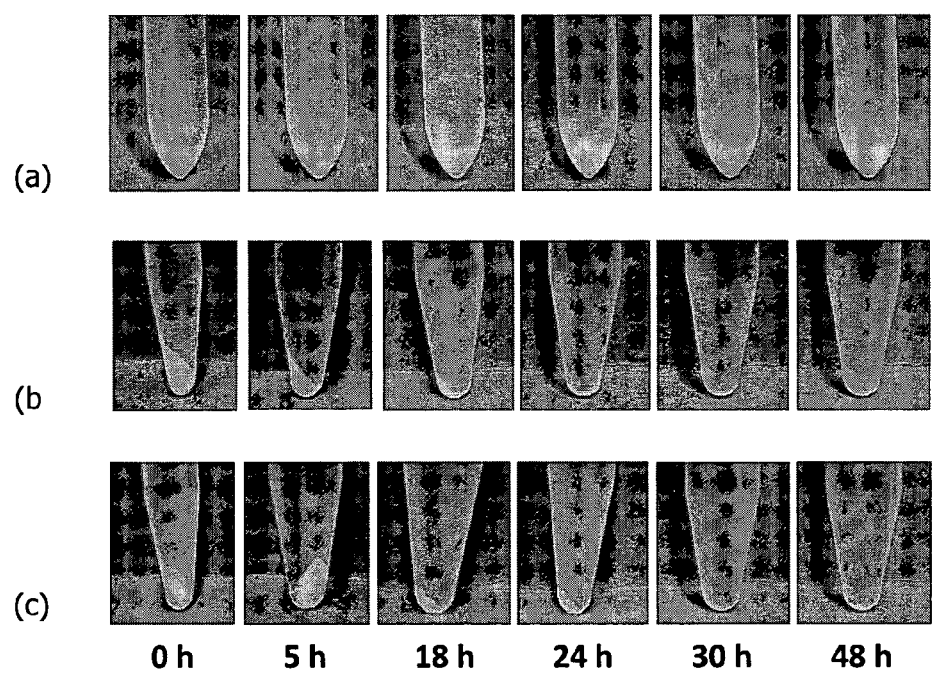

FIG. 26. Soluble starch deposit (after −20° C. storage) in SFM medium inoculated with wild type yeast *S. cerevisiae* s2 (a) and the sBCF2(b) and sBCF6(c) engineered strains.

Figure 27:
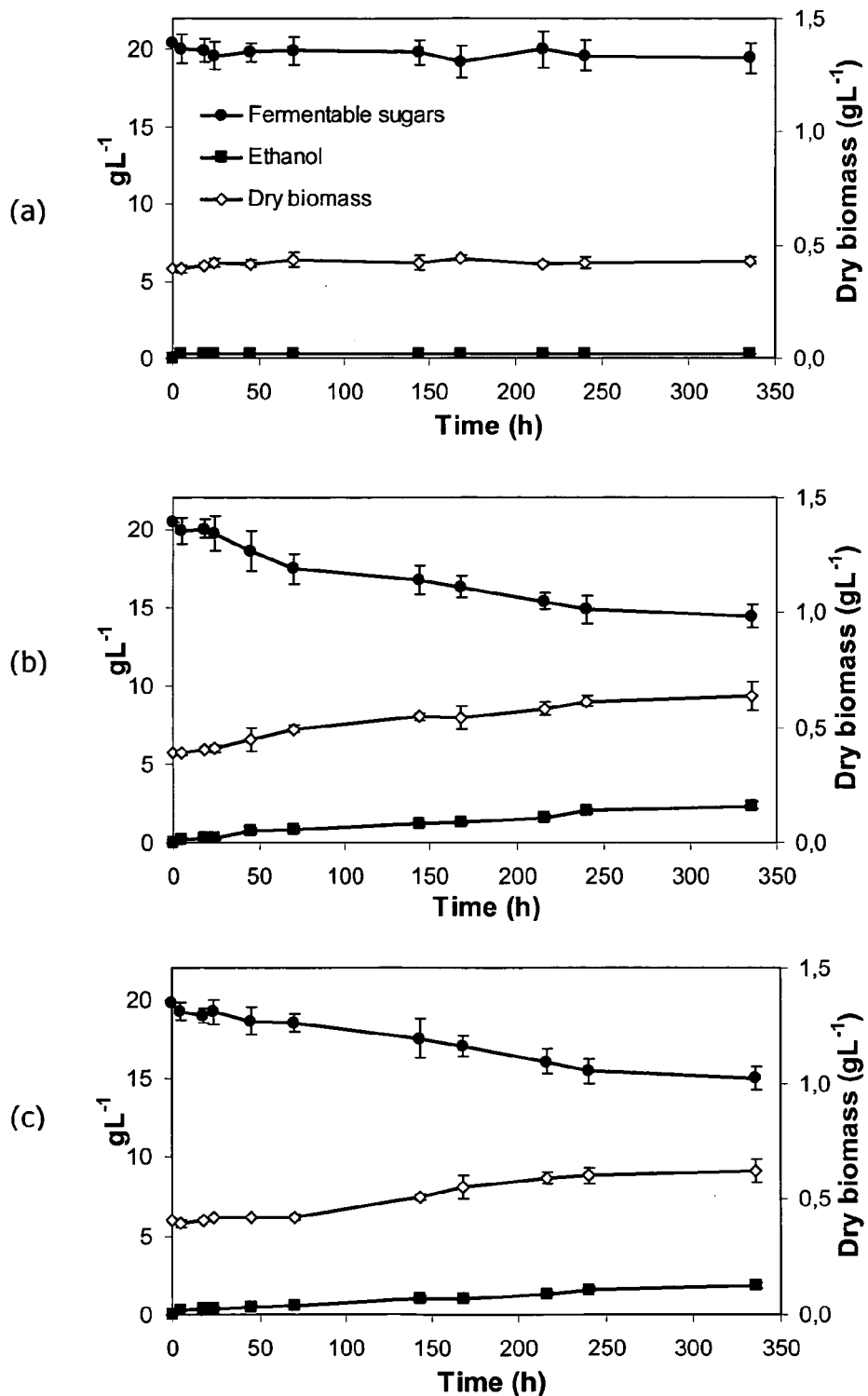

FIG. 27. Fermentation profiles of the wild type *S. cerevisiae* s2(a) and the sBCF2(b) and sBCF6(c) engineered strains anaerobically grown in RSFM medium. Ethanol and fermentable sugars concentrations (gL$^{-1}$) are indicated on the y-axis. Dry biomass (gL$^{-1}$) level is indicated on the secondary y-axis. The experiment was conducted in triplicate (±SD).

Figure 28:
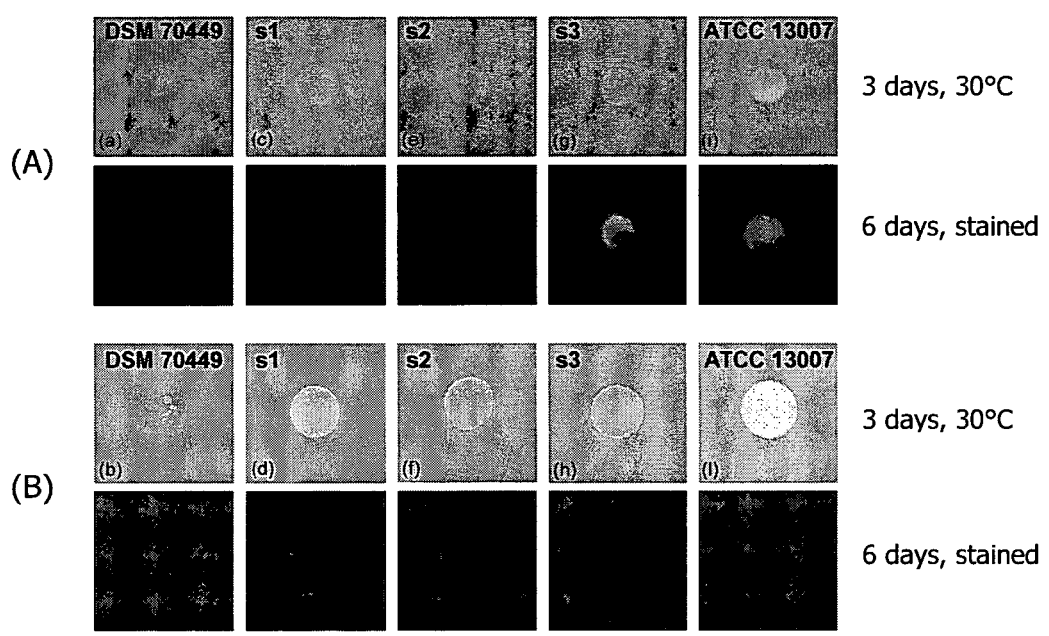

FIG. 28. Growth of *Saccharomyces* sp. strains on complete Wollum medium (A) and on minimal EMM plates (B). Reference strains (negative: *S. cerevisiae* DMS 70449; positive: *S. diastaticus* ATCC 13007) and potentially amylolytic strains (s1, s2, s3) were grown at 30° C. for 6 days and then stained with iodine solution.

Figure 29:
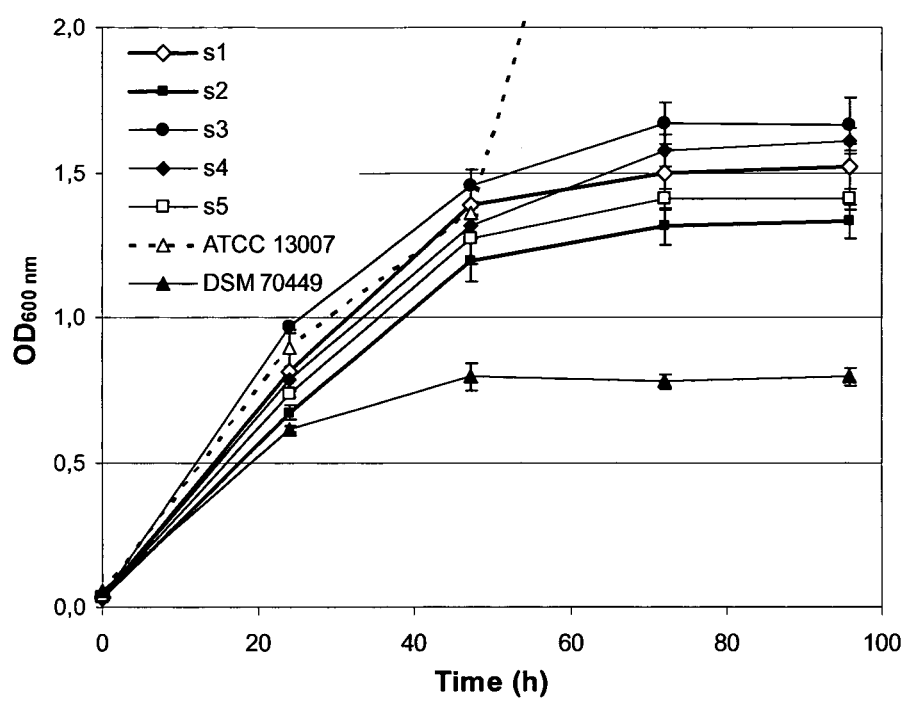

FIG. 29. Liquid cultures in YPS broth (supplemented with gL$^{-1}$: yeast extract, 10; peptone, 20 and soluble starch, 20) of potentially starch-degrading *S. cerevisiae* strains (s1-s5), *S. diastaticus* (ATCC 13007) and *S. cerevisiae* type strain (DSM 70449). Data are the means of three replicates (±SD).

Figure 30:
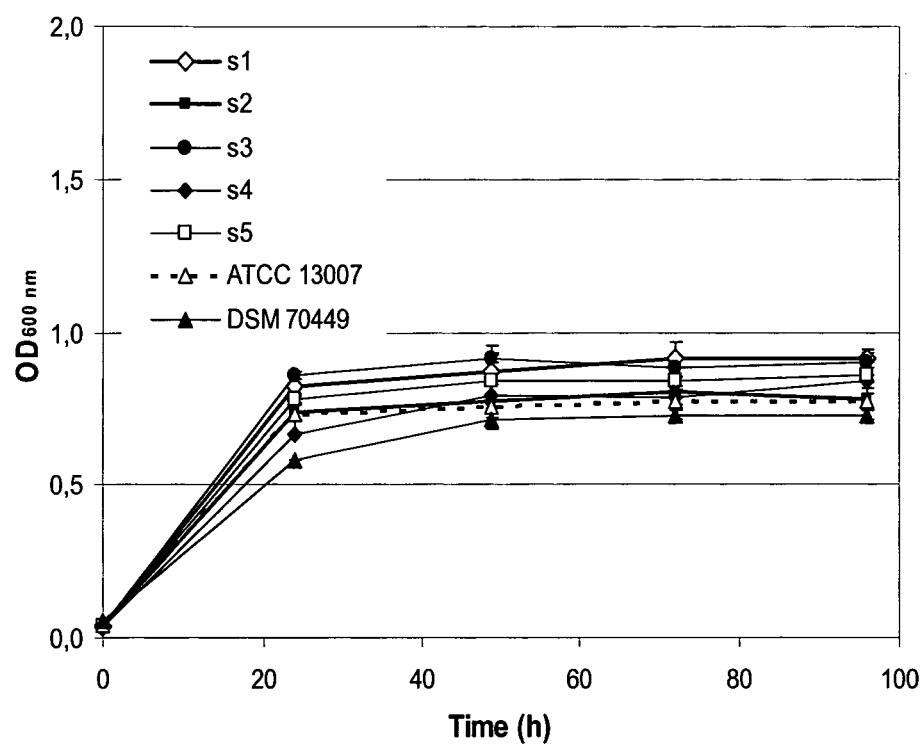

FIG. 30. Liquid cultures in YP broth (supplemented with gL$^{-1}$: yeast extract, 10 and peptone, 20) of potentially starch-degrading *S. cerevisiae* strains (s1-s5), *S. diastaticus* (ATCC 13007) and *S. cerevisiae* type strain (DSM 70449). Data are the means of three replicates (±SD).

Figure 31:
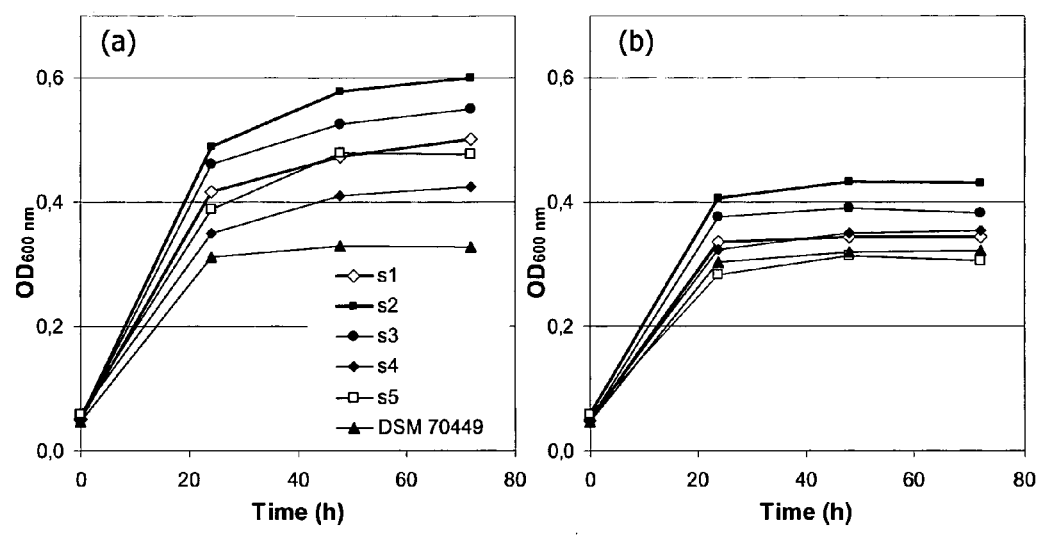

FIG. 31. Liquid cultures of potentially starch-degrading *S. cerevisiae* strains (s1-s5) in Minimal Medium Yeast with (a) or without (b) added soluble starch (5 gL$^{-1}$). *S. cerevisiae* DSM 70449 was used as negative control strain. Data represent the means of two replicates.

Figure 32:
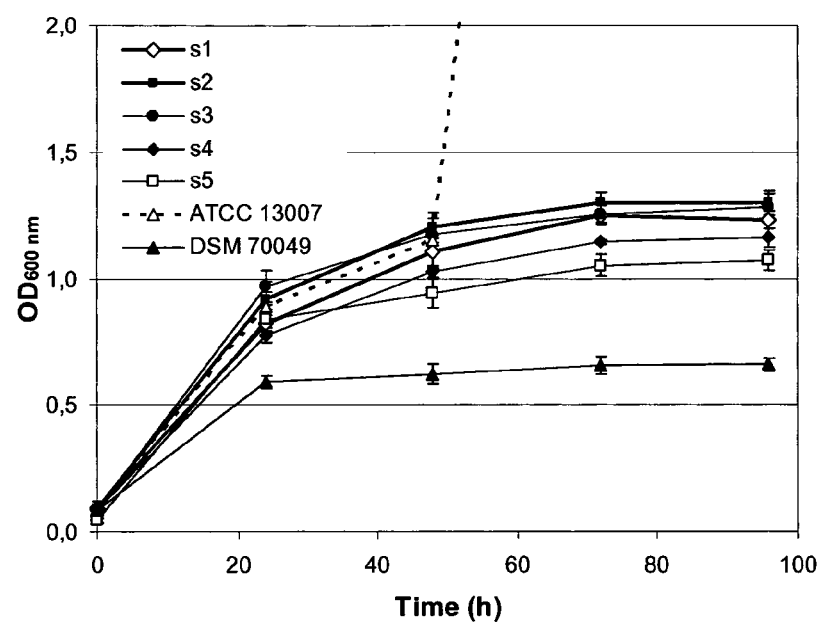

FIG. 32. Liquid cultures in EMM broth (20 gL$^{-1}$ soluble starch) of potentially starch-degrading *S. cerevisiae* strains (s1-s5), *S. diastaticus* (ATCC 13007) and *S. cerevisiae* type strain (DSM 70449). Data are the means of three replicates (±SD).

GLOSSARY OF TERMS

This section is intended to provide guidance on the interpretation of the words and phrases set forth below (and where appropriate grammatical variants thereof). Further guidance on the interpretation of certain words and phrases as used herein (and where appropriate grammatical variants thereof) may additionally be found in other sections of this specification.

As used herein, the singular forms "a", "an" and "the" include the plural references unless the content clearly dictates otherwise. Thus for example, reference to a composition containing "a compound" includes a reference to a mixture of two or more compounds. It should be noted that the term "or" is generally employed in the sense including "and/or" unless the context dictates otherwise.

As used herein, the term "about" as used in relation to a numerical value means, for example, within 50% (±50%) of the numerical value, preferably ±30%, ±20%, ±15%, ±10%, ±7%, ±5%, or ±1%. Where necessary, the word "about" may be omitted from the definition of the invention.

In the context of this specification, the term "comprising" means "including. Thus, for example, a composition or polypeptide "comprising" X may consist exclusively of X or may include one or more additional components. In some embodiments, "comprising" means "including principally, but not necessarily solely".

The term "control" sequences as used herein includes a reference to nucleic acid sequences which are operably linked to a polypeptide-encoding sequence and which allow or regulate expression of the coding sequence. Examples of control sequences will be well known to those skilled in the art and will include, for example, promoters, enhancers, transcriptional and translational stop sites, and other signal sequences.

The phrase "tested under essentially the same conditions" is intended to refer to the comparison of characteristics/parameters under conditions which provide for a meaningful comparison. Hence, the conditions used to conduct the comparisons should be the same to the extent that there are no variations in the test conditions which would materially affect the validity of the comparison. Where necessary, the word "essentially" may be omitted from the definition of the invention.

As used herein, "heterologous" in reference to a nucleic acid or protein includes a molecule that has been manipulated by human intervention so that it is located in a place other than the place in which it is naturally found. For example, a nucleic acid sequence from one organism (e.g. from one strain or species) may be introduced into the genome of another organism (e.g. of another strain or species), or a nucleic acid sequence from one genomic, locus may be moved to another genomic or extrachromasomal locus in the same organism. A heterologous protein includes, for example, a protein expressed from a heterologous coding sequence or a protein expressed from a recombinant gene in a cell that would not naturally express the protein.

The polypeptides and cells of the present invention may be "isolated". The term isolated as used herein means altered "by the hand of man" from its natural state; i.e., if it occurs in nature, it has been changed or removed from its original environment, or both. For example, a naturally occurring polypeptide naturally present in a cell is not "isolated", but the same polypeptide separated from the coexisting materials of its natural state is "isolated", as the term is employed herein.

The terms "mutant" and "mutation" include any detectable change in genetic material, e.g. DNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence.

The term "starch" refers to any material comprised of the complex polysaccharide carbohydrates of plant, comprised of amylose and amylopectin with the formula $(C_6H_{10}O_5)x$, wherein X can be any number.

The term "granular starch" refers to raw (unmodified) uncooked starch that has not been subjected to gelatinization. At about 25° C., starch granules start absorbing water, and as the temperature increases, the granules start to vibrate vigorously. Crystallinity decreases, and when the starch and water suspension is heated above a critical point, designated the pasting or gelatinisation temperature, the granules disintegrate to make a paste. The exact temperature of gelatinization depends on the specific starch, and can readily be determined by the skilled person.

The term "gelatinization" means the solubilization of a starch molecule by cooking to form a viscous suspension. The phrase "below the temperature of gelatinization" refers to a temperature less than the temperature which starts gelatinization.

"Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame.

The term "parent polypeptide" as used herein is used interchangeably with the term "reference polypeptide". In the case of a natural biological variant then the parent polypeptide will be a polypeptide as defined in (a) above. In the case of an active fragment of the invention then the parent polypeptide will be a polypeptide as defined in (a) or (b) above. In the case of a functional equivalent of the invention then the parent polypeptide will be a polypeptide as defined in (a), (b) or (c) above. In the case of a fusion protein of the invention then the parent polypeptide will be a polypeptide as defined in (a), (b), (c) or (d) above. In one embodiment the "parent polypeptide" may be a polypeptide whose sequence is explicitly recited herein (e.g. SEQ ID NO. 1, SEQ ID NO. 3, or SEQ ID NO. 2).

The term "phenotype" includes a detectable or outward characteristic of a cell determined by its genotype and modulated by its environment. Examples of phenotypes include the ability to produce proteins or compounds, the ability to produce certain amounts of a particular amino acid in a specified amount of time, level of gene expression, morphology, growth rate, enzyme activity, tolerance to low oxygen conditions etc.

The terms "polypeptide" and "protein" are used interchangeably and include any polymer of amino acids (dipeptide or greater) linked through peptide bonds or modified peptide bonds, whether produced naturally or synthetically. The polypeptides of the invention may comprise non-peptidic components, such as carbohydrate groups. Carbohydrates and other non-peptidic substituents may be added to a polypeptide by the cell in which the polypeptide is produced, and will vary with the type of cell. Polypeptides are defined herein, in terms of their amino acid backbone structures; substituents such as carbohydrate groups are generally not specified, but may be present nonetheless.

DETAILED DESCRIPTION OF THE INVENTION

As discussed above, the combination of alpha-amylases and glucoamylases has proved particularly useful in the processing of starch-containing material during the process of bioethanol production. However, only some alpha-amylases and glucoamylases possess the ability to hydrolyse raw starch.

Approximately 10% of amylolytic enzymes are able to hydrolyse linkages in raw or unmodified starch and these enzymes generally contain a Starch Binding Domain (SBD) (Coutinho and Reilly, 1997; Machovič & Janeč, 2006). Only a few enzymes have been identified to hydrolyse raw starch without the presence of a specialised binding domain (Machovič & Janeč (2006)). The SBD is a carbohydrate-binding module, which enhances the ability of the enzyme to degrade raw starch. The domain is responsible for starch binding and brings the catalytic site of the enzyme in closer proximity with the substrate, therefore increasing the rate of catalytic activity. SBDs are further discussed in Machovič & Janeč, 2006 Cell. Mol. Life. Sci. 63: 2710-2724.

The term "alpha-amylase" refers to the EC 3.2.1.1 class of enzymes (1,4-alpha-D-glucan glucanohydrolase) which display alpha-1,4-cleaving activity. The enzymes are endohydrolases, employ a retaining mechanism for hydrolysis (Enzyme Nomenclature, 1992) and belong to the glycoside hydrolase (GH) Family 13 and clan GH-H (MacGregor et al., 2001). They hydrolyse the 1,4-alpha-D-glucosidic linkages in polysaccharides containing three or more 1,4-alpha-linked D-glucose units. Hydrolysis reduces the molecular size of starch and therefore the viscosity of the starch solution. The alpha-amylases have considerably low sequence similarity, although four amino acids are invariant throughout the entire family of EC 3.2.1.1 (Hasegawa et al., 1999; Matsuura et al., 1980; Matsuura et al., 1984; Nakamura et al., 1992; Swift et al., 1991; Vihinen et al., 1990).

Glucoamylases (1,4-α-D-glucan glucohydrolase EC 3.2.1.3) belong to GH Family 15. Glucoamylases are inverting enzymes and hydrolyse the terminal 1,4-linked alpha-D-glucopyranosyl residues successively from non-reducing ends of starch chains to release beta-D-glucose in an exo-fashion. Most forms of the enzyme can rapidly hydrolyse 1,6-alpha-D-glucosidic bonds when the next bond in the sequence is 1,4-linked. The specific activity towards the 1,6-linkage is however only 0.2% of that for the 1,4-linkage.

Fungal glucoamylases contain a catalytic domain near the amino terminus. In enzymes with raw starch degrading ability, the catalytic domain is connected to a raw starch affinity site on the C-terminus (Fukuda et al., 1992; Hayashida et al., 1991) with an O-glycosylated polypeptide linker. When this C-terminal region was compared to glucoamylases and alpha-amylases of many strains, four areas of sequence similarity were identified (Svensson et al., 1989). Carbohydrate content of glucoamylases generally range from 10-20% of the MW and glycosylation plays an integral part in stability. Glycosylation does not seem to affect the protein's tertiary structure, however elimination of glycosylation leads to decreased enzyme secretion and thermal stability of the enzyme (Coutinho and Reilly, 1997; Williamson et al., 1992). A detailed review of the structure and function of Fungal glucoamylases may be found in Coutinho and Reilly, 1997 Proteins Struct. Funct. Genet. 29 (1997) 334-347 and in J. Sauer, et al. Biophys. Acta 1543 (2000) 275-293.

Further information of the structure and function of glucoamylases and alpha-amylases may be found in Christiansen et al. FEBS Journal 276 (2009) 5006-5029.

One of the embodiments of the present invention is to provide beneficial combinations of alpha-amylase and glucoamylase which may find utility in the bioethanol production industry on account of their ability to hydrolyse soluble starch and raw starch.

According to a first aspect of the invention, there is provided a host cell (preferably a microorganism) which expresses:
(i) TLG1 and SFA1; or
(ii) TLG1 and LKA1.

For the avoidance of doubt, the first aspect of the invention also extends to host cells which express all three of TLG1, SFA1 and LKA1.

For ease of reference the following combinations are referred to as the "glucoamylase and alpha-amylase combinations of the invention": (i) TLG1 and SFA1; (ii) TLG1 and LKA1; and (iii) TLG1, SFA1 and LKA1.

The terms "TLG1 protein"/"TLG1 polypeptide"/"TLG1" are used interchangeably in the present application and denote a protein which retains the glucoamylase activity of the *Thermomyces lanuginoses* TLG1 protein, which is preferably as set forth in SEQ. ID. NO.1.

In some embodiments, the TLG1 protein comprises (and in one embodiment consists of):
(a) a polypeptide comprising the sequence set forth in SEQ. ID. NO. 1;
(b) a natural biological variant of a polypeptide as defined in (a) above;
(c) an active fragment of a polypeptide as defined in (a) or (b);
(d) a functional equivalent of a polypeptide as defined in (a), (b) or (c); or
(e) a fusion protein comprising a polypeptide as defined in (a), (b), (c) or (d).

SEQ. ID. NO.1 represents the mature protein sequence of the *T. lanuginoses* TLG1 protein and is shown in FIG. 9 below, along with its native secretion signal (note the secretion signal does not form part of SEQ. ID. NO.1). The native secretion signal gets spliced off during secretion leaving the mature protein sequence. Further details of the TLG1 protein may be found in Thorsen et al. *Biochimica et Biophysica Acta* 1764 (2006) 671-676.

The terms "SFA1 protein"/"SFA1 polypeptide"/"SFA1" are used interchangeably in the present application and denote a protein which retains the alpha-amylase activity of the *Saccharomycopsis fibuligera* SFA1 protein which is preferably as set forth in SEQ. ID. NO.3. In some embodiments, the SFA1 protein comprises (and in one embodiment consists of):
(a) a polypeptide comprising the sequence set forth in SEQ ID NO: 3;
(b) a natural biological variant of a polypeptide as defined in (a) above;

(c) an active fragment of a polypeptide as defined in (a) or (b);
(d) a functional equivalent of a polypeptide as defined in (a), (b) or (c); or
(e) a fusion protein comprising a polypeptide as defined in (a), (b), (c) or (d).

SEQ. ID. NO.3 represents the mature protein sequence of the *S. fibuligera* SFA1 protein and is shown in FIG. 11 below, along with its native secretion signal (note the secretion signal does not form part of SEQ. ID. NO.3). The native secretion signal gets spliced off during secretion leaving the mature protein sequence.

The terms "LKA1 protein"/"LKA1 polypeptide"/"LKA1" are used interchangeably in the present application and denote a protein which retains the alpha-amylase activity of the *Lypomycis kononenkoae* LKA1 protein which is preferably as set forth in SEQ. ID. NO.2. In some embodiments the LKA1 protein comprises (and in one embodiment consists of):

(a) a polypeptide comprising the sequence set forth in SEQ. ID. NO. 2;
(b) a natural biological variant of a polypeptide as defined in (a) above;
(c) an active fragment of a polypeptide as defined in (a) or (b);
(d) a functional equivalent of a polypeptide as defined in (a), (b) or (c); or
(e) a fusion protein comprising a polypeptide as defined in (a), (b), (c) or (d).

SEQ. ID. NO.2 represents the mature protein sequence of the *L. kononenkoae* LKA1 protein and is shown in FIG. 10 below, along with the *Trichoderma reesei* xylanase 2 secretion signal (XYNSEC) (note the secretion signal does not form part of SEQ. ID. NO.2). The secretion signal gets spliced off during secretion leaving the mature protein sequence.

Natural Biological Variants

A natural biological variant may be described as, for example, an "allelic" "splice," or "polymorphic" variant.

An "allelic variant" is an alternative form of the TLG1, SFA1 or LKA1 polypeptide. Allelic variants are encoded by mutually exclusive forms of the same gene, occupying the same locus on homologous chromosomes, and governing the same biochemical or developmental process etc. Allelic variants may result from at least one mutation in the nucleic acid sequence and may result in altered mRNAs or in polypeptides whose structure or function may or may not be altered. Common mutational changes which give rise to allelic variants are generally ascribed to natural deletions, additions, or substitutions of nucleotides. Each of these types of changes may occur alone, or in combination with the others, one or more times in a given sequence.

A "splice variant" may have significant sequence identity to a reference molecule, but will generally have a greater or lesser number of amino acid residues due to alternate splicing during mRNA processing. The polypeptide may possess additional functional domains or lack domains that are present in the reference molecule. A splice variant may, for example, have less than about 99%, 97% 95%, 90%, 80%, 70% or alternatively less than about 60%, or alternatively less than about 50% sequence identity to a polypeptide according to (a) as defined above over its entire length. However, at least one or more portions of the splice variant may have at least about 70%, or alternatively at least about 85%, or alternatively at least about 95%, 97%, 98%, 99% or alternatively 100% sequence identity to a polypeptide according to (a).

The natural biological variants may have at least 40%, 50%, 60%, 70%, 80%, 85%, 90%, 92%, 95%, 97%, 98% or 99% sequence identity with a polypeptide according to (a) above (e.g. to SEQ ID NO.1, SEQ ID NO.3, or SEQ ID NO.1.

Active Fragments

Also included within the scope of the invention are "active fragments" wherein "active fragment" denotes a truncated protein that retains the enzymatic activity of the parent polypeptide. The fragments of the invention may contain single or multiple amino acid deletions from either terminus of the protein (i.e. from the amino and/or carboxyl terminus of the amino acid sequence) or from internal stretches of the primary amino acid sequence.

The fragments should comprise at least n consecutive amino acids from the parent sequence and, depending on the particular sequence, n preferably is 5 or more (for example, 5, 6, 7, 8, 9, 10, 12, 15, 17, 20, 30, 40, 50, 60, 70, 80, 100, 120, 140, 160, 180, 200, 220, 240, 260, 280, 300, 320, 340, 360, 380, 400, 420, 440, 460, 480 or more).

Such fragments may be "free-standing", i.e. not part of or fused to other amino acids or polypeptides, or they may be comprised within a larger polypeptide of which they form a part or region. When comprised within a larger polypeptide, the fragment of the invention most preferably forms a single continuous region. Additionally, several fragments may be comprised within a single larger polypeptide.

Also, it will be recognized by those skilled in the art that there may be critical areas within the protein which determine activity and which, as such, should be retained within the active fragment. In terms of such "critical areas" the reader is referred to the discussion below under "functional equivalents".

Functional Equivalent

The invention also includes functional equivalents of a polypeptide of (a), (b) or (c) as recited above.

The functionally-equivalent polypeptides according to this aspect of the invention include polypeptides that are homologous to a polypeptide as set forth in (a), (b) or (c) as recited above. In one embodiment there is provided a functionally-equivalent polypeptide which is homologous to a polypeptide whose sequence is explicitly recited herein (e.g. SEQ. ID. NO. 1, SEQ. ID. NO. 3 or SEQ. ID. NO. 2) or to a natural biological variant or an active fragment of any of these.

Two polypeptides are said to be "homologous" if the sequence of one of the polypeptides has a high enough degree of identity to the sequence of the other polypeptide. The phrases "percent identity", "% identity," "protein identity", "sequence identity" etc. as applied to polypeptide sequences, refer to the percentage of identical residue matches between at least two polypeptide sequences aligned using a standardized algorithm. Such an algorithm may insert, in a standardized and reproducible way, gaps in the sequences being compared in order to optimize alignment between two sequences, and therefore achieve a more meaningful comparison of the two sequences.

Percent identity may be determined using one or more computer algorithms or programs known in the art or described herein. For example the UWGCG Package provides the BESTFIT program which can be used to calculate sequence identity (for example used on its default settings) (Devereux et al (1984) Nucleic Acids Research 12, p 38'7-395). The PILEUP and BLAST (Basic Local Alignment Search Tool) algorithms can be used to calculate sequence identity or line up sequences (typically on their default settings), for example as described in Altschul S. F. (1993) J Mol Evol 36:290-300 and in Altschul, S, F et al (1990) J Mol Biol 215:403. Software for performing BLAST analyses is available from several sources, including the National Center for Biotechnology Information (NCBI), Bethesda, Md., and on the internet at, for example, "www.ncbi.nlm.nih.gov/".

Preferably, the default settings of the aforementioned algorithms/programs are used.

Typically, greater than 50% identity between two polypeptides is considered to be an indication of functional equivalence, provided that the activity of the reference polypeptide is retained. More preferred polypeptides have degrees of identity of greater than 60%, 65%, 70%, 75%, 80%, 82%, 85%, 87%, 90%, 92%, 95%, 97%, 98%, 99% or 99.5%, respectively.

Functionally-equivalent polypeptides according to the invention are intended to include polypeptides wherein at one or more positions there have been amino acid insertions, deletions, or substitutions, either conservative or non-conservative, provided that such changes result in a protein which retains activity of the parent polypeptide. Each of these types of changes may occur alone, or in combination with the others, one or more times in a given sequence. Such variants may for example be made using the methods of protein engineering and site-directed mutagenesis.

A "conservative" change is wherein a substituted amino acid has similar structural or chemical properties whilst a "non-conservative" change is wherein the substituted amino acid is structurally or chemically different. The terms "conservative substitution", "non-conservative substitutions", "non-polar amino acids", "polar amino acids", and "acidic amino acids" are all used consistently with the prior art terminology. Each of these terms is well-known in the art and has been extensively described in numerous publications, including standard biochemistry text books, such as "Biochemistry" by Geoffrey Zubay, Addison-Wesley Publishing Co., 1986 edition, which describes conservative and non-conservative substitutions, and properties of amino acids which lead to their definition as polar, non-polar or acidic.

In general, the non-polar amino acids Gly, Ala, Val, Ile and Leu; the non-polar aromatic amino acids Phe, Trp and Tyr; the neutral polar amino acids Ser, Thr, Cys, Gln, Asn and Met; the negatively charged amino acids Lys, Arg and His; the positively charged amino acids Asp and Glu, represent groups of conservative amino acids. This list is not exhaustive. For example, it is well known that Ala, Gly, Ser and sometimes Cys can substitute for each other even though they belong to different groups.

Whether an amino acid can be substituted at all (or deleted), or whether it can only be substituted by a conserved amino acid can be determined by comparing the amino acid sequence of one or more members of the protein family Amino acids that are identical in all the members of a protein family often cannot be substituted. Amino acids which are conserved can usually be substituted by other conserved amino acids without significantly affecting the protein's function. Finally, amino acids which are not conserved within a family can usually be freely substituted.

Guidance in determining which amino acid residues may be substituted, inserted, or deleted without abolishing biological activity may also be found using computer programs well known in the art, for example, LASERGENE software (DNASTAR). Guidance concerning how to make phenotypically silent amino acid substitutions is provided, for example, in J. U. Bowie et al., "Deciphering the Message in Protein Sequences: Tolerance to Amino Acid Substitutions," Science 247:1306-1310 (1990).

Also, it will be recognized by those skilled in the art that there may be critical areas on the protein which determine activity, such as the starch binding domain (SBD) and catalytic domain. The skilled person will appreciate that it may be desirable to take into account these areas when determining what changes to the amino acid sequence can be made. A detailed overview of SBDs may be found in Machovič & Janeč, 2006.

Amino acid residues essential to activity of the polypeptide, and therefore preferably not subject to alteration e.g. by substitution or deletion (or if substituted only substituted by conservative substitutions), may be identified according to procedures known in the art, such as site-directed mutagenesis or alanine-scanning mutagenesis (see, e.g., Cunningham and Wells, 1989, Science 244: 1081-1085). Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, Science 255: 306-312; Smith et al., 1992, Journal of Molecular Biology 224: 899-904; Wlodaver et al., 1992, FEBS Letters 309: 59-64).

Functional equivalents of the polypeptides of the invention also include polypeptides in which relatively short stretches (for example about 7 to 20 amino acids) have a high degree of homology (at least 60%, 70%, 80%, 85%, 87%, 90%, 92%, 95%, or 97%) with the reference polypeptide even though the overall homology between the two polypeptides may be much less. This is because important active or binding sites may be shared even when the general architecture of the protein is different.

Amino acid deletions, substitutions or additions remote from an active or binding site of a protein are generally more easily tolerated. In general, it is often possible to replace residues which form the tertiary structure, provided that residues performing a similar function are used. In other instances, the type of residue may be completely unimportant if the alteration occurs at a non-critical region of the protein.

In one embodiment there are provided functional equivalents in which one or more amino acids (e.g. between 1 and 30, 1 and 20, 1 and 10, 10 and 20, 5 and 10, 1 and 5, 1 and 3, 1 and 2 or just 1 amino acid) are independently substituted, deleted or added in any combination. In one embodiment there are less than 75, 50, 45, 40, 35, 30, 29, 28, 27, 26, 25, 24, 23, 22, 21, 20, 19, 18, 17, 16, 15, 14, 13, 12, 11, 10, 9, 8, 7, 6, 5, 4, 3 or 2 amino acid substitutions, additions, deletions or conservative substitutions. Especially preferred are silent substitutions, additions and deletions and conservative substitutions. Also preferred are changes which do not fall within the catalytic domain and/or SBD of the reference polypeptide.

In one embodiment there is provided a functional equivalent which contains one or more mutations. The mutations may each independently be a substitution, an insertion, or a deletion. Preferably, the functional equivalent comprises fewer than forty mutations (e.g. no more than 39, 35, 30, 25, 20, 19, 18, 17, 16, 15, 14, 13, 12, 11, 10, 9, 8, 7, 6, 5, 4, 3, 2 or 1 mutations). Each mutation preferably involves a single amino acid.

Each of the above-mentioned types of changes may occur alone, or in combination with the others, one or more times in a given sequence.

Ways of creating active fragments and functional equivalents are well established in the art. The polypeptide fragments and functional equivalents of the invention can for instance be identified either rationally, or via established methods of mutagenesis (see, for example, Watson, J. D. et al., "MOLECULAR BIOLOGY OF THE GENE", Fourth Edition, Benjamin/Cummings, Menlo Park, Calif., 1987).

Significantly, a random mutagenesis approach requires no a priori information about the gene sequence that is to be mutated. This approach has the advantage that it assesses the desirability of a particular mutant based on its function, and thus does not require an understanding of how or why the resultant mutant protein has adopted a particular conformation. Indeed, the random mutation of target gene sequences has been one approach used to obtain mutant proteins having desired characteristics (Leatherbarrow, R. 1986, *J. Prot. Eng.* 1: 7-16; Knowles, J. R., 1987, *Science* 236: 1252-1258; Shaw, W. V., 1987, *Biochem. J.* 246: 1-17; Gerit, J. A. 1987, *Chem. Rev.* 87: 1079-1105).

Alternatively, where a particular sequence alteration is desired, methods of site-directed mutagenesis can be employed. Thus, such methods may be used to selectively alter only those amino acids of the protein that are believed to be important (Craik, C. S., 1985, *Science* 228: 291-297; Cronin, et al., 1988, *Biochem.* 27: 4572-4579; Wilks, et al., 1988, *Science* 242: 1541-1544).

Fusion Proteins

The polypeptides of the invention may be "free-standing", i.e. not part of or fused to other amino acids or polypeptides or they may be comprised within a larger polypeptide of which they form a part or region. Hence, fusion proteins incorporating the polypeptides described above are contemplated in the present invention. Additional amino acid sequences may be fused at the N-terminus and/or the C-terminus of the polypeptides described above.

For example, it is often advantageous to include one or more additional amino acid sequences which may contain secretory or leader sequences, pro-sequences, or sequences which aid in for instance detection, expression, separation or purification of the protein or to endow the protein with additional properties as desired such as higher protein stability, for example during recombinant production. Techniques for producing fusion polypeptides are known in the art.

In some embodiments, TLG1 is expressed with a signal sequence, for example the native TLG1 signal sequence (see emboldened and underlined sequence in FIG. 9) or the *Trichoderma reesei* xylanase 2 secretion signal (XYNSEC).

In some embodiments, SFA1 is expressed with the native SFA1 signal sequence (see emboldened and underlined sequence in FIG. 11) or the *Trichoderma reesei* xylanase 2 secretion signal (XYNSEC).

In some embodiments, LKA1 is expressed with the *Trichoderma reesei* xylanase 2 secretion signal (XYNSEC) (see emboldened and underlined sequence in FIG. 10).

A fusion protein may be engineered to contain a cleavage site located between the sequence of a polypeptide of the invention and the sequence of a heterologous protein sequence so that the polypeptide may be cleaved and purified away from the heterologous protein sequence. In this context, by a "heterologous protein" and "heterologous polypeptide", we include a protein or an amino acid sequence which, in nature, is not found in association with a polypeptide of the invention.

In one embodiment, a fusion protein of the invention may be present in an active form. In other embodiments, the fusion protein may be present in an inactive form. For instance, a pro-sequence may be present which renders the protein inactive but when removed yields an active protein which retains the relevant enzymatic activity (i.e. the glucoamylase activity of SEQ ID NO.1 or the alpha-amylase activity of SEQ ID NO.3 or SEQ ID NO.2).

The activity of putative TLG1, SFA1 and LKA1 polypeptides (e.g. biological variants, active fragments, functional equivalents and fusion proteins) may be tested to verify that the relevant enzymatic activity (i.e. the glucoamylase activity of SEQ ID NO.1 or the alpha-amylase activity of SEQ ID NO.3 or SEQ ID NO.2) is retained.

In some embodiments, the TLG1 proteins (e.g. biological variants, active fragments, functional equivalents and fusion proteins) used in the present invention have at least 50%, 60%, 70%, 80%, 90%, 95% or 100% of the glucoamylase activity of the TLG1 protein as set forth in SEQ ID NO. 1 when tested under essentially the same conditions. In some preferred embodiments of the invention, the activity of the glucoamylase tested under essentially the same conditions will be at least 80%, 90%, 100%, 110%, 120%, 130%, 150% or 175% of the activity of the polypeptide as set forth in SEQ ID NO. 1. In some embodiments, the activity may be measured on a soluble starch substrate and in other embodiments the activity may be measured on a granular starch substrate (e.g. raw starch agar containing 2% corn starch, 2% peptone and 0.1% glucose).

In some embodiments, the SFA1 proteins (e.g. biological variants, active fragments, functional equivalents and fusion proteins) used in the present invention have at least 50%, 60%, 70%, 80%, 90%, 95% or 100% of the alpha-amylase activity of the SFA1 protein as set forth in SEQ ID NO. 3 when tested under essentially the same conditions. In some preferred embodiments of the invention, the activity of the alpha-amylase tested under essentially the same conditions will be at least 80%, 90%, 100%, 110%, 120%, 130%, 150% or 175% of the activity of the polypeptide as set forth in SEQ ID NO. 3. In some embodiments, the activity may be measured on a soluble starch substrate and in other embodiments the activity may be measured on a granular starch substrate (e.g. raw starch agar containing 2% corn starch, 2% peptone and 0.1% glucose).

In some embodiments, the LKA1 (e.g. biological variants, active fragments, functional equivalents and fusion proteins) proteins used in the present invention have at least 50%, 60%, 70%, 80%, 90%, 95% or 100% of the alpha-amylase activity of the LKA1 protein as set forth in SEQ ID NO. 2 when tested under essentially the same conditions. In some preferred embodiments of the invention, the activity of the alpha-amylase tested under essentially the same conditions will be at least 80%, 90%, 100%, 110%, 120%, 130%, 150% or 175% of the activity of the polypeptide as set forth in SEQ ID NO. 2. In some embodiments, the activity may be measured on a soluble starch substrate and in other embodiments the activity may be measured on a granular starch substrate (e.g. raw starch agar containing 2% corn starch, 2% peptone and 0.1% glucose).

Methods for evaluating enzymatic activity are well known in the art. Enzymatic activity may be measured in terms of U/mg, U/ml, nKat mL$^{-1}$, nanokatals per gram dry cell weight (nKat (g dw cells)$^{-1}$) or the like (U or IU is the international units used for enzyme activities; for conversion of nkat to U the conversion factor of 16.67 is used, thus 1 U=16.67 nkatals). 1 enzyme unit (U) is commonly defined as the amount of enzyme that catalyses the conversion of a given amount of substrate (typically 1 μmol or 1 nmol) per given amount of time (typically per minute). It may also be defined as the amount of enzyme that produces a given amount of product per given amount of time, or the amount of product released in the solution per unit time per ml or per g of dry cells. Where the enzyme is a glucoamylase (TLG1) the product is glucose and for alpha-amylase (LKA1 and SFA1) the product is reducing sugar. Specific activity is generally quoted as U/mg although the SI (katal kg$^{-1}$) may also be used. Specific activity is a measure of enzyme processivity and may in some embodiments be used as a measure of activity when comparing the activity of TLG1, SFA1 and LKA1 polypeptides with that of the reference polypeptide as set forth in SEQ ID NOs. 1, 3 and 2 respectively.

In some embodiments the TLG1 polypeptide (which may be a natural biological variant, an active fragment, a functional equivalent or fusion protein according to (b), (c), (d) or (e) above respectively) comprises the catalytic domain and/or the SBD of the TLG1 glucoamylase of SEQ ID NO: 1.

In some embodiments, the TLG1 polypeptide comprises a catalytic domain having at least 70%, 75%, 80%, 85%, 90%, 95%, 97%, 98% or 99% sequence identity to the catalytic domain of the TLG1 glucoamylase of SEQ ID NO: 1.

In some embodiments, the catalytic domain of the TLG1 polypeptide is a fragment of the catalytic domain of SEQ ID NO: 1. Preferably a fragment will encompass at least 60%, 70%, 80% or 90% of the amino acid residues of the catalytic domain of SEQ ID NO: 1.

In some embodiments, the TLG1 polypeptide comprises a starch binding domain having at least 70%, 75%, 80%, 85%, 90%, 95%, 97%, 98% or 99% sequence identity to the starch binding domain of the TLG1 glucoamylase of SEQ ID NO: 1.

In some embodiments, the starch binding domain of the TLG1 polypeptide is a fragment of the starch binding domain of SEQ ID NO: 1. Preferably a fragment will encompass at least 60, 70, 80 or 90 amino acid residues of the starch binding domain of SEQ ID NO: 1.

In some embodiments the SFA1 polypeptide (which may be a natural biological variant, an active fragment, a functional equivalent or fusion protein according to (b), (c), (d) or (e) above respectively) comprises the catalytic domain and/or the SBD of the SFA1 alpha-amylase of SEQ ID NO: 3.

In some embodiments, the SFA1 polypeptide comprises a catalytic domain having at least 70%, 75%, 80%, 85%, 90%, 95%, 97%, 98% or 99% sequence identity to the catalytic domain of the SFA1 alpha-amylase of SEQ ID NO: 3.

In some embodiments, the catalytic domain of the SFA1 polypeptide is a fragment of the catalytic domain of SEQ ID NO: 3. Preferably a fragment will encompass at least 60%, 70%, 80% or 90% of the amino acid residues of the catalytic domain of SEQ ID NO: 3.

In some embodiments, the SFA1 comprises a starch binding domain having at least 70%, 75%, 80%, 85%, 90%, 95%, 97%, 98% or 99% sequence identity to the starch binding domain of the SFA1 alpha-amylase of SEQ ID NO: 3.

In some embodiments, the starch binding domain of the SFA1 polypeptide is a fragment of the starch binding domain of SEQ ID NO: 3. Preferably a fragment will encompass at least 60, 70, 80 or 90 amino acid residues of the starch binding domain of SEQ ID NO: 3.

In some embodiments the LKA1 polypeptide (which may be a natural biological variant, an active fragment, a functional equivalent or fusion protein according to (b), (c), (d) or (e) above respectively) comprises the catalytic domain and/or the SBD of the LKA1 alpha-amylase of SEQ ID NO: 2.

In some embodiments, the LKA1 comprises a catalytic domain having at least 70%, 75%, 80%, 85%, 90%, 95%, 97%, 98% or 99% sequence identity to the catalytic domain of the LKA1 alpha-amylase of SEQ ID NO: 2.

In some embodiments, the catalytic domain of the LKA1 polypeptide is a fragment of the catalytic domain of SEQ ID NO: 3. Preferably a fragment will encompass at least 60%, 70%, 80% or 90% of the amino acid residues of the catalytic domain of SEQ ID NO: 2.

In some embodiments, the LKA1 comprises a starch binding domain having at least 70%, 75%, 80%, 85%, 90%, 95%, 97%, 98% or 99% sequence identity to the starch binding domain of the LKA1 alpha-amylase of SEQ ID NO: 2.

In some embodiments, the starch binding domain of the LKA1 polypeptide is a fragment of the starch binding domain of SEQ ID NO: 2. Preferably a fragment will encompass at least 60%, 70%, 80% or 90% of the amino acid residues of the starch binding domain of SEQ ID NO:2.

Techniques for introducing nucleic acid into cells so that they express a glucoamylase and alpha-amylase combination of the invention will be well known to those skilled in the art. The method of transforming a cell so that it expresses a glucoamylase and alpha-amylase combination of the invention forms a further aspect of the invention. Such cells may be used to hydrolyze raw starch.

"Transformation" describes a process by which nucleic acid (e.g. DNA or RNA) is introduced into a recipient cell. Transformation may occur under natural or artificial conditions according to various methods well known in the art, and may rely on any known method for the insertion of foreign nucleic acid sequences into a prokaryotic or eukaryotic host cell. In this way, heterologous nucleic acid may be expressed in the host cell. Reference to a transformed cell includes a reference to any descendants thereof which also comprise (and in some embodiments express) the introduced nucleic acid.

The method for transformation is selected based on the type of host cell being transformed and may include, but is not limited to, bacteriophage or viral infection, electroporation, nuclear microinjection, heat shock, lipofection, and particle bombardment, and protoplast fusion. General transformation techniques are known in the art (See, e.g., Ausubel et al Current Protocols in Molecular Biology; and Sambrook J et al. 2000. Molecular Cloning: A Laboratory Manual Cold Spring Harbor Laboratory, Cold Spring Harbor, N.Y. (Third Edition). Transformation of yeast cells is described in Sherman et al (1986) Methods In Yeast Genetics, A Laboratory Manual, Cold Spring Harbor, N.Y. See also Yamada et al (2009) which describes the creation of new yeast strains which were developed by mating two integrated haploid strains expressing the alpha-amylase or glucoamylase gene. In some embodiments, transformation may include polyploidization methods (optionally in combination with δ-integration). The combination of delta-integration and polyploidization methods may be used to obtain a significant overexpression of one or more heterologous proteins. Host cells expressing a glucoamylase and alpha-amylase combination of the invention and which are created by the mating of two different yeast with one expressing TLG1 and the other expressing SFA1 and/or LKA1 form part of the present invention.

In a preferred embodiment, there is provided a host cell of the first aspect of the invention which stably expresses at least one of TLG1, SFA1 and LKA1, and which preferably stably expresses TLG1 in combination with one or both of SFA1 and LKA1. In another embodiment, there is provided a host cell in accordance with the first aspect of the invention which only transiently expresses the inserted nucleic acid for limited periods of time. In one embodiment, by a "stably expressed protein" we include those instances where the encoding nucleic acid is capable of replication either as an autonomously replicating plasmid or as part of the host chromosome. In one embodiment, a "stably expressed protein" is still expressed after 30, 60, 90, 120 or 150 growth generations. Methods for verifying such stable expression will be known to those skilled in the art and include, for example, growth in sequential batch cultures using non-selective broths (see Cho K. M., Yoo Y. J. and Kang H. S., 1999 Enzyme and Microbial Technology, Volume 25, Number 1, 15 Jul. 1999, pp. 23-30 (8), δ-Integration of endo/exo-glucanase and β-glucosidase genes into the yeast chromosomes for direct conversion of cellulose to ethanol). After 30, 60, 90, 120 or 150 generations, protein expression is monitored and if confirmed the protein expression is considered stable.

In one embodiment, multiple copies of the heterologous genetic material (i.e. nucleic acid encoding TLG1 and SFA-1; TLG1 and LKA1; or TLG1 and SFA-1 and LKA1) are stably integrated into the host cell. An increase in the copy number of encoding sequences can be obtained by integrating at least one additional copy of the sequence into the host cell genome or by including an amplifiable selectable marker gene with the encoding polynucleotide where cells containing amplified copies of the selectable marker gene, and thereby additional copies of the polynucleotide, can be selected for by cultivating the cells in the presence of the appropriate selectable agent. The δ-integration system may find utility in the present invention and is further described in the Examples section of this specification.

In some embodiments, the glucoamylase (TLG1) and/or the alpha-amylase(s) (SFA1 and/or LKA1) is/are expressed by the host cell from nucleic acid which is codon-optimised for that host cell.

In some embodiments, the glucoamylase (TLG1) and/or the alpha-amylase(s) (SFA1 and/or LKA1) is/are expressed by the host cell from nucleic acid which has not been codon-optimised for that host cell so that the genes are the non-codon-optimised or wild-type or versions.

In some embodiments of the first aspect of the invention, the glucoamylase (TLG1) and alpha-amylase(s) (SFA1 and/or LKA1) are expressed as separate polypeptides. In other embodiments, the enzymes are expressed as bifunctional polypeptides (i.e. as TLG1 and SFA1; or TLG1 and LKA1). Where the host cell expresses TLG1, SFA1 and LKA1, then the polypeptides may be expressed as a trifunctional polypeptide, or as a bifunctional polypeptide and a separate polypeptide (e.g. SFA1 with LKA1 as bifunctional polypeptide along with TLG1 as a separate polypeptide).

In some embodiments, one or more (and preferably both/all three) of the expressed enzymes are secreted. This may involve the use of a "signal sequence" i.e. a sequence of amino acids bound to the N-terminal portion of a protein, which facilities the secretion of the mature form of a protein outside the cell. The mature form of the extracellular protein lacks the signal sequence, which is cleaved off during the secretion process. The terms "signal sequence", signal peptide", "secretion signal" and "leader peptide" and the like may be used interchangeably herein.

In some embodiments, one or more of the enzymes may be anchored on the cell wall of the host cell. Techniques to achieve secretion or anchoring of the enzymes will be well known to those skilled in the art.

In some embodiments, the host cell will be a genetically engineered host cell wherein one or more native genes have been inactivated. Gene inactivation may be accomplished by complete or partial deletion, by insertional inactivation or by any other means which renders a gene nonfunctional for its intended purpose (such that the gene is prevented from expression of a functional protein).

In some embodiments, the host cell of the first aspect of the invention is a fermentative organism, preferably one which is capable fermenting the hydrolysed starch to produce ethanol.

The host cells of the first aspect of the invention may be prokaryotic or eukaryotic cells including bacteria (gram negative and gram positive bacteria, for example *Zymomonas* sp., *Clostridium* sp., *Escherichia coli*, *Bacillus subtilis*, *S. typhimurium*, and *Serratia marcescens*), yeasts, filamentous fungi, plant cells, animal cells and insect cells. The cell of the first invention may be a cell of a higher organism such as a mammal or an insect, but is preferably a microorganism/microbial cell, e.g., a bacterial or a fungal (e.g. yeast) cell.

Where the host cell is a fungus, the fungus may be a filamentous fungus which term refers to all filamentous forms of the subdivision Eumycotina. Examples of filamentous fungi which may be used in the present invention may include, for example: *Trichoderma* sp., (e.g. *Trichoderma reesei*), *Penicillium* sp., *Humicola* sp. *Chrysosporium* sp., *Gliocladium* sp., *Aspergillus* sp. (e.g., *A. oryzae*, *A. niger*, *A. nidulans*, and *A. awamori*), *Fusarium* sp., *Neurospora* sp., *Hypocrea* sp., *Mucor*, and *Emericella* sp.

In other embodiments of the invention, the fungus is not a filamentous fungus. In one preferred embodiment of the first aspect of the invention, the microorganism is a yeast. Yeasts do not form an exact taxonomic or phylogenetic grouping but rather it is the colloquial name for single-celled members of the fungal divisions Ascomycota and Basidiomycota. The budding yeasts ("true yeasts") are classified in the order Saccharomycetales. Most reproduce asexually by budding, although a few do so by binary fission. Yeasts are unicellular, although some species with yeast forms may become multicellular through the formation of a string of connected budding cells known as pseudohyphae, or false hyphae as seen in most molds.

Exemplary yeast contemplated to be useful in the practice of the present invention are *Pichia* (Hansenula) spp. (e.g. *P. anomala*, *P. capsulate* and *P. angusta* (formerly *H. polymorpha*)), *Saccharomyces* spp. (e.g. *S. cerevisiae*, *S. italicus* and *S. rouxii*), *Yarrowia* (e.g. *Y. lipolytica*), *Kluyveromyces* spp. (e.g. *K. fragilis* and *K. lactis*), *Candida* spp. (e.g. *C. tropicales*), *Torulopsis* spp., *Torulaspora* spp., *Schizosaccharomyces* spp. (e.g. *S. pombe*), *Citeromyces* spp., *Pachysolen* spp., *Debaromyces* spp., *Metschunikowia* spp., *Rhodosporidium* spp., *Leucosporidium* spp., *Botryoascus* spp., *Sporidiobolus* spp., *Endomycopsis* spp., *Schwanniomyces* spp. (e.g. *S. occidentalis*) and the like.

In some embodiments the host cell is *S. cerevisiae*, with optionally a cell of the fourth aspect of the invention being used to express a glucoamylase and alpha-amylase combination of the invention. Thus, in some embodiments the host cell is s2 or a mutant or variant thereof which has been transformed to express a glucoamylase and alpha-amylase combination of the invention.

A second aspect of the invention is directed to a method for producing a composition comprising a glucoamylase and alpha-amylase combination of the invention (i.e. TLG1 in combination with one or both of SFA1 and LKA1), comprising culturing a host cell of the first aspect of the invention (and preferably a population of host cells of the first aspect of the invention) under suitable conditions for production of the glucoamylase and the alpha-amylase combination.

Suitable culture conditions may include liquid or solid media and may, for example, include shake flask cultivation, small scale or large scale fermentations (including continuous, batch and fed batch fermentations) in laboratory or industrial fermentors, with suitable medium containing physiological salts and nutrients.

The skilled person will be readily able to arrive at suitable nutrient conditions for the production of the glucoamylase and alpha-amylase combination of the invention. Suitable media are available from commercial suppliers or may be prepared according to published compositions (e.g., in catalogues of the American Type Culture Collection). Examples of suitable culture media may include YPD medium or selective complete medium (SC) (2% glucose and 0.17% yeast nitrogen base without amino acids). Growth factors, amino acids or other additives (e.g. antibiotics for selective pressure) may be added to such culture media as necessary. In cases where a glucoamylase or alpha-amylase coding sequence is under the control of an inducible promoter, the inducing agent (e.g., a sugar, metal salt or antimicrobial), is added to the medium at a concentration effective to induce expression. Other considerations, may comprise temperature and pH of the growth medium.

In some embodiments, the glucoamylase and alpha-amylase combination of the invention are recovered from the culture medium using techniques known in the art (e.g. separating the cells from the medium by centrifugation or filtration, precipitating proteinaceous components of the medium by means of a salt such as ammonium sulphate, followed by the use of chromatography such as ion exchange, affinity chromatography, or the like).

A third aspect of the invention provides a composition comprising a glucoamylase and alpha-amylase combination of the invention (i.e. TLG1 in combination with one or both of SFA1 and LKA1). Such a composition may be used to generate fermentable sugars from starch-containing material. This may, for example, be useful in processes for producing a fermentation product (e.g. alcohol such as ethanol) from a starch-containing material (see the fifth and sixth aspects of the invention below). In one embodiment the composition may comprise a pH buffering substance. In some embodiments the composition is a cell-free composition. In some embodiments the composition is free from other enzymes.

In a fourth aspect of the invention there is provided a strain of S. cerevisiae (herein designated as "s2") as deposited under the Budapest Treaty on the International Recognition of the Deposit of Microorganisms for the Purposes of Patent Procedure at DBVPG, Industrial Yeasts Collection, University of Perugia, Department of Applied Biology, Borgo 20 Giugno 74—06121 Perugia—Italy, under accession number 27P on 1 Apr. 2010 or a variant or mutant derived therefrom, and compositions or cultures comprising the same.

The depositor of s2 is University of Padova, Dipartimento di Biotecnologie agrarie dell' Universita' degli Studi di Padova. The address of University of Padova, Dipartimento di Biotecnologie agrarie dell'Universita' degli Studi di Padova is viale dell'Universitá 16-35020 Legnaro, Padova (Italy).

The phrase a "mutant derived from s2" is intended to be construed broadly. Thus, the term would include, for example, mutants which have been derived directly from s2 (i.e. from s2 per se and not from, say, a variant of s2) as well as mutants which have been indirectly derived from s2 (e.g. mutants which have been derived from a mutant or variant of s2, which mutant or variant has itself been derived from s2). For the avoidance of doubt, the term "s2 mutant" is used interchangeably with the phrase "mutant derived from s2".

Techniques for creating variants and mutants will be well known to those skilled in the art, e.g. exerting selective pressure for improved or new characteristics, using gene replacement techniques or classical chemical mutagenesis.

Examples of mutations which may be employed in the present invention include: the introduction of a stop codon; rearrangements; substitution mutations (e.g. missense and nonsense mutations); deletion mutations (the deletion of one or more nucleotides or the deletion of one or more codons); frame shift mutations; and insertions (the insertion or one or more nucleotides or the insertion of one or more codons). Methods for the introduction of mutations are well known in the art and can be readily accomplished by the skilled person. For example, site-directed mutagenesis which can be used to, for example, add, delete or change one or more nucleotides.

Mutations can be made to the native sequences using conventional techniques. The substrates for mutation can be an entire cluster of genes or only one or two of them; the substrate for mutation may also be portions of one or more of these genes. Techniques for mutation include preparing synthetic oligonucleotides including the mutations and inserting the mutated sequence into the gene of interest (e.g. a gene encoding a PKS or a subunit thereof etc.) using restriction endonuclease digestion. See, e.g., Kunkel, 1985, Proc. Natl. Acad. Sci. USA 82: 448; Geisselsoder et al., 1987, Biotechniques 5:786.

Alternatively, mutations can be created using a mismatched primer (generally 10-20 or 10-30 nucleotides in length) that hybridizes to the native nucleotide sequence, at a temperature below the melting temperature of the mismatched duplex. The primer can be made specific by keeping primer length and base composition within relatively narrow limits and by keeping the mutant base centrally located. See Zoller and Smith (1984), Methods Enzymol. 100:468. Primer extension is effected using DNA polymerase, the product cloned, and clones containing the mutated DNA, derived by segregation of the primer extended strand, selected. Identification can be accomplished using the mutant primer as a hybridization probe. The technique is also applicable for generating multiple point mutations. See, e.g., Dalbie-McFarland et al., 1982, Proc. Natl. Acad. Sci. USA 79: 6409.

PCR mutagenesis can also be used to effect the desired mutations. Random mutagenesis of selected portions of the nucleotide sequences encoding enzymatic activities can also be accomplished by several different techniques known in the art, e.g., by inserting an oligonucleotide linker randomly into a plasmid, by irradiation with X-rays or ultraviolet light, by incorporating incorrect nucleotides during in vitro DNA synthesis, by error-prone PCR mutagenesis, by preparing synthetic mutants, or by damaging plasmid DNA in vitro with chemicals, in accordance with the methods of the present invention.

Chemical mutagens include, for example, sodium bisulfite, nitrous acid, nitrosoguanidine, hydroxylamine, agents which damage or remove bases thereby preventing normal base-pairing such as hydrazine or formic acid, analogues of nucleotide precursors such as 5-bromouracil, 2-aminopurine, or acridine intercalating agents such as proflavine, acriflavine, quinacrine, and the like.

In some embodiments, a mutant comprises one or more (e.g. at least 1, 2, 3, 4, 5, 6, 7, 8, 9 or 10) mutated genes when compared with s2. In some embodiments, there are provided mutants which differ from s2 solely by the presence of one or more (e.g. at least 1, 2, 3, 4, 5, 6, 7, 8, 9 or 10) mutated genes, optionally in combination with one or more further genetic modifications which do not affect the phenotype of s2. Thus, in one embodiment there is provided a mutant which differs from s2 by a single mutated gene (optionally in combination with one or more further genetic modifications which do not affect the phenotype of s2). A mutated gene may carry one or more mutations (e.g. 1, 2, 3, 4, 5, 6, 7, 8, 9, 10 or more mutations) as compared with the corresponding gene in s2.

In some embodiments, there is provided a mutant or variant derived from s2 which has at 1, 2 or 3 characteristics selected from the group consisting of (i), (ii) and (iii) below:
(i) fermentative performance which is comparable or superior to s2 when measured under essentially the same conditions, wherein fermentative performance is measured in terms of ethanol yield obtained after a given period of fermentation and/or glucose remaining after a given period of fermentation;

(ii) growth rate in soluble starch which is comparable or superior to s2 when measured under essentially the same conditions; and (iii) amylolytic activity which is comparable or superior to s2 when measured under essentially the same conditions, wherein amylolytic activity is measured in terms of starch utilisation.

In some embodiments the mutant or variant possesses at least characteristic (i); in some embodiments at least characteristic (ii); and in some embodiments it possesses at least characteristic (iii).

In some embodiments, the mutant or variant possesses at least 2 characteristics selected from the above group (i.e. at least characteristics (i) and (ii); at least characteristics (i) and (iii); or at least characteristics (ii) and (iii)).

In some embodiments, the mutant or variant possesses all 3 characteristics (i), (ii) and (iii).

As discussed in Example 3, the presence of xylose may interfere with ethanol performance of the tested yeast. Accordingly, in some embodiments, fermentative performance (i.e. ethanol yield and/or glucose remaining) may be assessed in the presence of xylose (e.g. in the presence of 5% or 10% by weight xylose); in other embodiments fermentative performance may be assessed in the absence of xylose. In some embodiments, fermentative performance is assessed in the presence of xylose, and is also assessed in the absence of xylose.

In some embodiments, ethanol yield may be assayed as described for the generation of the data in Table 10, 11 or 12 (albeit with the number of replicates optionally being varied from that used to generate the data in Table 10, 11 or 12). Tables 10, 11 and 12 relate to fermentative ability on MNS medium supplemented with 20% glucose, 15% glucose and 5% xylose, 10% glucose and 10% xylose was assessed.

In relation to ethanol yield obtained after a given period of fermentation, by "comparable" we include where the ethanol yield (expressed as a % of the theoretical maximum (0.51 gg$^{-1}$ from glucose)) obtained with the mutant or variant is: (i) within ±7%, ±5%, ±3%, ±2.5%, ±2%, ±1.5% or ±1% of the ethanol yield obtained under essentially the same conditions with s2; or (ii) within ±7, ±5, ±4, ±3, ±2.5, ±2, ±1.5, ±1, ±0.5, or ±0.25 percentage points of the ethanol yield obtained under essentially the same conditions with s2. Percentage points (pp) are used herein to refer to the unit for the arithmetic difference of two percentages and are obtained by subtracting one percentage from another. Optionally, the comparison of ethanol yields is calculated to a probability level of 95% or greater (likewise, the comparison of other parameters/characteristics described herein may in some embodiments be calculated to a probability level of 95% or greater). In one embodiment, there is no statistically significant difference between the ethanol yields (P is <0.05).

In some embodiments, the glucose remaining after a given period of fermentation may be assayed as described for the generation of the data in Table 10, 11 or 12 (albeit with the number of replicates optionally being varied from that used to generate the data in Table 10, 11 or 12) where fermentative ability on MNS medium supplemented with 20% glucose, 15% glucose and 5% xylose, 10% glucose and 10% xylose was assessed.

In relation to the amount of glucose (gL$^{-1}$) remaining after a given period of fermentation, by "comparable" we refer to where the amount of glucose remaining following fermentation with the mutant or variant is: (i) within ±30%, ±20%, ±15%, ±10%, ±7%, ±5%, ±2.5%, or ±1% of the glucose remaining following fermentation with s2 under essentially the same conditions; or (ii) where the glucose remaining following fermentation with the mutant or variant does not differ by more than 3, 2.5, 2, 1.5, 1.0, 0.75, 0.5, 0.25, 0.2, or 0.1 g/L to that obtained with the s2 strain under essentially the same conditions.

Optionally, the comparison of glucose remaining is calculated to a probability level of 95% or greater. In one embodiment, there is no statistically significant difference between the amounts of glucose remaining (P is <0.05).

In some embodiments, growth rate in soluble starch may be assayed as described for the generation of the data in FIG. 32 (albeit with the number of replicates optionally being varied from that used to generate the data in FIG. 32). FIG. 32 relates to yeast growth in liquid cultures in EMM broth (20 gL-1 soluble starch).

In relation to growth rate in soluble starch, by "comparable" we include where the $OD_{600}$ value obtained with the mutant or variant is within ±25%, ±20%, ±15%, ±10%, ±7%, ±5%, ±2.5%, or ±1% of the $OD_{600}$ value obtained under essentially the same conditions with s2. The $OD_{600}$ values may be compared at, for example, 24 h, 48 h, 72 h or 96 h incubation. In one embodiment, there is no statistically significant difference between the $OD_{600}$ values (P is <0.05).

In some embodiments, amylolytic activity may be assayed as described for the generation of the data in Table (b) (albeit with the number of replicates optionally being varied from that used to generate the data in Table (b)). Table (b) relates to starch utilisation in EMM (20 gL-1 soluble starch) for 6 days at 30° C.

In relation to amylolytic activity, by "comparable" we include where starch utilised (gL$^{-1}$) by the mutant or variant is within ±25%, ±20%, ±15%, ±10%, ±7%, ±5%, ±2.5%, or ±1% of the starch utilised by s2 under essentially the same conditions. In one embodiment, there is no statistically significant difference (P<0.0.5) between the starch utilised by the mutant/variant and that by s2.

The term "variant" as used herein includes yeast which vary in one or more respects from s2. The term "variant" encompasses "mutants" but also encompasses yeast having one or more genetic modifications created by techniques/phenomena other than by mutagenesis, such as by recombinant technology.

The phrase a "variant derived from s2" is intended to be construed broadly. Thus, the term would include, for example, variants which have been derived directly from s2 (i.e. from s2 per se and not from, say, a variant or mutant of s2) as well as variants which have been indirectly derived from s2 (e.g. variants which have been derived from a mutant or variant of s2, which mutant or variant has itself been derived from s2). For the avoidance of doubt, the term "s2 variant" is used interchangeably with the phrase "variant derived from s2".

In some embodiments, the genome of s2 (or a variant or mutant thereof) may be augmented with genetic material (e.g. with one or more "control sequences" (e.g. promoters, terminators etc.)) and/or with one or more protein-encoding sequences) to create a variant. In this way, variants may be created which express one or more (e.g. at least 1, 2, 3, 4 or 5) heterologous proteins.

Where more than one heterologous protein is expressed, they may be expressed as separate polypeptides or as bifunctional polypeptides (or as multifunctional polypeptides where there are 3 or more heterologous proteins).

Signal sequences may be employed to achieve secretion of a heterologous protein. Secretion sequences include, for example, the native signal sequence of the heterologous protein and the *Trichoderma reesei* xylanase 2 secretion signal (XYNSEC).

In some embodiments, an s2 variant may have one or more genes of s2 inactivated. Gene inactivation may be accomplished by complete or partial deletion, by insertional inactivation or by any other means which renders a gene nonfunctional for its intended purpose (such that the gene is prevented from expression of a functional protein). Preferably, said inactivation of said one or more genes does not adversely affect fermentative performance, growth rate in soluble starch, or amylolytic activity. Thus, a variant which differs from s2 only by the inactivation of said one or more genes possesses comparable or superior fermentative performance, growth rate in soluble starch, and amylolytic activity to s2 when assessed as described above.

In some embodiments, there are provided s2 variants where the difference(s) between the variants and s2 (or a mutant thereof) comprise one or more (1, 2, 3, 4, 5 or 6) types of variation selected from the group consisting of:
  (i) the expression of one or more (e.g. 1, 2, 3, 4, 5 or more) heterologous proteins not expressed by s2;
  (ii) over or under expression of one or more (e.g. 1, 2, 3, 4, 5 or more) proteins;
  (iii) the expression of one or more (e.g. 1, 2, 3, 4, 5 or more) variant proteins, wherein the variant protein differs in at least one respect from its s2 counterpart beyond its amino acid sequence (e.g. in terms of its stability, activity etc.);
  (iv) alterations in one or more (e.g. 1, 2, 3, 4, 5 or more) non-coding regions of the genome of s2 (e.g. the modification of control sequences);
  (v) the inactivation of one or more genes (e.g. 1, 2, 3, 4, 5 or more genes); and
  (vi) one or more genetic modifications which do not affect the phenotype of s2 (e.g. phenotypically silent amino acid substitutions, alterations to non-functional regions of the genome etc).

Each of (i), (ii), (iii), (iv), (v) and (vi) represents a different type of variation. Thus, for instance a variant which comprises one type of variation may comprise variation type (i), in which case it expresses one or more heterologous proteins not expressed by s2. Each of these types of variation may occur alone, or in combination with one or more of the others.

Variation types (i) to (iii) and (v) bring about changes in phenotype. In some embodiments, variations of type (iv) bring about changes in phenotype. In other embodiments, variations of type (iv) do not bring about changes in phenotype. Variations of type (vi) are phenotypically silent.

In some embodiments, there are provided s2 variants wherein the difference(s) between the variants and s2 (or a mutant thereof) consist(s) of 1, 2, 3, 4, 5 or 6 types of variation selected from the list above. In some embodiments, there are provided s2 variants wherein the difference(s) between the variants and s2 (or a mutant thereof) consist(s) of variations selected from: variation types (i), (v) and (vi); variation types (i) and (vi); variation types (v) and (vi).

In terms of creating s2 variants, suitable techniques will be known to those skilled in the art (see also, for example, the discussion above of transformation in the context of the "first aspect" of the invention—this discussion applies mutatis mutandis to the fourth aspect of the invention). Thus, in some embodiments variants may be created through transformation of s2 or a mutant or variant thereof. Transformation may, for example, be used to create variants which express one or more (e.g. 1, 2, 3, 4, 5 or more) heterologous proteins which are not expressed by the deposited s2 strain. Transformation may include the combination of δ-integration and polyploidization methods in order to obtain high expression levels of one or more (e.g. 1, 2, 3, 4, 5 or more) heterologous proteins which are not expressed by the deposited s2 strain.

Examples of heterologous proteins which may be desirably expressed in a variant of the invention include amylolytic enzymes, which may optionally be capable of hydrolyzing raw starch. The amylolytic enzymes are preferably selected from the group consisting of alpha-amylases and glucoamylases. Preferably, the resulting variant expresses one or more (e.g. 1, 2, 3 or more) heterologous alpha-amylases and/or one or more (e.g. 1, 2, 3 or more) heterologous glucoamylases.

Thus, in some embodiments there is provided an s2 variant which expresses one or more heterologous alpha-amylases; preferably at least one (or all) of the one or more heterologous alpha-amylases is capable of hydrolyzing raw starch. Preferably at least one (or all) of the one or more alpha-amylases is expressed from a nucleic acid sequence which has been codon-optimised for expression by *S. cerevisiae*. Alternatively, at least one (or all) of the one or more alpha-amylases is expressed from a nucleic acid sequence which has not been codon-optimised for expression by *S. cerevisiae* (so that the gene(s) are the wild-type (non-codon-optimised) versions).

Similarly, an embodiment of the invention is also provided where an s2 variant expresses one or more heterologous glucoamylases; preferably at least one (or all) of the one or more glucoamylases is capable of hydrolyzing raw starch. Preferably at least one (or all) of the one or more glucoamylases is expressed from a nucleic acid sequence which has been codon-optimised for expression by *S. cerevisiae*. Alternatively, at least one (or all) of the one or more glucoamylases is expressed from a nucleic acid sequence which has not been codon-optimised for expression by *S. cerevisiae* (so that the gene(s) are the wild-type (non-codon-optimised) versions).

In some embodiments there are provided variants which express one, two or all three of: TLG1, SFA1 and LKA1 (in this regard see the first aspect of the invention). Thus, in one embodiment, an s2 variant expresses TLG1 and SFA1. In another embodiment, an s2 variant expresses TLG1 and LKA1. In another embodiment, an s2 variant expresses TLG1, SFA1 and LKA1. In some embodiments, the glucoamylase (TLG1) and alpha-amylase(s) (SFA1 and LKA1) are expressed as separate polypeptides. In an alternative embodiment, the enzymes are expressed as bifunctional polypeptides (i.e. as TLG1 and SFA1; or TLG1 and LKA1). Where TLG1, SFA1 and LKA1 are expressed, then the polypeptides may be expressed as a trifunctional polypeptide. In another embodiment, SFA1 and LKA1 could be expressed as a bifunctional polypeptide, and TLG1 as a separate polypeptide. In some embodiments, there are provided s2 variants where the difference(s) between the variant and s2 (or a mutant thereof) consist(s) of the expression of one, two or all three of: TLG1, SFA1 and LKA1 (e.g. TLG1 and SFA1, or TLG1 and LKA1), optionally in combination with: (i) one or more phenotypically silent variations; and/or (ii) one or more inactivated genes (e.g. 1, 2, 3, 4, 5 or more genes).

Other alpha-amylases which may be usefully expressed by a variant of the invention include, for example, fungal alpha-amylases or bacterial alpha-amylases. Examples of alpha-amylases include the following proteins and variants thereof: alpha-amylases from *Aspergillus* spp. (e.g. *A. kawachi*, *A. niger*, *A. awamori* (e.g. AMYL III), *A. oryzae*, alpha-amylases from *Bacillus* spp. (e.g. *B. stearothermophilus*, *B. amyloliquefaciens*, *B. subtilis*, *B. licheniformis*), alpha-amylases from *Lipomyces* spp. (e.g. *L. kononenkoae* (e.g. LKA2)), α-amylases from *Streptococcus* spp. (e.g. *S. bovis*) and alpha-amylases from *Saccharomyces* sp. (e.g. from *S. fibuligera* (e.g. SFA1). Chemically modified or protein engineered variants of the foregoing alpha-amylases may be used (see e.g.

above discussion of active fragments, functional equivalents and fusion proteins which applies here mutatis mutandis). In some embodiments, there are provided s2 variants where the difference(s) between the variant and s2 (or a mutant thereof) consist(s) of the expression of one, two or all three of: TLG1, SFA1 and LKA1 (e.g. TLG1 and SFA1, or TLG1 and LKA1), optionally in combination with: (i) one or more phenotypically silent variations; and/or (ii) one or more inactivated genes (e.g. 1, 2, 3, 4, 5 or more genes).

Other glucoamylases which may be usefully expressed by a variant of the invention include, for example, the following proteins and variants thereof: glucoamylases from *Aspergillus* spp. (e.g. *A. niger, A. awamori* (e.g. GA I), *A. kawachi, A. oryzae* (e.g. GLAA)), glucoamylases from *Rhizopus* spp. (e.g. *R. Oryzae* (e.g. GLAR), glucoamylases from *Humicola* spp. (e.g. *Humicola grisea* (e.g. GLA1), glucoamylases from *Talaromyces* spp. (e.g. *T. emersonii*), glucoamylases *Athelia* spp. (e.g. *A. rolfsii*) and glucoamylases from *Saccharomyces* sps. (e.g. *S. fibuligera* (e.g. SFG1 or GLU1) and *S. diastaticus*). Chemically modified or protein engineered variants of the foregoing glucoamylases may be used (see e.g. above discussion of active fragments, functional equivalents and fusion proteins which applies here mutatis mutandis).

In one embodiment there is provided an s2 variant which does not express a *R. oryzae* glucoamylase and/or does not express an alpha-amylase from *S. bovis*.

In one embodiment, there is provided an s2 variant which expresses the glucoamylase GA I polypeptide from *A. awamori* and/or the AMYLIII alpha-amylase polypeptide from *A. awamori*. The sgaI (sgaI refers to the synthetic (codon-optimised) version of the gene) and samylIII (sgaI refers to the synthetic (codon-optimised) version of the gene) nucleic acid and the corresponding protein sequences are provided in FIGS. 4 and 5 respectively. The skilled person will appreciate that active fragments, functional equivalents and fusion polypeptides of the GA I and AMYLIII polypeptide sequences may be made using techniques known in the art (see discussion above in relation to the first aspect of the invention regarding active fragments, functional equivalents and fusion proteins which applies here mutatis mutandis) and, as such these active fragments, functional equivalents and fusion proteins may be usefully expressed by s2 variants so that they exhibit glucoamylase and/or alpha-amylase activity.

In some embodiments, at least one of (and preferably all of) the one or more heterologous protein(s) expressed by the s2 variant are stably expressed. In other embodiments, the one or more heterologous proteins are only transiently expressed for limited periods of time.

In one embodiment, multiple copies of the genetic material encoding the one or more heterologous proteins may be stably integrated into s2 (or a mutant or variant thereof). An increase in the copy number of encoding sequences can be obtained by integrating at least one additional copy of the sequence into the host cell genome or by including an amplifiable selectable marker gene with the encoding polynucleotide where cells containing amplified copies of the selectable marker gene, and thereby additional copies of the polynucleotide, can be selected for by cultivating the cells in the presence of the appropriate selectable agent. The δ-integration system may also find utility in the present invention and is further described in the Examples section of this specification.

In one embodiment of the fourth aspect of the invention, there is provided a biologically pure culture of s2 or a mutant or variant derived therefrom (or a combination of the foregoing). By "a biologically pure culture" we include a culture which is substantially free of other organisms.

A fifth aspect of the invention relates to a process for producing a fermentation product, e.g. alcohol, from a starch-containing material using TLG1 in combination with one or both of SFA1 and LKA1.

A sixth aspect of the invention relates to a process for producing a fermentation product, e.g. alcohol, using s2 or a variant or mutant derived therefrom. Preferably, the fermentation product is produced from a starch-containing material.

By a "starch-containing material" any suitable starch-containing starting material, including granular or soluble starch, may be used. In some embodiments, the starch-containing material may comprise xylan. Examples of "starch-containing" material include plant-based substrates (which may be fractionated plant material, for example a cereal grain such as corn, which is fractionated into components such as fiber, germ, protein and starch (endosperm)), tubers, roots, stems, whole grains, corms, cobs, tall grasses, wheat, barley, rye, milo, sago, tapioca, rice peas, beans, arrow root, cassava, sweet potatoes, cereals, sugar-containing raw materials (e.g. molasses, fruit materials, sugar cane or sugar beet), potatoes, cellulose-containing materials (e.g. wood, wood residues, lignocelluloses, plant residues), wastes from agriculture (e.g. corn stover, rice straw, cereal, bran, damaged cereals, damaged potatoes, potato peel), non-cellulosic feed stocks such as sorghum, municipal waste (e.g. newspaper, waste paper), manure biomass, and agricultural residues etc. Furthermore, the starch-containing material may be used with or without pre-treatment. Accordingly, the starch may be used in its unmodified state or pre-treated such as with chemicals, or physical factors such as temperatures or enzymes.

The fermentation product produced in accordance with the fifth or sixth aspect of the invention may include, for example: alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); enzymes; and vitamins (e.g., riboflavin, B12, beta-carotene). Preferred fermentation processes include alcohol fermentation processes and anaerobic fermentation processes, as are well known in the art.

In one embodiment, the processes of the fifth and sixth aspect of the invention may comprise the following steps:
 (i) conversion of starch in the starch-containing material to yield fermentable sugars, which are then
 (ii) fermented (e.g. to alcohol) by a fermenting organism.

The starch in step (i) may optionally be raw, cooked starch, or starch contained in agricultural wastes-residues (i.e., cereal bran, damaged cereals, damaged potatoes, potato peel), or may be any other type of starch-containing material such as those listed above.

In the fifth aspect of the invention, step (i) may comprise the following steps: (a) liquification of the starch using SFA1 and/or LKA1; and (b) saccharification of the liquefied material obtained in step (a) using TLG1. One or more further enzymes may optionally be used in steps (i)(a) and/or step (i)(b).

The SFA1/LKA1 and the TLG1 may be provided in the reaction mix by various means, e.g. by one or more of the following means: (i) including a host cell of the first aspect of the invention in the reaction mix under conditions which are suitable for the expression of the enzymes; (ii) the use of exogenously added enzyme (an "exogenously added enzyme" being used to indicate that the enzyme per se is added to the reaction mix, as opposed to adding to the reaction mix a cell which expresses the enzyme); and (iii) including in the reaction mix a host cell which expresses only one of the aforesaid enzymes (i.e. TLG1, SFA1 or LKA1) or which expresses both SFA1 and LKA1 (but not TLG1).

Where, option (iii), is used multiple (i.e. 2 or more) different types of host cell may optionally be used so that 1, 2 or 3 of the SFA1, LKA1 and TLG1 enzymes are provided to the reaction mix. Accordingly, in some embodiments a host cell which expresses TLG1 is used and a host cell which expresses SFA1 and/or LKA1 is also used. Likewise, three different types of host cell may be used where each host cell expresses one of: SFA1, LKA1 and TLG1. It will be appreciated that the host cell(s) used in option (iii) is/are distinct from the host cells of the first aspect of the invention since those of the first aspect of the invention express TLG1 in combination with one or both of SFA1 and LKA1.

Combinations of the means (i), (ii) and (iii) may be used to provide the SFA1/LKA1 and the TLG1. (i), (ii) and (iii) may be used in combination with each other with different enzymes being provided in the reaction mix by different means and/or by one or more of the enzymes being provided in the reaction mix by more than one means (e.g. one or more enzymes may be provided by means (i) and (ii), (i) and (iii), (ii) and (iii) or by all three means).

Thus, in some embodiments the TLG1 and SFA1 is provided partly or wholly by including a host cell of the first aspect of the invention in the reaction mix under conditions which are suitable for the expression of both the TLG1 and SFA1. Similarly, TLG1 and LKA1 may be provided partly or wholly by including a host cell of the first aspect of the invention in the reaction mix under conditions which are suitable for the expression of both the TLG1 and LKA1. Where the combination of the invention used is TLG1 and SFA1 and LKA1 then all three of the enzymes may be partly or wholly provided by including a host cell of the first aspect of the invention in the reaction mix under conditions which are suitable for the expression of the TLG1, SFA1 and LKA1. Alternatively, where the combination of the invention used is TLG1 and SFA1 and LKA1, the SFA1 or the LKA1 (but not both in this embodiment) may be provided by some other means (e.g. means (ii) and/or (iii)). Where the host cell of the first aspect of the invention is a fermenting organism, it may also be used to ferment the sugars to produce a fermentation product such as ethanol (step (ii) above).

In some embodiments, the TLG1 is provided partly or wholly by the exogenous addition of the enzyme to the reaction mix. If SFA1 is used (in addition to, or as an alternative to LKA1), then the SFA1 may also be provided partly or wholly by the exogenous addition of the enzyme to the reaction mix, or it may be provided by including in the reaction mix a host cell which expresses SFA1, which host cell is distinct from a host cell of the first aspect of the invention. Similarly, if LKA1 is used (in addition to, or as an alternative to SFA1), then the LKA1 may also be provided partly or wholly by the exogenous addition of the enzyme to the reaction mix, or it may be provided by including in the reaction mix a host cell which expresses LKA1, which host cell is distinct from a host cell of the first aspect of the invention. The host cell expressing the SFA1 may be the same host cell or a different host cell to that expressing the LKA1. Where two or more enzymes are exogenously added to the reaction mix, the enzymes may be added simultaneously (e.g. as a single composition containing the two or more enzymes or as separate enzyme compositions) or sequentially.

In some embodiments, the TLG1 is provided partly or wholly by including in the reaction mix a host cell which expresses TLG1, which host cell is distinct from a host cell of the first aspect of the invention. If SFA1 is used (in addition to, or as an alternative to LKA1), then the SFA1 may be provided partly or wholly by the exogenous addition of the enzyme to the reaction mix or it may be provided by including in the reaction mix a further host cell which expresses SFA1, which second host cell is distinct from a host cell of the first aspect of the invention. Similarly, if LKA1 is used (in addition to, or as an alternative to SFA1), then the LKA1 may be provided partly or wholly by the exogenous addition of the enzyme to the reaction mix, or it may be provided by including in the reaction mix a host cell which expresses LKA1, which host cell is distinct from a host cell of the first aspect of the invention (i.e. it does not also express TLG1). The host cell expressing the LKA1 may be the same or a different host cell to that expressing the SFA1. Where a host cell is used which has fermentative ability then the host cell may be used in step (ii) to ferment the fermentable sugars.

With regard to the creation and characteristics of host cells which may be used in means (iii) above for providing SFA1/LKA1 and TLG1 in the reaction mix, the reader is directed to the discussion of the first aspect of the invention. With the notable exception that the host cells of the first aspect of the invention express TLG1 in combination with one or both of SFA1 and LKA1, the discussion of the host cells of the first aspect of the invention applies mutatis mutandis to the host cells which may be used as the source of the SFA1 and/or LKA1 or as the source of the TLG1 (but not TLG1 in combination with one or both of SFA1 and LKA1). Thus, for instance, the discussion on transformation of the host cells of the first aspect of the invention and the discussion on which types of cell may serve as a host cell (e.g. cells with fermentative ability, fungal cells, yeast cells such as *S. cerevisiae* etc.) applies here mutatis mutandis.

In some embodiments of the fifth aspect of the invention, in addition to SFA1 and/or LKA1 being used in the liquification of the starch, one or more further enzymes may be used to liquefy the starch, for instance one or more additional alpha-amylases may be used. Alternatively, the SFA1 and/or LKA1 may be used as the sole source of alpha-amylase activity used in the liquification of the starch.

In some embodiments of the fifth aspect of the invention, in addition to TLG1 being used to saccharify the liquefied material, one or more further enzymes may be used to saccharify the liquefied starch, for instance one or more additional glucoamylases may be used. Alternatively, the TLG1 may be used as the sole source of glucoamylase activity used in the saccharification of the liquefied starch.

As discussed below (see Example 3), s2 is a strain of *S. cerevisiae* which exhibits promising industrial fermentative traits. Thus, in the sixth aspect of the invention the fermentation step (step (ii) above) of the process comprises fermentation of the fermentable sugars by a cell of the fourth aspect of the invention. Thus, in some embodiments s2 is used. Likewise an s2 variant or an s2 mutant can be used. In one embodiment, one or more of s2 mutants and/or one or more variants can be used in the fermentation step, optionally in combination with s2.

In one embodiment, one or more further fermenting organisms (which is not s2 or a variant or mutant thereof) may additionally be used to ferment the sugars (e.g. in a sequential or concurrent manner). However, in another embodiment, no such further organisms are used to ferment the sugars. Accordingly, in one embodiment the only fermenting organisms used in the fermentation step are selected from the group consisting of: s2, s2 variants and s2 mutants.

When an s2 variant expresses a heterologous amylolytic enzyme (e.g. a heterologous amylolytic enzyme with raw starch hydrolyzing ability), then the variant may be used in step (i), i.e. in the conversion of the starch to yield fermentable sugars. In one embodiment of the sixth aspect of the invention, step (i) may comprise the following steps: (a) liquification of the starch, preferably in the presence of an alpha-amylase; and (b) saccharification of the liquefied material, preferably in the presence of a glucoamylase.

The variant may be used in step (i)(a) (starch liquification) and/or in step (i)(b) saccharification of the liquefied material. In one embodiment, an s2 variant which expresses one or more heterologous alpha-amylases (e.g. one or more alpha-amylases selected from the group consisting of: SFA1, LKA1 and the *A. awamori* AMYLIII) is used in step (i)(a) to liquefy the starch and/or an s2 variant which expresses one or more heterologous glucoamylases (e.g. TLG1 and/or GA I from *A. awamori*) is used in step (i)(b) to saccharify the liquefied material. The s2 variant used in step (i)(a) can be the same or different s2 variant as used in step (i)(b) (i.e. an s2 variant can be used in steps (i)(a) and (i)(b) where the variant expresses both a heterologous alpha-amylase and a heterologous glucoamylase, or 2 different variants could be used where e.g. one expresses a heterologous alpha-amylase, and the other expresses a heterologous glucoamylase). The s2 variant(s) used in step (a) can also be used in fermentation step (b), where optionally one or more further cells (i.e. one or more further cell types) can also be used to ferment the sugars (which one or more further cells may be selected from the group consisting of: s2, other s2 variants, s2 mutants and cells which are not s2, s2 variants or s2 mutants). In some embodiments, the s2 variant(s) used in step (a) are the only fermentative organisms to ferment the sugars in step (b).

In addition to, or as an alternative to, amylolytic activity being provided by an s2 variant, it will be appreciated that amylolytic enzymes may be provided from other sources: e.g. from the inclusion of one or more other cells in the reaction mix which express one or more enzymes with amylolytic activity and/or from the exogenous addition of one or more amylolytic enzymes to the reaction mix. Thus, for instance, alpha-amylase may be provided to the reaction mix by the inclusion of one or more other cells which express one or more alpha-amylases and/or by the exogenous addition of one or more alpha-amylase enzymes. Similarly, glucoamylase may be provided to the reaction mix by the inclusion of one or more other cells which express one or glucoamylases and/or by the exogenous addition of one or more glucoamylase enzymes. Examples of suitable alpha-amylases and glucoamylases will be known to those skilled in the art (see also the section above in relation to examples of alpha-amylases and glucoamylases which may be expressed by s2 (or a variant or mutant thereof) in the context of the fourth aspect of the invention: such alpha-amylases and glucoamylases may also be useful in the process of the sixth aspect of the invention and may, for example, be provided to the reaction mix by their exogenous addition or by the addition of one or more cells which expresses one or more of the enzyme). As mentioned above, a raw starch hydrolyzing (RSH) enzyme cocktail, Stargen 001 (Genencor) has been developed, which converts starch into dextrins at low temperatures (<48° C.) and hydrolyses dextrins into sugars during SSF. The cocktail contains an acid-stable alpha-amylase from *Aspergillus kawachi* and glucoamylase from *Aspergillus niger*. Such a preparation could be used in the sixth aspect of the invention to provide amylolytic activity in step (i)(a) and/or in step (i)(b). Likewise, Broin and Novozymes have also collaborated to produce the BPX (Broin project X) enzymes to hydrolyse raw starch in a non-cooking fermentation scenario (Berven, 2005). Thus, in some embodiments exogenously added enzyme and/or one or more cells other than an s2 variant is used in step (i)(a) and/or in step (i)(b) to provide amylolytic activity for the conversion of the starch to yield fermentable sugars. This may be particularly useful where s2 is used since the deposited s2 strain has not been transformed to express a heterologous alpha-amylase or glucoamylase.

In the process of the fifth and sixth aspect of the invention, step (i) is optionally preceded by the step of reducing the particle size of the starch-containing material. Reduction of particle size preferably occurs by milling. Wet milling or dry milling may be used, both processes being well known in the art. The milled material may then mixed with liquid to form a slurry of starch-containing material.

In some embodiments the slurry may be heated to above the gelatinization temperature of the starch and alpha-amylase may be added to liquefy the starch-containing material. Jet-cooking may be used to further gelatinize the slurry. After the starch-containing material has been liquefied using a combination of heat and liquefying enzymes (e.g. alpha-amylases) the mixture is cooled down and further treated with saccharifying enzymes, such as glucoamylases, to produce fermentable sugars. In other embodiments, the cooking step or exposure of the starch containing substrate to temperatures above the gelatinization temperate of the starch in the substrate may be eliminated, e.g. when one or more amylolytic enzymes (e.g. alpha-amylases, glucoamylases) are used in the process which are capable of hydrolysing raw starch to produce fermentable sugars. Therefore in some embodiments of the fifth and sixth aspects of the invention a fermentation product is produced from starch-containing material without gelatinization of the starch-containing material.

In the process of the fifth and sixth aspects of the invention, the saccharification in step (b) may be carried out using conditions well know in the art. Steps (i)(b) and (ii) of the processes of the fifth and sixth aspects of the invention may be carried out sequentially or simultaneously. Thus, in one embodiment the saccharification step and fermentation step are combined, therefore carrying out saccharification and fermentation simultaneously (SSF). In one embodiment, the liquification step can also be carried out simultaneously with the saccharification step and optionally also simultaneously with the fermentation step so that the liquification, saccharification and fermentation steps are performed simultaneously. This can be achieved by lowering the temperature when liquefying the starch to match that of saccharification and fermentation.

In the fifth aspect of the invention, the fermenting organism in step (ii) is preferably an alcohol (e.g. ethanol) producing microorganism. Methods of alcohol fermentations are described in the Alcohol textbook, a reference for the beverage, fuel and industrial alcohol industries, 3rd ed., eds K. A. Jacques et al., 1999, Nottingham University Press, UK. In some embodiments, the fermenting organism is a fungal cell, for instance a yeast cell, such as a yeast cell belonging to the *Saccharomyces* genus (e.g. *S. cerevisiae*). In one embodiment, the fermenting organism is the host cell of the first aspect of the invention (optionally supplemented by one or more further fermenting organisms which may be used in a sequential or concurrent manner). In another embodiment, the host cell of the first aspect of the invention is not used in the fermenting step and a different cell is used so that a consortium of two or more different cells/microorganisms is used, with the host cell of the first aspect of the invention being used in step (i) and then a further cell being used in fermentation step (ii).

Following fermentation, the fermentation product (e.g. alcohol) may optionally be recovered. Where alcohol is the fermentation product, then it may be recovered by, for example, distillation. Optionally, it may then be concentrated and/or further processed to render it more suitable/ready for its intended use. In one embodiment, the alcohol is ethanol. The ethanol may be used as, e.g., fuel ethanol, drinking ethanol, or as industrial ethanol.

Co-products of the processes of the fifth and sixth aspects of the invention may also be obtained. Examples of co-products may include distillers' grains (e.g. distillers dried grain (DDG) and Distillers Dried Grains with Solubles (DDGS)), germ, gluten meal, fiber, corn oil, and high protein animal feed. Moreover the biomass remaining after ethanol production could be used to produce biodiesel, and/or synthetic biofuels from products of thermochemical conversions and/or to generate heat. Thus, the processes of the fifth and sixth aspect of the invention may comprise recovering a coproduct from the fermentation process. Thus, the present invention further relates to generating biodiesel, biofuel, heat and/or carbon dioxide from the biomass remaining after ethanol production.

A seventh aspect of the invention provides a product obtainable or obtained by a process of the second, fifth or sixth aspects of the invention.

rotating wheel in Terrific Broth or on Luria-Bertani agar (Sambrook et al., 1989). Ampicillin for selection of resistant bacteria was added to a final concentration of 100 μg ml$^{-1}$. Fungal strains were cultivated at 30° C. on a rotary shaker set at 100 rpm. *Aspergillus* strains were cultivated in maltodextrin medium (5% maltodextrin, 0.6% NaNO$_3$, 0.15% KH$_2$PO$_4$, 0.05% MgSO$_4$, 0.05% KCl, and trace elements). The fungal strains were maintained at 30° C. on minimal medium (1% glucose, 0.6% NaNO$_3$, 0.2% neopeptone, 0.15% KH$_2$PO$_4$, 0.1% yeast extract, 0.1% casamino acids, 0.05% MgSO$_4$, 0.05% KCl, 2% agar and trace elements). *S. cerevisiae* strains were cultivated in either YPD medium (1% yeast extract, 2% peptone, and 2% glucose) or selective complete medium (SC) (2% glucose, and 0.17% yeast nitrogen base without amino acids) with additional growth factors and amino acids as necessary (without uracil (SC$^{-ura}$) or leucine (SC$^{-leu}$)) at 30° C. on a rotary shaker set at 100 rpm unless otherwise stated.

TABLE 1

Summary of plasmids and strains used in this Example

| Plasmids | Relevant genotype | Source or Reference |
|---|---|---|
| pDRIVE | bla | QIAGEN |
| pAZ1 | bla URA3 ENO1$_P$-XYN2-ENO1$_T$ | This laboratory |
| pBS-XYNSEC | bla XYNSEC | (Den Haan et al., 2007) |
| yXYNSEC | bla URA3 PGK1$_{PT}$ | (van Rooyen et al., 2005) |
| ySFI | bla URA3 PGK1$_P$-BGL1-PGK$_T$ | (van Rooyen et al., 2005) |
| *E. coli* XL1-Blue | MRF' endA1 supE44 thi-1 recA1 gyrA96 relA1 lac[F'proAB lacq ZΔM15 Tn10(tet)] | Stratagene |
| *S. cerevisiae* Y294 | α leu2-3, 112 ura3-52 his3 trp1-289 | ATCC 201160 |
| *A. awamori* | Wild type strain | CBS 115.52 |
| *A. oryzae* var. *oryzae* | Wild type strain | CBS 819.72 |

EXAMPLES

Example 1

Materials and Methods

Strains and Media

All chemicals, media components and supplements were of analytical grade standard. The genotypes and sources of the plasmids, yeast and bacterial strains used in the experiments are summarised in Table 1. Recombinant plasmids were constructed and amplified in *Escherichia coli* XL1-Blue. The bacterial strains were cultivated at 37° C. on a DNA Manipulations Standard protocols were followed for DNA manipulation (Sambrook et al., 1989). Restriction endonucleases and T4 DNA polymerase was supplied by either Roche or Fermentas. DNA fragments were eluted from agarose gels using phenol (Benson, 1984).

PCR Amplification

Sequence specific primers were designed for the *Trichoderma reesei* xylanase 2 secretion signal (XYNSEC) (xynsec-L, xynsec-R2), *A. oryzae* glucoamylase (glaA) (Aoryglu-left, Aoryglu-right), *A. awamori* α-amylase (amyl III) (Aawaamy-left, Aawaamy-right), and *A. awamori* glucoamylase (GA I) (Aawagluc-L, Aawagluc-R) (Table 2). The primers were designed to exclude the native signal peptides of the amylase genes. The PCR reaction was as follows: 200 ng template, 100 pmol of each primer, 0.2 mM each of deoxynucleoside triphosphate, reaction buffer supplied by the manufacturer, and TaKaRa Ex Taq™ (Takara Bio Inc.). *A. oryzae* and *A. awamori* total RNA was isolated after cultivation in maltodextrin medium (Plüddemann and van Zyl, 2003). mRNA was isolated from total RNA using the Fast Track mRNA isolation kit (Invitrogen). A first strand cDNA mix was amplified from the mRNA and used as template for the amylase gene sequence PCR.

TABLE 2

Summary of primers. Gene origin and Genbank accession numbers are listed.

| Gene (Genbank) | Organism | PCR primer sequence |
|---|---|---|
| XYNSEC (QM6a) | T. reesei | Xynsec-L: 5'-CTGAATTCAGGCCTCAACATGGTCTCCTTCACC-3'<br>Xynsec-R2: 5'-AGATCTTTTAAATACGTATCGCGAGCGCTTCTCCACAGCC-3' |
| glaA (D10698) | A. oryzae | Aoryglu-left: 5'-GATATCTACGTACAACCTGTCCTTAGACAGG-3'<br>Aoryglu-right: 5'-TCGCGACTCGAGTTACCGCCAAACATCGC-3' |
| GA I (AB083161) | A. awamori | Aawagluc-L: 5'-AGGCCTTACGTAACCTTGGATTCGTGGTTG-3'<br>Aawagluc-R: 5'-AAGCTTCTCGAGTTACCGCCAGGTGTCAGT-3'<br>Syngluc-L: 5'-CCCATCTGGTGACTTGTCT-3'<br>Syngluc-R: 5'-ACCGGTGGTAGTAGCAGTAG-3' |
| amyl III (AB083160) | A. awamori | Aawaamy-left: 5'-AGGCCTTACGTACTGTCAGCTGCAGAATGG-3'<br>Aawaamy-right: 5'-GGATCCAGATCTTTACCTCCACGTATCAACCA-3'<br>Synalpha-L: 5'-GCTGAATGGAGAACTCAATC-3'<br>Synalpha-R: 5'-TAGAGGTGGCAGTACAGGAG-3' |
| FUR1 | S. cerevisiae | FUR1-left: 5'-ATTTCTTCTTGAACCATGAAC-3'<br>FUR1-right: 5'-CTTAATCAAGACTTCTGTAGCC-3' |
| ENO1 | S. cerevisiae | ENO1-L: 5'-GGATCCACTAGTCTTCTAGGCGGGTTATC-3'<br>ENO1-R: 5'-AAGCTTGCGGCCGCAAAGAGGTTTAGACATTGG-3' |
| PGK1 | S. cerevisiae | PGKbeginprom: 5'-ACTGAAGCTTGGATCCTTAAAGATGCCG-3'<br>PGKendterm: 5'-ACTGAAGCTTGGCCAAGCTTTAACGAAC-3'<br>PGK1-left: 5'-CGGGATCCTTAAAGATGCCGATTTGG-3'<br>PGK1-right: 5'-CGGAATTCTATTTGTTGTAAAAAGTAGATAATTAC-3' |

Restriction enzyme sites are underlined

Construction of Plasmids for Secretion of Glucoamylase and Alpha-Amylase

Figure 3:
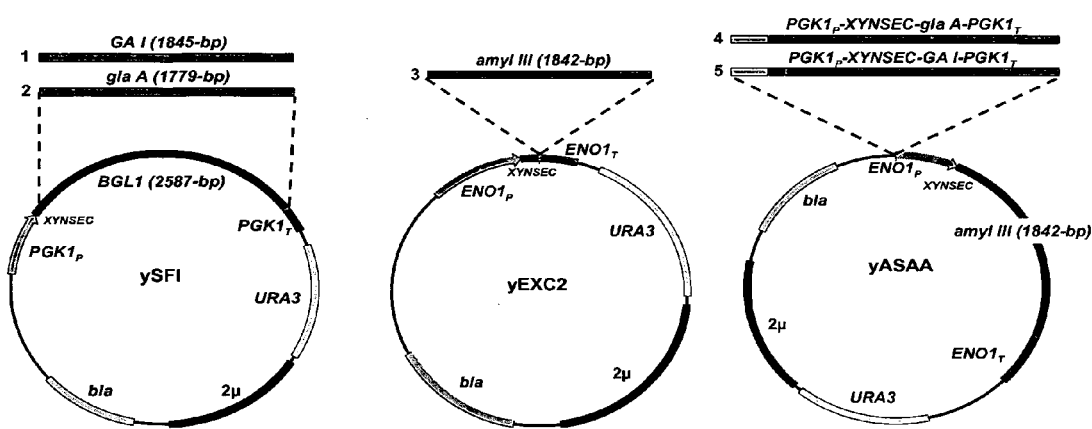

The 132-bp PCR amplified XYNSEC sequence fragment (amplified using the pBS-XYNSEC plasmid as template) was ligated into the commercial pDRIVE plasmid, and designated pDxynsec5. The yeast expression plasmid, designated yEXC2 was constructed as follows: the pAZ1 EcoRI-BglII T. reesei xyn2 fragment was replaced with the EcoRI-BglII XYNSEC fragment from pDxynsec5 (FIG. 3). Glucoamylase and alpha-amylase gene sequence fragments obtained by PCR were cloned into commercial plasmid pDRIVE. Sequences were verified as described elsewhere.

The gene fragments were sub-cloned into yeast expression plasmids as follows. The NruI-XhoI β-glucosidase (BGL1) fragment of ySFI (FIG. 3) was replaced with either the SnaBI-XhoI glaA fragment from pDOgluc13, or the StuI-XhoI GA I fragment from pDawagluc1. The resulting plasmids were designated yASOG and yASAG, respectively. The EcoRI-XhoI XYNSEC-GA I fragment of yASAG was replaced with the synthetic codon optimised EcoRI-XhoI sXYNSEC-sGA I fragment to yield plasmid ySYAG. The SnaBI-XhoI amyl III fragment from pDAawa2alpha was ligated in frame with the XYNSEC in yEXC2 (plasmid digested with NruI and XhoI), resulting in plasmid yASAA. The EcoRI-XhoI XYNSEC-amyl III fragment of yASAA was replaced with the synthetic codon optimised EcoRI-XhoI sXYNSEC-samyl III fragment to yield plasmid ySYAA. The PGK1$_P$-XYNSEC-glaA-PGK1$_T$ construct was removed from yASOG with KpnI and HindIII. The recessed 3' HindIII site was filled with Klenow fragment and the construct then sub-cloned into yASAA (plasmid digested with KpnI and BamHI, recessed 3' BamHI site filled with Klenow fragment) to generate plasmid yOGAA. The PGK1$_P$-XYNSEC-GA I-PGK1$_T$ cassette was removed from yASAG by digesting with HindIII and filling the recessed 3' terminus with Klenow fragment, followed by a partial digestion with KpnI to release the cassette from the plasmid. The cassette was then subcloned into yASAA (plasmid digested with KpnI and BamHI, recessed 3' BamHI site filled with Klenow fragment) to generate plasmid yAGAA. In a similar way, the codon optimised PGK1$_P$-sXYNSEC-sGA I-PGK1$_T$ cassette was inserted into ySYAA to yield ySYAGAA. Also, the EcoRI-XhoI XYNSEC-GA I fragment of yASAG was inserted into ySYAA to yield, yASAGSYAA.

Design of Codon Optimised Synthetic Gene Sequences

Sequences of the A. awamori GA I from plasmid yASAG and A. awamori amyl III from yASAA were used as template for design of sequences using only codons, which are favoured by S. cerevisiae (Sharp and Cowe, 1991). The codon adaptation index (CAI) for the wild type GA I and amyl III genes when expressed in S. cerevisiae was calculated as 0.115 and 0.132 respectively (Sharp and Li, 1987). A codon optimised version of the T. reesei XYNSEC was designed and used as secretion signal. All endonuclease restriction sites used frequently for cloning procedures in our laboratory were removed from within the designed genes (BamHI, BglII, EcoRI, EcoRV, HindIII, KpnI, NruI, SacI, SpeI, StuI and XhoI), and specific sites necessary for cloning purposes attached to the 5'- (StuI and EcoRI) and 3'-ends (XhoI and BglII) of the sequence. The designed sequences were used as template to synthetically produce the optimised genes (GenScript Corporation).

DNA Sequencing

The nucleotide sequences and open reading frames of the amylase fragments were determined with the dideoxy chain termination method using fluorescently labelled nucleotides on an ABI PRISM™ 3100 Genetic analyser. Sequence fragments were assembled manually in a word processing program. Sequence data was analysed with the PC based BLAST program (www.ncbi.nih.gov/BLAST) and protein sequences and restriction sites predicted and identified with the DNAMAN (version 4.1) software package (Lynnon Biosoft). Primer sequences are listed in Table 2.

Yeast Transformation

*S. cerevisiae* Y294 was transformed with the individual recombinant yeast expression plasmids using the dimethyl sulfoxide-lithium acetate method (Hill et al., 1991). Transformants were confirmed to be *S. cerevisiae* strains with PCR using PGK1, ENO1 or FUR1 sequence specific primers (Table 2). The presence of amylase genes in transformants was confirmed with PCR using gene specific primers (Table 2). Disruption of the uracil phosphoribosyltransferase (FUR1) gene in the *S. cerevisiae* transformants containing episomal plasmids was performed to ensure autoselection of the URA3-bearing expression plasmids in non-selective medium (Kern et al., 1990). Autoselective transformants (fur1::LEU2) were screened for on selection agar deficient in uracil and leucine (SC$^{ura-leu}$) and confirmed by PCR (Table 2).

Enzyme Assays

Raw starch hydrolysis by transformants was tested on raw starch agar (2% raw corn starch (Sigma), 2% peptone, and 0.1% glucose). Yeast cells were spotted onto the agar and incubated at 30° C. for 4 days. Afterwards the plates were stained with an iodine solution (3% KI, 0.3% iodine) to visualise clear hydrolysis zones.

Supernatant harvested from cultures cultivated in 250 ml baffled Erlenmeyer flasks containing 100 ml YPD medium for 3 days served as amylase source for liquid assays and was concentrated twenty times by freeze-drying. All buffers used in determining enzyme activity had a pH of 5.4 unless otherwise mentioned; as it was previously determined the yeast laboratory strain used preferred fermentation at pH 5.4-5.5 and 30° C.

Total amylase activity on soluble starch was determined in liquid assays using the DNS method (Miller, 1959). The substrate used was 0.1% soluble potato starch in citrate-phosphate buffer. Sodium azide (NaN$_3$) was added to a final concentration of 0.02% to inhibit microbial growth. The hydrolysing reaction was carried out at 30° C. for 30 minutes and the reducing glucose units produced were expressed as nanokatals per gram dry weight biomass (nkat (g DW cells)$^-$$^1$), which is defined as the enzyme activity needed to produce 1 nmol of glucose equivalents per second under the given assay conditions.

Amylase activity on raw starch was determined using a modified version of the DNS method. The substrate used was 2% raw corn starch in citrate-phosphate buffer. NaN$_3$ (0.02%) was added to inhibit microbial growth. The hydrolysing reaction was carried out at 30° C. for 90 minutes. The reaction was terminated after addition of DNS reagent and boiled for 15 minutes. The cooled reaction solution was centrifuged at 5000 rpm for 5 minutes to remove the retrograded starch gel. The reducing glucose units produced were expressed as nkat (g DW cells)$^{-1}$.

Optimum temperature for raw starch hydrolysis by glucoamylase on raw starch at pH 5.4 was determined using an adapted protocol (De Mot and Verachtert, 1985). One hundred micro liters of enzyme preparation (enzyme diluted in citrate-phosphate buffer with 20 mM CaCl$_2$) was incubated with 2% raw corn starch in 0.5 ml citrate-phosphate buffer at temperatures 30, 40, 50, 60, and 65° C. for 60 minutes. NaN$_3$ (0.02%) was added to inhibit microbial growth. The hydrolysis reaction was terminated by boiling in a water bath for 5 minutes. Glucose in a cooled sample was determined using the peroxidase-glucose oxidase method from a glucose assay kit (Sigma). One glucoamylase unit of activity (U) is defined as the amount of enzyme producing 1 µmol of glucose per minute under the specified conditions.

Alpha-Amylase activity was determined using the Red Starch assay from Megazyme. Activity was expressed as Cer-alpha Units per gram dry weight biomass (CU (g DW cells)$^-$$_1$). The optimum temperature for alpha-amylase hydrolysis at pH 5.4 was determined by applying the enzyme to the red starch substrate at temperatures 30, 40, 50, 60, and 70° C. The preferred pH for α-amylase hydrolysis at 30° C. was also determined by diluting enzyme in buffers with pH 4.0, 4.5, 5.0, 5.5, and 6.0.

To determine the specific activity of the GA I, an extracellular protein fraction of recombinant *A. awamori* glucoamylase was purified from a 4 day old YPD culture (3 liters) inoculated with Y294[yASAG]. The culture was centrifuged and filtered. The supernatant was concentrated ten-fold in the Diaflo Ultrafilter (Amicon). Recombinant glucoamylase supernatant (50 ml) was bound to 30% (w/v) raw corn starch by stirring for 18 hours, and recovered via centrifugation (10 minutes, 13,000 rpm). The glucoamylase was removed from the starch by stirring in 50 ml 1% (v/v) triethylamine, and subsequent centrifugation (10 minutes, 13,000 rpm). The supernatant was concentrated to 5 ml in the Diaflo Ultrafilter PM10 concentrator and dialysed with citrate-phosphate buffer (pH 4.0). The entire process was performed at 4-8° C.

Kinetic parameters were determined for the purified recombinant GA I. Up to 4 different raw starch (1, 2, 5, and 10% K$_m$) and maltose concentrations (0.2, 0.6, 1.0 and 1.5 mM K$_m$) were used for rate hydrolysis. Glucose liberated as a result of hydrolysis of the substrate by the enzyme over time was determined using the peroxidase-glucose oxidase method from a glucose assay kit (Sigma).

Electrophoresis and Zymogram Analysis

Recombinant enzymes were characterised by running the protein fractions on 7.5% acrylamide gels (7.5% acrylamide, 1.5 mM Tris (pH 8.8), 10% SDS, 10% ammonium persulfate and Temed) with 0.1% soluble starch for SDS-PAGE and overlay Zymogram analysis. The 5% stacking gel contained 30% acrylamide, 1.5 mM Tris (pH 6.8), 10% SDS, 10% ammonium persulfate and Temed. Loading buffer contained 60 mM Tris-HCL (pH 6.8), 25% glycerol, 2% SDS, 14 mM β-mercaptoethanol, and 0.1% bromophenol blue. The proteins were either left untreated (no boiling), denatured by boiling for 10 minutes, or de-N-glycosylated with PNGaseF (Biolabs Inc.) and then loaded onto the gels. SDS-PAGE was carried out at 4° C. and 150V for 90 minutes in Tris-glycine buffer (25 mM Tris, 250 mM glycine, 0.1% SDS). Gels were washed with citrate-phosphate buffer (pH 4.5) for 30 minutes at room temperature with gentle agitation to remove SDS. Gels were stained with Coomassie Brilliant Blue R250 in methanol, and de-stained with 10% acetic acid. For overlay gels, the de-stained gels were stained with an iodine solution (3% KI, 0.3% iodine) for 5 minutes.

Anaerobic Cultivation

Recombinant amylolytic yeast strains were cultivated in raw starch medium (RSYP) (2% raw corn starch (Sigma), 0.67% yeast nitrogen base (Difco) with amino acids, 2% peptone, and 0.05% glucose), soluble starch medium and glucose medium where the equivalent amount of raw starch was replaced with either soluble starch or glucose. The raw starch was sterilised with ethanol and dried at 30° C. overnight before adding to autoclaved medium. To prevent flocculation of yeast, 1 mM Aspirin (Sigma) was added to the raw starch before ethanol sterilisation (Strauss, 2005). Streptomycin (0.5 g l$^{-1}$) was added to prevent bacterial contamination under non-sterile raw starch conditions. Pre-cultures of Y294 [yxynsec] and Y294[yAGAA] grown to stationary phase in YPD medium were used as inoculum. Cells were washed with a salt solution (0.9% NaCl) to prevent medium and enzyme carry-over.

The inoculum of 10% v/v (±0.3 g l$^{-1}$) was inoculated in quadruplicate experiments using 120 ml glass serum bottles sealed with rubber stoppers containing 100 ml medium supplemented with 0.01 g l$^{-1}$ ergosterol and 0.42 g l$^{-1}$ Tween 80 (Yu et al., 1995). The contents of the serum bottles were mixed on a magnetic stirrer at 30° C. Samples were taken through a capped syringe needle pierced through the bottle stopper. Samples were periodically taken and yeast cells in the media were counted in duplicate on a haemocytometer for raw starch and soluble starch fermentations. The OD$_{600}$ was determined for cells grown in glucose.

Analytical Methods

Aerobic growth on glucose (YPD medium) was measured in triplicate in shake flask cultures as absorbance at OD$_{600}$. A calibration chart was prepared to correlate dry weights (DWs) with optical densities at OD$_{600}$ as well as cell counts determined using a haemocytometer. DWs were determined from 10 ml culture samples. Cells were collected on glass filters after filtration, washed several times with deionised sterile water, and dried in a microwave to constant weight (approximately 15 minutes. at 30% power).

Residual fermentable sugars present during anaerobic cultivations were determined in duplicate for each culture with the phenol-sulphuric method using glucose to create a linear standard (Dubois et al., 1956). Maltose, glycerol, acetate and ethanol concentrations were determined by high performance liquid chromatography (HPLC), with a Waters 717injector (Milford) and Agilent 1100 pump (PaloAlto). The compounds were separated on an Aminex HPX-87H column (Bio-Rad) at a column temperature of 45° C. with 5 mM H$_2$SO4 as mobile phase at a flow rate of 0.6 ml minute$^{-1}$ and subsequently detected with a Waters 410 refractive index detector.

Calculations

Maximum specific growth rates were calculated at specific time points on a growth curve in YPD and glucose medium as In OD$_{600}$ versus time (h$^{-1}$). In soluble starch and RSYP medium the g DW cells ml$^{-1}$ was converted to In OD$_{600}$ versus time (h$^{-1}$). A minimum of four adjacent points was used to calculate the value at a particular point on the curve during exponential growth phase.

Results

Plasmid and Amylolytic Yeast Strain Generation

*A. awamori* and *A. oryzae* were cultivated in maltodextrin medium, mRNA isolated and used for first strand cDNA synthesis. The glaA gene of *A. oryzae*, GA I gene of *A. awamori*, and amyl III gene of *A. awamori* were amplified by PCR from the cDNA and cloned into commercial plasmid pDRIVE before sub-cloning into yeast expression plasmids (FIG. 3). The glucoamylase and alpha-amylase genes were inserted in frame with the XYNSEC secretion signal for constitutive expression under the transcriptional control of the *S. cerevisiae* PGK1 and ENO1 promoters and terminators respectively. The resulting recombinant plasmids were transformed into *S. cerevisiae* Y294 (Table 3). A reference strain was constructed by transforming *S. cerevisiae* Y294 with a plasmid containing the PGK1 promoter and terminator, as well as the *T. reesei* secretion signal, but without an amylolytic gene. The strains constructed to harbour episomal plasmids were uracil (Ura$^+$) prototrophic. Genomic DNA isolated from the transformants served as template for PCR to confirm the presence of recombinant genes (data not shown). Autoselective strains were generated by FUR1 disruption and confirmed by PCR (data not shown).

TABLE 3

Summary of recombinant strains generated in this study

| Strains | Genotype | Strain designation | Amylase/s secreted |
|---|---|---|---|
| Y294 [fur1::LEU2 yXYNSEC] | bla URA3 PGK1$_{PT}$ | Y294[yXYNSEC] | none |
| Y294[fur1::LEU2 yASOG] | bla URA3 PGK1$_P$-XYNSEC-glaA-PGK1$_T$ | Y294[yASOG] | GLAA |
| Y294[fur1::LEU2 yASAG] | bla URA3 PGK1$_P$-XYNSEC-GA I-PGK1$_T$ | Y294[yASAG] | GA I |
| Y294[fur1::LEU2 yASAA] | bla URA3 ENO1$_P$-XYNSEC-amyl III-ENO1$_T$ | Y294[yASAA] | AMYL III |
| Y294[fur1::LEU2 yOGAA] | bla URA3 PGK1$_P$-XYNSEC-glaA-PGK1$_T$ ENO1$_P$-XYNSEC-amyl III-ENO1$_T$ | Y294[yOGAA] | GLAA and AMYL III |
| Y294[fur1::LEU2 yAGAA] | bla URA3 PGK1$_P$-XYNSEC-GA I-PGK1$_T$ ENO1$_P$-XYNSEC-amyl III-ENO1$_T$ | Y294[yAGAA] | GA I and AMYL III |
| Y294[fur1::LEU2 ySYAG] | bla URA3 PGK1$_P$-sXYNSEC-GA I-PGK1$_T$ | Y294[ySYAG] | sGA I |
| Y294[fur1::LEU2 ySYAA] | bla URA3 ENO1$_P$-sXYNSEC-amyl III-ENO1$_T$ | Y294[ySYAA] | sAMYL III |
| Y294 [fur1::LEU2 ySYAGAA] | bla URA3 PGK1$_P$-sXYNSEC-GA I-PGK1$_T$ ENO1$_P$-sXYNSEC-amyl III-ENO1$_T$ | Y294[ySYAGAA] | sGA I and sAMYL III |
| Y294 [fur1::LEU2 yASAGSYAA] | bla URA3 PGK1$_P$-XYNSEC-GA I-PGK1$_T$ ENO1$_P$-sXYNSEC-amyl III-ENO1$_T$ | Y294[yASAGSYAA] | GA I and sAMYL III |

Sequence Analysis

Figure 1:
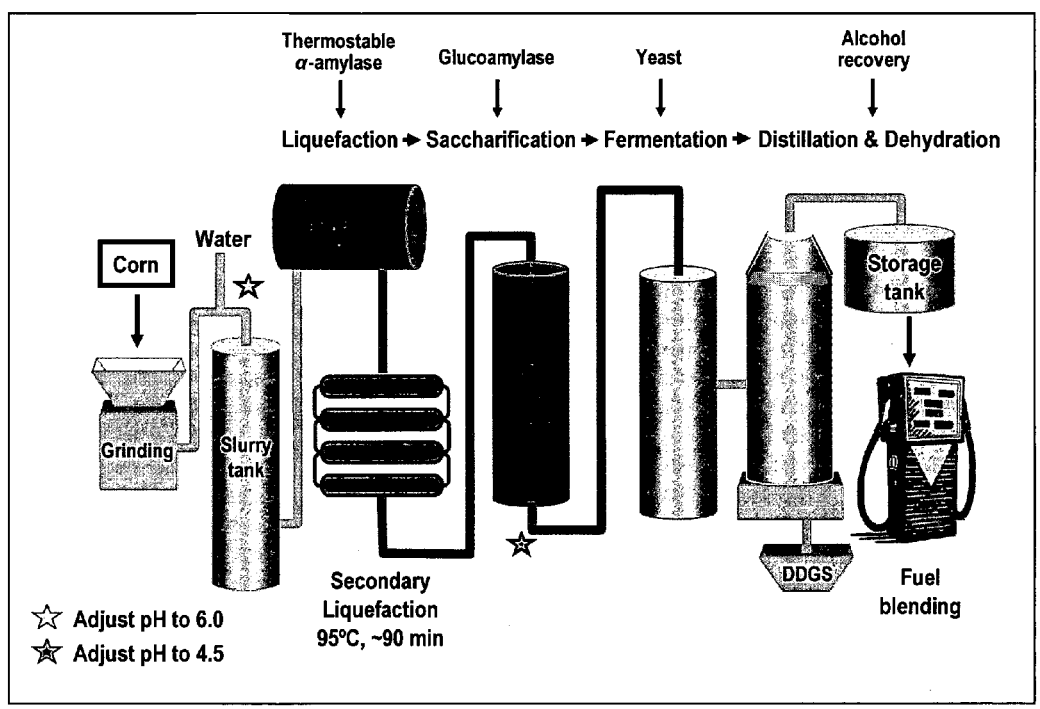
FIG. 1 shows conventional ethanol production process using corn as feedstock. Adapted from http://www.genencor.com/cms/resources/file/ebf95c076d3afc7/STARGEN%20Backgrounder.pdf.
Figure 2:
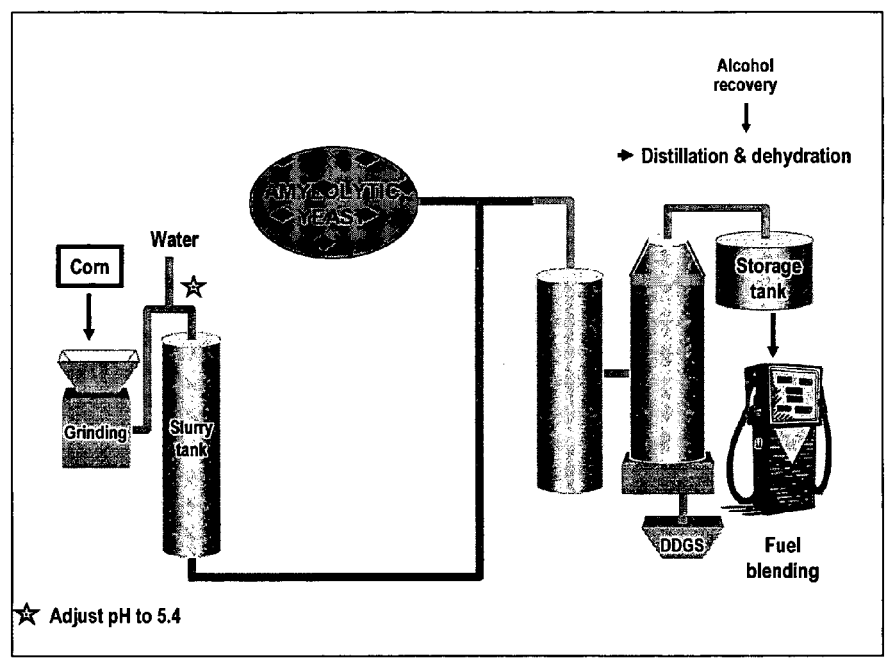
FIG. 2 Modification of the conventional ethanol production from corn. Amylolytic yeast is introduced to liquefy, saccharify and ferment raw starch to ethanol in a one-step process. Adapted from http://www.genencor.com/cms/resources/file/ebf95c076d3afc7/STARGEN%20Backgrounder.pdf FIG. 3 A schematic summary of the plasmids used to generate amylase expression cassettes in Example 1. The BGL1 gene from ySFI was replaced with *A. awamori* GA I (1) or *A. oryzae* glaA (2) in frame with XYNSEC. *A. awamori* amyl III (3) was inserted in frame with XYNSEC in yEXC2. The *A. oryzae* glaA (4) or *A. awamori* GA I (5) PGK1 promoter and terminator cassettes were inserted into yASAA. The synthetic codon optimised constructs were made similarly. The *S. cerevisiae* 2 micron autonomous replicating sequence (ARS2) is responsible for episomal replication of the plasmid and the bacterial β-lactamase (bla), and *S. cerevisiae* orotidine-5'-phosphate decarboxylase (URA3) are used as selectable markers.

Open reading frames for all the amylolytic genes were confirmed with sequencing. Furthermore predicted protein sequences were analysed for previously reported conserved regions and specific amino acids with specific functions in the genes (FIGS. 4 and 5). The sGA I protein sequence conformed to all sites (FIG. 2), including the minimal sequence identified around the Trp-597 (Trp-562 in mature protein (MP)) found to be essential for hydrolysis of raw starch (PLWYVTVTLPA) (Goto et al., 1994). The second conserved Trp-624 (Trp-590 in MP) residue involved in tighter binding and preparing the substrate for catalysis was also identified (Sorimachi et al., 1997). General acid and base catalysts Glu-213 (Glu-179 in MP) and Glu-434 (Glu-400 in MP) (Frandsen et al., 1994; Harris et al., 1993) as well as the Tyr-85, Trp-87, Arg-89, Asp-90, Trp-154, Glu-214, Arg-339, Asp-343, and Trp-351 residues which play a role in substrate transition-state stabilisation and or ground-state binding were conserved (Fierobe et al., 1996; Frandsen et al., 1995). The Gp-I region which is heavily O-glycosylated and TS rich was also identified. The glycosylation is responsible for enzyme stability en enhanced activity on raw starch (Goto et al., 1995; Goto et al., 1999). The Gp-I region is crucial for correct folding of the enzyme (Goto et al., 2004).

The sequence identified in glucoamylases essential for raw starch hydrolysis was also present in the sAMYL III, although not perfectly conserved (PEWSVTVSLPV versus PLWYVTVTLPA) (FIG. 5). The second conserved Trp was also present. Furthermore the TS rich region which promotes raw starch hydrolysis was also identified (Fukuda et al., 1992; Hayashida et al., 1989). The alpha-amylases have considerably low sequence similarity, although four amino acids are invariant (Hasegawa et al., 1999; Matsuura et al., 1980; Matsuura et al., 1984; Nakamura et al., 1992; Swift et al., 1991; Vihinen et al., 1990). These are the Arg-242 (Arg-204 in MP) and the three catalytic residues; Asp-244 (Asp-206 in MP), Glu-268 (Glu-230 in MP), and Asp-335 (Asp-297 in MP) (MP numbering of TAKA amylase sequence from A. oryzae). A further two invariant residues namely the H-160 and H-334 form the basis of conserved regions in the protein. These residues were also conserved in the AMYL III.

Recombinant Amylase Production and Characterisation

Figure 6:
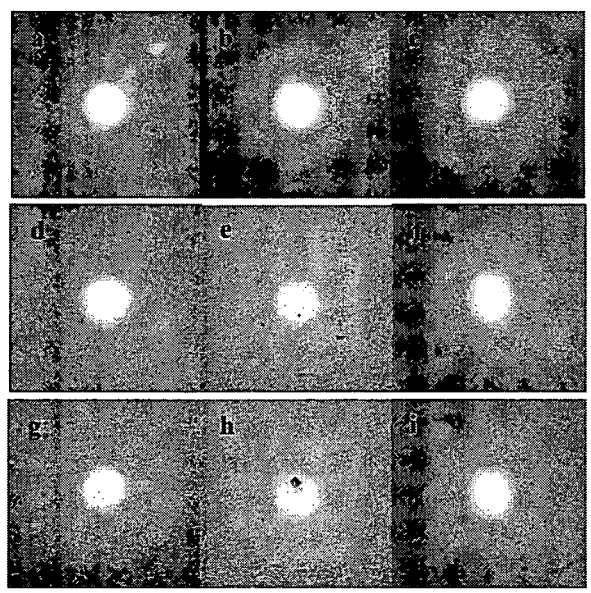
FIG. 6 Raw starch hydrolysis appears as clear zones around colonies secreting functional amylases. Strain (a) and (d) Y294[yxynsec] (reference strain), (b) Y294[yASOG] secreting GLAA, (c) Y294[yASAG] secreting GA I, (e) Y294[ySYAG] secreting sGA I, (f) Y294[OGAA] secreting GLAA and AMYL III, (g) Y294[yAGAA] secreting GA I and AMYL III, (h) Y294[ySYAGAA] secreting sGA I and sAMYL III, and (i) Y294[yASAGSYAA] secreting GA I and sAMYL III were grown for 4 days on agar containing raw starch and then stained with an iodine solution.
Figure 7:
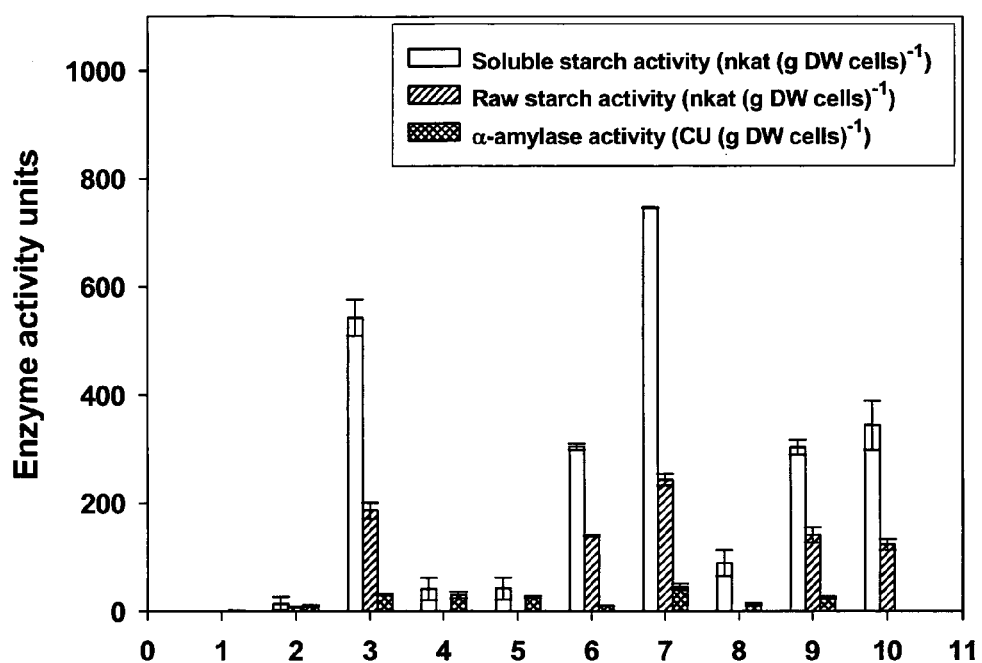
FIG. 7 Total amylase activity expressed as nkat g DW cells$^{-1}$ and alpha-amylase activity expressed as CU g DW cells$^{-1}$ for concentrated enzyme cocktails produced by the reference strain (1) Y294[yxynsec] and recombinant amylolytic yeast strains (2) Y294[yASOG], (3) Y294[yASAG], (4) Y294[yASAA], (5) Y294[yOGAA], (6) Y294[yAGAA], (7) Y294[ySYAG], (8) Y294[ySYAA], (9) Y294[ySYAGAA], and (10) Y294[yASAGSYAA]. Soluble and raw starch hydrolysing activity was determined at 30° C. and pH 5.4, and alpha-amylase activity at 50° C. and pH 5.4.

The ability of the amylolytic strains to produce functional amylases was visualised as cleared hydrolysis zones or halos in raw starch agar stained with iodine (FIG. 6). Amylolytic activity was confirmed in liquid assays. Raw starch and soluble starch activity was determined at the pH (pH 5.4) and temperature (30° C.) preferred by yeast during cultivation (FIG. 7). The Y294[yASAG] and Y294[ySYAG] strains secreting GA I and sGA I respectively produced the highest soluble as well as raw starch hydrolysing activity (186.4 nkat (g DW cells)$^{-1}$ (±14.98) and 243.6 nkat (g DW cells)$^{-1}$ (±10.70)) The cocktails containing GA I and AMYL III or sGA I and sAMYL III secreted by Y294[yAGAA] and Y294 [ySYAGAA] respectively, displayed very similar raw starch hydrolysing activities (139.66 nkat (g DW cells)$^{-1}$ (±1.27) and 141.42 nkat (g DW cells)$^{-1}$ (±13.85) respectively).

All alpha-amylase activity levels were very low compared to the amount of glucoamylase activity produced per gram DW cells. The strain secreting AMYL III (y294[yASAA]) produced more alpha-amylase activity per gram DW cells (30.1 CU (g DW cells)$^{-1}$ (±5.77)) than the Y294[ySYAA] strain secreting the optimised sAMYL III (13.1 CU (g DW cells)$^{-1}$ (±1.85)). The GA I and sGA I cocktails produced by Y294[yASAG] and Y294[ySYAG] respectively, showed alpha-amylase activity which was comparable to or higher than the level of alpha-amylase activity of the AMYL III cocktail secreted by Y294[yASAA].

The optimum temperature at pH 5.4 for raw starch activity was determined for the following enzyme cocktails; GA I secreted by Y294[yASAG], AMYL III secreted by Y294 [yASAA], GA I and AMYL III secreted by Y294[yAGAA], and sGA I and sAMYL III secreted by Y294[ySYAGAA] (Table 4). An optimum pH of 4.5 was measured at 30° C. for the AMYL III secreted by Y294[yASAA]. All the enzyme cocktails tested were stable at 30° C. and pH 5.4 for 52 hours as they retained more than 99% activity under these conditions.

TABLE 4

Summary of enzyme cocktail temperature preferences

| Strain | Enzymes | Temp.$^a$ at pH 5.4 |
| --- | --- | --- |
| Y294[yASAG] | GA I | 60 |
| Y294[yASAA] | AMYL III | 50 |
| Y294[yAGAA] | GA I and AMYL III | 40 |
| Y294[ySYAGAA] | sGA I and sAMYL III | 40 |

$^a$Optimum temperature at pH 5.4

The recombinant GA I was purified applying the adsorption characteristic of the enzyme, as the SBD will adhere to the starch granule. Kinetic parameters were determined and results are summarised in Table 5. The affinity for maltose was two-fold higher than for raw starch, and maximum specific activity towards raw starch was five-fold higher than for maltose.

TABLE 5

Kinetic parameters of GA I

| $K_m$ | $V_{max}$ | pH | Temperature | Reference |
| --- | --- | --- | --- | --- |
| $^a$3.574 µg ml$^{-1}$ | 11.603 | 4.0 | 50° C. | This study |
| $^b$1.648 mM | 2.410 | 4.0 | 50° C. | This study |
| $^b$1.82 mM | NR | 4.5 | 45° C. | (Fierobe et al., 1997) |
| $^b$1.09 mM | NR | 4.5 | 35° C. | (Allen et al., 1998) |

$^a$Raw corn starch substrate
$^b$Maltose substrate
NR Not reported

Characterisation of protein species by SDS-PAGE gel electrophoresis indicated that the GA I and AMYL III proteins were both hyper-glycosylated by the yeast and displayed broad protein species of 135-150 kDa (Chen et al., 1995; Jacks et al., 1995; Kovaleva et al., 1989; Romanos et al., 1992) (data not shown). After de-glycosylation the protein species were approximately 115 kDa. The size of the glucoamylase protein species was comparable to previous published data (Table 6). De-glycosylation was performed using an enzyme which removes only N-glycosylation. The difference in fragment size was therefore not substantial on an SDS-PAGE gel, as the proteins might contain O-glycosylation as well (Chen et al., 1995). Overlay Zymogram analysis indicated that both GA I and AMYL III were active and showed clear hydrolysis zones after iodine staining (data not shown).

TABLE 6

Summary of glucoamylase and alpha-amylase protein species secreted by native and *S. cerevisiae* hosts.

| Enzyme | Host | Mol mass (kDa) | Reference |
|---|---|---|---|
| *A. awamori* var. *kawachi* glucoamylase | *S. cerevisiae* | 120 | (Goto et al., 1997) |
| *A. awamori* glucoamylase | *S. cerevisiae* | 82[a] (66[b]) | (Khan et al., 2000) |
| *A. awamori* glucoamylase | *S. cerevisiae* | 84[a] | (Fierobe et al., 1997) |
| *A. awamori* glucoamylase | *S. cerevisiae* | 120 (115[c]) | (Chen et al., 1995) |
| *A. awamori* glucoamylase | *S. cerevisiae* | 120 (115[c]) | (Chen et al., 1994) |
| *A. awamori* α-amylase III | *A. awamori* | 90 | (Matsubara et al., 2004b) |
| *A. awamori* α-amylase III | *A. awamori* | 67[b] | (Matsubara et al., 2004b) |

[a]Determined by mass spectrometry
[b]Carbohydrate free MW in kDa
[c]De-N-glycosylated MW in kDa

Growth Kinetics of Amylolytic Strains Grown on Raw Starch, Soluble Starch and Glucose The anaerobic maximum specific growth rate of Y294[yAGAA] on raw starch (0.003 $h^{-1}$) was almost 30-fold lower than on soluble starch (0.085 $h^{-1}$). The anaerobic maximum specific growth rate of Y294[yAGAA] on glucose (0.248 $h^{-1}$) gave an indication of the expected growth rate when all the starch is converted to glucose for fermentation in a non-limiting step. The maximum specific growth rates for all the engineered strains determined during aerobic cultivation on glucose (YPD medium) in shake flasks ranged between 0.365-0.386 $h^{-1}$ and all strains reached an $OD_{600}$ of 6.2-7.1, which corresponded to 3.2-3.7 g $l^{-1}$ DW cells.

Figure 8:
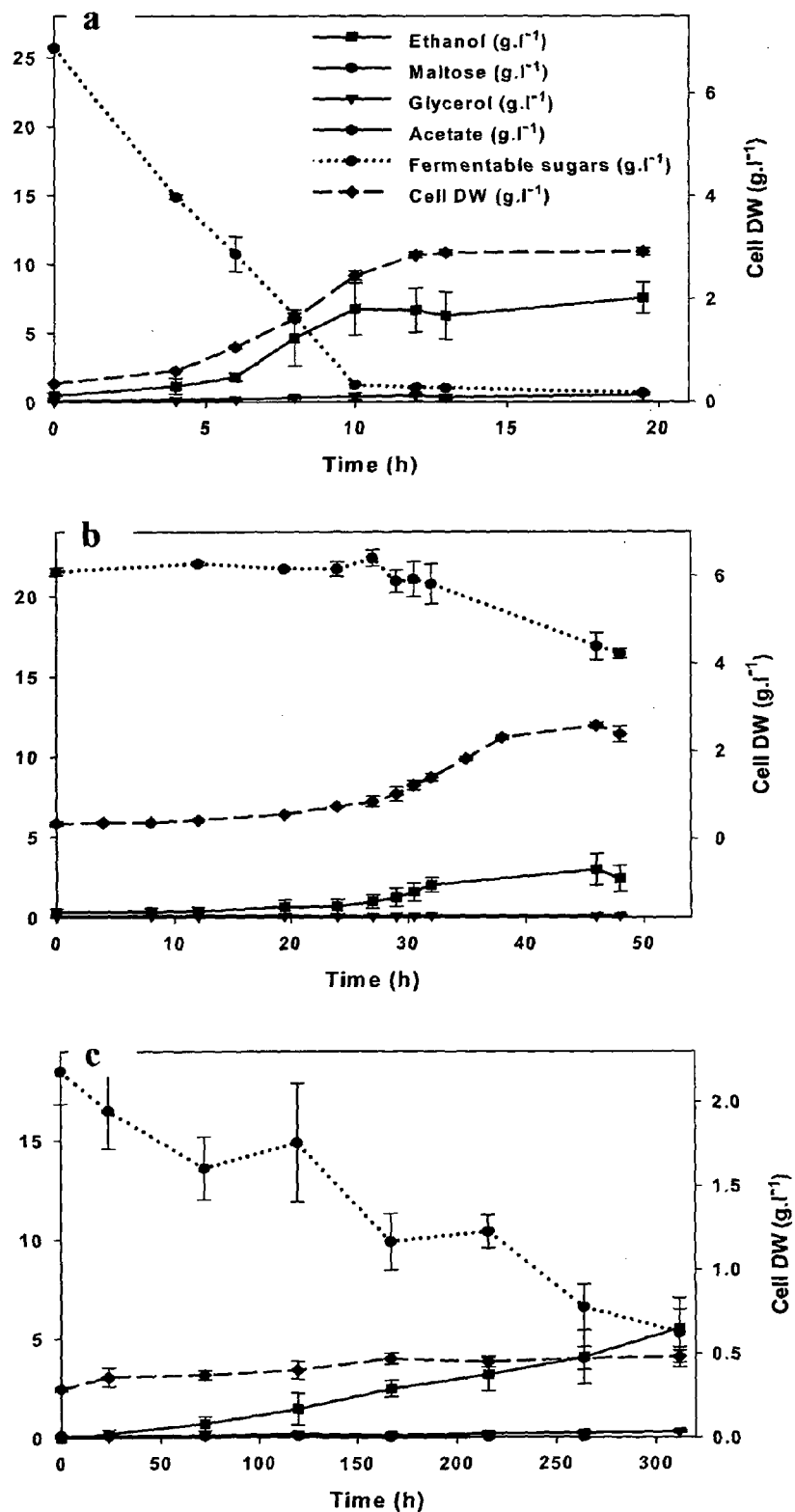
FIG. 8 Fermentation profiles of the Y294[yAGAA] strain cultivated anaerobically in serum bottles in a) 2.2% glucose medium, b) 2% soluble potato starch medium, and c) 2% RSYP medium (all starch media with added 0.05% glucose). Ethanol, maltose, glycerol and acetate levels (g l$^{-1}$) determined with HPLC, as well as fermentable sugars (g l$^{-1}$)

Ethanol, Biomass and By-Product Yields During Anaerobic Growth on Starch and Glucose The anaerobic fermentation profiles of the Y294[yAGAA] strain in glucose, soluble starch, and raw starch are presented in FIGS. 8*a-c*. The different yields of by-products from and carbon balances for anaerobic fermentation by the Y294[yAGAA] strain obtained in raw starch and glucose media are indicated in Table 7. The carbon balance for the fermentation in soluble starch medium could not be calculated accurately as glucose produced by enzyme hydrolysis interfered with total residual fermentable sugar determined with the phenol-sulphuric acid assay. $CO_2$ was estimated from the ethanol produced based on the assumption that one mol $CO_2$ is produced per mol ethanol. Y294[yAGAA] sustained growth on raw starch as sole carbon source and produced a maximum ethanol concentration of 5.5 g $l^{-1}$ after 312 hours of fermentation. A yield of 0.40 g of ethanol per gram available sugar from raw starch was calculated, which corresponds to 71% of the theoretical maximum of 0.56 g ethanol per g starch (Table 8). The maximum ethanol concentration from soluble starch was 3.0 g $l^{-1}$ after 46 hours. Y294[yAGAA] produced up to 7.1 g $l^{-1}$ ethanol after 19.5 hours cultivation in glucose.

TABLE 7

Product yields for anaerobic batch cultures of *S. cerevisiae* recombinant strains in serum bottles

| Strain | $\mu_{max}$ ($h^{-1}$) | Product Yields (g (g glucose)$^{-1}$) Biomass | Ethanol | Glycerol | Acetate | Carbon balance $Cmol_{in}/Cmol_{out}$ |
|---|---|---|---|---|---|---|
| Y294[yxynsec] [a] | 0 | — | — | — | — | — |
| Y294[yAGAA] [a] | 0.003 | 0.02 [c] | 0.40 | 0.02 | — | 0.83 |
| Y294[yAGAA] [b] | 0.248 | 0.13 [d] | 0.47 | 0.02 | 0 | 1.12 |

Strains cultivated in
[a] 20 g $l^{-1}$ raw starch and 0.5 g $l^{-1}$ glucose, and
[b] 22.5 g $l^{-1}$ glucose.
[c] inoculum of 0.29 g $l^{-1}$ DW cells increased to 0.49 g $l^{-1}$ DW cells during fermentation
[d] inoculum of 0.36 g $l^{-1}$ DW cells increased to 2.92 g $l^{-1}$ DW cells during fermentation
— indicates not determined.

TABLE 8

Ethanol production by strains cultivated in starch

| Strains | Sugar | Ethanol concentration | Ethanol productivity | Specific ethanol productivity | Ethanol Yield | Reference |
|---|---|---|---|---|---|---|
| Raw starch medium | | | | | | |
| G-5315-2 | 250 g $l^{-1}$ | 51 g $l^{-1}$ after 120 h | 0.675 g $l^{-1}$ $h^{-1}$ | | 0.20 (36%) [b] | (Ashikari et al., 1989) |
| YF207/pGA11/pUFLA | 200 g $l^{-1}$ | 61.8 g $l^{-1}$ after 72 h | 1.008 g $l^{-1}$ $h^{-1}$ | 0.069 g (g DW cells)$^{-1}$ $h^{-1}$ | 0.44 (79%) [b] | (Shigechi et al., 2004b) |
| YF237 (nf)/pGA11 (sd)/pSBAA2 (se) | 120 g $l^{-1}$ | 51 g $l^{-1}$ after 60 h | 1.283 g $l^{-1}$ $h^{-1}$ | 0.180 g (g DW cells)$^{-1}$ $h^{-1}$ | 0.46 (82%) [b] | (Khaw et al., 2006) |
| YF237 (nf)/pGA11 (sd)/pSBAA2 (sd) | 120 g $l^{-1}$ | 23 g $l^{-1}$ after 60 h | 0.305 g $l^{-1}$ $h^{-1}$ | 0.060 g (g DW cells)$^{-1}$ $h^{-1}$ | 0.38 (68%) [b] | (Khaw et al., 2006) |
| YF207 (f)/pGA11 (sd)/pSBAA2 (se) | 120 g $l^{-1}$ | 24 g $l^{-1}$ after 60 h | 0.321 g $l^{-1}$ $h^{-1}$ | 0.060 g (g DW cells)$^{-1}$ $h^{-1}$ | 0.45 (80%) [b] | (Khaw et al., 2006) |
| YF207 (f)/pGA11 (sd)/pSBAA2 (se) | 120 g $l^{-1}$ | 20 g $l^{-1}$ after 60 h | 0.208 g $l^{-1}$ $h^{-1}$ | 0.040 g (g DW cells)$^{-1}$ $h^{-1}$ | 0.20 (36%) [b] | (Khaw et al., 2006) |

TABLE 8-continued

Ethanol production by strains cultivated in starch

| Strains | Sugar | Ethanol concentration | Ethanol productivity | Specific ethanol productivity | Ethanol Yield | Reference |
|---|---|---|---|---|---|---|
| Y294[yAGAA] | 22.5 g l$^{-1}$ | 5.5 g l$^{-1}$ after 312 h | 0.018 g l$^{-1}$ h$^{-1}$ | 0.037 g (g DW cells)$^{-1}$ h$^{-1}$ | 0.40 (71%) [b] | This study |
| Soluble starch medium | | | | | | |
| YPG/AB | 48 g l$^{-1}$ | 21.5 g l$^{-1}$ after 70 h | 0.31 g l$^{-1}$ h$^{-1}$ | | 0.54 (96%) [b] | (Ülgen et al., 2002) |
| *Aspergillus awamori* and *Zymomonas mobilis* | 110 g l$^{-1}$ | 21 g l$^{-1}$ | | | 0.33 (59%) [b] | (Tanaka et al., 1986) |
| *Saccharomycopsis fibuligera* and *Zymomonas mobilis* | 33 g l$^{-1}$ | 9.7 g l$^{-1}$ after 25 h | 0.54 g l$^{-1}$ h$^{-1}$ | | 0.48 (86%) [b] | (Dostalek and Haggstrom, 1983) |
| Y294[yAGAA] | 22.5 g l$^{-1}$ | 3.0 g l$^{-1}$ after 312 h | 0.257 g l$^{-1}$ h$^{-1}$ | 0.022 g (g DW cells)$^{-1}$ h$^{-1}$ | [c] | This study |
| Glucose medium | | | | | | |
| Y294[yAGAA] | 22.5 g l$^{-1}$ | 7.1 g l$^{-1}$ after 312 h | 1.237 g l$^{-1}$ h$^{-1}$ | 0.125 g (g DW cells)$^{-1}$ h$^{-1}$ | 0.47 (92%) [d] | This study |

[a] Monomeric sugar equivalent determined from the sum of starch and glucose in medium.
[b] Ethanol yield as g (g consumed sugar)$^{-1}$ and % of theoretical maximum (0.56 g g$^{-1}$ from starch) indicated in brackets.
[c] Ethanol yield was not determined as glucose produced by enzyme hydrolysis interfered with measured total residual fermentable sugars.
[d] Ethanol yield as g g$^{-1}$ and % of theoretical maximum (0.51 g g$^{-1}$ from glucose) indicated in brackets.
(nf) denotes nonflocculent, (f) denotes flocculent, (sd) denotes surface displayed, (se) denotes secreted.
A blank space indicates that not enough data was presented to determine the value.

Discussion

A more efficient and cost effective conversion of starch to ethanol requires organisms producing enzymes which are capable of converting raw starch in a one-step process. Applying a raw starch utilising yeast in the starch conversion process will have all the benefits from a simultaneous SSF procedure, such as a lowered heating energy requirement and chemical usage. The added benefit will be elimination of the large cost associated with commercial enzyme purchase.

In this study, yeast was engineered to secrete both a raw starch hydrolysing glucoamylase and alpha-amylase from *Aspergillus awamori* origin, which allowed the yeast to sustain growth on raw starch as sole carbon source and ferment the hydrolysed substrate to ethanol, albeit a low maximum specific growth rate (0.003 h$^{-1}$). The generated strain (Y294 [yAGAA]) produced a maximum ethanol concentration of 5.5 g l$^{-1}$ after 312 hours of fermentation in 20 g l$^{-1}$ raw starch with 0.5 g l$^{-1}$ glucose. Although the volumetric ethanol productivity of the Y29[yAGAA] strain (0.018 g l$^{-1}$ h$^{-1}$) was much lower than the productivity determined for previously generated strains (0.208-1.283 g l$^{-1}$ h$^{-1}$) (Table 8), a yield of 0.40 g of ethanol per gram available sugar from raw starch was calculated, which corresponds to 71% of the theoretical maximum from starch. The yield compared well to calculated yields of strains previously engineered for raw starch conversion (Table 8).

Furthermore, the specific ethanol productivity of 0.037 g (g DW cells)$^{-1}$ h$^{-1}$ was comparable to a flocculent yeast strain co-displaying the *Rhizopus oryzae* glucoamylase and *Streptococcus bovis* alpha-amylase (0.04 g (g DW cells)$^{-1}$ h$^{-1}$). The flocculent strain produced up to 20 g ethanol after 60 hours in a medium containing 100 g raw starch with 10 g l$^{-1}$ glucose at an ethanol yield of 0.30 g g$^{-1}$ (36% of theoretical maximum). The group used an inoculum of 3.33 g cells per liter medium. In our study only 20 g l$^{-1}$ raw starch and 0.5 g l$^{-1}$ glucose was used in the medium and the cell inoculum was only 0.3 g l$^{-1}$. It is therefore speculated that by increasing the starch and glucose concentration in the medium and using a higher cell inoculum, the overall ethanol production of the Y294[yAGAA] strain will improve in a batch or even fed-batch fermentation system.

When the Y294[yAGAA] strain was cultivated in 20 g l$^{-1}$ soluble starch (with additional 0.5 g l$^{-1}$ glucose), an ethanol concentration of 3 g l$^{-1}$ was reached after 46 hours of fermentation. A higher ethanol concentration has been measured in a previous study, where up to 21.5 g l$^{-1}$ ethanol was produced after 70 hours in a controlled batch fermentation by a *S. cerevisiae* strain secreting separate polypeptides of *A. awamori* glucoamylase and *B. subtilis* alpha-amylase (Table 8). The Ülgen group's fermentation medium contained 40 g l$^{-1}$ soluble starch with additional 4 g l$^{-1}$ glucose, once again indicating that a higher starch and glucose concentration could increase ethanol concentration. Their strain showed a volumetric ethanol productivity of 0.310 g l$^{-1}$ h$^{-1}$, which is only 1.2-fold higher than the volumetric productivity of the Y294[yAGAA] strain (0.257 g l$^{-1}$ h$^{-1}$). Up to 9.7 g l$^{-1}$ ethanol was recorded during SSF with *Saccharomycopsis fibuligera* and *Zymomonas mobilis* after 25 hours of cultivation with an initial soluble starch concentration of 30 g l$^{-1}$ (Table 8). The volumetric productivity of ethanol was 0.54 g h$^{-1}$, which is 1.7-fold higher than for the Y294[yAGAA] strain.

The Y294[yAGAA] strain was cultivated in 22.5 g l$^{-1}$ glucose to determine ethanol produced in a non-limiting step as an indication whether enzyme production was a limiting factor in the generated strain. An ethanol concentration of up to 7.1 g was measured after 12 hours of fermentation. The volumetric ethanol productivity of the strain (1.237 g l$^{-1}$ h$^{-1}$) was well in line with the 1 g l$^{-1}$ h$^{-1}$ preferred by the industry for ethanol fermentation. The ethanol yield of 0.47 g g$^{-1}$ corresponded to 92% of the theoretical maximum from glucose. Enzyme production was thus too low to warrant high ethanol productivities in medium containing soluble or raw starch.

Various factors may contribute to a deficiency in adequate amounts of heterologously secreted enzymes or non-functional protein species. To prevent inefficient secretion of enzymes, the genes were fused to the *T. reesei* xylanase 2 secretion signal. Inefficient secretion of heterologous proteins has been observed in yeast and previously published work has shown that when using the native leader peptide from *A. awamori* glucoamylase, 5-12% of the activity was left within cells. The classical *S. cerevisiae* system for secretion of heterologous recombinant proteins utilising the *S. cerevisiae* α-factor leader sequence for secretion, and the endoprotease Kex2p (Lys-Arg) cleavage site for protein maturation was therefore utilised.

A second factor which may affect enzyme production is whether the engineered strain showed a metabolic burden as a result of heterologous enzyme secretion. A deleterious effect on growth was however not evident as the maximum specific growth rate for the Y294[yAGAA] determined during aerobic cultivation on glucose (YPD medium) was very similar to the maximum specific growth rate for the reference strain Y294[yxynsec] (0.37 h$^{-1}$ versus 0.38 h$^{-1}$).

Gene sequence may affect the functionality of expressed and secreted enzymes, as truncated genes or mutations may affect regions essential for enzyme activity and functionality. Sequencing confirmed open reading frames for the cloned gene sequences. Conserved residues in protein sequences indicated that translated proteins should be functional and effectively hydrolyse raw starch. Functionality of enzymes was visually confirmed by raw starch hydrolysis zones around yeast transformants in agar plates strained with iodine. Clear hydrolysis zones for secreted enzymes were visible in overlay Zymogram analysis, although protein species were hyper-glycosylated by the yeast. The specific soluble and raw starch activities of the enzymes were furthermore determined during liquid assays.

The characteristics of the enzymes were determined as the preferred temperature and pH of enzymes may indicate why their activity is less than optimal at the cultivation conditions preferred by the yeast. The GA I cocktail produced by Y294 [yASAG] had an optimum temperature of 60° C. at pH 5.4 and the activity dropped to only 67% of the maximum at 30° C. (Table 4). The optimum pH for raw starch activity at 30° C. could not be determined accurately, as the glycoside linkages between the glucose units become hydrolysable under acidic conditions. The strain producing both the GA I and AMYL III (y294[yAGAA]) had a lower temperature optimum of 40° C., which would be advantageous in a one-step fermentation scenario, as the cocktail showed 84% of the maximum activity at 30° C. (Table 4). Furthermore, the enzymes all remained very stable at 30° C. and pH 5.4 over 52 hours (>99%). The AMYL III showed the highest activity at 50° C. and pH 5.4, and only 33% activity was recorded at 30° C. The pH optimum of the enzyme was pH 4.5 at 30° C., and only 30% active at pH 5.4. These findings could indicate why low enzyme activity was measured during liquid assays or why no hydrolysis zones were visible for the strains secreting AMYL III or sAMYL III alone.

The affinity and maximum specific activity towards a substrate will give a further indication of how effective an enzyme will be in hydrolysing the substrate. The kinetic parameters of the purified GA I was therefore determined to calculate the enzyme's affinity ($K_m$) and maximum specific activity ($V_{max}$) for raw starch and maltose as substrate (Table 5). The affinity for maltose was two-fold higher than for raw starch, and maximum specific activity towards raw starch was five-fold higher than for maltose. The affinity of the GA I for maltose compared well with affinities reported in previous studies.

The rate of starch fermentation may be increased by increasing the engineered strain's performance, therefore increasing the level of glucoamylase and alpha-amylase expression. For this reason, glucoamylase and alpha-amylase sequences were designed using codons preferred by *S. cerevisiae*. The optimised GA I and AMYL III genes had CAI values of 0.921 and 0.923 respectively. Codon optimised genes offer the advantage of making gene expression less laborious for an organism harbouring the recombinant genes, as codons not frequently used by the organism are removed from the genes. This should increase gene expression.

Optimised gene sequences were synthesised and expressed in *S. cerevisiae*. Unfortunately applying the concept of codon adaptation did not improve recombinant protein production in the strain secreting both the sGA I and sAMYL III (FIG. 5). The Y294[yAGAA] and Y294[ySYAGAA] strains displayed similar raw starch hydrolysing activities at 30° C. per gram DW cells. The strains secreting the sGA I enzyme alone (Y294[ySYAG]) showed a 31% increase in raw starch hydrolysing activity per gram DW cells compared to the GA I secreted by Y294[yASAG]. The Y294[ySYAA] strain secreting the sAMYL III however displayed 56% less alpha-amylase activity per gram DW cells compared to AMYL III secreted from Y294[yASAA]. It can therefore be speculated that the negative effect of the sAMYL III counteracts the positive effect of the sGA I in Y294[ySYAGAA]. One possible avenue to be followed would be to express the sGA I and wild-type AMYL III as separate secreted polypeptides with the aim of increasing gene expression and therefore the rate of starch fermentation.

In conclusion, this study proved the concept that engineering yeast to secrete glucoamylase and α-amylase of *Aspergillus* origin alone yields an organism able to utilise raw starch as carbon source. The specific ethanol production rate of this strain on raw starch as carbon source (0.037 g (g DW cells)$^{-1}$ l$^{-1}$) was comparable to a previously engineered strain which was cultivated in a controlled batch fermentation with higher carbon source and ten-fold larger inoculum. It is therefore possible to increase ethanol production of the current strain in a more optimised fermentation system. An ethanol yield corresponding to 71% of the theoretical yield was observed. These preliminary serum bottle fermentations indicate that the generated strain is a promising raw starch converter. The GA I displayed an affinity ($K_m$) of 3.574 (µg ml$^{-1}$) and a maximum specific activity ($V_{max}$) of 11.604 towards raw corn starch. To our knowledge, this is the first study reporting on the affinity and specific activity of an enzyme for raw starch as substrate. Up to 140 nkat (g DW cells)$^{-1}$ raw starch hydrolysing activity was produced by the generated strain secreting both GA I and AMYL III. The Y294[yAGAA] and Y294 [ySYAGAA] strains displayed similar raw starch hydrolysing activities at 30° C. per gram DW cells. This could be due the lower expression of alpha-amylase, which counteracts the effect of the glucoamylase.

Example 2

Engineering New Amylolytic Yeast Strains for Industrial Ethanol Production

Strains and Media

All chemicals, media components and supplements were of analytical grade standard. Recombinant plasmids were constructed and amplified in *Escherichia coli* DH5α. The bacterial strains were cultivated at 37° C. on a rotating wheel in Luria-Bertani Broth (Sambrook et al., 1989). Ampicillin for selection of resistant bacteria was added to a final concentration of 100 µg ml⁻¹. Strains of *S. cerevisiae* were cultivated in either YPD medium (1% yeast extract, 2% peptone and 2% glucose) or selective complete medium (SC) (2% glucose and 0.17% yeast nitrogen base without amino acids) with addition growth factors and amino acids as necessary, at 30° C. on a rotary shaker set at 100 rpm.

DNA Manipulations

Restriction enzyme digestion, electrophoresis, DNA ligation, transformation and DNA preparation from *E. coli* were performed using the standard methods according to Sambrook et al. (1989). DNA fragments were purified from agarose gels by using phenol (Benson, 1984). Restriction enzymes and T4 DNA ligase were supplied by either Roche or Fermentas.

Design of Codon Optimised Synthetic Gene Sequences

Four new synthetic glucoamylase genes from various organisms were designed, together with 2 alpha-amylase genes. The glucoamylase genes were from *Rhizopus oryzay* (glaR), *Humicola grisea* (gla1), *Saccharomycopsis fibuligera* (GLU1) and *Thermomyces lanuginoses* (TLG1). The alpha-amylases were from *Lypomyces kononenkoae* (xsecLKA1) and *Saccharomyces fibuligera* (SFA1). Sequences of the different genes were used as template for design of synthetic sequences using only codons that are favoured by *S. cerevisiae* (Sharp and Cowe, 1991). A codon optimised version of the *Trichoderma reesei* xylanase 2 secretion signal (XYNSEC) was designed and used as secretion signal for all the genes, except for *Thermomyces lanuginoses* (TLG1) and *Saccharomyces fibuligera* (SFA1). The latter two genes contains its native secretion signals. All endonuclease restriction sites used frequently for cloning procedures in our laboratory were removed from within the designed genes (BamHI, BglII, EcoRI, EcoRV, HindIII, KpnI, NruI, SacI, SpeI, StuI and XhoI). Specific sites necessary for cloning purposes were attached to the 5'-(PacI, StuI and EcoRI) and 3'-ends (XhoI, BglII and AscI) of the sequence. The designed sequences were used as template to synthetically produce the optimised genes (GeneArt Corporation).

DNA Sequencing

The nucleotide sequences and open reading frames of the amylase fragments were determined with the dideoxy chain termination method using fluorescently labeled nucleotides on an ABI PRISM™ 3100 Genetic analyser. Sequence fragments were assembled manually in a word processing program. Sequence data was analysed with the PC based BLAST program (www.ncbi.nih.gov/BLAST) and protein sequences and restriction sites predicted and identified with the DNA-MAN (version 4.1) software package (Lynnon Biosoft).

At present we will only focus on the *Thermomyces lanuginoses* glucoamylase (TLG1) and the alpha-amylase from *Saccharomyces fibuligera* and *Lypomyces kononenkoae* (SFA1 and xsecLKA1 respectively). DNA sequences of these genes are indicated in FIGS. 9-11.

Construction of Integrative Plasmids for Secretion of Glucoamylase and Alpha-Amylase The delta integration vectors, pBKD1 and pBKD2, were used for the cloning of the synthetic genes. These two vectors differ in that pBKD1 contains the *S. cerevisiae* PGK1 (Phosphoglycerate Kinase) promoter and terminator sequences whereas pBKD2 contains the *S. cerevisiae* ENO1 (Enolase1) promoter and terminator sequences. These vectors allow multiple integration of the genes, due to the fact that integration is targeted to the δ-sequences of the yeast retrotransposon Ty1. This will ensure higher expressing levels of the newly synthesized glucoamylase and alpha-amylase.

Figure 12:
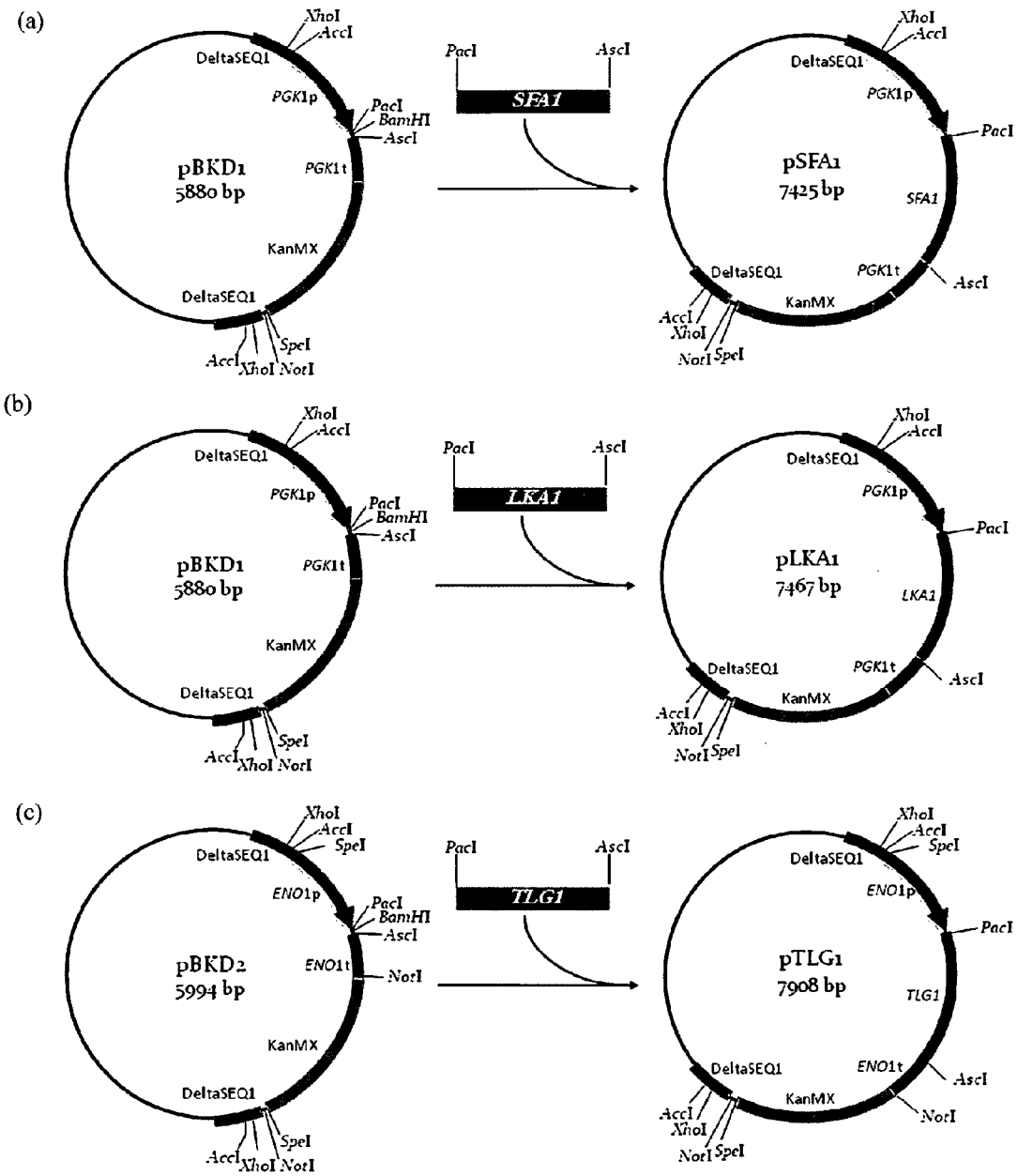

Glucoamylase and alpha-amylase gene sequence fragments were cloned into the commercial plasmid pDRIVE. Sequences were verified. The gene fragments were sub-cloned into yeast expression plasmids as follows: The codon optimised SFA1 gene was removed from the pDRIVE plasmid with PacI and AscI (FIG. 12). The gene fragment was then sub-cloned into pBKD1 (plasmid digested with PacI and AscI) to generate plasmid pSFA1. In a similar way, the codon optimized xsecLKA1 gene was subcloned into pBKD1 to generate plasmid pLKA1. Similarly, the codon optimized TLG1 gene was subcloned into pBKD2, generating pTLG1.

The ENO1P-TLG1-ENO1T cassette was removed from pTLG1 by digesting with SpeI and NotI to release the cassette from the plasmid. The cassette was then subcloned into pSFA1 (plasmid digested with SpeI and NotI) to generate plasmid pTLGSFA (FIG. 13). In a similar way the ENO1P-TLG1-ENO1T cassette was inserted into pLKA to yield pTLGLKA.

Electrotransformation of Yeast Strains with Delta Vectors

The wild type *S. cerevisiae* yMH1000 was transformed with XhoI digested pSFA, pLKA, pTLG, pTLGSFA and pTLGLKA integrative plasmids for multi-copy chromosomal integration.

Host cells, grown overnight in YPD broth, were harvested in Eppendorf tubes by centrifugation at 4000 rpm for 1 min, washed twice with distilled deionized water and finally suspended in 1 mL of electroporation buffer containing 1 M sorbitol and 20 mM HEPES. After centrifugation at 4000 rpm for 1 min, the pellet was resuspended in 200 µL of electroporation buffer. The resuspended cells (50 µL) were transferred into electroporation cuvettes (0.2 cm electrode, BiopRad). After adding 10 µg of linearized plasmid, an electric pulse of 1.4 kV, 200 ohm was applied with various capacitances by using Gene-Pulser. In this pulsed cuvette, 1 mL of YPD supplemented with 1 M sorbitol was added. The cuvette was incubated for 3 h at 30° C.

The recombinant cells were plated onto YPD plates (containing 1 M sorbitol) supplemented with geneticin (200 µg mL⁻¹) for selective pressure. The yeast Transformants were transferred onto soluble starch agar plates at 30° C. for 3 days. The recombinant colonies expressing the amylase gene were surrounded by a clear halo due to starch hydrolysis.

Enzyme Assays

Raw starch hydrolysis by transformants was tested on soluble, as well as, raw starch agar (2% corn starch, 2% peptone and 0.1% glucose). For plates containing raw starch, the starch was covered with ethanol. It was then left overnight in the laminar flow to allow for evaporation of the ethanol. The dry, sterile starch was then added to the autoclaved media. Yeast cells were spotted onto the agar and incubated at 30° C. for 3 days. The plates were stained afterwards with an iodine solution (3% KI, 0.3% iodine) to visualize clear hydrolysis zones.

The ability of the Amylolytic strains to produce functional amylases was visualized as cleared hydrolysis zones or halos on agar plates containing soluble and raw starch respectively, stained with iodine (FIG. 14).

The strain secreting *Thermomyces lanuginoses* glucoamylase (TLG1) and *Saccharomycopsis fibuligera* alpha-amylase (SFA1) produced the highest soluble as well as raw starch hydrolyzing activity.

Example 3

Selection and Development of an Efficient Amylolytic Yeast Strain for Industrial Ethanol Production Screening for the Production of Extracellular Hydrolytic Enzymes by *Saccharomyces cerevisiae* and non-*Saccharomyces* Strains.

The media used in this work are reported in Table (a) below. All chemicals, media components and supplements were of analytical grade standard.

TABLE (a)

Summary of media used in this study.

| Medium | Reference or supplier |
|---|---|
| Edimburgh Minimal Medium (EMM) | Favaro et al., 2008 |
| Minimal Medium Yeast (MMY) | Favaro et al., 2008 |
| Nutrient Agar (NA) | DIFCO |
| Wollum medium | Wollum et al., 1982 |

Screening for the Production of Extracellular Hydrolytic Enzymes by Saccharomyces cerevisiae and Non-Saccharomyces Strains.

Yeast Strains

Two hundred and twenty S. cerevisiae strains and 180 non-Saccharomyces isolates were screened for their amylolytic activities. S. cerevisiae DSM 70449 was used as reference negative strain while S. diastaticus ATCC 13007, having glucoamylolytic activity, was used as positive control strain.

All strains were isolated from different oenological environments. All cultures were identified by means of conventional morphological, physiological and biochemical procedures according to the latest taxonomic guidelines (Yarrow, 1998).

Media and Screening Procedure.

Calibrated suspensions ($A_{600nm}$=0.8, corresponding to an average cell concentration of $10^6$ mL$^{-1}$) of 24 h yeast cells were used to inoculate purified agar plates. Petri dishes were checked for the presence of enzymatic activity after incubation at 30° C. for 6-14 days.

Starch-Degrading Activity (StA).

Yeast strains were screened for their ability to hydrolyse soluble potato starch (Sigma and BDH) on NA medium supplemented with 0.2% starch and on Wollum medium containing (gL$^{-1}$): Yeast Extract (Difco), 1; Na$_2$NO$_3$, 1; KCl, 0.5; MgSO$_4$, 0.5; starch, 10 and agar, 17.

After incubation, Petri dishes were flooded with iodine solution (Wollum, 1982). A pale yellow zone around colonies in a blue medium indicated starch degrading activity (StA).

Positive strains for StA were grown also on agar plates of YPS (gL$^{-1}$: yeast extract, 10; peptone, 10 and starch, 20) and EMM containing gL$^{-1}$: KHC$_8$H$_4$O$_4$, 3; Na$_2$HPO$_4$, 2.2; NH$_4$Cl, 5; starch, 20 and agar, 17. Cultures were aerobically incubated at 30° C. for 6 days and then monitored for the production of starch degradation halos after iodine solution staining.

Extensive Biochemical, Physiological and Genetic Study on the Starch-Hydrolytic Mechanism Showed by S. Cerevisiae Strains.

Determination of Amylolytic Activity in Liquid Media.

The starch-degrading activity of the thirteen S. cerevisiae strains selected was assessed in different liquid broths: YPS, YP (YPS without soluble starch) as complete media and EMM and MMY as minimal media.

S. cerevisiae DSM 70449 and S. diastaticus ATCC 13007 were used as negative and positive control strain, respectively. Yeast cells, grown to stationary phase in YPD broth, were inoculated to an $A_{600nm}$ of 0.06 to 0.09. Cell growth was monitored by measuring absorbance ($A_{600nm}$) at 12 h intervals. EMM was chosen for investigating the growth on- and the utilisation of starch. The exhausted EMM broth after 6 days incubation was determined for starch concentration. Residual starch was estimated by UV-method (Boehringer Mannheim/R-Biopharm). Every experiment was carried out in triplicate.

Screening for the Production of Extracellular Amylolytic Enzymes by S. Cerevisiae and Non-Saccharomyces Strains.

Two hundred and twenty S. cerevisiae strains and 180 non-Saccharomyces yeasts were screened for the production of amylolytic enzymes. The results derived from three experiments, each with two replicates. From the collection of non-Saccharomyces strains tested, no isolate was found effective for the production of starch-degrading enzymes.

Thirteen strains of S. cerevisiae were selected as potential amylolytic yeasts on the basis of their starch degradation halos. All isolates produced cell biomass and hydrolysing activity on both tested selective media.

The selection of high fermentative S. cerevisiae strains with potential starch-degrading abilities was unexpected since the species is considered in literature unable to use and ferment polysaccharides, such as cellulose, xylan and starch (Lynd et al., 2002).

In order to confirm this unpredicted finding, the selected strains were evaluated for their amylolytic activities on different agar media. They were grown on YEPS complete medium and on media with progressively decreased additives (yeast extract and peptone) which could supply to yeasts other carbon sources. All strains grew well on complete medium (data not shown) and slowly on Wollum, supplemented with only 1 g L$^{-1}$ yeast extract (FIG. 28A). Moreover, the isolates grew also on the minimal medium EMM that lacks any biological nitrogen source (FIG. 28B).

The FIG. 28 shows the growth, after 3 days incubation at 30° C., of the potentially amylolytic S. cerevisiae strains (c-d; e-f, g-h) on complete Wollum and minimal EMM plates. The type strain S. cerevisiae DSM 70449, used in the experiments as negative control, showed a very feeble growth pattern (FIG. 28 a-b). S. diastaticus ATCC 13007, having glucoamylolytic activity, grew very well on both media (FIG. 28 i-l).

After 6 days incubation, Petri dishes were flooded with iodine solution. In FIG. 28, the halos of the strains were compared. Complete Wollum medium (FIG. 28A) seems to support amylolytic activity better than EMM agar: the halos around the colonies grown on Wollum medium were larger in diameter than those on the minimal medium (FIG. 28B). However, the presence of a weak starch-degrading activity on EMM plates is clear evidence of the ability of the S. cerevisiae strains to use starch as the only carbon source.

Extensive Biochemical, Physiological and Genetic Study on the Starch-Hydrolytic Mechanism Showed by S. cerevisiae Strains.

Thirteen S. cerevisiae strains showed the potential of starch-hydrolysis when incubated on complete and minimal media supplemented with soluble starch as the only carbon source. Their capability was further evaluated with multi-disciplinary approaches in order to look into this possible new starch-hydrolytic mechanism. The research was carried out by means of a) studies on their amylolytic activity in liquid cultures, b) definition of a reliable method for in vitro enzymatic assays c) genetic identification of putative glucoamylolytic sequence(s) in S. cerevisiae strains.

Determination of Amylolytic Activity in Liquid Media.

All potentially amylolytic yeasts were checked for their ability to grow in different broths using starch. To evaluate if starch-hydrolysing ability in S. cerevisiae strains is dependent on medium composition, both complete (YPD) and minimal media (MMY and EMM) were used.

Firstly, their starch degrading activity was checked in complete YPS broth supplemented with soluble starch (20 gL$^{-1}$).

The selected strains grew at good levels reaching $OD_{600}$ values up to 1.6. However, the isolates showed variable ability to use starch as carbon source. In FIG. 29 the growth in liquid cultures of five strains, selected for their highest growth rate, is reported.

The growth of S. cerevisiae type strain DSM 70449 was much slower: the yeast, used as negative control, reached an $OD_{600}$ of only about 0.75 after 48 h incubation at 30° C. (FIG. 29).

As expected, S. diastaticus ATCC 13007 performed the best growth rate and after 48 h incubation it resulted induced by soluble starch for the production of extracellular glucoamylases. The strain reached a final $OD_{600}$ of 8.5 after 4 days incubation.

To test whether the growth of S. cerevisiae strains was depending closely on soluble starch and not on peptone or yeast extract added to the complete YPS medium, the strains were also grown in modified YP broth without starch (FIG. 30). Yeasts did not exhibit growth comparable to that shown in the same medium supplemented with starch.

The thirteen strains were also cultured in MMY medium supplemented with starch (5 $gL^{-1}$). As indicated in FIG. 31a, the five strains with the highest growth rate in YPS broth, confirmed their ability to use soluble starch as carbon source. The negative strain DSM 70449 gave no significant growth in terms of measurable absorbance: the yeast grew only up to 0.3 ($OD_{600}$) after a prolonged incubation at 30° C.

However, on the basis of the growth exhibited by amylolytic yeasts, MMY formulation could be a limiting factor for their enzymatic activity on soluble starch. Once incubated in the same medium without starch, the strains grew at levels slightly higher than those showed in MMY supplemented with soluble starch (FIG. 31b). For example, S. cerevisiae s2 was able to grow up to 0.43 ($OD_{600}$) after 48 h incubation while, in the presence of starch as available carbon source, it grew only up to 0.57. This evidence may be due to the MMY restricted amount of any component essential for amylase production by S. cerevisiae strains. This suggestion is consistent with that of De Mot and Verachtert (1987) who reported that amylase secretion by yeast is highly dependent on medium composition. Therefore, MMY broth could be not effective for supporting amylolytic enzymes production or activity by the selected yeasts.

The five strains with the highest growth rate in YPS broth (FIG. 29) were grown also in Edinburgh Minimal Medium (EMM). Data reported in FIG. 32 indicate that amylolytic yeasts grew well on soluble starch in a liquid minimal medium, too. All wild type strains showed starch degrading activity within 72 h incubation at 30° C.

The presence of starch in the broth was essential for the yeast growth: in EMM medium formulated without the polysaccharide, the yeasts showed only limited growth within 24 h incubation. Moreover, the addition of glucose at the concentration equivalent to that present as impurities of starch into fresh EMM (0.18 $gL^{-1}$) did not sustain the extra growth of potentially amylolytic strains (data not shown). Thus, the greater number of generations accomplished by the cells in the minimal broth was ascribed to result from starch utilisation.

S. cerevisiae DSM 70449 grew up to 0.65 $OD_{600}$ within 72 h incubation. This growth was probably due to the presence in the broth of a small amount of potassium hydrogen phthalate, utilised by yeast for growth. On the other hand, S. diastaticus resulted more proficient in growth rate. After 48 h incubation, the yeast showed consistent growth on soluble starch. Therefore, its glucoamylases should support the cell growth much better than the putative starch-degrading enzymes of the selected S. cerevisiae strains.

Analyses of the residual starch in exhausted EMM broth seem to confirm this hypothesis: as reported in Table (b), while S. diastaticus hydrolysed 75% of the soluble starch, S. cerevisiae strains were able to use no more than 6%.

TABLE (b)

Starch utilisation by Saccharomyces sp. strains grown in EMM (20 $gL^{-1}$ soluble starch) for 6 days at 30° C. Data are the means of three independent experiments (± SD).

| Strain | Starch in exhausted medium ($gL^{-1}$) | Starch utilised by strain ($gL^{-1}$) |
|---|---|---|
| ATCC 13007 | 4.25 (±0.24) | 15.75 |
| s1 | 18.72 (±0.19) | 1.28 |
| s2 | 18.94 (±0.19) | 1.06 |
| s3 | 19.15 (±0.18) | 0.85 |
| s4 | 19.09 (±0.23) | 0.91 |
| s5 | 19.12 (±0.16) | 0.88 |
| DSM 70449 | 19.77 (±0.13) | 0.23 |

The deficiency observed in S. cerevisiae strains could be probably due to the activity of different enzymes involved in starch degradation. Alternatively, the yeasts could have glucoamylase(s) with lower enzymatic efficiency than that secreted by S. diastaticus ATCC 13007.

Discussion.

In contrast to the accepted view that S. cerevisiae cannot use starch as a sole carbon source for growth, thirteen wild type strains of this species were found able of utilise starch in both complete and minimal broths. Heterogeneity in growth rate was also observed, suggesting that there is some genetic variability in the starch growth phenotype.

Their growth and starch-utilising capability were strongly dependent on the media composition. Complete medium supported amylolytic activity better than minimal broths. These results were consistent with the literature on yeast amylase (De Mot and Verachtert, 1987; Fogarty and Kelly, 1979; Pandey et al., 2000; Sun et al., 2009; Vihinen and Mantsiila, 1989). Gupta et al. (2003), in a recent review, indicated pH, nitrogen and phosphate sources as the main physico-chemical parameters affecting microbial amylase production.

The highest growth rates were indeed detected in YPS complete medium. However, the complex additives (yeast extract and peptone) included in YPS formulation supplies other carbon sources that yeast can metabolise. In EMM broth, which was supplemented only with $NH_4Cl$ as nitrogen source, the strains proved effective for their growth on soluble starch.

Selection of Wild Type S. cerevisiae Strains with Properties for Industrial Bioethanol Application Five potentially amylolytic S. cerevisiae strains (named as s1, s2, s3, s4, s5) with the highest growth rate on soluble starch were evaluated for their fermentative ability on MNS medium supplemented with different concentrations of glucose and/or xylose: 20% glucose, 15% glucose and 5% xylose, 10% glucose and 10% xylose. The following method was described by Delfini (1995). Every glass serum bottle was filled with 100 mL of MNS medium and then sealed with rubber stoppers. Pre-cultures of S. cerevisiae strains were inoculated with an average cell concentration of $7.5 \times 10^6$ cells per bottle and incubated in static condition at 25° C. S. cerevisiae H1 was used as a benchmark strain. Two S. cerevisiae isolates, named as F6 and F9, were used as control strains from the collection of S. cerevisiae selected for their high fermentative vigour (Dipartimento di Biotecnologie Agrarie, University of Padova). The experiments were carried out in triplicate.

The fermentation vigour was monitored daily by measuring flask weight loss in relation to $CO_2$ production. Results were reported, as grams of glucose utilised per 100 mL of MSN medium, by a conversion factor of 2.118. Samples were drawn after 7 and 21 days, filtered through 0.22-μm filters and analyzed for detection of glucose, xylose, xylitol, glycerol and ethanol by HPLC as described in van Zyl et al. (1999).
Engineering S. cerevisiae Yeasts by Introducing the sgaI Glucoamylase Gene from Aspergillus awamori and/or amylIII Amylase Gene from A. awamori.
Recombinant Strains and Plasmids The genotypes and sources of the plasmids, yeast and bacterial strains used in these experiments are summarised in Table 9.

terminator sequences whereas pBKD2 contains the S. cerevisiae ENO1 (EnolaseI) promoter and terminator sequences.
Dominant Marker Resistance Tests.

To establish their dominant marker resistance, the wild type S. cerevisiae strains s1, s2, F6 and H1 were grown in YPD broth at 30° C. for 24 h. Yeast cells were serially diluted in NaCl (0.9%) and plated onto YPD agar supplemented with increasing amounts of geneticin (0, 50, 100, 150, 200, 300 μg $mL^{-1}$) or zeocin (0, 50, 100, 150, 200 μg $mL^{-1}$). After 24 h incubation at 30° C., each strain was then evaluated for geneticin and zeocin sensibility.
Electrotransformation of Yeast Strains with Delta Vectors.

The wild type S. cerevisiae strains s1, s2, F6 and H1 were transformed with XhoI digested pBCFsgaI, pBCFamylIII and pBGA integrative plasmids for multi-copy chromosomal integration.

Host cells, grown overnight in YPD broth, were harvested in Eppendorf tubes by centrifugation at 4000 rpm for 1 min,

TABLE 9

Summary of plasmids and strains constructed for the development of an efficient amylolytic S. cerevisiae strain (*TEF1 promoter and terminator from Ashbya gossypii).

| Plasmid/Strains | Relevant genotype or phenotype | Source |
|---|---|---|
| ySYAG | bla URA3 PGK1$_P$-XYNSEC-sgaI-PGK1$_T$ | Stellenbosch Univ. |
| yASAA | bla URA3 ENO1$_P$-XYNSEC-amylIII-ENO1$_T$ | Stellenbosch Univ. |
| pBKD1 | amp δ-sites-TEF$_P$-KanMX-TEF$_T$-δ-sites* | Stellenbosch Univ. |
| pBKD2 | amp δ-sites-TEF$_P$-KanMX-TEF$_T$-δ-sites* | Stellenbosch Univ. |
| pBZD1 | amp δ-sites-TEF$_P$-ShBle-TEF$_T$-δ-sites* | Stellenbosch Univ. |
| pBCFsgaI | amp δ-sites-PGK1$_P$-XYNSEC-sgaI-PGK1$_T$-Shble-δ-sites | This work |
| pBCFamylIII | amp δ-sites-ENO1$_P$-XYNSEC-amylIII-ENO1$_T$-KanMX-δ-sites | This work |
| pBGA | amp δ-sites-PGK1$_P$-XYNSEC-sgaI-PGK1$_T$-KanMX-ENO1$_P$-XYNSEC-amylIII-ENO1$_T$-δ-sites | This work |
| E. coli XL1-Blue | MRF' endA1 supE44 thi-1 recA1 gyrA96 relA1 lac [F'proAB lacq ZΔM15 Tn10(tet)] | Stratagene (USA) |
| S. cerevisiae LH3 | H1 recombinant strain with sgaI multiple copy integration | This work |
| S. cerevisiae LH4 | H1 recombinant strain with sgaI multiple copy integration | This work |
| S. cerevisiae LH18 | H1 recombinant strain with sgaI multiple copy integration | This work |
| S. cerevisiae sBCF2 | s2 recombinant strain with sgaI multiple copy integration | This work |
| S. cerevisiae sBCF6 | s2 recombinant strain with sgaI multiple copy integration | This work |

Recombinant plasmids were constructed and amplified in E. coli XL1-Blue. The bacterial strains were cultured at 37° C. on a rotating wheel in Terrific Broth or on LB agar (Sambrook et al., 1989). Ampicillin was added to a final concentration of 100 μg $mL^{-1}$ for the selection of resistant bacteria.
DNA Manipulations.

Restriction enzyme digestion, electrophoresis, DNA ligation, transformation and DNA preparation from E. coli were performed using the standard methods according to Sambrook et al. (1989). DNA fragments were purified from agarose gels by using the GENE CLEAN kit (BIO 101, Inc., Vista, Calif., USA) or phenol (Benson, 1984). Restriction enzymes, Klenow fragment, and T4 DNA ligase were supplied by either Roche or Fermentas.
Construction of Integrative Plasmids for Secretion of Glucoamylase and α-Amylase.

A synthetic glucoamylase gene (sgaI) from A. awamori and the amylIII alpha-amylase gene from A. awamori were selected for the construction of new integrative vectors targeted to the δ-sequences of the yeast retrotransposon Ty1. The fungal sgaI and amylIII sequences, encoding proficient raw starch degrading glucoamylase and alpha-amylase respectively are shown in FIGS. 4 and 5. Both genes were subcloned into the pBKD1 and pBKD2 integrative plasmids. These two vectors differ in that pBKD1 contains the S. cerevisiae PGK1 (Phosphoglycerate Kinase) promoter and washed twice with distilled deionized water and finally suspended in 1 mL of electroporation buffer containing 1 M sorbitol and 20 mM HEPES. After centrifugation at 4000 rpm for 1 min, the pellet was resuspended in 200 μL of electroporation buffer. The resuspended cells (50 μL) were transferred into electroporation cuvettes (0.2 cm electrode, Bio-Rad). After adding 10 μg of linearized plasmid, an electric pulse of 1.4 kV, 200 ohm was applied with various capacitances by using Gene-Pulser (Bio-Rad Lab., Hercules, Calif., USA). In this pulsed cuvette, 1 mL of YPD supplemented with 1 M sorbitol was added. The cuvette was incubated for 3 h at 30° C.

The recombinant cells were plated onto YPD plates (containing 1M sorbitol) supplemented with zeocin (75-100 μg $mL^{-1}$) or geneticin (200-300 μg $mL^{-1}$) for selective pressure. The yeast transformants were transferred onto soluble starch agar plates at 30° C. for 3 days. The plates were transferred to 4° C. for 24 h to allow the starch to precipitate. Recombinant colonies expressing the amylase gene were surrounded by a clear halo due to starch hydrolysis.
Evaluation of Mitotic Stability of the Transformants.

To study mitotic stability of the obtained mutants, the transformants with the largest starch hydrolysis halos were grown in sequential batch cultures. The integrants were cultivated in non-selective YPD broth (10 mL) on a rotating wheel and transferred (1% v/v) to fresh YPD after glucose depletion.

After 30, 60 and 120 generations, recombinant strains were plated onto YPD and incubated at 30° C. for 24 h. Up to 250 colonies for each transformant were replicated onto soluble starch agar with and without zeocin (100 μg mL$^{-1}$) or geneticin (300 μg mL$^{-1}$) as well as on YPD plates (with and without antibiotics). The stable transformants remained resistant to antibiotics and displayed hydrolytic activity on starch.

Enzymatic Assays.

Stable mitotic transformants were studied for their ability to produce SgaI recombinant protein in the following broths: YPD, 2×SC (supplemented with gL$^{-1}$: glucose, 20 and yeast nitrogen base without amino acids, 13.4) and 2×SC supplemented also with 7.5 gL$^{-1}$ yeast extract, then referred to as 2×SC-modified.

The enzymatic assays were conducted with wild type S. cerevisiae H1 and its mitotically stable recombinants LH3, LH4, LH18 as well as with wild type S. cerevisiae s2 and the recombinant strains sBCF2 and sBCF6.

Yeast cells were aerobically grown at 30° C. up to 168 h. Five mL samples were withdrawn at 24 h intervals. After centrifugation (5000 rpm for 5 min), the supernatant was used for the assays and the pellets were used for the determination the dry biomass. For dry biomass determination, cell pellets were washed several times with deionised sterile water and dried in an oven (80° C.) to constant weight.

Samples of supernatant (50 μL) were mixed with 450 μL of the substrate (2% corn starch or 0.1% potato soluble starch in a 4.5 pH 0.05M citrate-phosphate buffer. The hydrolysing reaction was carried out at 30° C. for 36 minutes and at 50° C. for 12 minutes.

The optimal pH for glucoamylase hydrolysis at 50° C. was determined by adding supernatant samples in citrate-phosphate buffers with the following pH values: 5.0-5.4-6.0 and 7.5. The enzymatic reactions were stopped by boiling in a waterbath for 5 minutes. Glucose concentration in a cooled sample was determined using the peroxidase-glucose oxidase method from a glucose assay kit (Boehringer Mannheim/R-Biopharm). Enzymatic activities were expressed as nanokatals per mL (nKat mL$^{-1}$) that is defined as the enzyme activity needed to produce 1 nmol of glucose per second per mL of culture. In addition, enzymatic activities were reported also as nanokatals per gram dry cell weight (nKat (g dw cells)$^{-1}$), which is defined as the enzyme activity needed to produce 1 nmol of glucose per second per gram dry cell weight. Two experiments were carried out in triplicate and each enzymatic assay was repeated three times.

Fermentation Studies.

Recombinant amylolytic yeast strains were cultivated in: a) Raw Starch Fermentation Medium (RSFM) supplemented with (g L$^{-1}$) raw corn starch (Sigma) 20; yeast nitrogen base 6.7; peptone 20 and glucose 0.5, b) Starch Fermentation Medium (SFM) and c) Glucose Fermentation Medium (GFM) where the equivalent amount of raw starch was replaced with either soluble potato starch (Sigma) or glucose.

The raw starch was sterilised with ethanol and dried at 30° C. overnight before adding to filter-sterilized medium. Streptomycin (Sigma) was added (0.5 g L$^{-1}$) to prevent bacterial contamination under non-sterile raw starch conditions.

Fermentation experiments were performed at 30° C. in two different systems: fermentation flasks on orbital shaker and serum bottles sealed with rubber stoppers on multistirrer.

Precultures of S. cerevisiae s2 and recombinant strains sBCF2 and sBCF6 grown to stationary phase in YPD medium were used as inoculum. Cells were washed with a salt solution (0.9% NaCl) and used to inoculate 10% (v/v) 100 mL medium in triplicate experiments using 120 mL glass serum bottles or 120 mL Erlenmeyer flasks. Bottles and flasks were sealed with rubber stoppers, incubated at 30° C. and mixed on a magnetic stirrer or on an orbital shaker, respectively.

Samples were taken through a capped syringe needle pierced through the bottle stopper. Yeast cells were counted in triplicate using a Thoma chamber (depth, 0.02 mm) for raw starch fermentations. Anaerobic growth on glucose and starch fermentation medium was measured in triplicate as absorbance at 600 nm.

Analytical Methods.

A calibration chart was prepared to correlate dry weights (dw) with optical densities ($OD_{600}$) as well as cell counts determined using a Thoma chamber. Dry cell weights were determined from 5 mL culture samples. Cells were collected after centrifugation (5000 rpm, 5 min), washed several times with deionised sterile water, and dried in an oven (80° C.) to constant weight.

Residual fermentable sugars present during anaerobic cultivations were determined in duplicate for each culture with the glucose and starch assay kit (Boehringer Mannheim/R-Biopharm) while raw starch concentration was determined with phenol-sulphuric acid method using glucose as standard (Dubois et al., 1956).

Ethanol concentrations were analysed by ethanol assay kit (Boehringer Mannheim/R-Biopharm) and by HPLC. Ethanol analysis was performed with high-performance anion-exchange chromatography with pulsed amperometric detection (HPAEC-PAD). Ethanol was separated with an Aminex HPX-87H column (Bio-Rad, Hercules, USA) at 65° C. with 5 mM $H_2SO_4$ as the mobile phase, at a flow rate of 0.5 mL min$^{-1}$. The system (Shimadzu, Kyoto, Japan) was equipped with refractive index detector (Shimadzu) and cation-H refill cartridge (Bio-Rad, Hercules, USA) prior to the column.

Calculations.

The ethanol yield (g g$^{-1}$ consumed sugar) from glucose or starch was calculated as the amount of ethanol produced per gram of consumed sugar. The volumetric productivity (Q) was based on grams of ethanol produced per liter of culture medium per hour: (gL$^{-1}$)h$^{-1}$.

The highest volumetric productivity value of each strain was defined as maximum volumetric productivity ($Q_{max}$).

The specific productivity (q), based on the respective volumetric productivity divided by the correspondent dry cell weight value, was also calculated. The highest specific productivity value ($q_{max}$) was defined as the maximum specific productivity of the strains.

Development of an Efficient Amylolytic Yeast Strain for Industrial Ethanol Production.

Selection of Wild Type S. cerevisiae Strains with Proper Traits for Industrial Bioethanol Application.

Production of bioethanol from agricultural residues requires a fermenting organism converting all sugars of the raw material to ethanol in high yield and with high rate. The main properties for an industrial yeast strain are: (1) process water economy, (2) inhibitor tolerance, (3) ethanol yield, and (4) specific ethanol productivity. Moreover, the complete substrate utilisation is one of the prerequisites to render lignocellulosic ethanol processes economically competitive. This means that all types of sugars in cellulose, starch and hemicellulose must be converted to ethanol, and that microorganisms must efficiently perform this conversion under industrial conditions.

In addition to easily metabolised sugars, industrial substrates may also contain a mixture of unusual sugars. The simultaneous presence of multiple monosaccharides may pose limitations such as incomplete substrate utilisation and inhibition of sugar uptake pathways.

In this study, the five *S. cerevisiae* strains with the most interesting amylolytic capability were tested for their robustness and fermentative vigour in defined medium with low amounts of additives and high sugar levels. MNS broth, chosen for fermentation trials, has been used in several works for the comparison of yeast fermentative abilities (Agnolucci et al., 2007; Delfini and Formica, 2001). Glucose and xylose were selected as representative of hexose and pentose sugars since they are abundantly present as substrates in the industrial scale ethanol processes. It is known that wild type *S. cerevisiae* does not utilise xylose for growth, but the presence of the sugar in the medium could interfere with the ethanol performance of the tested yeast strains.

Delfini method was followed using MNS medium with different concentrations of glucose and/or xylose above within this Example (i.e. Example 3).

FIG. 15 shows the yeast fermentative performance on MNS supplemented with glucose (20%) reported both as cumulative sugar utilisation (grams of consumed glucose per 100 mL of MNS medium) and daily glucose consumption rate.

The strains displayed variable sugar utilisation kinetics. Four to five yeasts were able to utilise all sugar available in the medium while strain s3 exhibited lower fermentative ability. The potentially amylolytic strains performed remarkable fermentative vigour since they consumed glucose with a rate much higher than *S. cerevisiae* H1, used as reference strain. Interestingly, the ability of the five yeasts was comparable also with that showed by F6 and F9 strains, selected among the high fermentative yeasts of the collection belonging to the Department of Agricultural Biotechnology (University of Padova).

The yeasts produced significant daily sugar consumption and two strains showed the highest rate of about 5 grams at the third incubation day (FIG. 15). The data obtained following Delfini method were confirmed by HPLC analysis of samples taken at the end of fermentation (Table 10).

The best fermentative activities were performed by the strains s1, s2 and F6 that produced the highest ethanol levels. Their ethanol yield was interesting: 0.47, 0.48 and 0.46 g ethanol per gram of consumed glucose, respectively. Glycerol was produced by all yeasts in small amount.

The fermentative ability of the *S. cerevisiae* strains were tested also on MNS supplemented with glucose (15%) and xylose (5%) as reported in FIG. 16. The presence of xylose seemed to affect glucose consumption. After 21 days of incubation, indeed, the medium still contained 1% glucose.

However, the five strains displayed interesting fermentative performance also in the presence of high xylose concentration. In particular the isolates s1, s2 and s4 showed the highest glucose utilisation. Strain H1 consumed the glucose available at rate similar to *S. cerevisiae* F6 that exhibited the best cumulative sugar consumption.

In FIG. 16*b*, the yeasts were compared for daily glucose uptake. The rate of utilisation was influenced by the presence of xylose. The strain s2 confirmed high fermentative vigour with values slightly lower than those exhibited in MNS 20% glucose (FIG. 15*b*). The isolate F6, even if at a consumption rate significantly slower than in MNS 20% glucose, showed high vigour at the beginning of fermentation. As a result, the strain showed one of the best fermentative performances.

H1 isolate seemed to be slightly affected by xylose: in both MNS media, *S. cerevisiae* H1 displayed the maximum sugar consumption rate of about 4 grams glucose per day.

The HPLC analysis showed that all strains were able to convert little amounts of xylose into xylitol (Table 11). However, the majority of the pentose was still present at the end of fermentation. The alcohol conversion efficiency was remarkable in the strains s2, s3, s4 with ethanol yields of about 0.47 g g$^{-1}$ which corresponds to 92% of the theoretical maximum yield of 0.51 g ethanol per g glucose.

TABLE 10

Product formation by *S. cerevisiae* strains after 21 days fermentation at 25° C. in MNS with glucose (200 gL$^{-1}$) as substrate.

| Product (gL$^{-1}$) | H1 | s1 | s2 | s3 | s4 | s5 | F6 | F9 |
|---|---|---|---|---|---|---|---|---|
| Substrate remaining | | | | | | | | |
| Glucose | 15.2 | 3.1 | — | 21.2 | — | 2.5 | — | 28.0 |
| Products formed | | | | | | | | |
| Glycerol | 7.3 | 5.3 | 5.9 | 6.3 | 5.5 | 7.2 | 6.5 | 5.9 |
| Ethanol | 84.8 | 93.3 | 95.6 | 85.7 | 87.9 | 87.1 | 93.9 | 79.6 |
| Ethanol yield [a] | 0.46 | 0.47 | 0.48 | 0.48 | 0.44 | 0.44 | 0.47 | 0.46 |
| | (90%) | (91%) | (94%) | (94%) | (86%) | (86%) | (92%) | (91%) |

[a] Ethanol yield as g g$^{-1}$ and % of theoretical maximum (0.51 g g$^{-1}$ from glucose) indicated in brackets.

TABLE 11

Product formation by *S. cerevisiae* strains after 21 days fermentation at 25° C. in MNS with glucose (150 gL$^{-1}$) and xylose (50 gL$^{-1}$) as substrates.

| Product (gL$^{-1}$) | H1 | s1 | s2 | s3 | S4 | s5 | F6 | F9 |
|---|---|---|---|---|---|---|---|---|
| Substrate remaining | | | | | | | | |
| Glucose | 10.9 | 8.6 | 3.7 | 3.2 | — | 15.0 | 5.5 | 20.0 |
| Xylose | 46.0 | 45.3 | 44.8 | 45.0 | 44.5 | 44.2 | 44.7 | 45.4 |
| Products formed | | | | | | | | |
| Xylitol | 3.6 | 3.5 | 4.8 | 3.8 | 4.1 | 4.8 | 4.0 | 4.0 |
| Glycerol | 5.7 | 5.1 | 5.3 | 4.9 | 5.5 | 6.0 | 6.2 | 5.9 |
| Ethanol | 60.6 | 59.6 | 68.6 | 64.7 | 65.5 | 58.0 | 62.4 | 56.6 |
| Ethanol yield [a] | 0.46 (85%) | 0.42 (83%) | 0.47 (92%) | 0.44 (86%) | 0.44 (86%) | 0.43 (84%) | 0.43 (85%) | 0.44 (85%) |

[a] Ethanol yield as g g$^{-1}$ and % of theoretical maximum (0.51 g g$^{-1}$ from glucose) indicated in brackets.

The yeasts were also incubated in MNS supplemented with glucose and xylose at 10% each (FIG. 17).

Sugar consumption was slower than those reported in the other two MNS broths. As a result, the glucose utilisation rate was lower and the highest values were obtained earlier, after two days of fermentation. Strains s2 and H1 presented the most consistent fermentative vigour (about 3.0 grams) which was 1.5-fold that shown by isolate F9 (FIG. 17b). As reported in Table 12, xylitol conversion was limited although the medium was supplemented with high xylose concentration. The alcohol productions were significantly influenced by the presence of the xylose: the yeasts produced less consistent ethanol levels. *S. cerevisiae* s2 showed the most important yield of about 0.43 g ethanol per gram of glucose consumed, corresponding to nearly 84% of the maximum theoretical yield result, the glucose utilisation rate was lower and the highest values were obtained earlier, after two days of fermentation. Strains s2 and H1 presented the most consistent

TABLE 12

Product formation by *S. cerevisiae* strains after 21 days fermentation at 25° C. in MNS with glucose (100 gL$^{-1}$) and xylose (100 gL$^{-1}$) as substrates.

| Product (gL$^{-1}$) | H1 | s1 | s2 | s3 | S4 | s5 | F6 | F9 |
|---|---|---|---|---|---|---|---|---|
| Substrate remaining | | | | | | | | |
| Glucose | — | — | — | — | — | — | — | — |
| Xylose | 97.4 | 93.3 | 95.8 | 94.5 | 95.5 | 96.0 | 95.2 | 95.4 |
| Products formed | | | | | | | | |
| Xylitol | 2.9 | 3.7 | 3.1 | 3.5 | 3.3 | 3.1 | 3.5 | 3.3 |
| Glycerol | 5.2 | 4.9 | 5.3 | 7.9 | 4.8 | 4.6 | 5.3 | 4.5 |
| Ethanol | 37.0 | 40.5 | 43.0 | 33.9 | 36.5 | 32.0 | 39.4 | 30.9 |
| Ethanol yield [a] | 0.37 (73%) | 0.40 (79%) | 0.43 (84%) | 0.34 (66%) | 0.37 (72%) | 0.32 (63%) | 0.39 (77%) | 0.31 (61%) |

[a] Ethanol yield as g g$^{-1}$ and % of theoretical maximum (0.51 g g$^{-1}$ from glucose) indicated in brackets.

On the basis of the fermentative kinetics reported in FIGS. 15, 16 and 17, the strains s1, s2 and F6 were selected in order to start a molecular biology programme for the development of an efficient amylolytic yeast. The isolate H1 was also included as reference strain.

Integrative Plasmids Construction.

The glucoamylase sgaI codon-optimised gene of *Aspergillus awamori* and the amylIII α-amylase gene from *A. awamori* were inserted in frame with the XYNSEC secretion signal (Den Haan et al., 2007) for constitutive expression under the transcriptional control of the *S. cerevisiae* PGK1 and ENO1 promoters and terminators, respectively.

The yeast integrative expression plasmids were constructed as follows. The XYNSEC-amylIII sequence was retrieved from yASAA by digesting with EcoRI, treated with Klenow enzyme and then digested with BglII. The resulting fragment was sub-cloned into pBKD2 (vector digested with PacI, treated with T4 DNA polymerase and digested with BamHI).

The XYNSEC-sgaI fragment was retrieved from ySYAG with an EcoRI and BglII digestion (FIG. 19). The recessed 3' EcoRI site was filled in with Klenow enzyme and the fragment was then ligated with pBKD1 vector (digested with PacI, treated with T4 DNA polymerase and digested with BamHI) to generate plasmid pBKsgaI.

The KanMX gene (G418 resistance) of the vector pBKsgaI was replaced with the Shble gene (Zeocin resistance) removed from the plasmid pBZD 1 digested with EcoRI and SpeI. The final integrative plasmid was named pBCFsgaI (FIG. 19).

To obtain a unique δ-vector for both glucoamylase and α-amylase expressions in *S. cerevisiae*, the pBCFamylIII was digested with SpeI and NotI. The resulting fragment was ligated into the SpeI site of pBKsgaI to obtain the final vector construct, pBGA (FIG. 20).

Amylolytic Yeast Strain Generation.

The integrative plasmids constructed contain a unique XhoI site in the δ-sequence for an efficient homologous recombination into yeast chromosomes. However, since the amylIII gene contains a XhoI site, partial XhoI digestion were conducted with plasmids pBCFamylIII (FIG. 18) and pBGA (FIG. 20). All vectors were digested with XhoI and used to transform S. cerevisiae s1, s2, F6 and H1 previously selected as the most promising fermentative yeasts.

Unlike laboratory haploid strains of S. cerevisiae, wild type isolates lack selective genetics markers and thus could only be transformed with vectors containing dominant selection markers such as zeocin gene (Shble, in pBCFsgaI plasmid) and geneticin gene (KanMX, in pBCFamylIII and pBGA constructs). The resistance to these antibiotics were determined for the S. cerevisiae strains and is reported in Table 13.

TABLE 13

Dominant selection marker resistance of S. cerevisiae strains s1, s2, F6 and H1 grown on YPD plate supplemented with increasing concentration of geneticin and zeocin.

| S. cerevisiae strains | s1 | s2 | F6 | H1 |
|---|---|---|---|---|
| Geneticin ($\mu g\ mL^{-1}$) | | | | |
| 0 | ++++ | ++++ | ++++ | ++++ |
| 50 | ++ | ++++ | ++++ | ++++ |
| 100 | + | +++ | +++ | ++ |
| 150 | ng | + | ++ | + |
| 200 | ng | ng | ng | ng |
| 300 | ng | ng | ng | ng |
| Zeocin ($\mu g\ mL^{-1}$) | | | | |
| 0 | ++++ | ++++ | ++++ | ++++ |
| 50 | ng | ng | ng | ng |
| 100 | ng | ng | ng | ng |
| 150 | ng | ng | ng | ng |
| 200 | ng | ng | ng | ng |

(++++: consistent growth; ng: no growth).

The concentration of 200-300 ($\mu g\ mL^{-1}$) and 75-100 ($\mu g\ mL^{-1}$) of geneticin and zeocine, respectively, were chosen for the selection of the recombinants. Yeast cells were prepared as described above (see heading "Engineering S. cerevisiae yeasts by introducing the sgaI glucoamylase from Aspergillus awamori and/or amylIII amylase gene grom A. awamori) and transformed through electroporation. The electroporated cells were plated on selective YPD agar, supplemented with zeocin or geneticin, and then tested for amylolytic activity on soluble and raw starch agar media. The integrated yeasts with the largest starch hydrolysis halos were selected and maintained on agar plates for further analysis. The number of the obtained recombinants from each wild type host strain is reported in Table 14.

TABLE 14

Recombinant strains obtained with electro-transformation of wild type S. cerevisiae strains with pBCFsgaI, pBCFamylIII and pBGA integrative plasmids. Stable transformants maintained both antibiotic resistance and amylolytic activity after 120 growth generations in non selective YPD.

| | pBCFsgaI | | pBCFamylIII | | pBGA | |
|---|---|---|---|---|---|---|
| S. cerevisiae strains | n. obtained | n. stable | n. obtained | n. stable | n. obtained | n. stable |
| s1 | 32 | — | 6 | — | — | — |
| s2 | 25 | 2 | 21 | — | 6 | — |
| F6 | 16 | — | 36 | — | 3 | — |
| H1 | 87 | 3 | 27 | — | 4 | — |

To study their mitotic stability, all mutants were grown in sequential batch cultures using non-selective YPD broth. The majority of the yeasts lost the phenotype of both resistance to antibiotic and amylolytic activity as the number of generations increased. After 120 generations, only five engineered strains were found to be mitotically stable. They displayed both resistance to zeocin and hydrolytic ability on soluble starch. As reported in Table 14, all stable recombinants were engineered for the multiple integration of the codon-optimised synthetic gene sgaI. The mutant strains of S. cerevisiae s2 were named sBCF2 and sBCF6 while the integrants of S. cerevisiae H1 were named LH3, LH4 and LH18.

Expression of sgaI Gene in Engineered Yeasts.

The ability of the amylolytic strains to produce functional amylases was confirmed as hydrolysis halos in both raw and soluble starch agar plates (data not shown). The enzymatic activity of engineered yeasts was then detected in liquid assays. Firstly, the strains were evaluated for the production of the recombinant SgaI in three different broths: 2×SC, 2×SC-modified and YPD. Cultivation media and mainly their nitrogen sources, indeed, could influence the production of heterolougus proteins by engineered microbial strains.

The glucoamylolytic activities of sBCF2 and LH4, reported here as representative of the others recombinant strains, are shown in FIGS. 21 and 22. The enzymatic assays were conducted at 50° C. in citrate-phosphate buffer (pH 4.5) with 0.1% soluble starch.

As expected, the sgaI gene fused to the PGK1 promoter was constitutively expressed since the engineered yeasts constantly showed significant enzymatic activity; highest values were obtained after 72 hour incubation.

Media supplements influenced the production of SgaI by recombinant yeasts. All strains produced the maximum enzymatic activities once grown in rich YPD broth, containing both yeast extract and peptone. Therefore, the medium was selected for further enzymatic studies. The glucoamylolytic activity of the stable transformants secreting SgaI was monitored each 24 hour in three buffers at pH 4.5, 6.0 and 7.5. Highest values, reported in Table 15, were obtained after 72 hour incubation. The strains sBCF2 and LH4 produced the most efficient soluble starch hydrolysing ability.

The SgaI protein works better in acid conditions: the enzyme produced significantly lower values at pH 6.0, while at higher pH value no detectable hydrolytic activity was recorded.

On the basis of the preliminary enzymatic assays reported above, the glucoamylolytic activity of SgaI was tested at pH values of 4.5-5.0 and 6.0 (FIG. 23). The 5.4 pH was also investigated since it has been reported as optimal for the SgaI of A. awamori (de Villiers, 2008).

TABLE 15

Glucoamylolytic activity (nKat $mL^{-1}$) of engineered strains LH3, LH4, LH18, sBCF2, sBCF6 and their respective wild type yeast S. cerevisiae H1 and s2. The enzymatic activity was measured on cell-free supernatants after 72 h incubation in YPD broth. The assays were performed at 50° C. in citrate-phosphate buffer (0.1% soluble starch) at 4.5-6.0-7.5 pH.

| | Glucoamylolytic activity at 50° C. (nKat $mL^{-1}$) | | |
|---|---|---|---|
| | pH 4.5 | pH 6.0 | pH 7.5 |
| S. cerevisiae H1 | ND | ND | ND |
| S. cerevisiae LH3 | 0.72 ± 0.05 | 0.52 ± 0.06 | ND |
| S. cerevisiae LH4 | 2.35 ± 0.18 | 1.42 ± 0.15 | ND |
| S. cerevisiae LH18 | 0.63 ± 0.06 | 0.41 ± 0.05 | ND |
| S. cerevisiae s2 | ND | ND | ND |
| S. cerevisiae sBCF2 | 1.79 ± 0.15 | 1.20 ± 0.12 | ND |
| S. cerevisiae sBCF6 | 1.08 ± 0.09 | 0.65 ± 0.08 | ND |

ND: not detectable.
The experiment was conducted in triplicate (±SD).

In FIG. 23, the glucoamylolytic activity of SgaI secreted by the strains LH4 and sBCF2 is reported. An optimal pH of 4.5 was measured and the enzymatic activity decreased as the pH increased. Only about 72% and 58% of the maximum glucoamylolytic activity was still detectable at pH 5.4 and 6.0, respectively.

Raw starch and soluble starch activity was determined at the optimal pH and temperature incubation for SgaI (pH 4.5, 50° C.). The assays were also conducted at 30° C., growth temperature preferred by the yeast (Table 16).

TABLE 16

Glucoamylolytic activity (nkat (g dw cells)$^{-1}$) of the engineered *S. cerevisiae* strains and their respective wild type yeasts (s2 and H1) grown in YPD broth for 72 hours. The assays were performed at 30° and 50° C. in citrate-phosphate buffer at 4.5 with either 0.1% soluble starch or 2% raw starch.

| | Soluble starch | | Raw starch | |
|---|---|---|---|---|
| *S. cerevisiae* strains | 50° C. | 30° C. | 50° C. | 30° C. |
| H1 | ND | ND | ND | ND |
| LH3 | 993.5 ± 87.5 | 281.5 ± 26.0 | 594.1 ± 127.5 | 174.2 ± 16.5 |
| LH4 | 3218.3 ± 327.2 | 834.2 ± 77.4 | 1232.0 ± 137.3 | 360.1 ± 40.0 |
| LH18 | 1151.7 ± 120.5 | 317.2 ± 32.1 | 694.4 ± 97.3 | 196.9 ± 19.9 |
| s2 | ND | ND | ND | ND |
| sBCF2 | 2122.4 ± 245.4 | 624.7 ± 35.6 | 1040.8 ± 65.9 | 315.3 ± 38.1 |
| sBCF6 | 1778.8 ± 122.1 | 489.1 ± 36.4 | 855.6 ± 75.4 | 224.4 ± 17.2 |

The values are the means of the results obtained from two experiments conducted in triplicate (±SD).
ND: not detectable.

The yeast sBCF2, engineered strain of *S. cerevisiae* s2, showed remarkable soluble as well as raw starch hydrolysing activity. Among H1 recombinants, the highest enzymatic activity was produced by the strain LH4 with a glucoamylolytic activity of 3218 and 1232 nkat(g dw cells)$^{-1}$ on soluble and raw starch, respectively.

Fermentation Studies.

The two recombinant yeasts sBCF2 and sBCF6 were selected for fermentation studies from glucose, soluble and raw starch. Although the strains produced enzymatic activity lower than LH4, they originated from the parental yeast s2, a much more efficient fermentative strain than H1 as reported above.

The fermentation experiments were conducted in two different systems described above (see heading "Engineering *S. cerevisiae* yeasts by introducing the sgaI glucoamylase from *Aspergillus awamori* and/or amylIII amylase gene grom *A. awamori*). The ethanol yield displayed by the yeasts were similar in both fermentation procedures but the magnetic multi-stirring significantly enhanced the yeast ethanol productivity. Therefore, the results obtained with multi-stirring method will be presented.

The anaerobic growth rate and the fermentative performance from glucose were compared between sBCF2 and sBCF6 strains and the wild type yeast s2. As shown in FIG. 24, no notable differences were observed when the yeasts were grown in GFM medium (glucose 20.25 gL$^{-1}$).

Glucose was rapidly depleted and the strains produced up to 9.9 gL$^{-1}$ ethanol after 24 h. Their ethanol yield of about 0.49 gg$^{-1}$ corresponded to 96% of the theoretical maximum yield from glucose. As indicated in Table 17, the major fermentative parameters considered in this study were similar in all strains.

The engineered strains were also used for direct ethanol fermentation from soluble starch (FIG. 25 and Table 17). The stable transformants, sBCF2 and sBCF6, hydrolysed 69% and 63% of the soluble starch and produced 5.4 and 4.8 gL$^{-1}$ of ethanol after 48 h, respectively (FIGS. 25*b* and 25*c*). As expected, the parental yeast s2 did not convert starch into ethanol after long incubation at 30° C. (FIG. 25*a*).

The sBCF2 strain showed an ethanol yield of 0.44 g ethanol per gram of consumed starch (79% of theoretical maximum) while strain sBCF6 produced a yield of 0.42, corresponding to 76% of the theoretical yield (0.56 gg$^{-1}$).

TABLE 17

Ethanol production by the engineered *S. cerevisiae* strains (sBCF2 and sBCF6) and their wild type yeast (s2).

| *S. cerevisiae* strains | Sugar[a] gL$^{-1}$ | Ethanol gL$^{-1}$ | Q (volumetric productivity) (gL$^{-1}$)h$^{-1}$ | $Q_{max}$ (gL$^{-1}$)h$^{-1}$ | q (specific productivity) g(g dw cell)$^{-1}$h$^{-1}$ | $q_{max}$ g(g dw cell)$^{-1}$h$^{-1}$ | Ethanol Yield |
|---|---|---|---|---|---|---|---|
| Raw starch medium | | | | | | | |
| sBCF2 | 20.25 | 2.4 after 336 h | 0.007 | 0.016 (45 h) | 0.011 | 0.035 (45 h) | 0.41 (72%)[b] |
| sBCF6 | 20.25 | 1.8 after 336 h | 0.005 | 0.011 (45 h) | 0.010 | 0.025 (45 h) | 0.40 (72%)[b] |
| Soluble starch medium | | | | | | | |
| sBCF2 | 20.25 | 5.4 after 48 h | 0.11 | 0.23 (18 h) | 0.040 | 0.12 (18 h) | 0.44 (79%)[b] |
| sBCF6 | 20.25 | 4.8 after 48 h | 0.10 | 0.11 (18 h) | 0.037 | 0.08 (18 h) | 0.42 (76%)[b] |
| Glucose medium | | | | | | | |
| s2 | 20.25 | 9.9 after 24 h | 0.41 | 0.70 (6 h) | 0.136 | 0.32 (6 h) | 0.49 (96%)[c] |
| sBCF2 | 20.25 | 9.8 after 24 h | 0.41 | 0.64 (6 h) | 0.135 | 0.29 (6 h) | 0.49 (95%)[c] |
| sBCF6 | 20.25 | 9.9 after 24 h | 0.41 | 0.66 (6 h) | 0.135 | 0.25 (6 h) | 0.49 (96%)[c] |

[a] Sugar equivalent amounts determined from the sum of starch and glucose in medium.
[b] Ethanol yield as g (g consumed sugar)$^{-1}$ and % of theoretical maximum (0.56 g g$^{-1}$ from starch) indicated in brackets.
[c] Ethanol yield as g g$^{-1}$ and % of theoretical maximum (0.51 g g$^{-1}$ from glucose) indicated in brackets.

As reported in Table 17, the final volumetric productivity (Q) was similar for both engineered yeasts but the maximum ethanol productivity ($Q_{max}$) of the sBCF2 strain (0.23 gL$^{-1}$ h$^{-1}$) was approximately two-fold that of the sBCF6 yeast (0.11 gL$^{-1}$ h$^{-1}$).

The conversion rate of starch to ethanol was also found to be much more efficient in the case of sBCF2 (FIG. 25b), especially up to 18 h of fermentation. The comparison of the residual starch deposits seems to confirm this finding (FIG. 26).

The yeast sBCF2 hydrolysed the major amount of starch within 24 h incubation (FIG. 26b), while sBCF6 showed slower starch hydrolysing ability (FIG. 26c). As expected, the wild type strain did not use the polysaccharide for growth: the amount of starch was constant in the SFM medium during the entire fermentation (FIG. 26a).

Each recombinant yeast was also evaluated for direct ethanol production from raw starch in anaerobic conditions (FIG. 27). The strains, sBCF2 and sBCF6, consumed 32% and 25% of the raw starch and produced 2.4 and 1.8 gL$^{-1}$ of ethanol, respectively. The alcohol yields were similar, corresponding to 72% of the theoretical maximum yield (Table 17). Moreover, both strains displayed similar fermentative profiles.

However, the fermentation with sBCF2 was faster than that of sBCF6: the maximum ethanol productivity ($Q_{max}$) of sBCF2, (0.016 gL$^{-1}$)h$^{-1}$, was approximately 1.5-fold higher than sBCF6 (Table 17). Considering the maximum ethanol specific productivity ($q_{max}$) the sBCF2 displayed a value of 0.035 g (g dw cell)$^{-1}$h$^{-1}$ after 45 h of incubation which was 1.4-fold higher than sBCF6 value.

Discussion

The wild type yeasts, showing interesting amylolytic activities, have distinct physiological properties rendering them suitable for large scale fermentation.

Firstly, they originated from different fermentation plants and are specifically adapted to the oenological environment. In addition, wild type strains are generally adapted for efficient fermentation in grape musts with high sugar content (up to 260 gL$^{-1}$), and/or in environments with high alcohol content (up to 15% v/v), low pH (3.0-3.5), often with limiting amounts of nitrogen, lipids and vitamins.

The availability of such isolates as candidates for metabolic engineering programs is crucial in order to assure successful introduction of novel recombinant strains into industrial ethanol processes. Whereas strain development by recombinant techniques is performed in genetically defined laboratory yeasts in particular media, the typical industrial production microbe is genetically undefined and adapted to perform in poor, toxic and nutrient-limited broths.

The potentially amylolytic yeasts were further evaluated for their fermentative vigour in defined medium with high sugar levels. MNS broth, used in this study, was designed in order to simulate natural musts with defined supplements and additives (Delfini, 1995). The broth could be considered quite similar to several poor industrial media (Dahod, 1999; Miller and Churchill, 1986). In Table 18, MNS composition is compared with that of two commonly used defined broths in the recombinant yeast development: defined mineral medium (DMM; Verduyn et al., 1992) and synthetic complete (SC) medium equivalent to supplemented YNB broth (Difco).

TABLE 18

Composition of defined media used in the development of yeast strains for industrial applications.

| Components (gL$^{-1}$) | MNS | DMM | SC (YNB + Suppl) |
|---|---|---|---|
| (NH$_4$)$_2$SO$_4$ | 0.3 | 5 | 5 |
| (NH$_4$)$_2$HPO$_4$ | 0.3 | — | — |
| KH$_2$PO$_4$ | 1 | 3 | 1 |
| MgSO$_4$•7H$_2$O | 0.5 | 0.5 | 0.5 |
| NaCl | 0.1 | — | 0.1 |
| Malic Acid | 2 | — | — |
| Tartaric Acid | 3 | — | — |
| Vitamins (mgL$^{-1}$) | | | |
| Biotin | 0.02 | 0.05 | 0.002 |
| D-Pantothenic Acid | 0.4 | 1 | 0.4 |
| myo-Inositol | 2 | 25 | 2 |
| Nicotinic Acid | 0.4 | 1 | 0.4 |
| Thiamine | 0.4 | 1 | 0.4 |
| Pyridoxine | 0.4 | 1 | 0.4 |
| p-Aminobenzoic Acid | 0.2 | 0.2 | 0.2 |
| Riboflavin | — | — | 0.2 |
| Folic Acid | — | — | 0.002 |
| Trace elements (mgL$^{-1}$) | | | |
| H$_3$BO$_3$ | 0.5 | 1 | 0.5 |
| CuSO$_4$•5H$_2$O | 0.04 | 0.3 | 0.04 |
| KI | 0.1 | 0.1 | 0.1 |
| NaMoO$_4$•2H$_2$O | 0.2 | 0.4 | 0.2 |
| ZnSO$_4$•7H$_2$O | 0.4 | 4.5 | 0.4 |
| FeSO$_4$•7H$_2$O | — | 3 | — |
| FeCl$_3$•6H$_2$O | 0.4 | — | 0.2 |
| MnCl$_2$•2H$_2$O | — | — | — |
| MnSO$_4$•4H$_2$O | — | — | 0.4 |
| EDTA | — | 15 | — |
| CaCl$_2$•2H$_2$O | 100 | 4.5 | 100 |

TABLE 18-continued

Composition of defined media used in the development of yeast strains for industrial applications.

| Components (gL$^{-1}$) | MNS | DMM | SC (YNB + Suppl) |
|---|---|---|---|
| Supplements (mgL$^{-1}$) | | | |
| Adenin (hemisulfate salt) | — | — | 40 |
| L-arginine | — | — | 20 |
| L-aspartic acid | — | — | 100 |
| L-glutamic acid (hemisulfate salt) | — | — | 100 |
| L-histidine | — | — | 20 |
| L-leucine | — | — | 60 |
| L-lysine (mono-HCl) | — | — | 30 |
| L-methionine | — | — | 20 |
| L-phenylalanine | — | — | 50 |
| L-serine | — | — | 375 |
| L-threonine | — | — | 200 |
| L-tryptophan | — | — | 40 |
| L-tyrosine | — | — | 30 |
| L-valine | — | — | 150 |
| Uracil | — | — | 20 |

YNB medium is a chemically defined broth that can be supplemented to satisfy auxotrophic requirements of yeast mutants used in metabolic engineering, then referred to as SC medium.

DM medium contains almost all components of YNB medium (Table 18), however, some nutrients are present in higher concentration than in YNB broth. The DMM medium is commonly used to obtain quantitative physiological data for yeast strains. The broth has been designed to assure that concentrations of vitamins and trace elements do not exercise growth limitation.

As reported in Table 18, MNS broth is characterized by the lowest amounts of components, macro and micro-nutrients. Yeast strains able to grow and efficiently ferment with limiting nutrients could be very interesting for industrial scale applications.

From this point of view, the fermentation kinetics of the tested wild type S. cerevisiae strains are promising. Yeasts, selected for their potentially amylolytic abilities, displayed high fermentative vigour in all MNS media tested.

However, the strains showed some genetic variability in the fermentative phenotype. Once incubated in 20% glucose, few isolates converted rapidly glucose into ethanol at high levels: the strains s2 and F6 exhibited consistent glucose consumption rate and ethanol yield (FIG. 15). Their efficiency was even more consistent than that of S. cerevisiae H1, used as reference industrial strain.

All yeasts were influenced by the xylose addition in MNS broth (FIGS. 16 and 17). Glucose consumption rates and ethanol yields decreased as the xylose concentration increased. Since S. cerevisiae is unable to utilise xylose as fermentative substrates, this finding could be explained considering that the yeast uptakes xylose by facilitated diffusion even though the sugar is not a natural substrate.

S. cerevisiae indeed takes up xylose mainly through non-specific hexose transporters encoded by the HXT gene family. However, their affinity for xylose is much lower than that for glucose and the xylose uptake through the transporters is strongly inhibited by glucose.

Therefore, all yeast strains were affected by xylose which, present in high concentrations, may have acted as alternative substrate for specific and non-specific hexose transporters. In addition, xylose was initially reduced to xylitol, as indicated by the limited amounts of xylitol detected in MNS supplemented with either 5 or 10% xylose (Table 11 and 12). The first enzyme in the xylose-utilising pathway is xylose reductase (XR), which converts xylose to xylitol. Thus, the yeast strains should have XR enzyme(s) rendering them able of converting xylose into xylitol. The suggestion is consistent with previous works that have described xylose reductase activities in wild type S. cerevisiae strains.

Since one of the main properties for an industrial strain is the ability to ferment in the presence of a mixture of unusual sugars and under nutrient limitation, the yeasts performing the highest ethanol yields in MNS broths were selected. Thus the isolates s1, s2, F6 and H1 were used as host strains for the development of industrial amylolytic yeasts.

To successfully express amylolytic sequences in the selected S. cerevisiae strains, the construction of new delta vectors was necessary subcloning sgaI, sinthetic glucoamylase gene from A. awamori and/or amylIII alpha-amylase gene from A. awamori, into integrative plasmids.

Chromosomal integration is an effective method for introducing heterologous genes in S. cerevisiae. The segregational instability of plasmid vectors is avoided and, for structurally stable insertions, the cloned gene copy number can be maintained at its optimum value.

In this study, genes integration was targeted to δ-sequences of S. cerevisiae. This elements are the long terminal repeats of retrotransposons Ty1 and Ty2 (Boeke and Sandmeyer, 1991). In addition to their close association with Ty1 and Ty2, δ-sequences also occur as isolated elements. Because there exist about 30 copies of Ty1 and 425 copies of δ-sequences dispersed throughout the haploid yeast genome, this δ-integration system makes possible to integrate more copies of genes into yeast chromosomes than other conventional integration procedures.

Three integrative delta vectors were constructed for the expression of amylIII alpha-amylase gene (FIG. 18), sgaI synthetic glucoamylase (FIG. 19) and both amylolytic sequences (FIG. 20). However, the majority of the integrants, obtained by electroporation method, revealed mitotically unstable (Table 14) and only five stable yeasts secreting SgaI were selected.

The maintenance of both zeocin resistance and amylolytic activity phenotype does not necessarily mean that these recombinant strains should be efficient amylolytic yeasts. For this reason, the stable integrants were tested for their glucoamylolytic activities and fermentative performance from glucose, soluble and raw starch.

Firstly, the engineered strains were evaluated for the production of the heterologous protein in different broths. Media supplements were shown to have the major influence on the production of SgaI. In particular, yeast extract and peptone enhanced the glucoamylase secretion by recombinant strains (FIGS. 21 and 22). In YPD broth supplemented with both additives the enzymatic activity was about 1.4 and 1.8-fold higher than those detected in the supernatant of cultures grown in 2×SC-modified and 2×SC media, respectively.

The choice of nitrogen source in media for the production of heterologous proteins can be crucial. For instance, inconsistency in complex components such as yeast extract can limit the reproducibility of industrial fermentation performance, resulting in 2-3 fold differences in heterologous protein production levels.

The remarkable enzymatic activity produced by the engineered yeasts secreting SgaI indicated that the choice of cloning sgaI in frame with *T. reesei* xylanase 2 secretion signal was effective. The XYNSEC signal avoided the inefficient secretion of the recombinant enzyme, one of the main factors negatively affecting the adequate production of heterologous extracellular proteins. The phenomenon has been observed in yeast and it has been shown that when using the native leader peptide from *A. awamori* glucoamylase, 5-12% of the activity was left within cells.

The enzymatic studies on SgaI activity revealed an optimal pH value of 4.5 (FIG. 23). The glucoamylolytic activity was also influenced by temperature incubation and substrate (Table 16): at 30° C. incubation, the enzymatic activity was nearly 28% of the maximum value obtained at 50° C., optimal temperature for the enzyme. As expected, on unmodified corn starch, the integrated strains produced about 50% of their enzymatic activity performed on soluble starch.

Among the recombinant strains, sBCF6 and LH4 exhibited the most important activity on both raw and soluble starch (Table 16). Their efficient enzymatic abilities should be related to the high number of integrated gene copies as compared to those inserted in the other yeasts. However, further genetic studies are required to confirm this hypothesis.

The engineered strains sBCF2 and sBCF6, once grown in GFM medium (glucose 20.25 $gL^{-1}$), produced ethanol with yield similar to that of the parental yeast s2 (Table 19). This result could indicate that multiple gene integrations did not significantly affect the yeast fermentative performance.

The recombinant strains efficiently convert soluble starch into ethanol (FIG. 25). The maximum ethanol concentration was 5.4 and 4.8 $gL^{-1}$ after 48 hours for sBCF2 and sBCF6, respectively. Their fermentative abilities was compared to that of previously engineered strains (Table 19) and their starch conversion capacity resulted similar. A higher ethanol concentration has been measured in a previous work, where up to 14.3 $gL^{-1}$ ethanol was produced after 140 hours in a controlled batch fermentation with *S. cerevisiae* SR93 secreting Sta1 glucoamylase. However, the yeasts developed in this study showed comparable volumetric productivity levels (Table 19). Moreover, the yields of ethanol per gram of consumed starch were similar to the yield of *S. cerevisiae* SR93, constructed by integrating sta1 glucoamylase gene of *S. diastaticus*.

At the end of the fermentation, only about 66% of starch was hydrolysed by the recombinant yeasts (FIG. 24). In addition, after 20 h, the starch to ethanol conversion rate of both strains decreased notably. This result may be explained considering that SgaI glucoamylase could efficiently cleave only α-1,4 linkages.

This suggestion seems to be confirmed by the fermentation kinetics of the recombinant strains grown in raw starch medium. The yeast sBCF2 produced the maximum ethanol concentration of 2.4 $gL^{-1}$ after 336 hours of fermentation (FIG. 26). As reported in Table 15, its volumetric ethanol productivity, 0.007 $(gL^{-1})h^{-1}$, was much lower than the productivity determined for previously generated strains, 0.31-0.46 $(gL^{-1})h^{-1}$. However, the strains showed ethanol yield comparable with those exhibited by yeasts recently engineered with glucoamylase and α-amylase for raw starch conversion (Yamada et al., 2009).

TABLE 19

Ethanol production by *S. cerevisiae* strains engineered for the multiple integration of amylolytic genes.

| *S. cerevisiae* strains | Sugar[a] $gL^{-1}$ | Ethanol $gL^{-1}$ | Q (volumetric productivity) $(gL^{-1})h^{-1}$ | Ethanol Yield | Reference |
| --- | --- | --- | --- | --- | --- |
| Raw starch medium | | | | | |
| MT8-1SS | 110.00 | 26.0 after 84 h | 0.31 | 0.45 (80%)[b] | Yamada et al., 2009 |
| NBRC1440SS | 110.00 | 28.0 after 84 h | 0.33 | 0.52 (93%)[b] | Yamada et al., 2009 |
| MN8140SS | 110.00 | 39.0 after 84 h | 0.46 | 0.44 (79%)[b] | Yamada et al., 2009 |
| sBCF2 | 20.25 | 2.4 after 336 h | 0.007 | 0.41 (72%)[b] | This study |
| sBCF6 | 20.25 | 1.8 after 336 h | 0.005 | 0.40 (72%)[b] | This study |
| Soluble starch medium | | | | | |
| SR93 | 55.00 | 14.3 after 140 h | 0.10 | 0.48 (85%)[b] | Nakamura et al., 1997 |
| sBCF2 | 20.25 | 5.4 after 48 h | 0.11 | 0.44 (79%)[b] | This study |
| sBCF6 | 20.25 | 4.8 after 48 h | 0.10 | 0.42 (76%)[b] | This study |
| Glucose medium | | | | | |
| s2 | 20.25 | 9.9 after 24 h | 0.41 | 0.49 (96%)[c] | This study |
| sBCF2 | 20.25 | 9.8 after 24 h | 0.41 | 0.49 (95%)[c] | This study |
| sBCF6 | 20.25 | 9.9 after 24 h | 0.41 | 0.49 (96%)[c] | This study |

[a]Sugar equivalent amounts determined from the sum of starch and glucose in medium.
[b]Ethanol yield as g (g consumed sugar)$^{-1}$ and % of theoretical maximum (0.56 g $g^{-1}$ from starch) indicated in brackets.
[c]Ethanol yield as g $g^{-1}$ and % of theoretical maximum (0.51 g $g^{-1}$ from glucose) indicated in brackets.

Although the recombinant strains sBCF2 and sBCF6 secreted the sole glucoamylase enzyme, their raw starch fermentative capacity should be considered promising. Indeed, the yeasts, described in Yamada et al (2009), were developed by mating two integrated haploid strains expressing the α-amylase or glucoamylase gene.

The limited amount of ethanol produced by the sgaI expressing yeasts seemed to confirm that the codon optimised glucoamylase could efficiently hydrolyse only α-1,4 linkages. Indeed, the strains consumed low amount (up to 32%) of the available raw starch (FIG. 26).

Since the engineered yeasts were able to ferment all glucose available in the GFM medium (FIG. 24), the main factor limiting ethanol fermentation from both soluble and raw starch seems to be the inability of SgaI to hydrolyse α-1,6 linkages.

The co-expression of sgaI and other amylolytic genes in the constructed strains is in progress in order to increase their starch conversion efficiency. Furthermore, this study reported the first multiple integration of a codon optimised glucoamylase gene into wild type *S. cerevisiae* strains. The use of the synthetic sgaI gene should have increased gene expression making it less laborious for the host strain, since codons not frequently used by *S. cerevisiae* are removed from the glucoamylase sequence.

The constructing strategy adopted in this work proved effective and could be applied to other genes encoding efficient extracellular enzymes in order to achieve high expression levels in wild type yeasts.

It will be understood that the invention has been described by way of example only and modifications may be made whilst remaining within the scope and spirit of the invention.

REFERENCES

Agnolucci M., Scarano S., Santoro S., Sassano C., Toffanin A. and Nuti M., 2007, Genetic and phenotypic diversity of autochthonous *Saccharomyces* spp. strains associated to natural fermentation of 'Malvasia delle Lipari'. Lett Appl Microbiol 45, 657-662.

Allen M J, Coutinho P M, and Ford C F (1998) Stabilization of *Aspergillus awamori* glucoamylase by proline substitution and combining stabilizing mutations. Protein Eng 11:783-788

Ashikari T, Kunisaki S, Matsumoto N, Amachi T, and Yoshizumi H (1989) Direct fermentation of raw corn to ethanol by yeast transformants containing a modified *Rhizopus* glucoamylase gene. Appl Microbiol Biotechnol 32:129-133

Belshaw N J and Williamson G (1993) Specificity of the binding domain of glucoamylase 1. Eur J Biochem 211: 717-724

Benson S A (1984) A rapid procedure of isolation of DNA fragments from agarose gels. Biotechniques 2:66-67

Boeke J. D. and Sandmeyer S. B., 1991, Yeast transposable elements. In: Broach J., Jones E. and Pringle J. (Eds) The molecular and cellular biology of the yeast *Saccharomyces*: genome dynamics, protein synthesis, and energetics. Cold Spring Harbor Laboratory Press, Cold Spring Harbor, N.Y. Chen H M, Ford C, and Reilly P J (1994) Substitution of asparagine residues in *Aspergillus awamori* glucoamylase by site-directed mutagenesis to eliminate N-glycosylation and inactivation by deamidation. Biochem J 301: 275-281

Chen H M, Ford C, and Reilly P J (1995) Identification and elimination by site-directed mutagenesis of thermolabile aspartyl bonds in *Aspergillus awamori* glucoamylase. Protein Eng 8:575-582

Coutinho P M and Reilly P J (1997) Glucoamylase structural, functional, and evolutionary relationships. *Proteins* 29:334-347

Dahod S. K., 1999, Raw material selection and medium development for industrial fermentation processes. In: Demain A. L. and Davies J. E. (Eds) Manual of industrial microbiology and biotechnology. 2nd edition. ASM Press, Washington D.C.

De Mot R. and Verachtert H., 1987, Some microbiological and biochemical aspects of starch bioconversion by amylolytic yeasts. Critic Rev Biotechnol 5, 259-272.

Delfini C., 1995, Scienza e tecnica di microbiologia enologica. Edizioni Ii lievito, Asti.

Delfini C. and Formica J. V., 2001, Wine microbiology: science and technology. Marcel Dekker Inc Publisher, New York.

De Mot R and Verachtert H (1985) Purification and characterization of extracellular amylolytic enzymes from the yeast *Filobasidium capsuligenum*. Appl Environ Microbiol 50:1474-1482 de Villiers T., 2008, Fungal enzymes and microbial systems for industrial processing. Ph.D. thesis, Department of Microbiology, Stellenbosch University.

Den Haan R, McBride J E, La Grange D C, Lynd L R, and van Zyl W H (2007) Functional expression of cellobiohydrolases in *Saccharomyces cerevisiae* towards one-step conversion of cellulose to ethanol. Enzyme Microb Tech 40:1291-1299

Dostalek M and Haggstrom M (1983) Mixed culture of *Saccharomycopsis fibuligera* and *Zymomonas mobilis* in starch-use of oxygen as a regulator. Eur J Appl Microbiol Biotechnol 17:269-274

Dubois M, Gilles K A, Hamilton J K, Rebers P A, and Smith F (1956) Colorimetric method for determination of sugars and related substances. Anal Chem 28:350-356

Enzyme Nomenclature (1992). New York, Academic Press, and supplements thereto: Suppl 1, *Eur. J. Biochem.* 1994, 223, 1-5., Suppl 2, *Eur. J. Biochem.* 1995, 232, 1-6, Suppl 3, *Eur. J. Biochem.* 1996, 237, 1-5., Suppl 4, *Eur. J. Biochem.* 1997, 250, 1-6., Suppl 5, *Eur. J. Biochem.* 1999, 264, 610-650., Suppl 6, http://www.chem.qmul.ac.uk/iubmb/enzyme/supplements/sup6/, Suppl 7, http://www.chem.qmul.ac.uk/iubmb/enzyme/supplements/sup7/, Suppl 8, http://www.chem.qmul.ac.uk/iubmb/enzyme/supplements/sup8/.

Favaro L., Basaglia M. and Casella S., 2008, Could *Saccharomyces cerevisiae* convert agricultural by-products? Proceedings of Venice 2008, Second International Symposium on Energy from Biomass and Waste (9 pp). 17-20 November, Venice, Italy.

Fierobe H P, Stoffer B B, Frandsen T P, and Svensson B (1996) Mutational modulation of substrate bond-type specificity and thermostability of glucoamylase from *Aspergillus awamori* by replacement with short homologue active site sequences and thiol/disulfide engineering. Biochemistry 35:8696-8704

Fierobe H P, Mirgorodskaya E, Frandsen T P, Roepstorff P, and Svensson B (1997) Overexpression and characterization of *Aspergillus awamori* wild-type and mutant glucoamylase secreted by the methylotrophic yeast *Pichia pastoris*: comparison with wild-type recombinant glucoamylase produced using *Saccharomyces cerevisiae* and *Aspergillus niger* as hosts. Prot Exp Purification 9:159-170

Fogarty W. M. and Kelly C. T., 1979, Starch degrading enzymes of microbial origin. Prog Ind Microbiol 15, 87-150.

Frandsen T P, Dupont C, Lehmbeck J, Stoffer B, Sierks M R, Honzatko R B, and Svensson B (1994) Site-directed mutagenesis of the catalytic base Glutamic-acid-400 in glucoamylase from *Aspergillus niger* and of Tyrosine-48 and Glutamine-401, Both hydrogen-bonded to the gamma-carboxylate group of Glutamic-acid-400. Biochemistry 33:13808-13816

Frandsen T P, Christensen T, Stoffer B, Lehmbeck J, Dupont C, Honzatko R B, and Svensson B (1995) Mutational analysis of the roles in catalysis and substrate recognition of arginines 54 and 305, aspartic acid 309, and tryptophan 317 located at subsites 1 and 2 in glucoamylase from *Aspergillus niger*. Biochemistry 34:10162-10169

Fukuda K, Teramoto Y, Goto M, Sakamoto J, Mitsuiki S, and Hayashida S (1992) Specific inhibition by cyclodextrins of raw starch digestion by fungal glucoamylase. Biosci Biotechnol Biochem 56:556-559

Goto M, Semimaru T, Furukawa K, and Hayashida S (1994) Analysis of the raw starch-binding domain by mutation of a glucoamylase from *Aspergillus awamori* var. *kawachi* expressed in *Saccharomyces cerevisiae*. Appl Environ Microbiol 60:3926-3930

Goto M, Kuwano E, Kanlayakrit W, and Hayashida S (1995) Role of the carbohydrate moiety of a glucoamylase from *Aspergillus awamori* var. *kawachi* in the digestion of raw starch. Biosci Biotechnol Biochem 59:16-20

Goto M, Ekino K, and Furukawa K (1997) Expression and functional analysis of a hyperglycosylated glucoamylase in a parental host, *Aspergillus awamori* var. *kawachi*. Appl Environ Microbiol 63:2940-2943

Goto M, Shinoda N, Oka T, Sameshima Y, Ekino K, and Furukawa K (2004) Thr/Ser-rich domain of *Aspergillus* glucoamylase is essential for secretion. Biosci Biotechnol Biochem 68:961-963

Goto M, Tsukamoto M, Kwon I, Ekino K, and Furukawa K (1999) Functional analysis of O-linked oligosaccharides in threonine/serine-rich region of *Aspergillus* glucoamylase by expression in mannosyltransferase-disruptants of yeast. Eur J Biochem 260:596-602

Gupta R., Gigras P., Mohapatra H., Goswami V. K. and Chauhan B., 2003, Microbial alpha-amylases: a biotechnological perspective. Process Biochem 38, 1599-1616.

Harris E M S, Aleshin A E, Firsov L M, and Honzatko R B (1993) Refined structure for the complex of 1-deoxynojirimycin with glucoamylase from *Aspergillus awamori* Var X100 to 2.4-Angstrom resolution. Biochemistry 32:1618-1626

Hasegawa K, Kubota M, and Matsuura Y (1999) Roles of catalytic residues in alpha-amylases as evidenced by the structures of the product-complexed mutants of a maltotetraose-forming amylase. Protein Eng 12:819-824

Hayashida S, Nakahara K, Kanlayakrit W, Kara T, and Teramoto Y (1989) Characteristics and function of raw-starch-affinity site on *Aspergillus awamori* var. *kawachi* glucoamylase I molecule. Agric Biol Chem 53:143-149

Hayashida S, Teramoto Y, and Kira I (1991) Promotive and inhibitory effects of raw starch adsorbable fragments from pancreatic alpha-amylase on enzymatic digestions of raw starch. *Agric Biol Chem* 55:1-6

Hill J, Donald K A, and Griffiths D E (1991) DMSO-enhanced whole cell yeast transformation. Nucleic Acids Res 19:5791

Jacks A J, Sorimachi K, Gal-Coeffet M F, Williamson G, Archer D B, and Williamson M P (1995) 1H and 15N assignments and secondary structure of the starch-binding domain of glucoamylase from *Aspergillus niger*. Eur J Biochem 233:568-578

Kern L, de Montigny J, Jund R, and Lacroute F (1990) The FUR1 gene of *Saccharomyces cerevisiae*: cloning, structure and expression of wild-type and mutant alleles. Gene 88:149-157

Khan S M A, Reilly P J, and Ford C (2000) Thermal and molecular characterization of *Aspergillus awamori* glucoamylase catalytic and starch-binding domains. Starch-Starke 52:385-397

Khaw T S, Katakura Y, Koh J, Kondo A, Ueda M, and Shioya S (2006) Evaluation of performance of different surface-engineered yeast strains for direct ethanol production from raw starch. Appl Microbiol Biotechnol 70:573-579

Kondo A, Shigechi H, Abe M, Uyama K, Matsumoto T, Takahashi S, Ueda M, Tanaka A, Kishimoto M, and Fukuda H (2002) High-level ethanol production from starch by a flocculent *Saccharomyces cerevisiae* strain displaying cell-surface glucoamylase. Appl Microbiol Biotechnol 58:291-296

Kovaleva I E, Novikova L A, and Luzikov V N (1989) Synthesis and secretion of bacterial alpha-amylase by the yeast *Saccharomyces cerevisiae*. Febs Lett 251:183-186

Lynd L. R., Weimer P. J., van Zyl W. H. and Pretorius I. S., 2002, Microbial cellulose utilization: fundamentals and biotechnology. Microbiol. Mol Biol Rev 66, 506-577.

MacGregor E A, Janecek S, and Svensson B (2001) Relationship of sequence and structure to specificity in the alpha-amylase family of enzymes. Biochim Biophys Acta 1546:1-20

Machovič & Janeč (2006) Cell. Mol. Life. Sci. 63: 2710-2724.

Matsubara T, Ben Ammar Y, Anindyawati T, Yamamoto S, Ito K, Iizuka M, and Minamiura N (2004a) Degradation of raw starch granules by alpha-amylase purified from culture of *Aspergillus awamori* KT-11. J Biochem Mol Biol 37:422-428

Matsubara T, Ben Ammar Y, Anindyawati T, Yamamoto S, Ito K, Iizuka M, and Minamiura N (2004b) Molecular cloning and determination of the nucleotide sequence of raw starch digesting alpha-amylase from *Aspergillus awamori* KT-11. J Biochem Mol Biol 37:429-438

Matsuura Y, Kusunoki M, Harada W, and Kakudo M (1984) Structure and possible catalytic residues of Taka-amylase A. J Biochem (Tokyo) 95:697-702

Matsuura Y, Kusunoki M, Harada W, Tanaka N, Iga Y, Yasuoka N, Toda H, Narita K, and Kakudo M (1980) Molecular structure of taka-amylase A. I. Backbone chain folding at 3 A resolution. J Biochem (Tokyo) 87:1555-1558

Matsuura Y (2002) A possible mechanism of catalysis involving three essential residues in the enzyme of alpha-amylase family. *Biologia, Bratislava* 57:21-27

Miller G-L (1959) Use of dinitrosalicyclic acid reagent for determination of reducing sugars. Anal Chem 31:426-428

Miller T. and Churchill B. W., 1986, Substrates for large-scale fermentations. In: Demian A. L. and Solomon N. A. (Eds) Manual of industrial microbiology and biotechnology. ASM Press, Washington D.C.

Murai T, Ueda M, Yamamura M, Atomi H, Shibasaki Y, Kamasawa N, Osumi M, Amachi T, and Tanaka A (1997) Construction of a starch-utilizing yeast by cell surface engineering. Appl Environ Microbiol 63:1362-1366

Murai T, Yoshino T, Ueda M, Haranoya I, Ashikari T, Yoshizumi H, and Tanaka A (1998) Evaluation of the function of arming yeast displaying glucoamylase on its cell surface by direct fermentation of corn to ethanol. J Ferment Bioeng 86:569-572

Nakamura A, Haga K, Ogawa S, Kuwano K, Kimura K, and Yamane K (1992) Functional relationships between cyclodextrin glucanotransferase from an alkalophilic *Bacillus* and alpha-amylases. Site-directed mutagenesis of the conserved two Asp and one Glu residues. Febs Lett 296:37-40

Nakamura Y, Kobayashi F, Ohnaga M, and Sawada T (1997) Alcohol fermentation of starch by a genetic recombinant yeast having glucoamylase activity. Biotechnol Bioeng 53:21-25

Pandey A., Nigam P., Soccol C. R., Soccol V. T., Singh D. and Mohan R., 2000, Advances in microbial amylases. Biotechnol Appl Biochem 31, 135-152.

Plüddemann A and van Zyl W H (2003) Evaluation of *Aspergillus niger* as host for virus-like particle production, using the hepatitis B surface antigen as a model. Curr Genet 43:439-446

Romanos M A, Scorer C A, and Clare J J (1992) Foreign gene expression in yeast: a review. Yeast 8:423-488

Sambrook J, Fritsch E F, and Maniatis T (1989) Molecular cloning: A laboratory manual. Vol. 2. Cold Spring Harbor Laboratory Press, Cold Spring Harbor, N.Y.

Sharp P M and Cowe E (1991) Synonymous codon usage in *Saccharomyces cerevisiae*. Yeast 7:657-678

Sharp P M and Li W H (1987) The codon Adaptation Index—a measure of directional synonymous codon usage bias, and its potential applications. Nucleic Acids Res 15:1281-1295

Shigechi H, Uyama K, Fujita Y, Matsumoto T, Ueda M, Tanaka A, Fukuda H, and Kondo A (2002) Efficient ethanol production from starch through development of novel flocculent yeast strains displaying glucoamylase and co-displaying or secreting alpha-amylase. J Mol Cat B-Enz 17:179-187

Shigechi H, Koh J, Fujita Y, Matsumoto T, Bito Y, Ueda M, Satoh E, Fukuda H, and Kondo A (2004b) Direct production of ethanol from raw corn starch via fermentation by use of a novel surface-engineered yeast strain codisplaying glucoamylase and alpha-amylase. Appl Environ Microbiol 70:5037-5040

Sorimachi K, Gal-Coeffet M F, Williamson G, Archer D B, and Williamson M P (1997) Solution structure of the granular starch binding domain of *Aspergillus niger* glucoamylase bound to beta-cyclodextrin. Structure 5:647-661

Strauss, C. J. (2005) The role of lipids in the flocculation of *Saccharomyces cerevisiae*. Thesis/Dissertation. University of the Free State Sun H., Zhao P., Ge X., Xia Y., Hao Z., Liu J. and Peng M., 2009, Recent advances in microbial raw starch degrading enzymes. Appl Biochem Biotechnol, DOI 10.1007/s12010-009-8579-y.

Svensson B, Jespersen H, Sierks M R, and MacGregor E A (1989) Sequence homology between putative raw-starch binding domains from different starch-degrading enzymes. Biochem J 264:309-311

Swift H J, Brady L, Derewenda Z S, Dodson E J, Dodson G G, Turkenburg J P, and Wilkinson A J (1991) Structure and molecular model refinement of *Aspergillus oryzae* (TAKA) alpha-amylase: an application of the simulated-annealing method. Acta Crystallogr B 47:535-544

Tanaka H, Kurosawa H, and Murakami H (1986) Ethanol production from starch by a coimmobilized mixed culture system of *Aspergillus awamori* and *Zymomonas mobilis*. Biotechnol Bioeng 28:1761-1768

Ülgen K Ö, Saygili B, Önsan Z I, and Kirdar B (2002) Bioconversion of starch into ethanol by a recombinant *Saccharomyces cerevisiae* strain YPG-AB. Process Biochem 37:1157-1168 van Rooyen R, Hahn-Hägerdal B, La Grange D C, and van Zyl W H (2005) Construction of cellobiose-growing and fermenting *Saccharomyces cerevisiae* strains. J Biotechnol 120:284-295 van Zyl C., Prior B. A., Kilian S. G. and Brandt E. V., 1993, Role of D-ribose as a cometabolite in D-xylose metabolism by *Saccharomyces cerevisiae*. Appl Environ Microbiol 59, 1487-1494.

van Zyl W. H., Eliasson A., Hobley T. and Hahn-Hagerdal B., 1999, Xylose utilisation by recombinant strains of *Saccharomyces cerevisiae* on different carbon sources. Appl Microbiol Biotechnol 52, 829-833.

Vihinen M. and Mantsiila P., 1989, Microbial amylolytic enzymes, Crit. Rev Biochem Mol Biol 24, 329-418.

Vihinen M, Ollikka P, Niskanen J, Meyer P, Suominen I, Karp M, Holm L, Knowles J, and Mantsala P (1990) Site-directed mutagenesis of a thermostable alpha-amylase from *Bacillus stearothermophilus*: putative role of three conserved residues. J Biochem (Tokyo) 107:267-272

Williamson G, Belshaw N J, Noel T R, Ring S G, and Williamson M P (1992) O-glycosylation and stability. Unfolding of glucoamylase induced by heat and guanidine hydrochloride. Eur J Biochem 207:661-670

Wollum A. G., 1982, In: Methods in soil analysis Part 2. Chemical and microbiological properties. Agron Monograph n. 9. ASA-SSSA, U.S.A.

Yamada R., Bito Y., Adachi T., Tanaka T., Ogino C., Fukuda H. and Kondo A., 2009, Efficient production of ethanol from raw starch by a mated diploid *Saccharomyces cerevisiae* with integrated alpha-amylase and glucoamylase genes. Enzyme Microb Technol 44, 344-349.

Yarrow D., 1998, Methods for the isolation, maintenance and identification of yeasts. In: Kurtzman C. P. and Fell J. W. (Eds) The Yeasts, A Taxonomic Study, Elsevier Sci Publ Amsterdam.

Yu S, Jeppsson H, and Hahn-Hägerdal B (1995) Xylulose fermentation by *Saccharomyces cerevisiae* and xylose-fermenting yeast strains. Appl Microbiol Biotechnol 44:314-320

---

The invention claimed is:

1. A host cell which expresses a *Thermomyces lanuginosus* glucoamylase 1 (TLG1) protein and at least one of a *Saccharomycopsis fibuligera* alpha-amylase 1 (SFA1) protein and a *Lypomyces kononenkoae* alpha-amylase 1 (LKA1) protein, wherein:
the sequence of the TLG1 protein comprises a sequence which has at least 70% identity to SEQ ID NO: 1;
the sequence of the SFA1 protein comprises a sequence which has at least 70% identity to SEQ ID NO: 3;
the sequence of the LKA1 protein comprises a sequence which has at least 70% identity to SEQ ID NO: 2, and
the host cell is a yeast;
and wherein the proteins which are expressed by the host cell are capable of converting an uncooked grain starch-containing material to a fermentation product.

2. The host cell according to claim 1, wherein:
the sequence of the TLG1 protein comprises a sequence which has at least 80% identity to SEQ ID NO: 1;
the sequence of the SFA1 protein comprises a sequence which has at least 80% identity to SEQ ID NO: 3; and/or
the sequence of the LKA1 protein comprises a sequence which has at least 80% identity to SEQ ID NO: 2.

3. The host cell according to claim 1, wherein:
the sequence of the TLG1 protein comprises a sequence which has at least 90% identity to SEQ ID NO: 1;
the sequence of the SFA1 protein comprises a sequence which has at least 90% identity to SEQ ID NO: 3; and/or
the sequence of the LKA1 protein comprises a sequence which has at least 90% identity to SEQ ID NO: 2.

4. The host cell according to claim 1, wherein:
the sequence of the TLG1 protein comprises a sequence which is identical to SEQ ID NO: 1;
the sequence of the SFA1 protein comprises a sequence which is identical to SEQ ID NO: 3; and/or
the sequence of the LKA1 protein comprises a sequence which is identical to SEQ ID NO: 2.

5. The host cell according to claim 1, which expresses the *Thermomyces lanuginosus* TLG1 protein and the *Saccharomycopsis fibuligera* SFA1 protein.

6. The host cell according to claim 1, which expresses the *Thermomyces lanuginosus* TLG1 protein and the *Lypomyces kononenkoae* LKA1 protein.

7. The host cell according to claim 1, which expresses the *Thermomyces lanuginosus* TLG1 protein, the *Saccharomycopsis fibuligera* SFA1 protein and the *Lypomyces kononenkoae* LKA1 protein.

8. The host cell according to claim 1, wherein the fermentation product is selected from the group consisting of an alcohol, organic acid, ketone, amino acid, gas, enzyme and vitamin.

9. The host cell according to claim 8, wherein the alcohol is selected from the group consisting of ethanol, methanol and butanol.

10. A process for producing a fermentation product, the process comprising the steps of using a host cell which expresses a *Thermomyces lanuginosus* glucoamylase 1 (TLG1) protein and at least one of a *Saccharomycopsis fibuhgera* alpha-amylase 1 (SFA1) protein and a *Lypomyces kononenkoae* alpha-amylase 1 (LKA1) protein to convert grain starch in a starch-containing material to the fermentation product, wherein:
the sequence of the TLG1 protein comprises a sequence which has at least 70% identity to SEQ ID NO: 1;
the sequence of the SFA1 protein comprises a sequence which has at least 70% identity to SEQ ID NO: 3;
the sequence of the LKA1 protein comprises a sequence which has at least 70% identity to SEQ ID NO: 2;
the host cell is a yeast; and
wherein the starch-containing material is uncooked grain starch.

11. The process according to claim 10, wherein:
the sequence of the TLG1 protein comprises a sequence which has at least 80% identity to SEQ ID NO: 1;
the sequence of the SFA1 protein comprises a sequence which has at least 80% identity to SEQ ID NO: 3; and/or
the sequence of the LKA1 protein comprises a sequence which has at least 80% identity to SEQ ID NO: 2.

12. The process according to claim 10, wherein:
the sequence of the TLG1 protein comprises a sequence which has at least 90% identity to SEQ ID NO: 1;
the sequence of the SFA1 protein comprises a sequence which has at least 90% identity to SEQ ID NO: 3; and/or
the sequence of the LKA1 protein comprises a sequence which has at least 90% identity to SEQ ID NO: 2.

13. The process according to claim 10, wherein:
the sequence of the TLG1 protein comprises a sequence which is identical to SEQ ID NO: 1;
the sequence of the SFA1 protein comprises a sequence which is identical to SEQ ID NO: 3; and/or
the sequence of the LKA1 protein comprises a sequence which is identical to SEQ ID NO: 2.

14. The process according to claim 10, wherein the host cell expresses the *Thermomyces lanuginosus* TLG1 protein and the *Saccharomycopsis fibuligera* SFA1 protein.

15. The process according to claim 10, wherein the host cell expresses the *Thermomyces lanuginosus* TLG1 protein and the *Lypomyces kononenkoae* LKA1 protein.

16. The process according to claim 10, wherein the host cell expresses the *Thermomyces lanuginosus* TLG1 protein, the *Saccharomycopsis fibuligera* SFA1 protein and the *Lypomyces kononenkoae* LKA1 protein.

17. The process according to claim 10, wherein the fermentation product is selected from the group consisting of an alcohol, organic acid, ketone, amino acid, gas, enzyme and vitamin.

18. The process according to claim 17, wherein the alcohol is selected from the group consisting of ethanol, methanol and butanol.

* * * * *

SEQUENCE LISTING

```
<160> NUMBER OF SEQ ID NOS: 13

<210> SEQ ID NO 1
<211> LENGTH: 592
<212> TYPE: PRT
<213> ORGANISM: Thermomyces lanuginosus
<220> FEATURE:
<221> NAME/KEY: misc_feature
<223> OTHER INFORMATION: 1_SEQ ID NO 1 Mature protein sequence of the
      synthetic glucoamylase gene sequence of Thermomyces lanuginoses

<400> SEQUENCE: 1
```

```
Glu Thr Thr Val Pro His Ala Thr Gly Ser Leu Asp Asp Phe Leu Ala
1               5                   10                  15

Ala Gln Ser Pro Ile Ala Phe Gln Gly Ile Leu Asn Asn Ile Gly Pro
            20                  25                  30

Ser Gly Ala Tyr Ser Glu Gly Val Asn Pro Gly Val Val Ile Ala Ser
        35                  40                  45

Pro Ser Lys Gln Asp Pro Asp Tyr Phe Tyr Thr Trp Val Arg Asp Ala
50                  55                  60

Ala Leu Thr Val Gln Tyr Leu Val Glu Glu Leu Val Ala Gly Asn Ala
65                  70                  75                  80

Ser Leu Gln Phe Leu Ile Gln Asp Tyr Ile Ser Ser Gln Ala Arg Leu
                85                  90                  95

Gln Thr Val Glu Asn Pro Ser Gly Ser Leu Ser Ser Gly Gly Leu Gly
            100                 105                 110

Glu Pro Lys Phe His Val Asp Glu Thr Ala Phe Thr Asp Ser Trp Gly
            115                 120                 125

Arg Pro Gln Arg Asp Gly Pro Pro Leu Arg Ala Ile Ala Met Ile Ser
    130                 135                 140

Phe Ala Asn Tyr Leu Ile Asp Asn Gly His Gln Ser Thr Val Glu Asp
145                 150                 155                 160

Ile Ile Trp Pro Ile Gly Arg Asn Asp Leu Ser Tyr Val Ser Gln His
                165                 170                 175

Trp Asn Glu Thr Thr Phe Asp Ile Trp Glu Glu Val His Ser Ser Ser
            180                 185                 190

Phe Phe Thr Thr Ala Val Gln Tyr Arg Ala Leu Val Gln Gly Ser Ala
            195                 200                 205

Leu Ala Ser Lys Leu Gly His Thr Cys Asp Asn Cys Gly Ser Gln Ala
    210                 215                 220

Pro Gln Ile Leu Cys Phe Leu Gln Ser Tyr Trp Thr Gly Ser His Ile
225                 230                 235                 240

Leu Ala Asn Thr Gly Gly Gly Arg Ser Gly Lys Asp Val Ser Thr Ile
                245                 250                 255

Leu Gly Val Ile Gly Ser Phe Asp Pro Asn Ala Asp Cys Asp Asp Val
            260                 265                 270

Thr Phe Gln Pro Cys Ser Ala Arg Ala Leu Ala Asn His Lys Gln Val
        275                 280                 285

Val Asp Ser Phe Arg Ser Ile Tyr Ala Ile Asn Ala Gly Ile Pro Ser
    290                 295                 300

Gly Ser Ala Val Ala Val Gly Arg Tyr Pro Glu Asp Val Tyr Gln Gly
305                 310                 315                 320

Gly His Pro Trp Tyr Leu Thr Thr Ala Ala Ala Ala Glu Gln Leu Tyr
                325                 330                 335

Asp Ala Ile Tyr Gln Trp Asn His Val Gly His Ile Asp Ile Asn Ala
            340                 345                 350

Val Asn Leu Asp Phe Phe Lys Ser Ile Tyr Pro Ser Ala Ala Glu Gly
        355                 360                 365

Thr Tyr Thr Ser Asp Ser Ser Thr Phe Gln Asp Ile Ile Ser Ala Val
    370                 375                 380

Arg Thr Tyr Ala Asp Gly Phe Leu Ser Val Ile Glu Lys Tyr Thr Pro
385                 390                 395                 400

Pro Asp Asn Leu Leu Ala Glu Gln Phe His Arg Glu Thr Gly Ile Pro
                405                 410                 415

Leu Ser Ala Ala Ser Leu Thr Trp Ser Tyr Ala Ala Leu Asn Thr Ala
```

```
              420                 425                 430
Ala Gln Arg Arg Ala Ser Ile Val Pro Ser Pro Trp Asn Ser Asn Ser
            435                 440                 445

Thr Asp Leu Pro Asp Lys Cys Ser Ala Thr Ser Ala Thr Gly Pro Tyr
450                 455                 460

Ala Thr Pro Thr Asn Thr Ala Trp Pro Thr Thr Thr Gln Pro Pro Glu
465                 470                 475                 480

Arg Pro Ala Cys Thr Pro Pro Ser Glu Val Thr Leu Thr Phe Asn Ala
            485                 490                 495

Leu Val Asp Thr Ala Phe Gly Gln Asn Ile Tyr Leu Val Gly Ser Ile
            500                 505                 510

Pro Glu Leu Gly Ser Trp Asp Pro Ala Asn Ala Leu Leu Met Ser Ala
            515                 520                 525

Lys Ser Trp Thr Ser Gly Asn Pro Val Trp Thr Leu Ser Ile Ser Leu
            530                 535                 540

Pro Ala Gly Thr Ser Phe Glu Tyr Lys Phe Ile Arg Lys Asp Asp Gly
545                 550                 555                 560

Ser Ser Asp Val Val Trp Glu Ser Asp Pro Asn Arg Ser Tyr Asn Val
            565                 570                 575

Pro Lys Asp Cys Gly Ala Asn Thr Ala Thr Val Asn Ser Trp Trp Arg
            580                 585                 590

<210> SEQ ID NO 2
<211> LENGTH: 475
<212> TYPE: PRT
<213> ORGANISM: Lypomycis kononenkoae
<220> FEATURE:
<221> NAME/KEY: misc_feature
<223> OTHER INFORMATION: 2_SEQ ID NO 2 Mature protein sequence of the
      synthetic alpha-amylase gene sequence of Lypomycis kononenkoae

<400> SEQUENCE: 2

Thr Ala Ala Glu Trp Lys Glu Leu Ser Ile Tyr Gln Val Ile Thr Asp
1               5                   10                  15

Arg Phe Ala Thr Thr Asn Leu Thr Ala Pro Asp Cys Trp Ile Arg Ala
                20                  25                  30

Tyr Cys Gly Gly Thr Trp Lys Gly Leu Glu Arg Lys Leu Asp Tyr Ile
            35                  40                  45

Gln Asn Met Gly Phe Asp Ala Val Trp Ile Ser Pro Val Ile His Asn
        50                  55                  60

Ile Glu Val Asn Thr Thr Trp Gly Phe Ala Phe His Gly Tyr Trp Gly
65                  70                  75                  80

Asp Asp Pro Tyr Arg Leu Asn Glu His Phe Gly Thr Ala Ala Asp Leu
                85                  90                  95

Lys Ser Leu Ser Asp Ser Leu His Ala Arg Gly Met Ser Leu Met Val
            100                 105                 110

Asp Val Val Ile Asn His Leu Ala Ser Tyr Thr Leu Pro Gln Asp Val
            115                 120                 125

Asp Tyr Ser Leu Tyr Pro Ala Pro Phe Asn Thr Ser Ser Ala Phe His
        130                 135                 140

Gln Pro Cys Pro Ile Asp Phe Ser Asn Gln Ser Ser Ile Glu Asp Cys
145                 150                 155                 160

Trp Leu Val Thr Glu Pro Ala Pro Ala Leu Val Asp Leu Lys Asn Glu
                165                 170                 175

Asp Gln Val Ile Leu Asp Ala Leu Ile Asn Ser Val Val Asp Leu Val
            180                 185                 190
```

Glu Thr Tyr Asp Ile Asp Gly Ile Arg Leu Asp Thr Ala Arg His Val
            195                 200                 205

Pro Lys Pro Ser Leu Ala Lys Phe Gln Glu Lys Val Gly Val Phe Val
            210                 215                 220

Thr Gly Glu Ala Leu Asn Gln Ser Val Pro Tyr Val Ala Gln Tyr Gln
225                 230                 235                 240

Gly Pro Leu Asn Ser Ala Ile Asn Tyr Pro Leu Trp Tyr Ala Leu Val
            245                 250                 255

Asp Ser Phe Met Gly Arg Thr Thr Phe Asp Tyr Leu Glu Ser Val Val
            260                 265                 270

Lys Ser Glu Gln Ala Thr Phe Ser Asp Ala His Ala Leu Thr Asn Phe
            275                 280                 285

Leu Asp Asn Gln Asp Gln Pro Arg Phe Ala Ser Tyr Leu Gly Asp Gly
            290                 295                 300

Asn Gly Asp Asp Val Leu Arg Asp Glu Asn Ala Ala Thr Phe Leu Phe
305                 310                 315                 320

Phe Val Ser Gly Ile Pro Val Ile Tyr Tyr Gly Phe Glu Gln Arg Phe
            325                 330                 335

Asp Gly Gly Phe Asp Pro Val Asn Arg Glu Pro Met Trp Thr Ser Gly
            340                 345                 350

Tyr Asn Thr Ser Thr Pro Leu Tyr Asn Tyr Leu Ala Arg Leu Asn Ala
            355                 360                 365

Ile Arg Lys Tyr Ala Ala Ser Ile Thr Gly Thr Gln Val Phe Tyr Ser
            370                 375                 380

Asp Asp Thr Val Phe Leu Gly Ser Gly Val Ser His Met Ala Met Gln
385                 390                 395                 400

Arg Gly Pro Leu Val Ile Val Leu Thr Asn Val Gly Gln His Ile Ile
            405                 410                 415

Asp Asn Thr Gly Tyr Thr Val Thr Gly Ser Gln Phe Ser Ala Gly Asp
            420                 425                 430

Ser Leu Thr Asp Leu Val Ser Cys Thr Lys Val Lys Val Val Gly Ala
            435                 440                 445

Asn Gly Thr Phe Thr Ser Pro Ser Asn Gly Gly Lys Ala Arg Ile Trp
            450                 455                 460

Ile Lys Ser Lys Tyr Ala Gly Lys Phe Cys Ser
465                 470                 475

<210> SEQ ID NO 3
<211> LENGTH: 468
<212> TYPE: PRT
<213> ORGANISM: Saccharomycopsis fibuligera
<220> FEATURE:
<221> NAME/KEY: misc_feature
<223> OTHER INFORMATION: 3_SEQ ID NO 3 Mature protein sequence of the
      synthetic alpha-amylase gene sequence of Saccharomycopsis
      fibuligera

<400> SEQUENCE: 3

Glu Thr Asn Ala Asp Lys Trp Arg Ser Gln Ser Ile Tyr Gln Ile Val
1               5                   10                  15

Thr Asp Arg Phe Ala Arg Thr Asp Gly Asp Thr Ser Ala Ser Cys Asn
            20                  25                  30

Thr Glu Asp Arg Leu Tyr Cys Gly Gly Ser Phe Gln Gly Ile Ile Lys
            35                  40                  45

Lys Leu Asp Tyr Ile Lys Asp Met Gly Phe Thr Ala Ile Trp Ile Ser
            50                  55                  60

```
Pro Val Glu Asn Ile Pro Asp Asn Thr Ala Tyr Gly Tyr Ala Tyr
 65                  70                  75                  80

His Gly Tyr Trp Met Lys Asn Ile Tyr Lys Ile Asn Glu Asn Phe Gly
                 85                  90                  95

Thr Ala Asp Asp Leu Lys Ser Leu Ala Gln Glu Leu His Asp Arg Asp
                100                 105                 110

Met Leu Leu Met Val Asp Ile Val Thr Asn His Tyr Gly Ser Asp Gly
            115                 120                 125

Ser Gly Asp Ser Ile Asp Tyr Ser Glu Tyr Thr Pro Phe Asn Asp Gln
        130                 135                 140

Lys Tyr Phe His Asn Tyr Cys Leu Ile Ser Asn Tyr Asp Gln Ala
145                 150                 155                 160

Gln Val Gln Ser Cys Trp Glu Gly Asp Ser Ser Val Ala Leu Pro Asp
                165                 170                 175

Leu Arg Thr Glu Asp Ser Asp Val Ala Ser Val Phe Asn Ser Trp Val
            180                 185                 190

Lys Asp Phe Val Gly Asn Tyr Ser Ile Asp Gly Leu Arg Ile Asp Ser
        195                 200                 205

Ala Lys His Val Asp Gln Gly Phe Phe Pro Asp Phe Val Ser Ala Ser
210                 215                 220

Gly Val Tyr Ser Val Gly Glu Val Phe Gln Gly Asp Pro Ala Tyr Thr
225                 230                 235                 240

Cys Pro Tyr Gln Asn Tyr Ile Pro Gly Val Ser Asn Tyr Pro Leu Tyr
                245                 250                 255

Tyr Pro Thr Thr Arg Phe Phe Lys Thr Thr Asp Ser Ser Ser Ser Glu
            260                 265                 270

Leu Thr Gln Met Ile Ser Ser Val Ala Ser Ser Cys Ser Asp Pro Thr
        275                 280                 285

Leu Leu Thr Asn Phe Val Glu Asn His Asp Asn Glu Arg Phe Ala Ser
290                 295                 300

Met Thr Ser Asp Gln Ser Leu Ile Ser Asn Ala Ile Ala Phe Val Leu
305                 310                 315                 320

Leu Gly Asp Gly Ile Pro Val Ile Tyr Tyr Gly Gln Glu Gln Gly Leu
                325                 330                 335

Ser Gly Lys Ser Asp Pro Asn Asn Arg Glu Ala Leu Trp Leu Ser Gly
            340                 345                 350

Tyr Asn Lys Glu Ser Asp Tyr Tyr Lys Leu Ile Ala Lys Ala Asn Ala
        355                 360                 365

Ala Arg Asn Ala Ala Val Tyr Gln Asp Ser Ser Tyr Ala Thr Ser Gln
370                 375                 380

Leu Ser Val Ile Phe Ser Asn Asp His Val Ile Ala Thr Lys Arg Gly
385                 390                 395                 400

Ser Val Val Ser Val Phe Asn Asn Leu Gly Ser Ser Gly Ser Ser Asp
                405                 410                 415

Val Thr Ile Ser Asn Thr Gly Tyr Ser Ser Gly Glu Asp Leu Val Glu
            420                 425                 430

Val Leu Thr Cys Ser Thr Val Ser Gly Ser Ser Asp Leu Gln Val Ser
        435                 440                 445

Ile Gln Gly Gly Gln Pro Gln Ile Phe Val Pro Ala Lys Tyr Ala Ser
450                 455                 460

Asp Ile Cys Ser
465
```

<210> SEQ ID NO 4
<211> LENGTH: 1954
<212> TYPE: DNA
<213> ORGANISM: Aspergillus awamorii
<220> FEATURE:
<221> NAME/KEY: misc_feature
<223> OTHER INFORMATION: 4_sGA gene sequence of A. awamori

<400> SEQUENCE: 4

| | | | | | | |
|---|---|---|---|---|---|---|
| gaattccaac | atggtttcct | tcacttcttt | gttggccggt | gtcgctgcca | tttctggtgt | 60 |
| cttggctgct | ccagctgctg | aagttgaacc | agttgccgtc | gaaaagagaa | ctttggattc | 120 |
| ctggttgtct | aacgaagcca | ctgttgctag | aactgctatt | ttgaacaaca | tcggtgccga | 180 |
| cggtgcttgg | gtttccggtg | ctgactccgg | tattgttgtt | gcttccccat | ccaccgataa | 240 |
| cccagactac | ttctacacct | ggactagaga | ctccggtttg | gtcattaaga | ctttggttga | 300 |
| cttgttcaga | aacggtgata | ctgacttgtt | gtctaccatt | gaacactaca | tttcttccca | 360 |
| agctatcatc | caaggtgttt | ccaacccatc | tggtgacttg | tcttccggtg | gtttgggtga | 420 |
| accaaagttc | aacgtcgatg | aaaccgctta | cactggttct | ggggtagac | acaaagaga | 480 |
| tggtccagcc | ttgagagcta | ctgccatgat | cggtttcggt | caatggttgt | tggataacgg | 540 |
| ttacacttcc | gctgctaccg | aaatcgtttg | gccattggtt | agaaacgact | tgtcctacgt | 600 |
| cgctcaatac | tggaaccaaa | ccggttacga | cttgtgggaa | gaagttaacg | ttcttcttt | 660 |
| cttcaccatc | gccgtccaac | acagagcctt | ggttgaaggt | tccgctttcg | ctaccgctgt | 720 |
| cggttcctct | tgttcctggt | gtgattctca | agctccacaa | atcttgtgtt | acttgcaatc | 780 |
| tttctggacc | ggttcttaca | tcttggctaa | cttcgattcc | tctagatccg | gtaaggacac | 840 |
| caacactttg | ttgggttcta | tccacacctt | cgatccagaa | gctggttgtg | acgactctac | 900 |
| tttccaacca | tgttctccaa | gagctttggc | taaccacaag | gaagtcgttg | actctttcag | 960 |
| atccatctac | accttgaacg | acggtttgtc | cgattctgaa | gctgttgctg | tcggtagata | 1020 |
| cccagaagat | tcctactaca | acggtaaccc | atggttcttg | tgtactttgg | ctgctgctga | 1080 |
| acaattgtac | gacgctttgt | accaatggga | taagcaaggt | tccttggaaa | ttactgacgt | 1140 |
| ctccttggac | ttcttcaagg | ctttgtactc | tggtgctgct | actggtactt | actcctcttc | 1200 |
| ctcttctacc | tactcctcca | ttgtttccgc | tgttaagacc | ttcgctgatg | gtttcgtttc | 1260 |
| tatcgtcgaa | acccacgctg | cttccaacgg | ttccttgtcc | gaacaattcg | acaagtctga | 1320 |
| cggtgatgaa | ttgtctgcta | gagacttgac | ctggtcttac | gctgctttgt | tgaccgctaa | 1380 |
| caacagaaga | aactctgttg | ttccaccatc | ttggggtgaa | acttccgctt | cttccgttcc | 1440 |
| aggtacttgt | gctgccactt | ctgcttccgg | tacttactct | tccgtcactg | ttacctcctg | 1500 |
| gccatccatc | gtcgctaccg | gtggtactac | cactactgct | actaccaccg | ttctggtgg | 1560 |
| tgtcacctcc | acttccaaga | ccaccaccac | tgcttctaag | acctccacca | ctacttcttc | 1620 |
| cacttcttgt | accaccccaa | ctgctgttgc | cgtcactttc | gatttgactg | ccactaccac | 1680 |
| ctacggtgaa | aacatttact | tggtcggttc | catttctcaa | ttgggtgact | gggaaacctc | 1740 |
| cgacggtatc | gctttgtctg | ccgacaagta | caccctcttct | aacccattgt | ggtacgttac | 1800 |
| tgttactttg | ccagctggtg | aatctttcga | atacaagttc | atcagagttg | aatctgatga | 1860 |
| ttctgttgaa | tgggaatctg | acccaaacag | agaatacacc | gttccacaag | cctgtggtga | 1920 |
| atccaccgct | accgttactg | acacctggag | ataa | | | 1954 |

<210> SEQ ID NO 5

```
<211> LENGTH: 647
<212> TYPE: PRT
<213> ORGANISM: Aspergillus awamorii
<220> FEATURE:
<221> NAME/KEY: misc_feature
<223> OTHER INFORMATION: 5_Predicted protein sequence of the sGA gene
      sequence of A. awamori

<400> SEQUENCE: 5

Met Val Ser Phe Thr Ser Leu Leu Ala Gly Val Ala Ala Ile Ser Gly
1               5                   10                  15

Val Leu Ala Ala Pro Ala Ala Glu Val Glu Pro Val Ala Val Glu Lys
            20                  25                  30

Arg Thr Leu Asp Ser Trp Leu Ser Asn Glu Ala Thr Val Ala Arg Thr
        35                  40                  45

Ala Ile Leu Asn Asn Ile Gly Ala Asp Gly Ala Trp Val Ser Gly Ala
    50                  55                  60

Asp Ser Gly Ile Val Val Ala Ser Pro Ser Thr Asp Asn Pro Asp Tyr
65                  70                  75                  80

Phe Tyr Thr Trp Thr Arg Asp Ser Gly Leu Val Ile Lys Thr Leu Val
                85                  90                  95

Asp Leu Phe Arg Asn Gly Asp Thr Asp Leu Leu Ser Thr Ile Glu His
            100                 105                 110

Tyr Ile Ser Ser Gln Ala Ile Ile Gln Gly Val Ser Asn Pro Ser Gly
        115                 120                 125

Asp Leu Ser Ser Gly Gly Leu Gly Glu Pro Lys Phe Asn Val Asp Glu
    130                 135                 140

Thr Ala Tyr Thr Gly Ser Trp Gly Arg Pro Gln Arg Asp Gly Pro Ala
145                 150                 155                 160

Leu Arg Ala Thr Ala Met Ile Gly Phe Gly Gln Trp Leu Leu Asp Asn
                165                 170                 175

Gly Tyr Thr Ser Ala Ala Thr Glu Ile Val Trp Pro Leu Val Arg Asn
            180                 185                 190

Asp Leu Ser Tyr Val Ala Gln Tyr Trp Asn Gln Thr Gly Tyr Asp Leu
        195                 200                 205

Trp Glu Glu Val Asn Gly Ser Ser Phe Phe Thr Ile Ala Val Gln His
    210                 215                 220

Arg Ala Leu Val Glu Gly Ser Ala Phe Ala Thr Ala Val Gly Ser Ser
225                 230                 235                 240

Cys Ser Trp Cys Asp Ser Gln Ala Pro Gln Ile Leu Cys Tyr Leu Gln
                245                 250                 255

Ser Phe Trp Thr Gly Ser Tyr Ile Leu Ala Asn Phe Asp Ser Ser Arg
            260                 265                 270

Ser Gly Lys Asp Thr Asn Thr Leu Leu Gly Ser Ile His Thr Phe Asp
        275                 280                 285

Pro Glu Ala Gly Cys Asp Asp Ser Thr Phe Gln Pro Cys Ser Pro Arg
    290                 295                 300

Ala Leu Ala Asn His Lys Glu Val Val Asp Ser Phe Arg Ser Ile Tyr
305                 310                 315                 320

Thr Leu Asn Asp Gly Leu Ser Asp Ser Glu Ala Val Ala Val Gly Arg
                325                 330                 335

Tyr Pro Glu Asp Ser Tyr Tyr Asn Gly Asn Pro Trp Phe Leu Cys Thr
            340                 345                 350

Leu Ala Ala Ala Glu Gln Leu Tyr Asp Ala Leu Tyr Gln Trp Asp Lys
        355                 360                 365
```

Gln Gly Ser Leu Glu Ile Thr Asp Val Ser Leu Asp Phe Phe Lys Ala
    370                 375                 380

Leu Tyr Ser Gly Ala Ala Thr Gly Thr Tyr Ser Ser Ser Ser Ser Thr
385                 390                 395                 400

Tyr Ser Ser Ile Val Ser Ala Val Lys Thr Phe Ala Asp Gly Phe Val
                405                 410                 415

Ser Ile Val Glu Thr His Ala Ala Ser Asn Gly Ser Leu Ser Glu Gln
            420                 425                 430

Phe Asp Lys Ser Asp Gly Asp Glu Leu Ser Ala Arg Asp Leu Thr Trp
        435                 440                 445

Ser Tyr Ala Ala Leu Leu Thr Ala Asn Asn Arg Arg Asn Ser Val Val
450                 455                 460

Pro Pro Ser Trp Gly Glu Thr Ala Ser Ser Val Pro Gly Thr Cys
465                 470                 475                 480

Ala Ala Thr Ser Ala Ser Gly Thr Tyr Ser Ser Val Thr Val Thr Ser
                485                 490                 495

Trp Pro Ser Ile Val Ala Thr Gly Gly Thr Thr Thr Ala Thr Thr
            500                 505                 510

Thr Gly Ser Gly Gly Val Thr Ser Thr Ser Lys Thr Thr Thr Thr Ala
            515                 520                 525

Ser Lys Thr Ser Thr Thr Thr Ser Ser Thr Ser Cys Thr Thr Pro Thr
    530                 535                 540

Ala Val Ala Val Thr Phe Asp Leu Thr Ala Thr Thr Thr Tyr Gly Glu
545                 550                 555                 560

Asn Ile Tyr Leu Val Gly Ser Ile Ser Gln Leu Gly Asp Trp Glu Thr
                565                 570                 575

Ser Asp Gly Ile Ala Leu Ser Ala Asp Lys Tyr Thr Ser Ser Asn Pro
            580                 585                 590

Leu Trp Tyr Val Thr Val Thr Leu Pro Ala Gly Glu Ser Phe Glu Tyr
        595                 600                 605

Lys Phe Ile Arg Val Glu Ser Asp Asp Ser Val Glu Trp Glu Ser Asp
610                 615                 620

Pro Asn Arg Glu Tyr Thr Val Pro Gln Ala Cys Gly Glu Ser Thr Ala
625                 630                 635                 640

Thr Val Thr Asp Thr Trp Arg
                645

<210> SEQ ID NO 6
<211> LENGTH: 1975
<212> TYPE: DNA
<213> ORGANISM: Aspergillus awamorii
<220> FEATURE:
<221> NAME/KEY: misc_feature
<223> OTHER INFORMATION: 6_sAMYL III gene sequence of A. awamori

<400> SEQUENCE: 6
aggcctgaat tccaacatgg tttccttcac ctccttgttg gccggtgtcg ctgctatctc     60
cggtgtcttg gctgctccag ctgctgaagt tgaaccagtc gctgtcgaaa agagattgtc    120
tgccgctgaa tggagaactc aatctatcta cttcttgttg accgacagat cggtagaac    180 tgataactct accaccgcca cctgtaacac cggtgaccaa atctactgtg gtggttcctg    240
gcaaggtatc atcaaccact ggactacat tcaaggtatg ggtttcactg ctatctggat    300
ctctccaatt actgaacaat tgccacaaga tacctctgac ggtgaagcct accacgtta    360 ctggcaacaa aagatttaca acgtcaactc caacttcggt actgctgatg acttgaagtc    420

```
tttgtctgac gctttgcacg ccagaggtat gtacttgatg gttgacgtcg tcccaaacca      480
catgggttac gccggtaacg gtaacgacgt tgactactcc gttttcgacc cattcgattc      540
ttcctcctac ttccacccat actgtttgat taccgactgg gacaacttga ctatggtcca      600
agactgttgg gaaggtgata ctattgtctc cttgccagac ttgaacacca ctgaaactgc      660
tgtcagaacc atctggtacg attgggtcgc tgacttggtt ccaactact  ctgttgatgg      720
tttgagaatt gactccgtcg aagaagtcga accagatttc ttcccaggtt accaagaagc      780
tgccggtgtt tactgtgtcg gtaagttga  caacggtaac ccagctttgg attgtccata      840
ccaaaagtac ttggacggtg ttttgaacta cccaatttac tggcaattgt tgtacgcttt      900
cgaatcctct tctggttcta tctccaactt gtacaacatg attaagtccg ttgcctccga      960
ctgttctgat ccaaccttgt tgggtaactt cattgaaaac cacgacaacc caagattcgc     1020
ttcttacact tccgactact ctcaagctaa gaacgtcttg tcttacatct tcttgtctga     1080
tggtatccca atcgtttacg ctggtgaaga caacactac  tctggtggtg acgttccata     1140
caacagagaa gctacttggt tgtccggtta cgacacctcc gctgaattgt acacttggat     1200
cgctactacc aacgccatca gaaagttggc catctccgct gattctgact acatcactta     1260
cgctaacgac ccaatctaca ccgattctaa cactatcgcc atgagaaagg gtacttccgg     1320
ttctcaaatt atcaccgtct gtccaacaa  gggttcctct ggttcttcct acaccttgac     1380
tttgtccggt tctggttaca cctctggtac taagttgatc gaagcctaca cctgtacttc     1440
tgttactgtt gactctaacg gtgacattcc agtcccaatg gcttctggtt tgccaagagt     1500
tttgccacca gcttctgttg tcgactcttc ttctttgtgt ggtggttctg gtaacactac     1560
cactactact accgctgcta cttctacttc taaggccact acctcttcct cctcctcttc     1620
tgctgctgct accacttctt cctcctgtac tgccacctct actaccttgc caattacttt     1680
cgaagaattg gttaccacta cttacggtga agaagtttac ttgtctggtt ccatctctca     1740
attgggtgaa tgggatacct ccgacgctgt taagttgtct gctgacgatt acacctcctc     1800
taacccagaa tggtctgtca ctgtttcttt gccagttggt actaccttcg aatacaagtt     1860
cattaaggtt gatgaaggtg ttctgtcac  ctgggaatct gacccaaaca gagaatacac     1920
tgttccagaa tgtggttccg gttccggtga aactgtcgtc gacacttgga gataa          1975
```

<210> SEQ ID NO 7
<211> LENGTH: 652
<212> TYPE: PRT
<213> ORGANISM: Aspergillus awamorii
<220> FEATURE:
<221> NAME/KEY: misc_feature
<223> OTHER INFORMATION: 7_Predicted protein sequence of the sAMYL III
      gene sequence of A. awamori

<400> SEQUENCE: 7

```
Met Val Ser Phe Thr Ser Leu Leu Ala Gly Val Ala Ala Ile Ser Gly
1               5                   10                  15

Val Leu Ala Ala Pro Ala Ala Glu Val Glu Pro Val Ala Val Glu Lys
            20                  25                  30

Arg Leu Ser Ala Ala Glu Trp Arg Thr Gln Ser Ile Tyr Phe Leu Leu
        35                  40                  45

Thr Asp Arg Phe Gly Arg Thr Asp Asn Ser Thr Thr Ala Thr Cys Asn
    50                  55                  60

Thr Gly Asp Gln Ile Tyr Cys Gly Gly Ser Trp Gln Gly Ile Ile Asn
65                  70                  75                  80
```

```
His Leu Asp Tyr Ile Gln Gly Met Gly Phe Thr Ala Ile Trp Ile Ser
                85                  90                  95
Pro Ile Thr Glu Gln Leu Pro Gln Asp Thr Ser Asp Gly Glu Ala Tyr
            100                 105                 110
His Gly Tyr Trp Gln Gln Lys Ile Tyr Asn Val Asn Ser Asn Phe Gly
        115                 120                 125
Thr Ala Asp Asp Leu Lys Ser Leu Ser Asp Ala Leu His Ala Arg Gly
    130                 135                 140
Met Tyr Leu Met Val Asp Val Val Pro Asn His Met Gly Tyr Ala Gly
145                 150                 155                 160
Asn Gly Asn Asp Val Asp Tyr Ser Val Phe Asp Pro Phe Asp Ser Ser
                165                 170                 175
Ser Tyr Phe His Pro Tyr Cys Leu Ile Thr Asp Trp Asp Asn Leu Thr
            180                 185                 190
Met Val Gln Asp Cys Trp Glu Gly Asp Thr Ile Val Ser Leu Pro Asp
        195                 200                 205
Leu Asn Thr Thr Glu Thr Ala Val Arg Thr Ile Trp Tyr Asp Trp Val
    210                 215                 220
Ala Asp Leu Val Ser Asn Tyr Ser Val Asp Gly Leu Arg Ile Asp Ser
225                 230                 235                 240
Val Glu Glu Val Glu Pro Asp Phe Phe Pro Gly Tyr Gln Glu Ala Ala
                245                 250                 255
Gly Val Tyr Cys Val Gly Glu Val Asp Asn Gly Asn Pro Ala Leu Asp
            260                 265                 270
Cys Pro Tyr Gln Lys Tyr Leu Asp Gly Val Leu Asn Tyr Pro Ile Tyr
        275                 280                 285
Trp Gln Leu Leu Tyr Ala Phe Glu Ser Ser Gly Ser Ile Ser Asn
    290                 295                 300
Leu Tyr Asn Met Ile Lys Ser Val Ala Ser Asp Cys Ser Asp Pro Thr
305                 310                 315                 320
Leu Leu Gly Asn Phe Ile Glu Asn His Asp Asn Pro Arg Phe Ala Ser
                325                 330                 335
Tyr Thr Ser Asp Tyr Ser Gln Ala Lys Asn Val Leu Ser Tyr Ile Phe
            340                 345                 350
Leu Ser Asp Gly Ile Pro Ile Val Tyr Ala Gly Glu Glu Gln His Tyr
        355                 360                 365
Ser Gly Gly Asp Val Pro Tyr Asn Arg Glu Ala Thr Trp Leu Ser Gly
    370                 375                 380
Tyr Asp Thr Ser Ala Glu Leu Tyr Thr Trp Ile Ala Thr Thr Asn Ala
385                 390                 395                 400
Ile Arg Lys Leu Ala Ile Ser Ala Asp Ser Asp Tyr Ile Thr Tyr Ala
                405                 410                 415
Asn Asp Pro Ile Tyr Thr Asp Ser Asn Thr Ile Ala Met Arg Lys Gly
            420                 425                 430
Thr Ser Gly Ser Gln Ile Ile Thr Val Leu Ser Asn Lys Gly Ser Ser
        435                 440                 445
Gly Ser Ser Tyr Thr Leu Thr Leu Ser Gly Ser Gly Tyr Thr Ser Gly
    450                 455                 460
Thr Lys Leu Ile Glu Ala Tyr Thr Cys Thr Ser Val Thr Val Asp Ser
465                 470                 475                 480
Asn Gly Asp Ile Pro Val Pro Met Ala Ser Gly Leu Pro Arg Val Leu
                485                 490                 495
Pro Pro Ala Ser Val Val Asp Ser Ser Ser Leu Cys Gly Gly Ser Gly
```

|  |  |  | 500 |  |  |  |  | 505 |  |  |  | 510 |  |  |
|---|---|---|---|---|---|---|---|---|---|---|---|---|---|---|
| Asn | Thr | Thr | Thr | Thr | Thr | Thr | Ala | Ala | Thr | Ser | Thr | Ser | Lys | Ala | Thr |
|  |  |  | 515 |  |  |  |  | 520 |  |  |  | 525 |  |  |
| Thr | Ser | Ser | Ser | Ser | Ser | Ala | Ala | Ala | Thr | Thr | Ser | Ser | Ser | Cys |
|  |  | 530 |  |  |  |  | 535 |  |  |  | 540 |  |  |  |
| Thr | Ala | Thr | Ser | Thr | Thr | Leu | Pro | Ile | Thr | Phe | Glu | Glu | Leu | Val | Thr |
| 545 |  |  |  |  | 550 |  |  |  |  | 555 |  |  |  |  | 560 |
| Thr | Thr | Tyr | Gly | Glu | Glu | Val | Tyr | Leu | Ser | Gly | Ser | Ile | Ser | Gln | Leu |
|  |  |  | 565 |  |  |  |  | 570 |  |  |  |  | 575 |  |  |
| Gly | Glu | Trp | Asp | Thr | Ser | Asp | Ala | Val | Lys | Leu | Ser | Ala | Asp | Asp | Tyr |
|  |  |  | 580 |  |  |  |  | 585 |  |  |  | 590 |  |  |
| Thr | Ser | Ser | Asn | Pro | Glu | Trp | Ser | Val | Thr | Val | Ser | Leu | Pro | Val | Gly |
|  |  | 595 |  |  |  |  | 600 |  |  |  | 605 |  |  |  |
| Thr | Thr | Phe | Glu | Tyr | Lys | Phe | Ile | Lys | Val | Asp | Glu | Gly | Gly | Ser | Val |
|  |  | 610 |  |  |  |  | 615 |  |  |  | 620 |  |  |  |
| Thr | Trp | Glu | Ser | Asp | Pro | Asn | Arg | Glu | Tyr | Thr | Val | Pro | Glu | Cys | Gly |
| 625 |  |  |  |  | 630 |  |  |  |  | 635 |  |  |  |  | 640 |
| Ser | Gly | Ser | Gly | Glu | Thr | Val | Val | Asp | Thr | Trp | Arg |  |  |  |  |
|  |  |  | 645 |  |  |  |  | 650 |  |  |  |  |  |  |  |

<210> SEQ ID NO 8
<211> LENGTH: 1914
<212> TYPE: DNA
<213> ORGANISM: Thermomyces lanuginosus
<220> FEATURE:
<221> NAME/KEY: misc_feature
<223> OTHER INFORMATION: 8_Synthetic glucoamylase gene sequence of
      Thermomyces lanuginoses

<400> SEQUENCE: 8

```
ggtaccgaat tcaggcctgg atccttaatt aaaaatgttg ttccaaccaa ctttgtgtgc    60
tgctttgggt ttggctgctt tgattgttca aggtggtgaa gctagaccag aaactactgt   120
tccacatgct actggttctt tggatgattt tttggctgct caatctccaa ttgcttttca   180
aggtattttg aacaatattg gtccatctgg tgcttattct gaaggtgtta atccaggtgt   240
tgttattgct tctccatcta acaagatcc agattacttt tacacttggg ttagagatgc    300
tgctttaact gttcaatact ggttgaaga attggttgct ggtaatgctt ctttgcaatt   360
cttgattcaa gattacattt cttcacaagc tagattgcaa actgttgaaa tccatctgg   420
ttctttgtca tctggtggtt tgggtgaacc aaaatttcat gttgatgaaa ctgcttttac   480
tgattcttgg ggaaggccac aaagagatgg tccaccattg agagctattg ctatgatttc   540
tttcgctaac tacttgattg ataacggtca tcaatctact gttgaggaca tcatttggcc   600
aattggtaga aatgatttgt cttacgtttc tcaacattgg aatgaaacta ctttcgatat   660
ttgggaagaa gttcattctt cttcattttt cactactgct gttcaatata gagctttggt   720
tcaaggttct gctttggctt ctaaattggg tcatacttgt gataattgtg ttctctcaagc   780
tccacaaatt ttgtgtttct tgcaatctta ttggactggt tctcatattt tggctaatac   840
tggtggtggt agatcaggta agatgtttc tactatttg ggtgttattg gttcttttga    900
tccaaatgct gattgtgatg atgttacttt tcaaccatgt tctgctagag ctttggctaa   960
tcataaacaa gttgttgatt ctttcagatc aatttacgct attaatgctg gtattccatc   1020
aggttctgct gttgctgttg gaagataccc tgaagatgtt tatcaaggtg tcatccatg    1080
gtatttgact actgctgctg ctgcagaaca attgtatgat gcaatttacc aatggaatca   1140
```

-continued

```
tgttggtcat attgatatta acgctgttaa cttggatttt ttcaagtcaa tttatccatc   1200
tgctgctgaa ggtacttata cttctgattc ttctactttc caagacatca tttctgctgt   1260
tagaacttat gctgatggtt tcttgtctgt tattgaaaaa tacactccac cagataattt   1320
gttggctgaa caatttcata gagaaacagg tattccattg tctgctgctt cattgacttg   1380
gtcttatgct gctttgaata cagctgctca agaagagct tctattgttc catctccatg    1440
gaactctaat tctactgatt tgccagataa atgttctgct acatctgcta ctggtccata   1500
tgctacacca actaatactg cttggccaac tactactcaa ccaccagaaa gaccagcttg   1560
tactccacca tctgaagtta ctttgacttt taacgctttg gttgatactg cttttggtca   1620
aaacatttac ttggttggtt ctattccaga attgggttct gggacccag ctaatgcttt    1680
gttgatgtct gctaaatctt ggacttctgg taatccagtt tggactttgt ctatttcttt   1740
gccagctggt acttcttttg aatacaagtt cattagaaag gatgatggtt cttctgatgt   1800
tgtttgggaa tctgatccaa atagatcata caatgttcca aaagattgtg gtgctaatac   1860
tgctactgtt aattcttggt ggagataata aggcgcgcca gatctctcga gctc         1914
```

<210> SEQ ID NO 9
<211> LENGTH: 617
<212> TYPE: PRT
<213> ORGANISM: Thermomyces lanuginosus
<220> FEATURE:
<221> NAME/KEY: misc_feature
<223> OTHER INFORMATION: 9_Protein sequence of the synthetic
      glucoamylase gene sequence of Thermomyces lanuginoses

<400> SEQUENCE: 9

```
Met Leu Phe Gln Pro Thr Leu Cys Ala Ala Leu Gly Leu Ala Ala Leu
1               5                   10                  15

Ile Val Gln Gly Gly Glu Ala Arg Pro Glu Thr Thr Val Pro His Ala
            20                  25                  30

Thr Gly Ser Leu Asp Asp Phe Leu Ala Ala Gln Ser Pro Ile Ala Phe
        35                  40                  45

Gln Gly Ile Leu Asn Asn Ile Gly Pro Ser Gly Ala Tyr Ser Glu Gly
    50                  55                  60

Val Asn Pro Gly Val Val Ile Ala Ser Pro Ser Lys Gln Asp Pro Asp
65                  70                  75                  80

Tyr Phe Tyr Thr Trp Val Arg Asp Ala Ala Leu Thr Val Gln Tyr Leu
                85                  90                  95

Val Glu Glu Leu Val Ala Gly Asn Ala Ser Leu Gln Phe Leu Ile Gln
            100                 105                 110

Asp Tyr Ile Ser Ser Gln Ala Arg Leu Gln Thr Val Glu Asn Pro Ser
        115                 120                 125

Gly Ser Leu Ser Ser Gly Gly Leu Gly Glu Pro Lys Phe His Val Asp
    130                 135                 140

Glu Thr Ala Phe Thr Asp Ser Trp Gly Arg Pro Gln Arg Asp Gly Pro
145                 150                 155                 160

Pro Leu Arg Ala Ile Ala Met Ile Ser Phe Ala Asn Tyr Leu Ile Asp
                165                 170                 175

Asn Gly His Gln Ser Thr Val Glu Asp Ile Ile Trp Pro Ile Gly Arg
            180                 185                 190

Asn Asp Leu Ser Tyr Val Ser Gln His Trp Asn Glu Thr Thr Phe Asp
        195                 200                 205

Ile Trp Glu Glu Val His Ser Ser Phe Phe Thr Thr Ala Val Gln
    210                 215                 220
```

Tyr Arg Ala Leu Val Gln Gly Ser Ala Leu Ala Ser Lys Leu Gly His
225                 230                 235                 240

Thr Cys Asp Asn Cys Gly Ser Gln Ala Pro Gln Ile Leu Cys Phe Leu
            245                 250                 255

Gln Ser Tyr Trp Thr Gly Ser His Ile Leu Ala Asn Thr Gly Gly Gly
        260                 265                 270

Arg Ser Gly Lys Asp Val Ser Thr Ile Leu Gly Val Ile Gly Ser Phe
    275                 280                 285

Asp Pro Asn Ala Asp Cys Asp Val Thr Phe Gln Pro Cys Ser Ala
290                 295                 300

Arg Ala Leu Ala Asn His Lys Gln Val Val Asp Ser Phe Arg Ser Ile
305                 310                 315                 320

Tyr Ala Ile Asn Ala Gly Ile Pro Ser Gly Ser Ala Val Ala Val Gly
                325                 330                 335

Arg Tyr Pro Glu Asp Val Tyr Gln Gly Gly His Pro Trp Tyr Leu Thr
            340                 345                 350

Thr Ala Ala Ala Glu Gln Leu Tyr Asp Ala Ile Tyr Gln Trp Asn
        355                 360                 365

His Val Gly His Ile Asp Ile Asn Ala Val Asn Leu Asp Phe Phe Lys
        370                 375                 380

Ser Ile Tyr Pro Ser Ala Ala Glu Gly Thr Tyr Thr Ser Asp Ser Ser
385                 390                 395                 400

Thr Phe Gln Asp Ile Ile Ser Ala Val Arg Thr Tyr Ala Asp Gly Phe
            405                 410                 415

Leu Ser Val Ile Glu Lys Tyr Thr Pro Pro Asp Asn Leu Leu Ala Glu
            420                 425                 430

Gln Phe His Arg Glu Thr Gly Ile Pro Leu Ser Ala Ala Ser Leu Thr
        435                 440                 445

Trp Ser Tyr Ala Ala Leu Asn Thr Ala Ala Gln Arg Arg Ala Ser Ile
    450                 455                 460

Val Pro Ser Pro Trp Asn Ser Asn Ser Thr Asp Leu Pro Asp Lys Cys
465                 470                 475                 480

Ser Ala Thr Ser Ala Thr Gly Pro Tyr Ala Thr Pro Thr Asn Thr Ala
                485                 490                 495

Trp Pro Thr Thr Thr Gln Pro Pro Glu Arg Pro Ala Cys Thr Pro Pro
            500                 505                 510

Ser Glu Val Thr Leu Thr Phe Asn Ala Leu Val Asp Thr Ala Phe Gly
            515                 520                 525

Gln Asn Ile Tyr Leu Val Gly Ser Ile Pro Glu Leu Gly Ser Trp Asp
        530                 535                 540

Pro Ala Asn Ala Leu Leu Met Ser Ala Lys Ser Trp Thr Ser Gly Asn
545                 550                 555                 560

Pro Val Trp Thr Leu Ser Ile Ser Leu Pro Ala Gly Thr Ser Phe Glu
            565                 570                 575

Tyr Lys Phe Ile Arg Lys Asp Asp Gly Ser Ser Asp Val Val Trp Glu
            580                 585                 590

Ser Asp Pro Asn Arg Ser Tyr Asn Val Pro Lys Asp Cys Gly Ala Asn
        595                 600                 605

Thr Ala Thr Val Asn Ser Trp Trp Arg
610                 615

<210> SEQ ID NO 10
<211> LENGTH: 1587

```
<212> TYPE: DNA
<213> ORGANISM: Lypomycis kononenkoae
<220> FEATURE:
<221> NAME/KEY: misc_feature
<223> OTHER INFORMATION: 10_Synthetic alpha-amylase gene sequence of
      Lypomycis kononenkoae

<400> SEQUENCE: 10
ggtaccgaat tcaggcctgg atccttaatt aaaaatggtt tctttcactt ctttgttggc      60
tggtgttgct gctatttctg gtgttttggc tgctccagct gctgaagttg aaccagttgc     120
tgttgaaaaa agaactgctg ctgaatggaa agaattgtca atttaccaag ttattactga     180
tagattcgct actactaatt tgactgctcc agattgttgg attagagctt attgtggtgg     240
tacttggaaa ggtttggaaa gaaagttgga ttacattcaa aatatgggtt ttgatgctgt     300
ttggatttct ccagttattc ataacattga agttaatact acttgggggtt ttgcttttca     360
tggttattgg ggtgatgatc catatagatt gaatgaacat tttggtactg ctgctgattt     420
gaaatctttg tctgattctt gcatgctag aggaatgtct ttgatggttg atgttgttat     480
taatcatttg gcttcatata ctttgccaca agatgttgat tattctttgt atccagctcc     540
atttaatact tcatctgctt ttcatcaacc atgtccaatt gatttttcta accaatcttc     600
tattgaagat tgttggttgg ttactgaacc agctccagct ttggttgatt tgaagaacga     660
agatcaagtt attttggatg ctttgattaa ctctgttgtt gatttggttg aaacttacga     720
tattgatggt attagattgg atactgctag acatgttcca aaaccatctt tggctaagtt     780
tcaagaaaaa gttggtgttt ttgttactgg tgaagcattg aatcaatctg ttccatacgt     840
tgctcaatat caaggtccat tgaactctgc tattaactat ccattgtggt atgctttagt     900
tgattctttt atgggtagaa ctactttga ttacttggaa tctgttgtta aatctgaaca     960
agctactttt tctgatgctc atgctttgac taatttcttg gataatcaag atcaaccaag    1020
atttgcttct tatttgggtg atggtaatgg tgatgatgtt ttgagagatg aaaatgctgc    1080
tactttttg ttttttcgttt ctggtattcc agttatctac tacggtttcg aacaaagatt    1140
tgatggtggt tttgatccag ttaatagaga accaatgtgg acttctggtt ataatacttc    1200
tactccattg tataattact tggctagatt gaatgctatt agaaaatacg ctgcttctat    1260
tactggtact caagtttttt actctgatga tactgttttt ttgggttctg gtgtttctca    1320
tatggctatg caaagaggtc cattggttat tgttttgact aatgttggtc aacatattat    1380
tgataacact ggttatactg ttactggttc tcaattttct gctggtgatt ctttgactga    1440
tttggtttct tgtactaagg ttaaagttgt tggtgctaat ggtactttta cttctccatc    1500
taatggtggt aaagctagaa tttggattaa atctaagtac gctggtaagt tctgttctta    1560
ataaggcgcg ccagatctct cgagctc                                        1587
```

<210> SEQ ID NO 11
<211> LENGTH: 508
<212> TYPE: PRT
<213> ORGANISM: Lypomycis kononenkoae
<220> FEATURE:
<221> NAME/KEY: misc_feature
<223> OTHER INFORMATION: 11_Protein sequence of the synthetic
      alpha-amylase gene sequence of Lypomycis kononenkoae

<400> SEQUENCE: 11

Met Val Ser Phe Thr Ser Leu Leu Ala Gly Val Ala Ala Ile Ser Gly
1               5                   10                  15

Val Leu Ala Ala Pro Ala Ala Glu Val Glu Pro Val Ala Val Glu Lys

-continued

```
             20                  25                  30
Arg Thr Ala Ala Glu Trp Lys Glu Leu Ser Ile Tyr Gln Val Ile Thr
             35                  40                  45

Asp Arg Phe Ala Thr Thr Asn Leu Thr Ala Pro Asp Cys Trp Ile Arg
 50                  55                  60

Ala Tyr Cys Gly Gly Thr Trp Lys Gly Leu Glu Arg Lys Leu Asp Tyr
 65                  70                  75                  80

Ile Gln Asn Met Gly Phe Asp Ala Val Trp Ile Ser Pro Val Ile His
                 85                  90                  95

Asn Ile Glu Val Asn Thr Thr Trp Gly Phe Ala Phe His Gly Tyr Trp
                100                 105                 110

Gly Asp Asp Pro Tyr Arg Leu Asn Glu His Phe Gly Thr Ala Ala Asp
                115                 120                 125

Leu Lys Ser Leu Ser Asp Ser Leu His Ala Arg Gly Met Ser Leu Met
    130                 135                 140

Val Asp Val Val Ile Asn His Leu Ala Ser Tyr Thr Leu Pro Gln Asp
145                 150                 155                 160

Val Asp Tyr Ser Leu Tyr Pro Ala Pro Phe Asn Thr Ser Ser Ala Phe
                165                 170                 175

His Gln Pro Cys Pro Ile Asp Phe Ser Asn Gln Ser Ser Ile Glu Asp
                180                 185                 190

Cys Trp Leu Val Thr Glu Pro Ala Pro Ala Leu Val Asp Leu Lys Asn
    195                 200                 205

Glu Asp Gln Val Ile Leu Asp Ala Leu Ile Asn Ser Val Val Asp Leu
    210                 215                 220

Val Glu Thr Tyr Asp Ile Asp Gly Ile Arg Leu Asp Thr Ala Arg His
225                 230                 235                 240

Val Pro Lys Pro Ser Leu Ala Lys Phe Gln Glu Lys Val Gly Val Phe
                245                 250                 255

Val Thr Gly Glu Ala Leu Asn Gln Ser Val Pro Tyr Val Ala Gln Tyr
                260                 265                 270

Gln Gly Pro Leu Asn Ser Ala Ile Asn Tyr Pro Leu Trp Tyr Ala Leu
    275                 280                 285

Val Asp Ser Phe Met Gly Arg Thr Thr Phe Asp Tyr Leu Glu Ser Val
    290                 295                 300

Val Lys Ser Glu Gln Ala Thr Phe Ser Asp Ala His Ala Leu Thr Asn
305                 310                 315                 320

Phe Leu Asp Asn Gln Asp Gln Pro Arg Phe Ala Ser Tyr Leu Gly Asp
                325                 330                 335

Gly Asn Gly Asp Asp Val Leu Arg Asp Glu Asn Ala Ala Thr Phe Leu
                340                 345                 350

Phe Phe Val Ser Gly Ile Pro Val Ile Tyr Tyr Gly Phe Glu Gln Arg
    355                 360                 365

Phe Asp Gly Gly Phe Asp Pro Val Asn Arg Glu Pro Met Trp Thr Ser
    370                 375                 380

Gly Tyr Asn Thr Ser Thr Pro Leu Tyr Asn Tyr Leu Ala Arg Leu Asn
385                 390                 395                 400

Ala Ile Arg Lys Tyr Ala Ala Ser Ile Thr Gly Thr Gln Val Phe Tyr
                405                 410                 415

Ser Asp Asp Thr Val Phe Leu Gly Ser Gly Val Ser His Met Ala Met
                420                 425                 430

Gln Arg Gly Pro Leu Val Ile Val Leu Thr Asn Val Gly Gln His Ile
    435                 440                 445
```

```
Ile Asp Asn Thr Gly Tyr Thr Val Thr Gly Ser Gln Phe Ser Ala Gly
    450                 455                 460

Asp Ser Leu Thr Asp Leu Val Ser Cys Thr Lys Val Lys Val Val Gly
465                 470                 475                 480

Ala Asn Gly Thr Phe Thr Ser Pro Ser Asn Gly Gly Lys Ala Arg Ile
                485                 490                 495

Trp Ile Lys Ser Lys Tyr Ala Gly Lys Phe Cys Ser
                500                 505

<210> SEQ ID NO 12
<211> LENGTH: 1545
<212> TYPE: DNA
<213> ORGANISM: Saccharomycopsis fibuligera
<220> FEATURE:
<221> NAME/KEY: misc_feature
<223> OTHER INFORMATION: 12_Synthetic alpha-amylase gene sequence of
      Saccharomycopsis fibuligera

<400> SEQUENCE: 12
ggtaccgaat tcaggcctgg atccttaatt aaaaatgcaa atttctaagg ctgctttgtt      60
ggcttctttg gctgctttgg tttatgctca accagttact ttgtttaaga gagaaactaa     120
cgctgataag tggagatcac aatcaattta ccaaattgtt actgatagat cgctagaac     180 tgatggtgat acttctgctt cttgtaatac tgaagataga ttgtattgtg gtggttcttt     240
tcaaggtatt atcaagaagt tggattacat taaggatatg ggttttactg ctatttggat     300
ttctccagtt gttgaaaata ttccagataa tactgcttat ggttatgctt atcatggtta     360
ctggatgaaa acatttaca agattaacga aaattttggt actgctgatg atttgaaatc     420
tttggctcaa gaattgcatg atagagacat gttgttgatg ttgatattg ttactaatca     480 ttacggttct gatggttctg gtgattctat tgattactct gaatacactc catttaacga     540
tcaaaagtac ttccataact actgtttgat ttctaactat gatgatcaag ctcaagttca     600
atcttgttgg gaaggtgatt cttctgttgc tttgccagat ttgagaactg aagattctga     660
tgttgcttct gtttttaact cttgggttaa ggattttgtt ggtaactatt ctattgatgg     720
tttgagaatt gattctgcta acatgttga tcaaggtttt tttccagatt ttgtttctgc     780
ttctggtgtt tattctgttg gtgaagtttt tcaaggtgat ccagcttata cttgtccata     840
ccaaaattac attccaggtg tttctaatta tccattgtac tacccaacta ctagatttt     900 caagactact gattcttctt cttctgaatt gactcaaatg atttcttcag ttgcttcttc     960
ttgttctgat ccaactttgt tgactaattt cgttgaaaac catgataatg aaagatttgc    1020
ttctatgact tctgatcaat ctttgatttc aaacgctatt gcttttgttt tgtgggtga    1080 tggtattcca gttatctact acggtcaaga acaaggtttg tctggtaaat ctgatccaaa    1140
caatagagaa gcattgtggt tgtctggtta taacaaagaa tctgattact acaagttgat    1200
tgctaaagct aatgctgcta gaaatgctgc tgtttatcaa gattcttctt acgctacttc    1260
tcaattgtct gttattttct ctaacgatca tgttattgct actaaaagag ttctgttgt    1320 ttctgttttc aacaatttgg gttcttctgg ttcttcagat gttactattt ctaacactgg    1380
ttattcttca ggtgaagatt tggttgaagt tttgacttgt tctactgttt ctggttcatc    1440
tgatttgcaa gtttctattc aaggtggtca accacaaatt tttgttccag ctaagtatgc    1500
ttctgatatt tgttcttaat aaggcgcgcc agatctctcg agctc                    1545

<210> SEQ ID NO 13
```

```
<211> LENGTH: 494
<212> TYPE: PRT
<213> ORGANISM: Saccharomycopsis fibuligera
<220> FEATURE:
<221> NAME/KEY: misc_feature
<223> OTHER INFORMATION: 13_Protein sequence of the synthetic
      alpha-amylase gene sequence of Saccharomycopsis fibuligera

<400> SEQUENCE: 13
```

| Met | Gln | Ile | Ser | Lys | Ala | Ala | Leu | Leu | Ala | Ser | Leu | Ala | Ala | Leu | Val |
|---|---|---|---|---|---|---|---|---|---|---|---|---|---|---|---|
| 1 | | | | 5 | | | | | 10 | | | | | 15 | |

Tyr Ala Gln Pro Val Thr Leu Phe Lys Arg Glu Thr Asn Ala Asp Lys
              20                  25                  30

Trp Arg Ser Gln Ser Ile Tyr Gln Ile Val Thr Asp Arg Phe Ala Arg
         35                  40                  45

Thr Asp Gly Asp Thr Ser Ala Ser Cys Asn Thr Glu Asp Arg Leu Tyr
     50                  55                  60

Cys Gly Gly Ser Phe Gln Gly Ile Ile Lys Lys Leu Asp Tyr Ile Lys
 65                  70                  75                  80

Asp Met Gly Phe Thr Ala Ile Trp Ile Ser Pro Val Val Glu Asn Ile
                 85                  90                  95

Pro Asp Asn Thr Ala Tyr Gly Tyr Ala Tyr His Gly Tyr Trp Met Lys
             100                 105                 110

Asn Ile Tyr Lys Ile Asn Glu Asn Phe Gly Thr Ala Asp Asp Leu Lys
         115                 120                 125

Ser Leu Ala Gln Glu Leu His Asp Arg Asp Met Leu Leu Met Val Asp
    130                 135                 140

Ile Val Thr Asn His Tyr Gly Ser Asp Gly Ser Gly Asp Ser Ile Asp
145                 150                 155                 160

Tyr Ser Glu Tyr Thr Pro Phe Asn Asp Gln Lys Tyr Phe His Asn Tyr
                165                 170                 175

Cys Leu Ile Ser Asn Tyr Asp Asp Gln Ala Gln Val Gln Ser Cys Trp
            180                 185                 190

Glu Gly Asp Ser Ser Val Ala Leu Pro Asp Leu Arg Thr Glu Asp Ser
        195                 200                 205

Asp Val Ala Ser Val Phe Asn Ser Trp Val Lys Asp Phe Val Gly Asn
    210                 215                 220

Tyr Ser Ile Asp Gly Leu Arg Ile Asp Ser Ala Lys His Val Asp Gln
225                 230                 235                 240

Gly Phe Phe Pro Asp Phe Val Ser Ala Ser Gly Val Tyr Ser Val Gly
                245                 250                 255

Glu Val Phe Gln Gly Asp Pro Ala Tyr Thr Cys Pro Tyr Gln Asn Tyr
            260                 265                 270

Ile Pro Gly Val Ser Asn Tyr Pro Leu Tyr Tyr Pro Thr Thr Arg Phe
        275                 280                 285

Phe Lys Thr Thr Asp Ser Ser Ser Ser Glu Leu Thr Gln Met Ile Ser
    290                 295                 300

Ser Val Ala Ser Ser Cys Ser Asp Pro Thr Leu Leu Thr Asn Phe Val
305                 310                 315                 320

Glu Asn His Asp Asn Glu Arg Phe Ala Ser Met Thr Ser Asp Gln Ser
                325                 330                 335

Leu Ile Ser Asn Ala Ile Ala Phe Val Leu Leu Gly Asp Gly Ile Pro
            340                 345                 350

Val Ile Tyr Tyr Gly Gln Glu Gln Gly Leu Ser Gly Lys Ser Asp Pro
        355                 360                 365

-continued

```
Asn Asn Arg Glu Ala Leu Trp Leu Ser Gly Tyr Asn Lys Glu Ser Asp
    370                 375                 380

Tyr Tyr Lys Leu Ile Ala Lys Ala Asn Ala Ala Arg Asn Ala Ala Val
385                 390                 395                 400

Tyr Gln Asp Ser Ser Tyr Ala Thr Ser Gln Leu Ser Val Ile Phe Ser
                405                 410                 415

Asn Asp His Val Ile Ala Thr Lys Arg Gly Ser Val Val Ser Val Phe
            420                 425                 430

Asn Asn Leu Gly Ser Ser Gly Ser Ser Asp Val Thr Ile Ser Asn Thr
        435                 440                 445

Gly Tyr Ser Ser Gly Glu Asp Leu Val Glu Val Leu Thr Cys Ser Thr
    450                 455                 460

Val Ser Gly Ser Ser Asp Leu Gln Val Ser Ile Gln Gly Gly Gln Pro
465                 470                 475                 480

Gln Ile Phe Val Pro Ala Lys Tyr Ala Ser Asp Ile Cys Ser
                485                 490
```